(12) United States Patent
Jiang et al.

(10) Patent No.: US 7,491,707 B1
(45) Date of Patent: Feb. 17, 2009

(54) SYNTHETIC LIPID-A-ANALOGS AND USES THEREOF

(75) Inventors: Zi-Hua Jiang, Edmonton (CA); Mimi Bach, Edmonton (CA); Damayanthi Yalamati, Edmonton (CA); Rao Koganty, Edmonton (CA); Michael Longenecker, Edmonton (CA)

(73) Assignee: Biomira, Inc., Edmonton, Alberta (CA)

( * ) Notice: Subject to any disclaimer, the term of this patent is extended or adjusted under 35 U.S.C. 154(b) by 0 days.

(21) Appl. No.: 10/130,055

(22) PCT Filed: Nov. 15, 2000

(86) PCT No.: PCT/US00/31281

§ 371 (c)(1),
(2), (4) Date: Apr. 3, 2003

(87) PCT Pub. No.: WO01/36433

PCT Pub. Date: May 25, 2001

Related U.S. Application Data

(60) Provisional application No. 60/164,928, filed on Nov. 15, 1999.

(51) Int. Cl.
*A61K 31/7016* (2006.01)
*A61K 9/127* (2006.01)

(52) U.S. Cl. .................. 514/53; 536/123.13; 424/450; 424/812

(58) Field of Classification Search ................ 536/55.2, 536/123.13
See application file for complete search history.

(56) References Cited

U.S. PATENT DOCUMENTS

| | | | |
|---|---|---|---|
| 4,912,094 A | 3/1990 | Myers et al. | 514/54 |
| 5,134,230 A * | 7/1992 | Kusama et al. | 536/117 |
| 5,554,372 A * | 9/1996 | Hunter | 424/280.1 |
| 5,648,343 A * | 7/1997 | Carlson | 514/53 |
| 2005/0048076 A1* | 3/2005 | Apicella et al. | 424/190.1 |

FOREIGN PATENT DOCUMENTS

| | | | |
|---|---|---|---|
| EP | 0330715 | | 9/1989 |
| EP | 0536969 | | 3/1993 |
| WO | WO 95/14026 | * | 5/1995 |

OTHER PUBLICATIONS

Wang, Y. et al "Acid and base hydrolysis of Lipid A . . ." J. Mass Sprectrom. (1996) vol. 31, pp. 138-149.*
Karunaratne, D. et al "Characterization of Lipid A . . ." Arch. Biochem. Biophys. (1992) vol. 299, No. 2, pp. 368-376.*
Grabarek, J. et al "Modulation of human platelet . . ." J. Clin. Invest. (1988) vol. 82, pp. 964-971.*
Schromm, A. et al "The charge of endotoxin molecules influences their conformation . . ." J. Immunol. (1998) vol. 161, pp. 5464-5471.*
Rietschel, E. et al "Bacterial endotoxin: molecular relationships . . ." FASEB J. (1994) vol. 8, pp. 217-225.*
Imoto, M. et al "Chemical synthesis of a biosynthetic precursor of lipid A . . ." Bull. Chem. Soc. Jpn. (1987) vol. 60, pp. 2197-2204.*
Samuel, J. et al "immunogenicity and antitumor activity . . ." Int. J. Cancer (1998) vol. 75, pp. 295-302.*
Alving, Carl, *Lipopolysaccharide, Lipid A, and Liposomes Containing Lipid A as Immunologic Adjuvants*, Immunobiol., vol. 187, pp. 430-446, 1993.
Charon, et al., *Chemical Synthesis and Immunological Activities of Glycolipids Structurally Related to Lipid A*, Biochemistry, vol. 24, pp. 2736-2742, 1985.
Christ et al., *E5531, a Pure Endotoxin Antagonist of High Potency*, Science, vol. 268, pp. 80-83, Apr. 7, 1995.
Fink, et al., *Adoptive immunotherapy of Gram-negative sepsis: Use of monoclonal antibodies to lipopolysaccharide*, Critical Care Medicine, vol. 21, No. 2, pp. S32-S39, 1993.
Fujishima, et al., *New synthetic immunomodulators combining a 4-O-phosphono-D-glucosamine derivative related to bacteria lipid A with 1-deoxy-N-acetylmuramoyl dipeptide analogs*, Carbohydrate Research, vol. 167, pp. 317-324, 1987.
Goldman, et al., *Analysis of Lipopolysaccharide Biosynthesis in Salmonella typhimurium and Escherichia coli by Using Agents Which Specifically Block Incorporation of 3-Deoxy-D-manno-Octulosonate*, Journal of Bacteriology, vol. 170, No. 5, pp. 2185-2191, May 1988.
Goldman, et al., *Inhibition of lipopolysaccharide synthesis in Agrobacterium tumefaciens and Aeromonas salmonicida*, Journal of General Microbiology, vol. 138, pp. 15271533, 1992.

Monosaccharide and disaccharide Lipid-A analogs containing new lipid structures and two examples thereof Kiso, et al., *Synthesis of 2-Deoxy-4-O-Phosphono-3-O-Tetradecanoyl-2-[(3/R)—and (3s)-3-Tetradecanoyloxytetradecanamidol]-D-Glucose: A Diastereoisomeric Pair of 4-O-Phosphono-D-Glucosamine Derivatives (GLA-27) Related to Bacterial Lipid A*, Carbohydrate Research, vol. 148, pp. 221-234, 1986.

Kotani, et al., *Immunobiological Activities of Synthetic Lipid A Analogs with Low Endotoxicity*, Infection and Immunity, vol. 54, No. 3, pp. 673-682, Dec. 1986.

Kotani, et al., *Low Endotoxic Activities of Synthetic Salmonella-Type Lipid A with an Additional Acyloxyacyl Group on the 2-Amino Group of β) 1-6 ) Glucosamine Disaccharide 1,4'-Bisophosphate*, Infection and Immunity, vol. 52, No. 3, pp. 872-884, Jun. 1986.

Onishi, et al., *Antibacterial Agents That Inhibit Lipid A Biosynthesis*, Science, vol. 274, pp. 980-982, Nov. 8, 1996.

Sato, et al., *Synthetic Lipid A Analog with Low Endotoxicity, Dt-5461, Prevents Lethal Endotoxemia*, Infection and Immunity, vol. 63, No. 8, pp. 2859-2866, Aug. 1995.

Takahashi, et al., *Requirement of a Properly Acylated β(1-6)-D-Glucosamine Disaccharide Bisphosphate Structure for Efficient Manifestation of Full Endotoxic and Associated Bioactivities of Lipid A*, Infection and Immunity, vol. 65, No. 1, pp. 57-68, Jan. 1987.

Takayama, et al., *Separation and Characterization of Toxic and Nontoxic Forms of Lipid A*, Reviews of Infectious Diseases, vol. 6, No. 4, pp. 439-443, Jul.-Aug. 1984.

Takayama, et al., *Use of Endotoxin in Cancer Immunotherapy and Characterization of Its Nontoxic but Active Lipid A Components*, pp. 219-233, American Chemical Society, 1983.

Ulrich, et al., *Monophosphoryl Lipid A as an Adjuvant: Past Experiences and New Directions*, Pharm. Biotechnol., vol. 6, pp. 495-525, 1995.

Vaara, Martti, *Lipid A: Target for Antibacterial Drugs*, Science, vol. 274, pp. 939-940, Nov. 8, 1996.

Von Eschen, Kenneth B., *Monophosphoryl Lipid A and Immunotherapy*, vol. II: Immunopharmacology and pathophysiology, D.C. Morrison and J. L. Ryan (eds.), CRC Press, Boca Raton, Ann Arbor, London, Tokyo, pp. 411-428, 1992.

Werner, et al., *Immunostimulating agents: what next? A review of their present and potential medical applications*, Eur. J. Biochem., vol. 242, pp. 1-19, 1996.

\* cited by examiner

*Primary Examiner*—Leigh C Maier
(74) *Attorney, Agent, or Firm*—Iver P. Cooper

(57) ABSTRACT

New synthetic Lipid-A analogs based on monosaccharide (1) and disaccharide (2) derivatives were designed and prepared in the present invention. Both structures (1) and (2) incorporate novel lipid structures (3) and (4) that are not found in nature. Also, novel disaccharide Lipid-A structures (2) that incorporate novel contingents of uniform lipids and where $R_1$, $R_4$ and $R_5$ are the same substitution group of structure (III) were synthesized. Liposome formulations containing totally synthetic components such as synthetic Lipid-A and synthetic lipopeptide derived from tumor-associated MUC1 mucin are described along with their therapeutic utility. Comparative test results of immunostimulating properties and toxicity of Lipid-A analogs (1) and (2) are included.

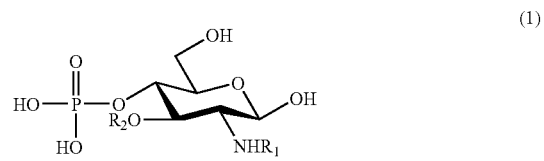

(1)

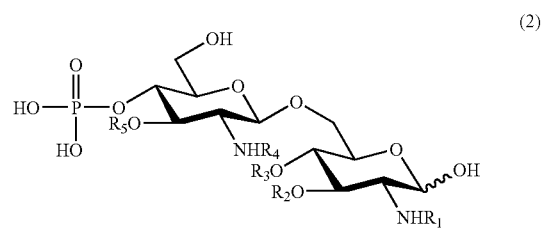

(2)

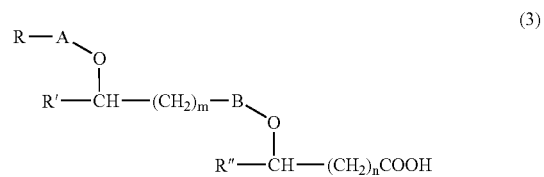

(3)

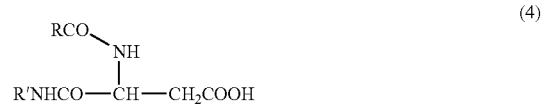

(4)

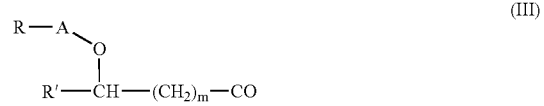

(III)

69 Claims, 35 Drawing Sheets

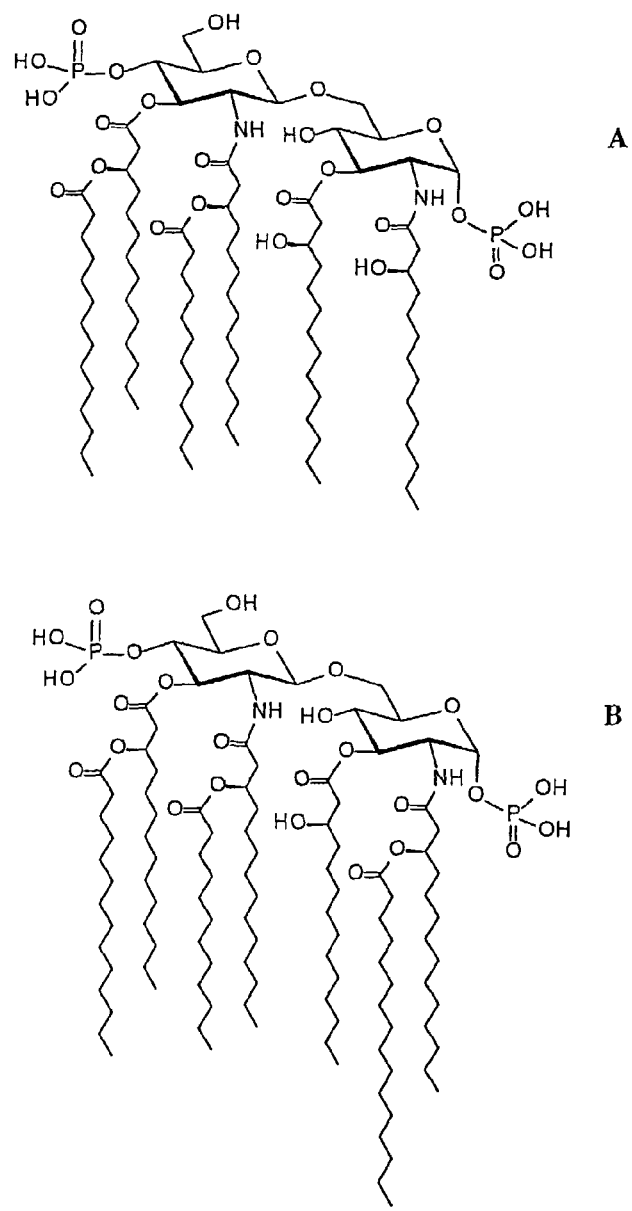
FIG. 1 Examples of natural Lipid-A structures, A from *E. coli* and B from *Salmonella* strains

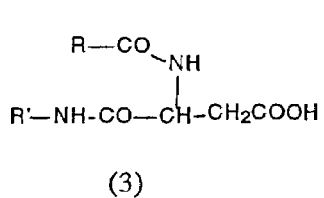
(3)
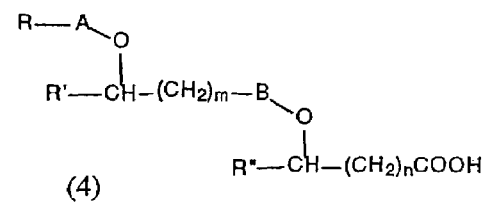
(4)
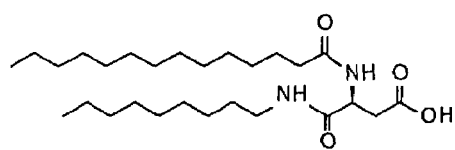
5
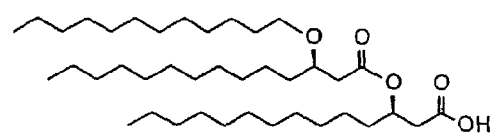
23
FIG. 2   New lipid acids (3) and (4) and two examples thereof

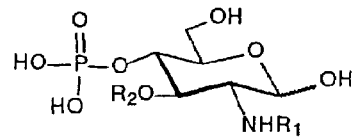
(1)
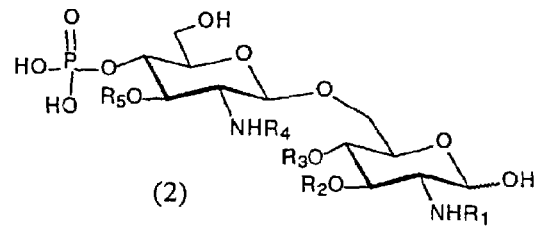
(2)
at least one of $R_1$, $R_2$, $R_3$, $R_4$ and $R_5$ has the lipid structure (I) or (II)
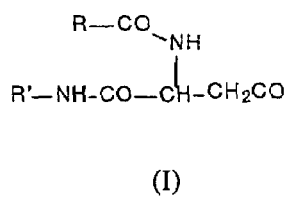
(I)
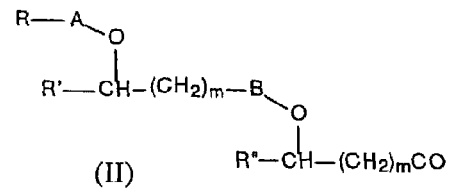
(II)
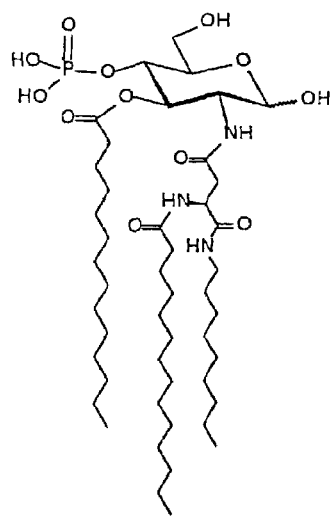
33
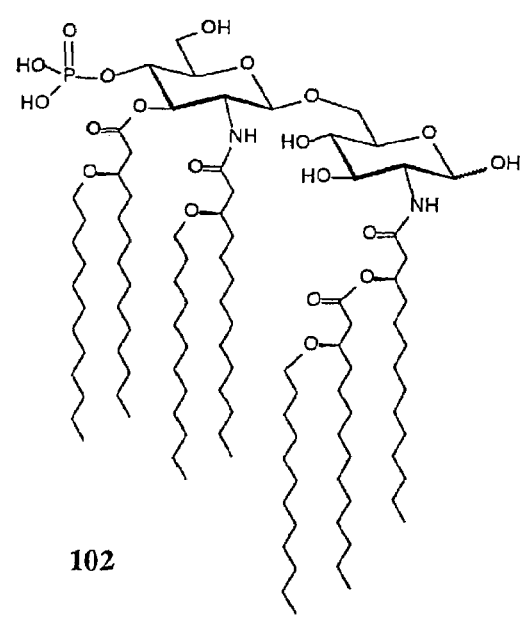
102
FIG. 3   Monosaccharide and disaccharide Lipid-A analogs containing new lipid structures and two examples thereof

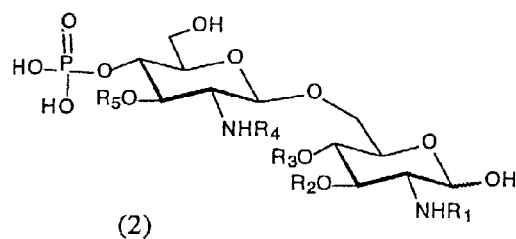
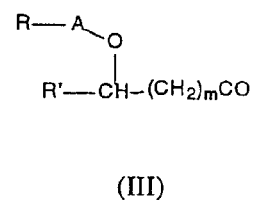
$R_1$, $R_4$ and $R_5$ are the same substitution group of structure (III)
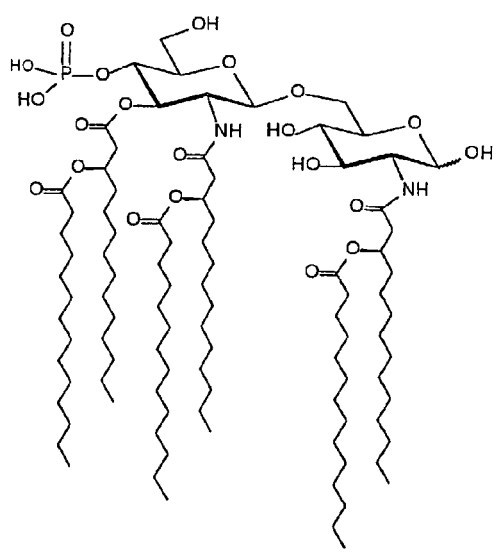
54
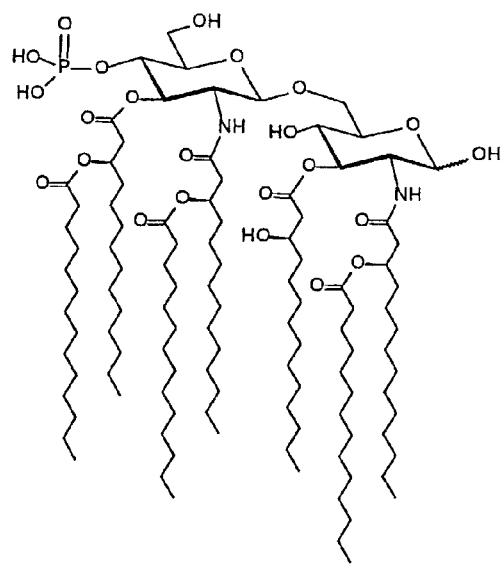
86
FIG. 4   Disaccharide Lipid-A analogs with uniform di-lipid chains and two examples thereof

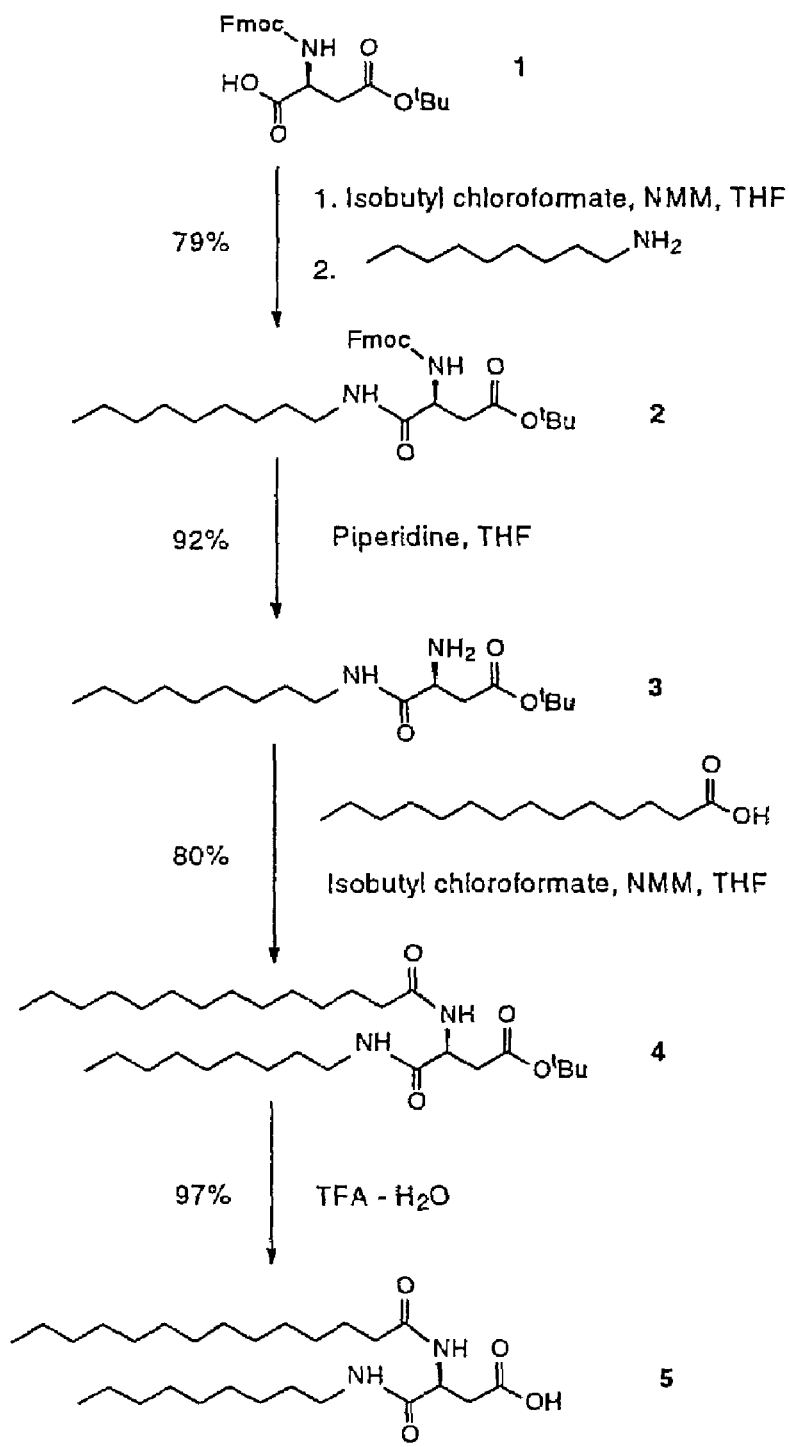
FIG. 5  Synthesis of lipid 5

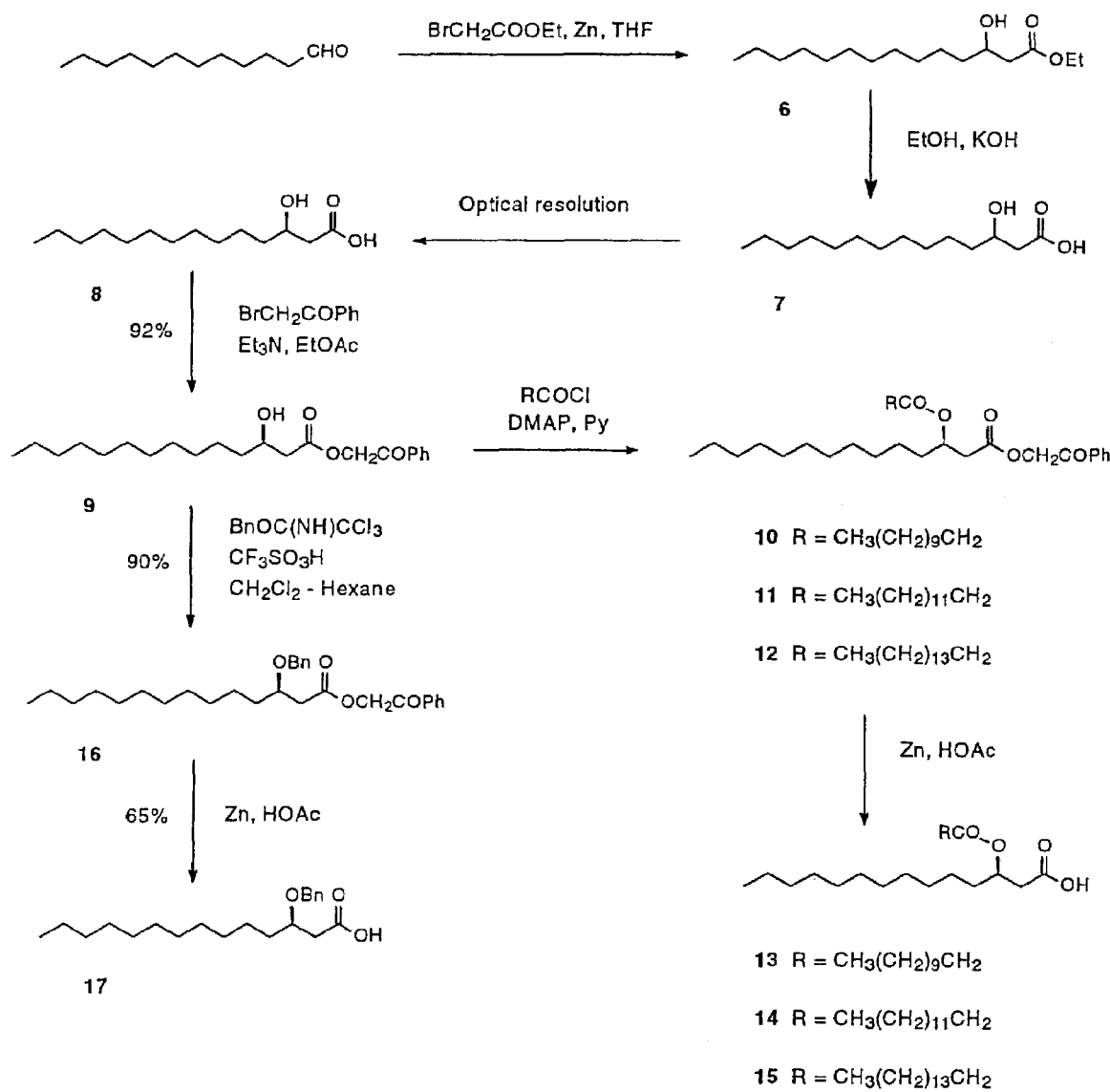
FIG. 6 Synthesis of lipids

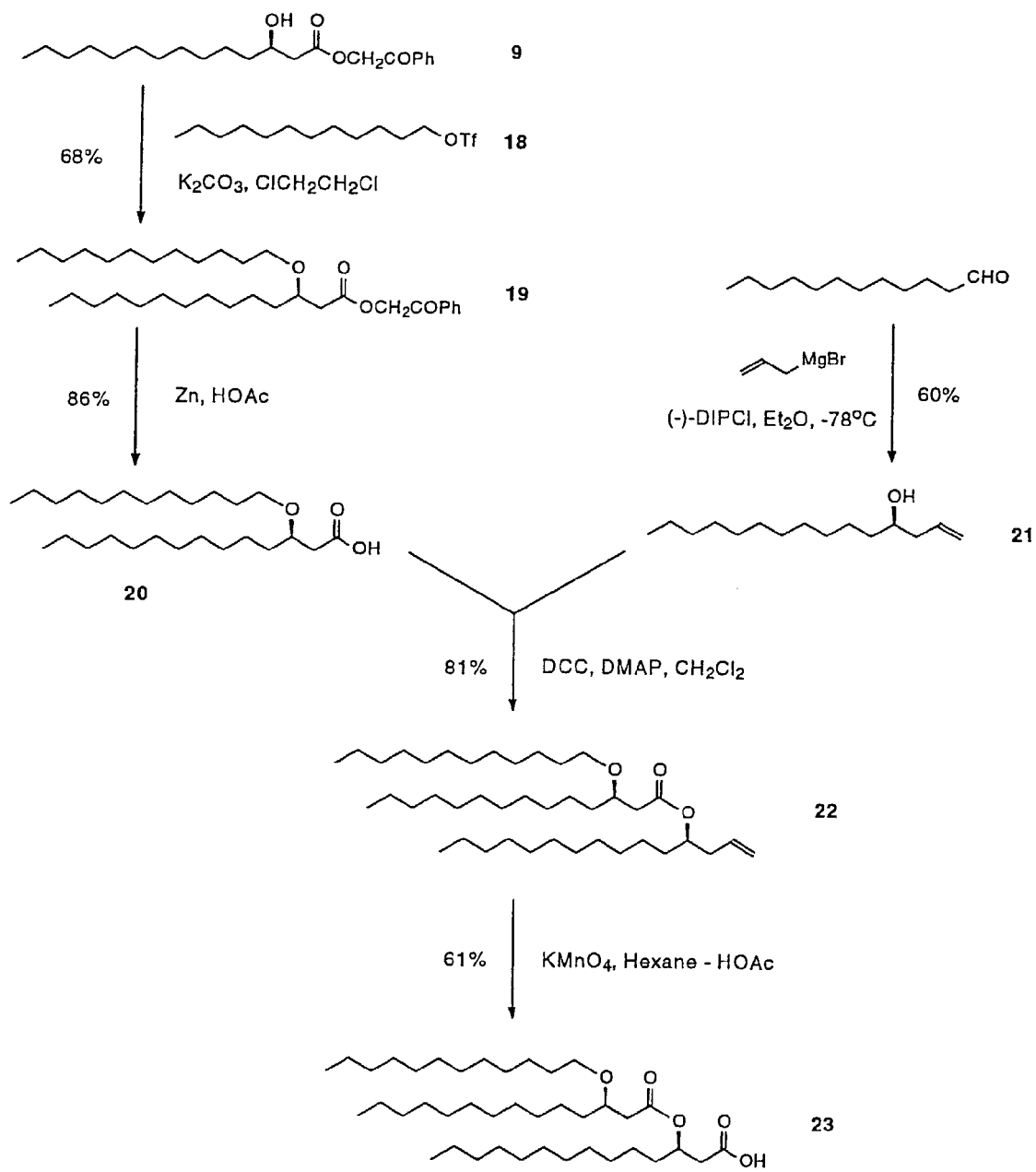
FIG. 7    Synthesis of tri-lipid acid 23

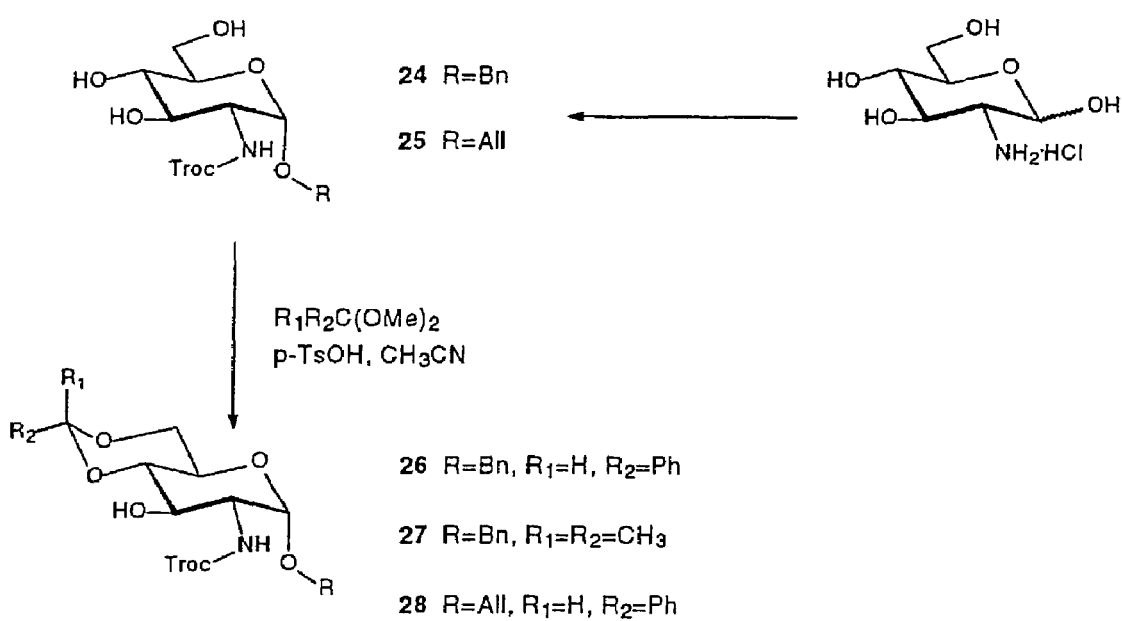
FIG. 8  Synthesis of glucosamine derivatives

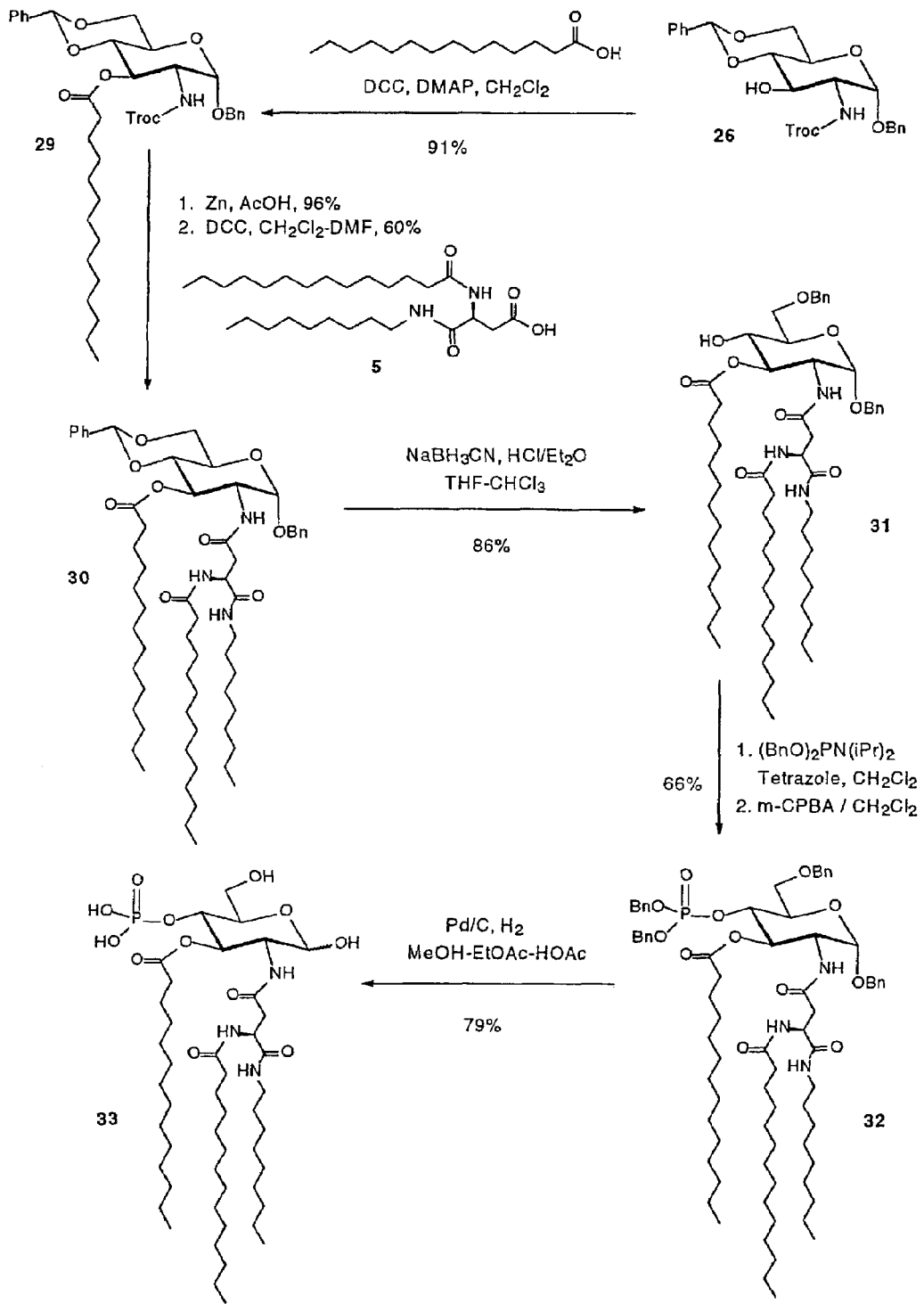
FIG. 9 Synthesis of compound 33

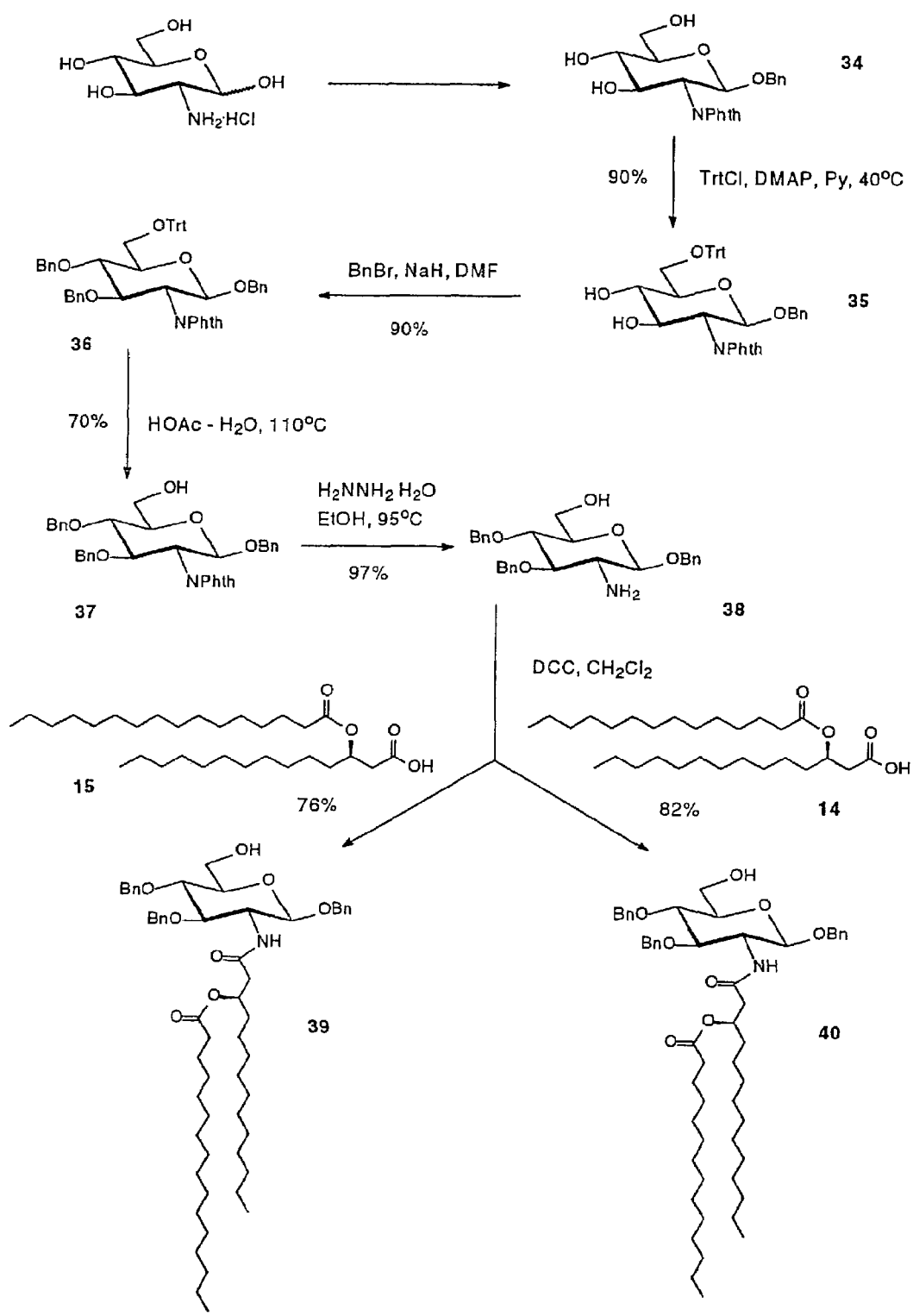
FIG. 10   Synthesis of glycosylation acceptors

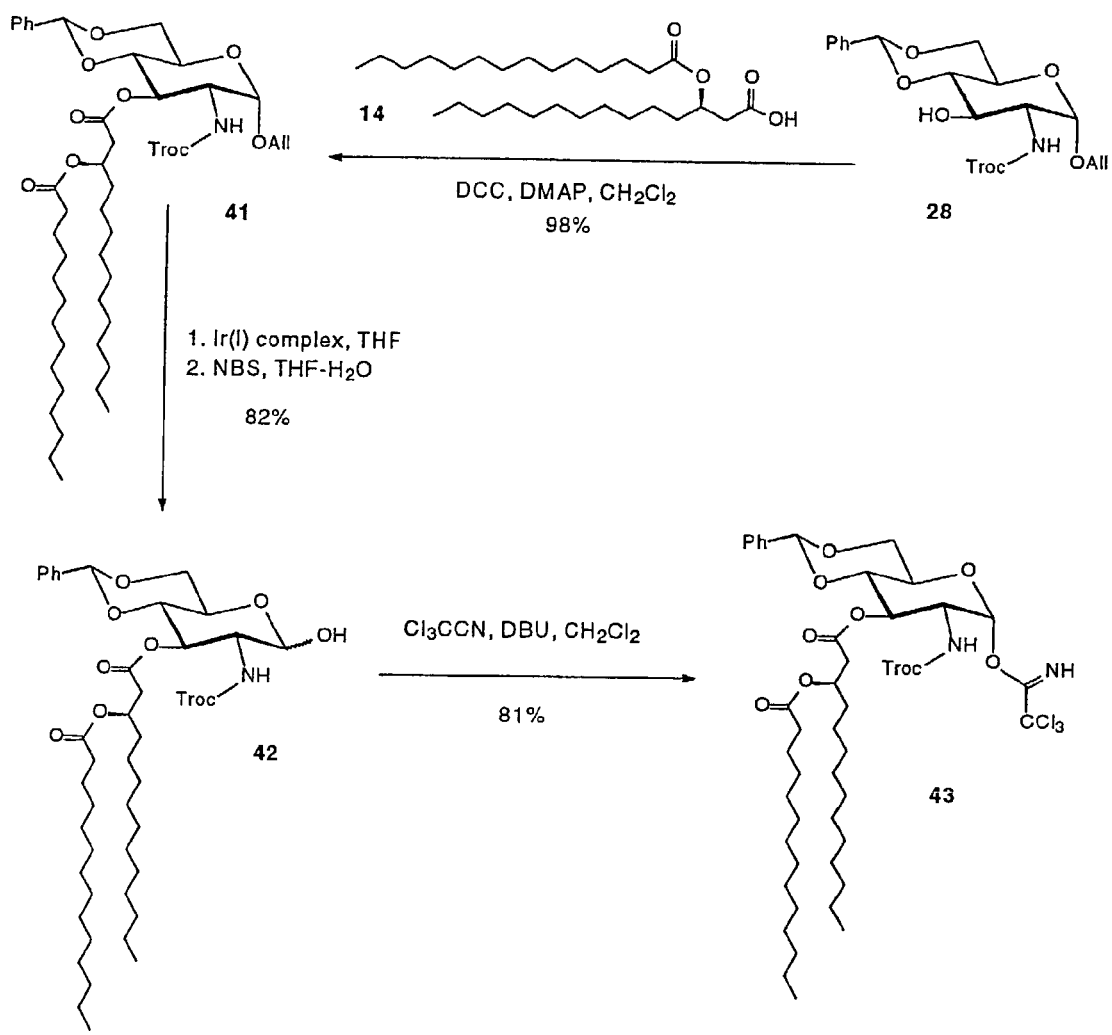
FIG. 11   Synthesis of glycosylation donor 43

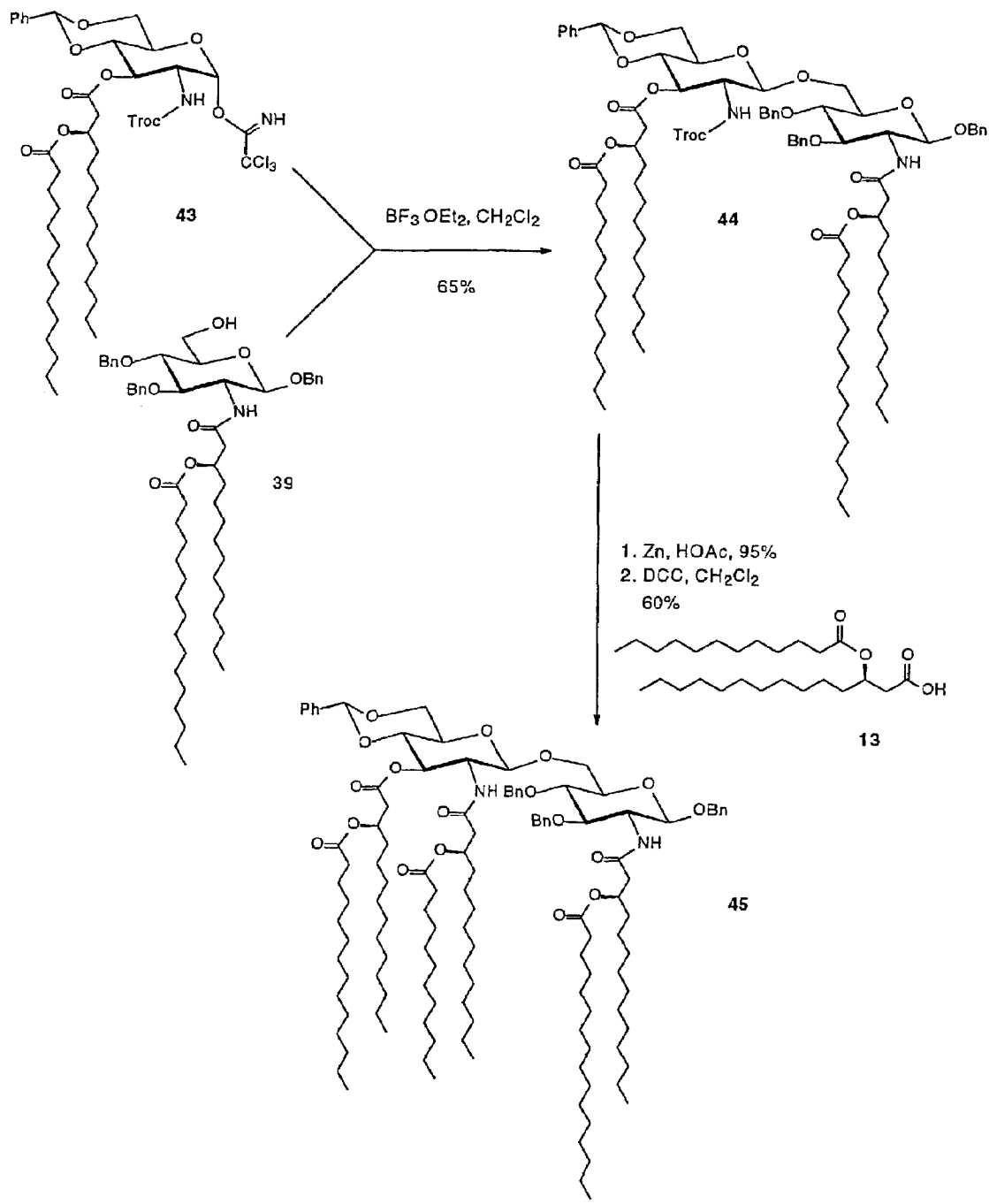
FIG. 12  Synthesis of disaccharide 45

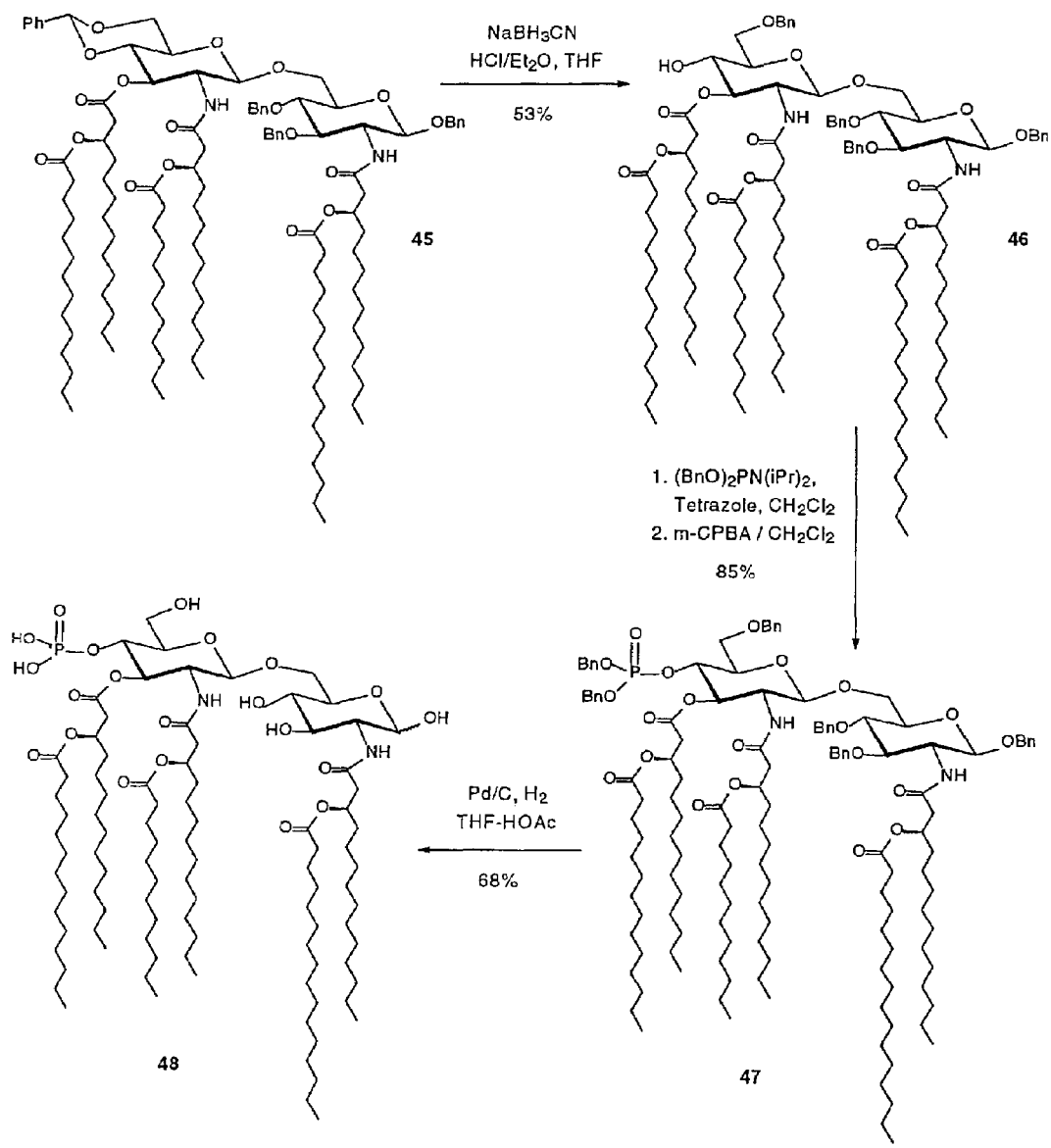
FIG. 13  Synthesis of compound 48

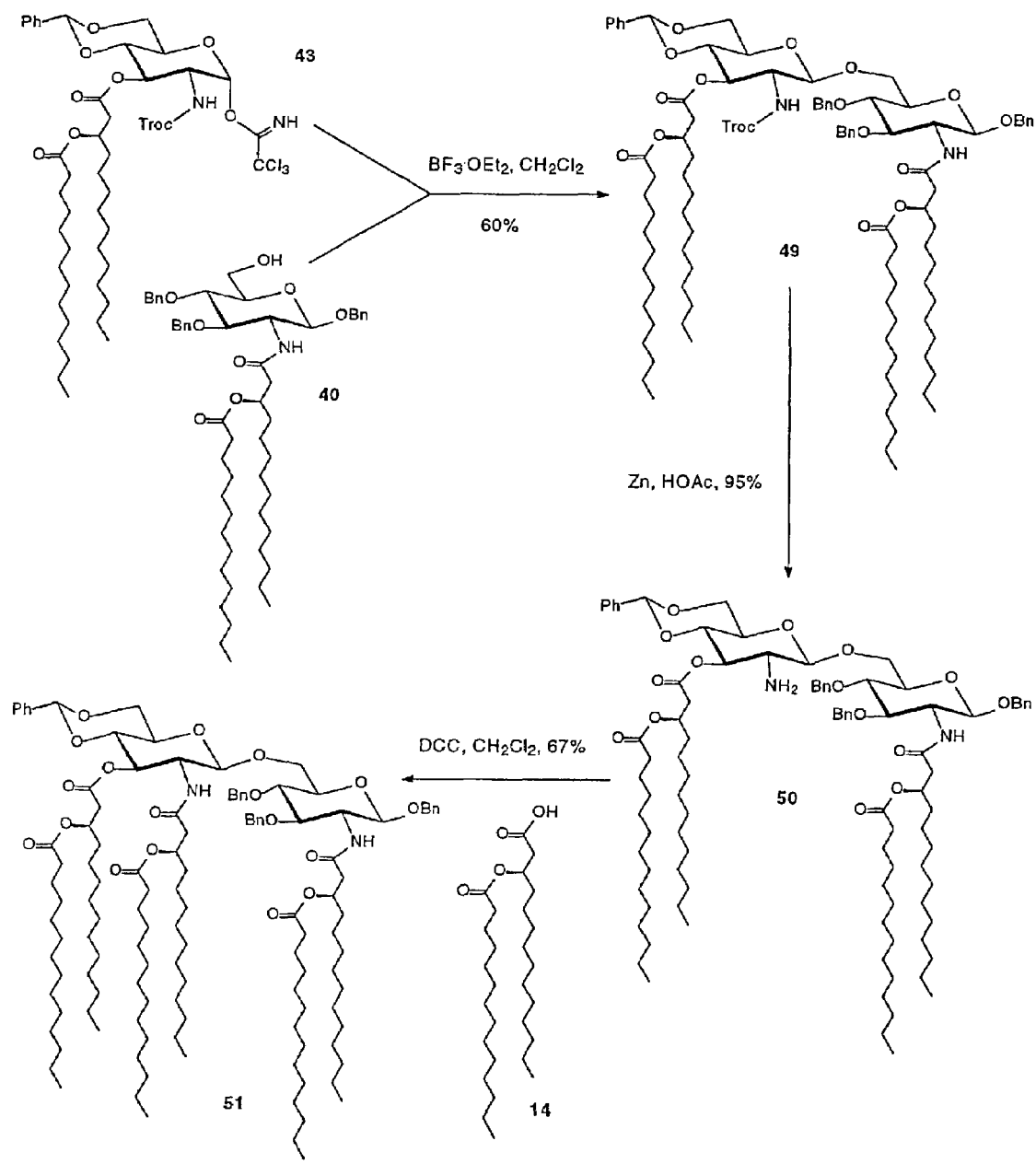
FIG. 14 Synthesis of disaccharide 51

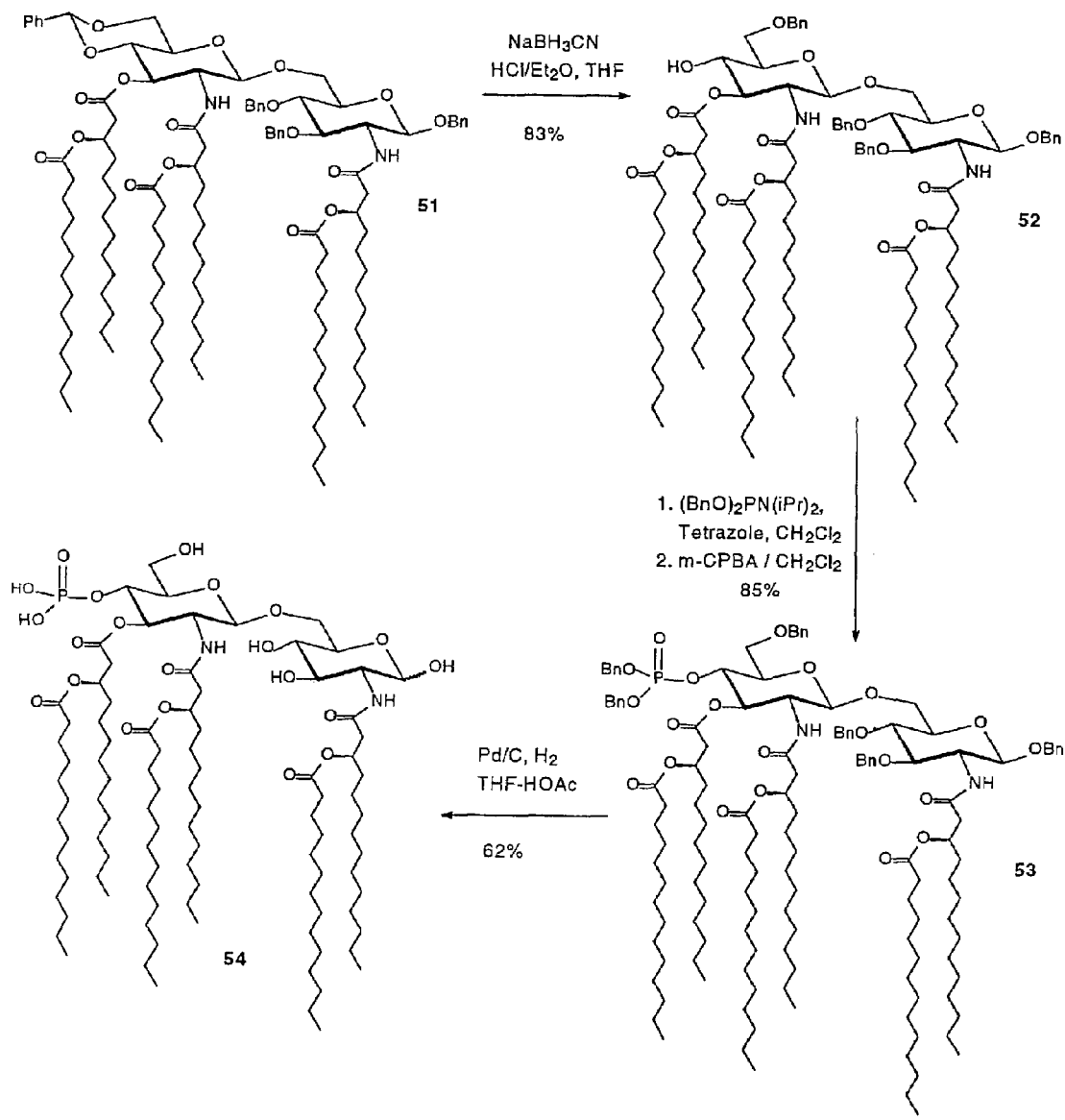
FIG. 15  Synthesis of compound 54

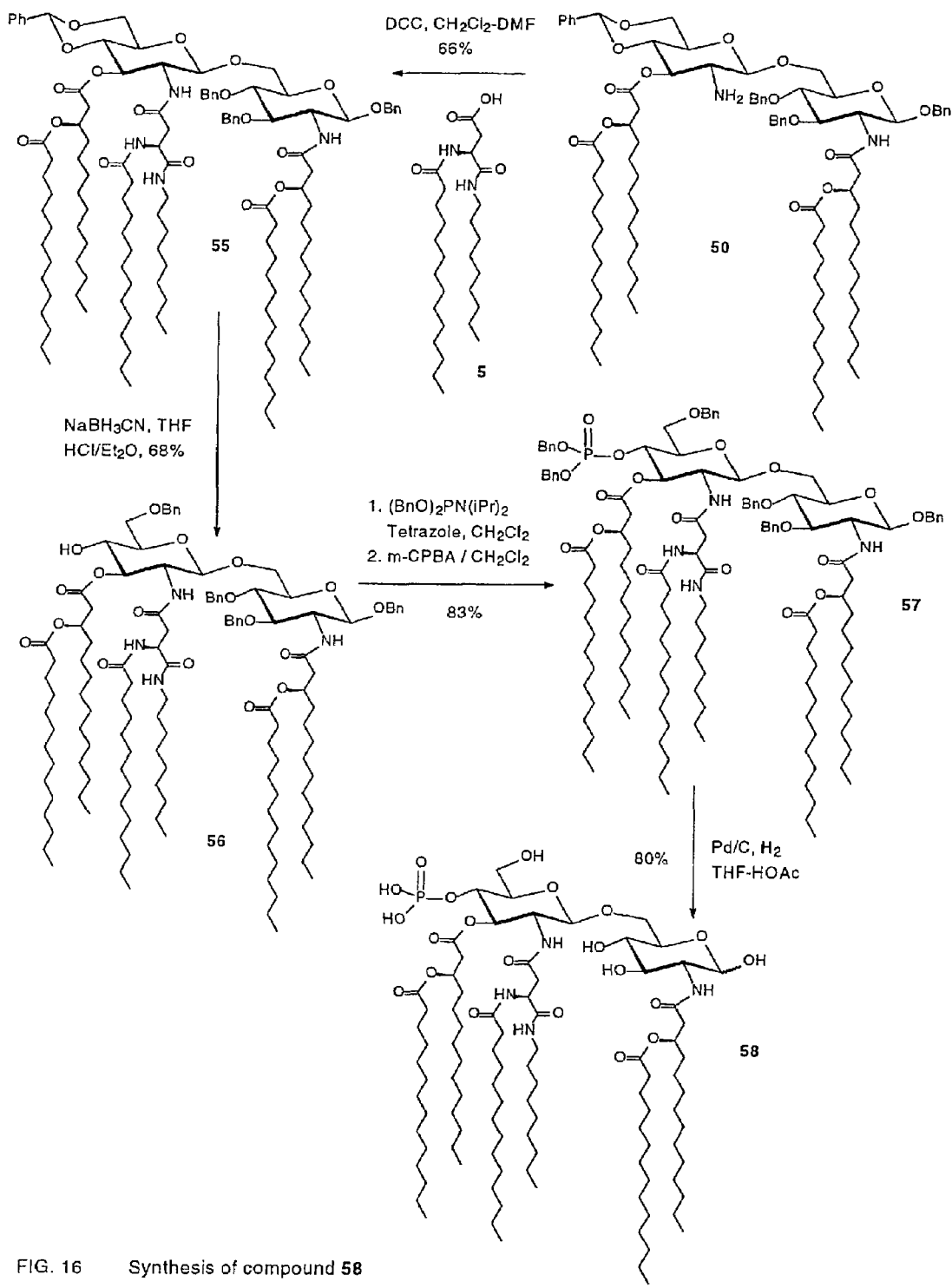
FIG. 16  Synthesis of compound 58

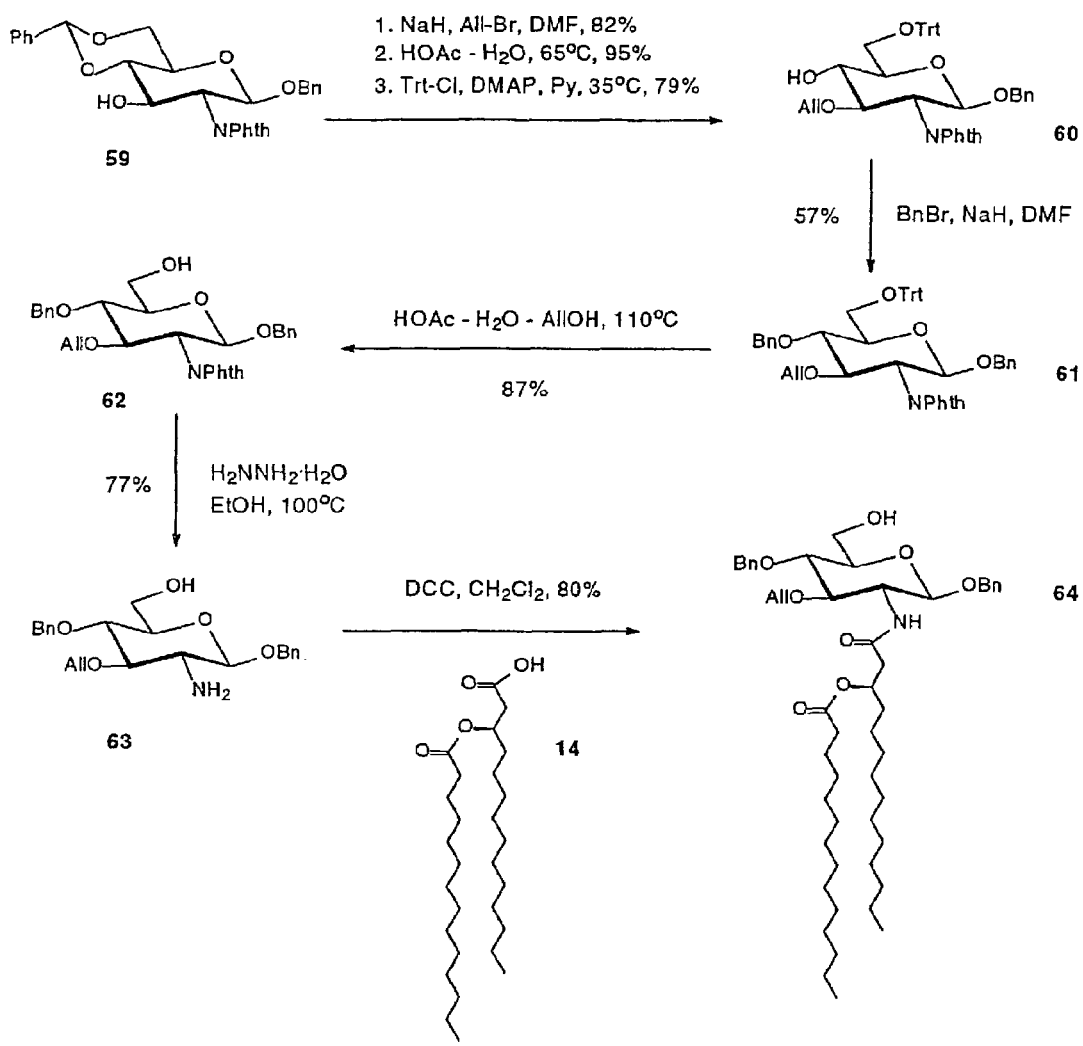
FIG. 17  Synthesis of glycosylation acceptor 64

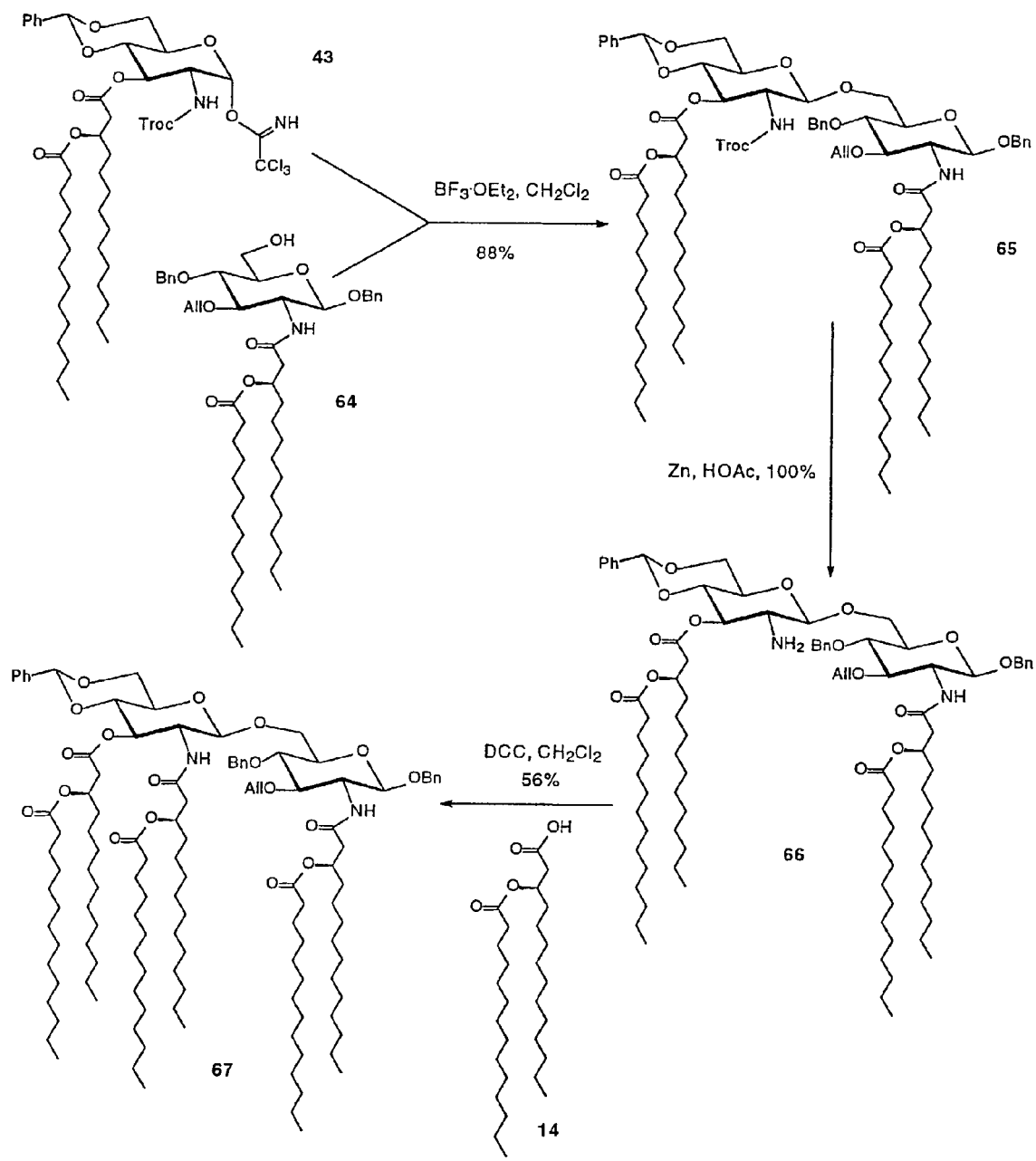
FIG. 18   Synthesis of disaccharide 67

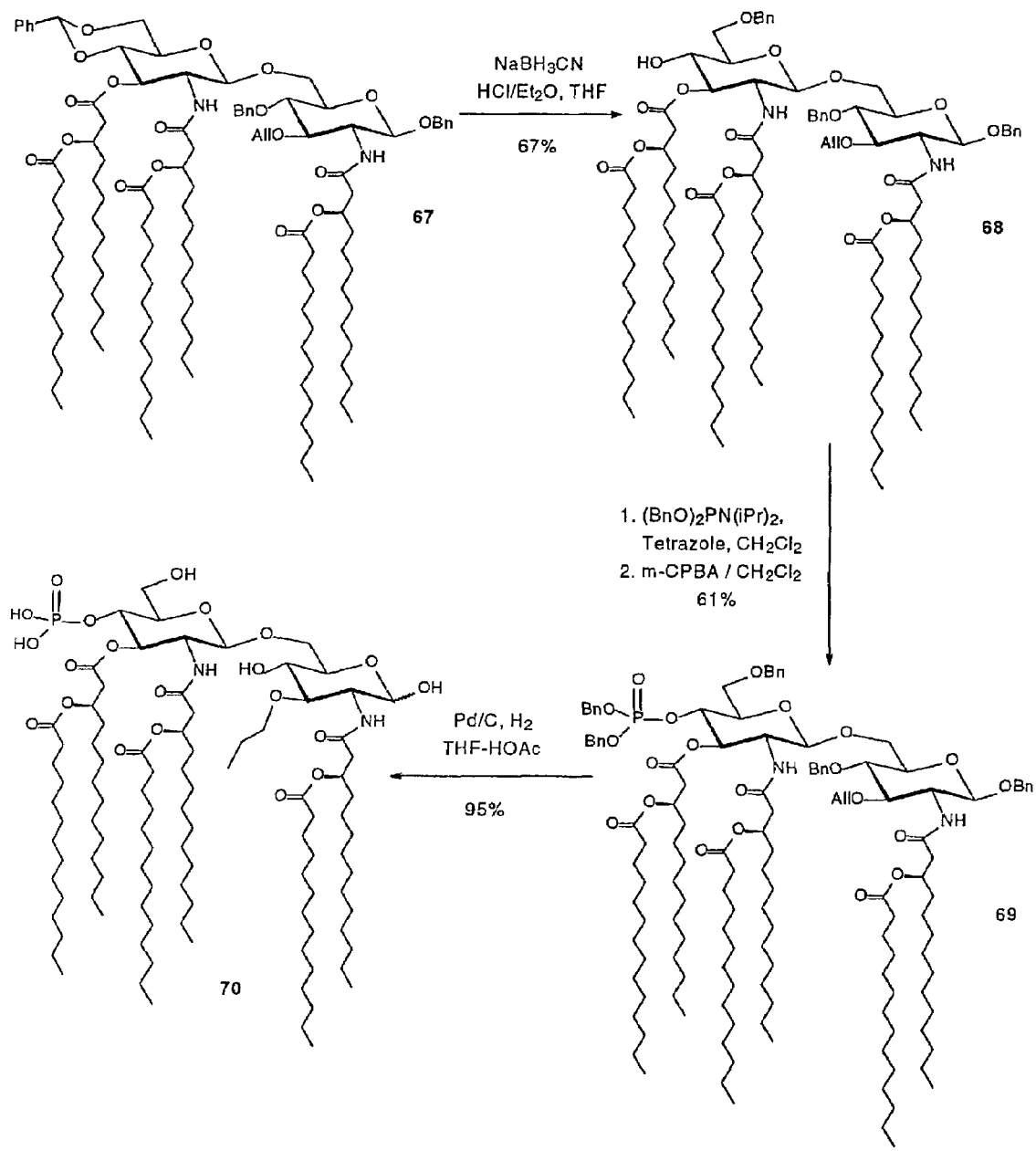
FIG. 19  Synthesis of compound 70

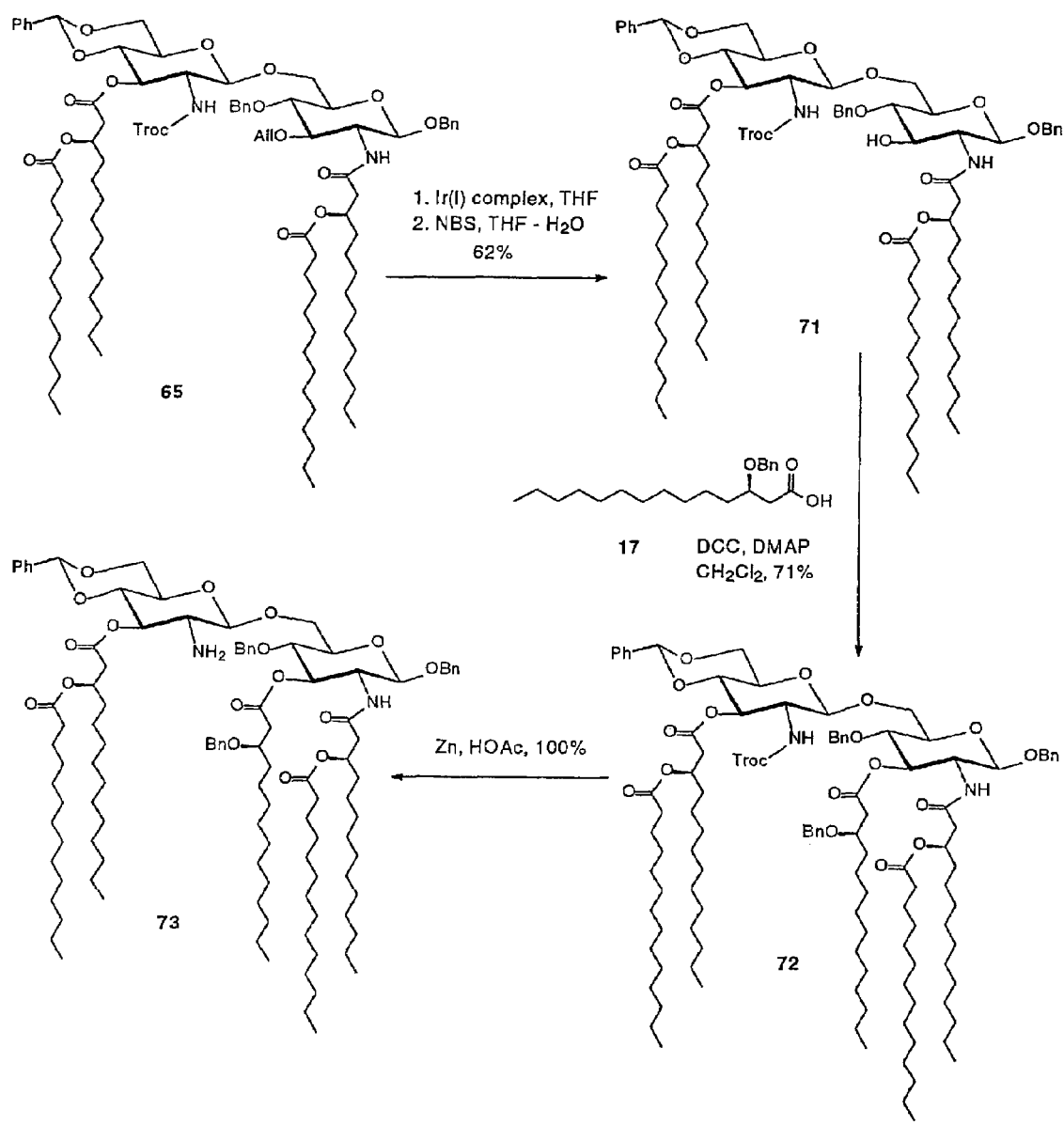
FIG. 20  Synthesis of amine 73

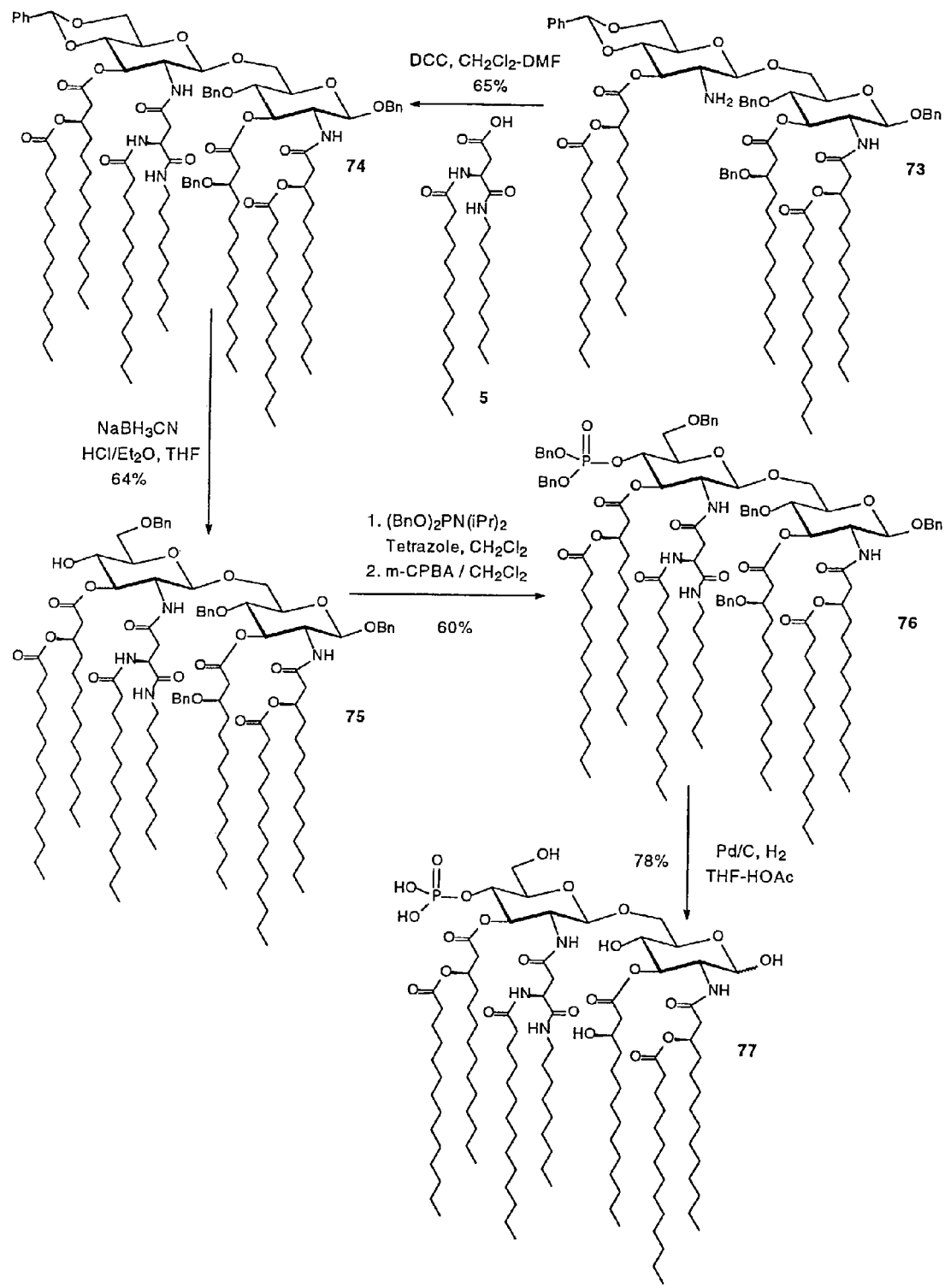
FIG. 21 Synthesis of compound 77

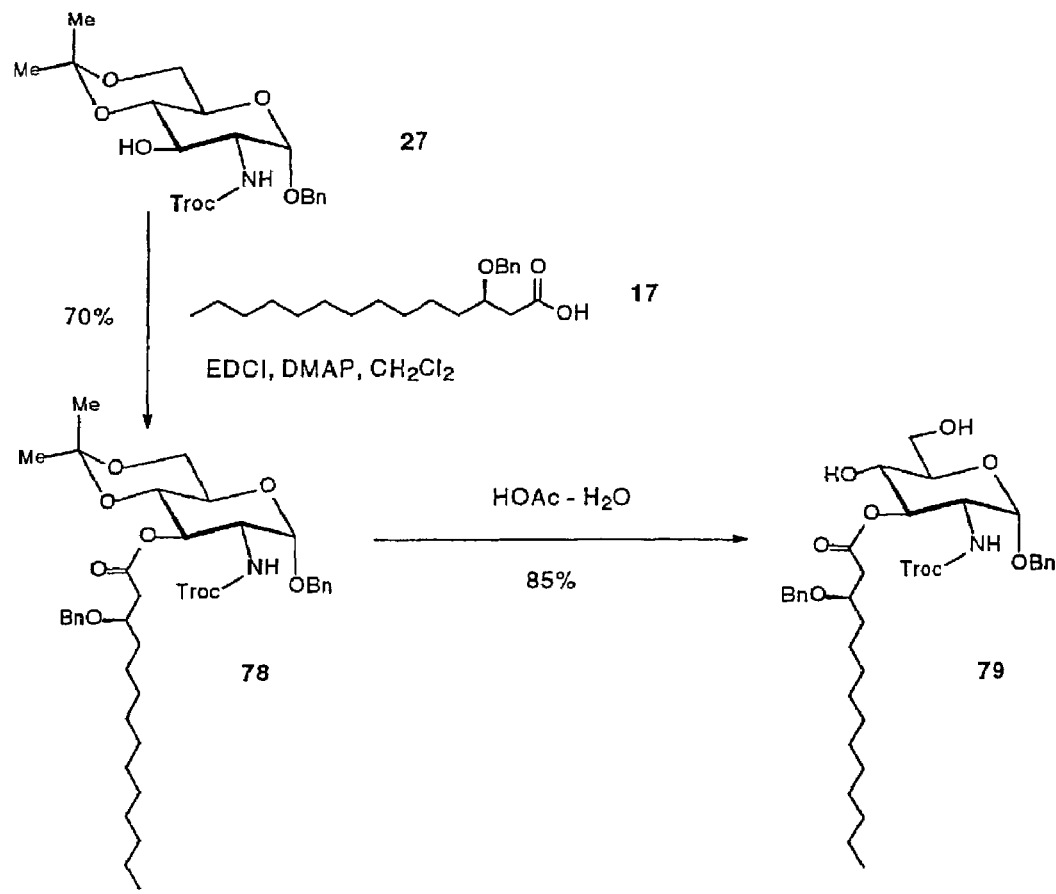
FIG. 22  Synthesis of glycosylation acceptor 79

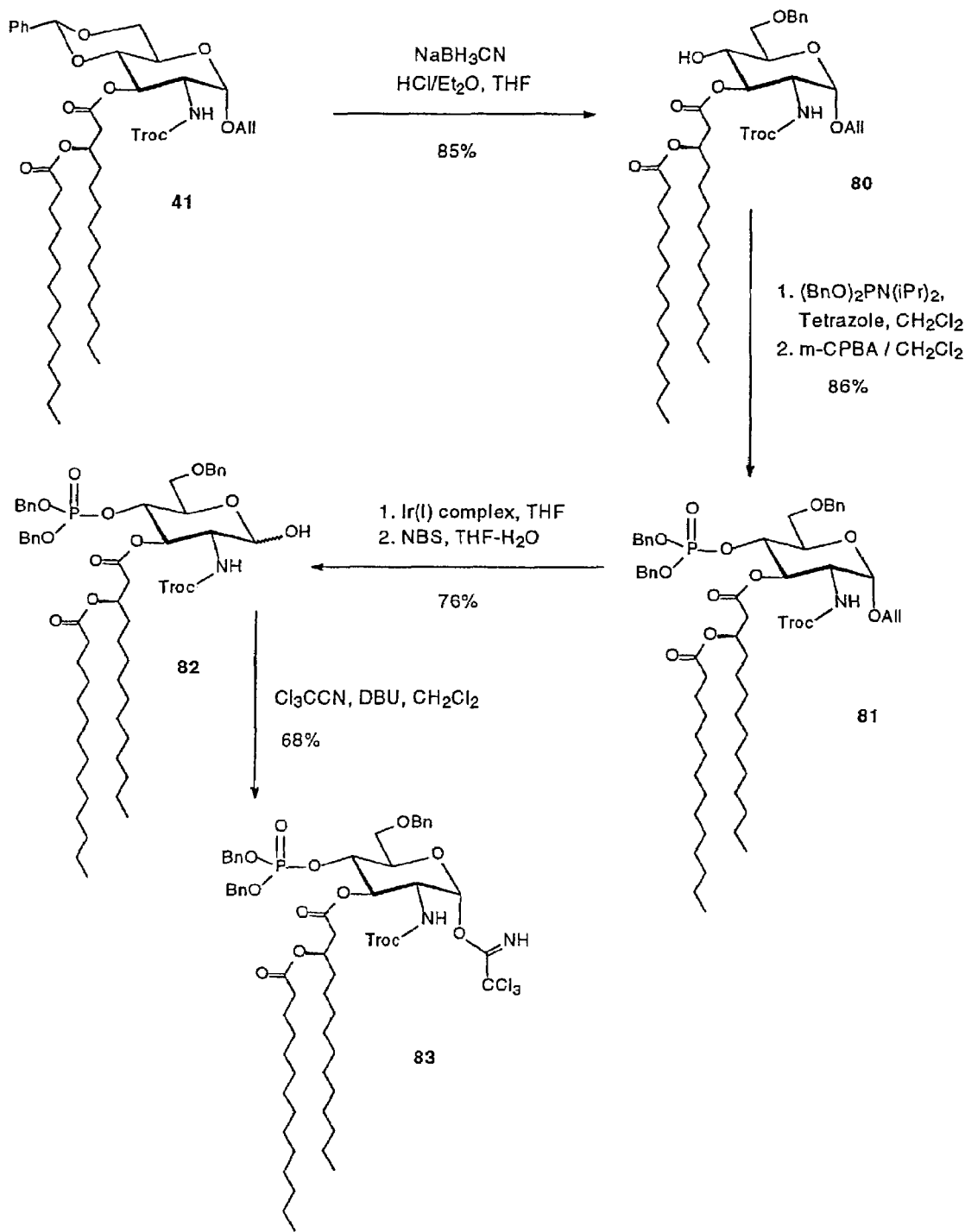
FIG. 23 Synthesis of glycosylation donor 83

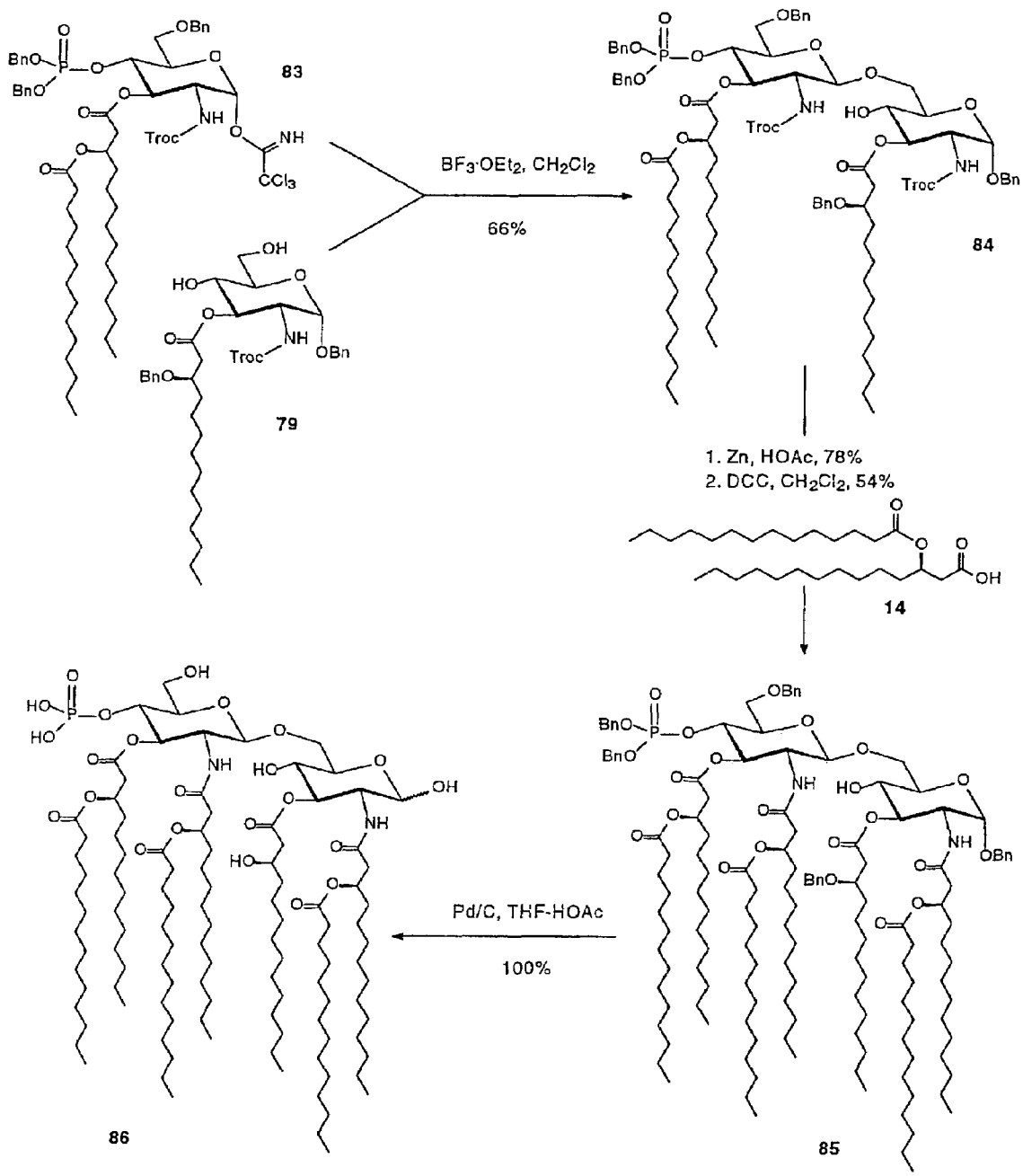
FIG. 24 Synthesis of compound 86

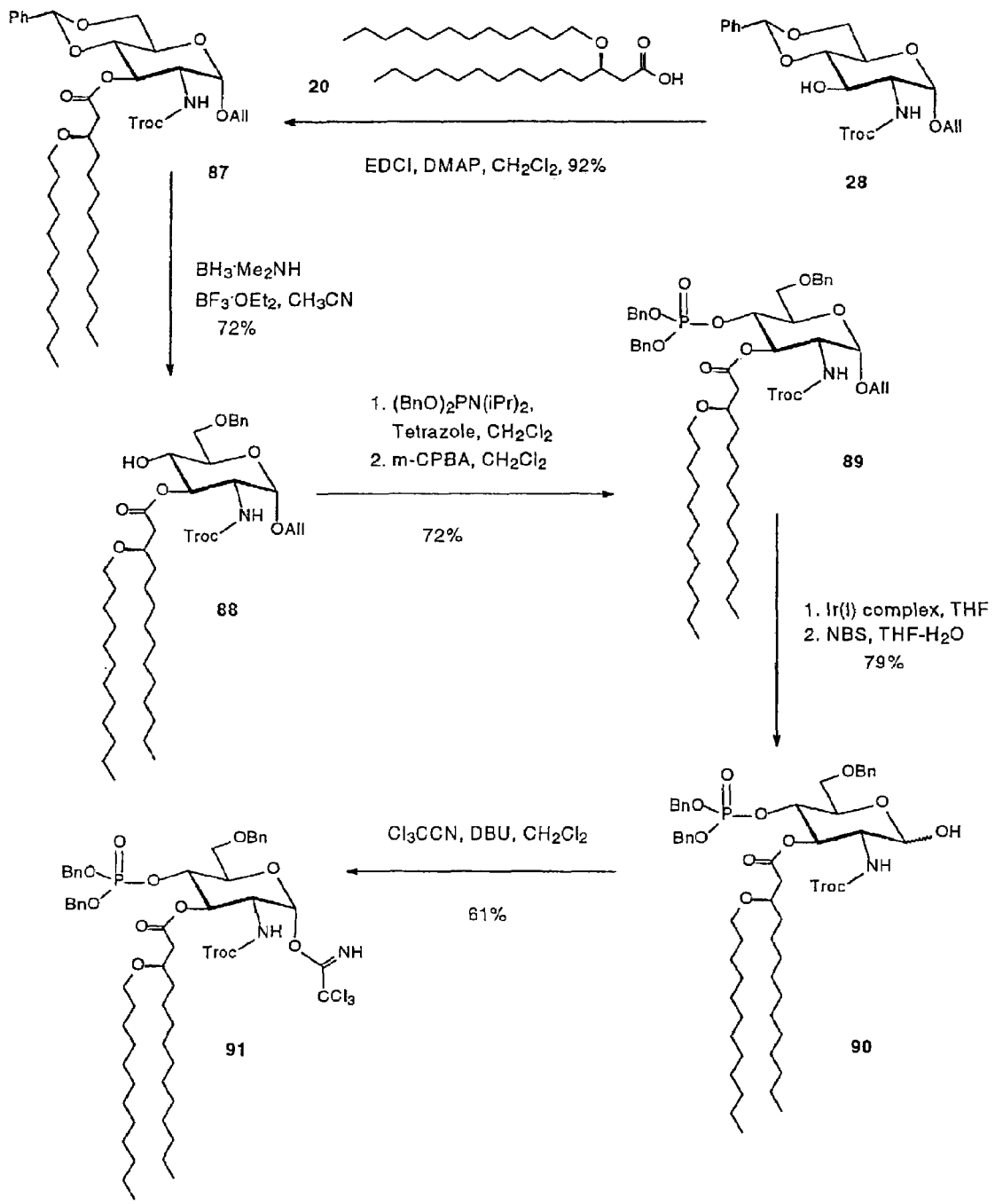
FIG. 25 Synthesis of glycosylation donor 91

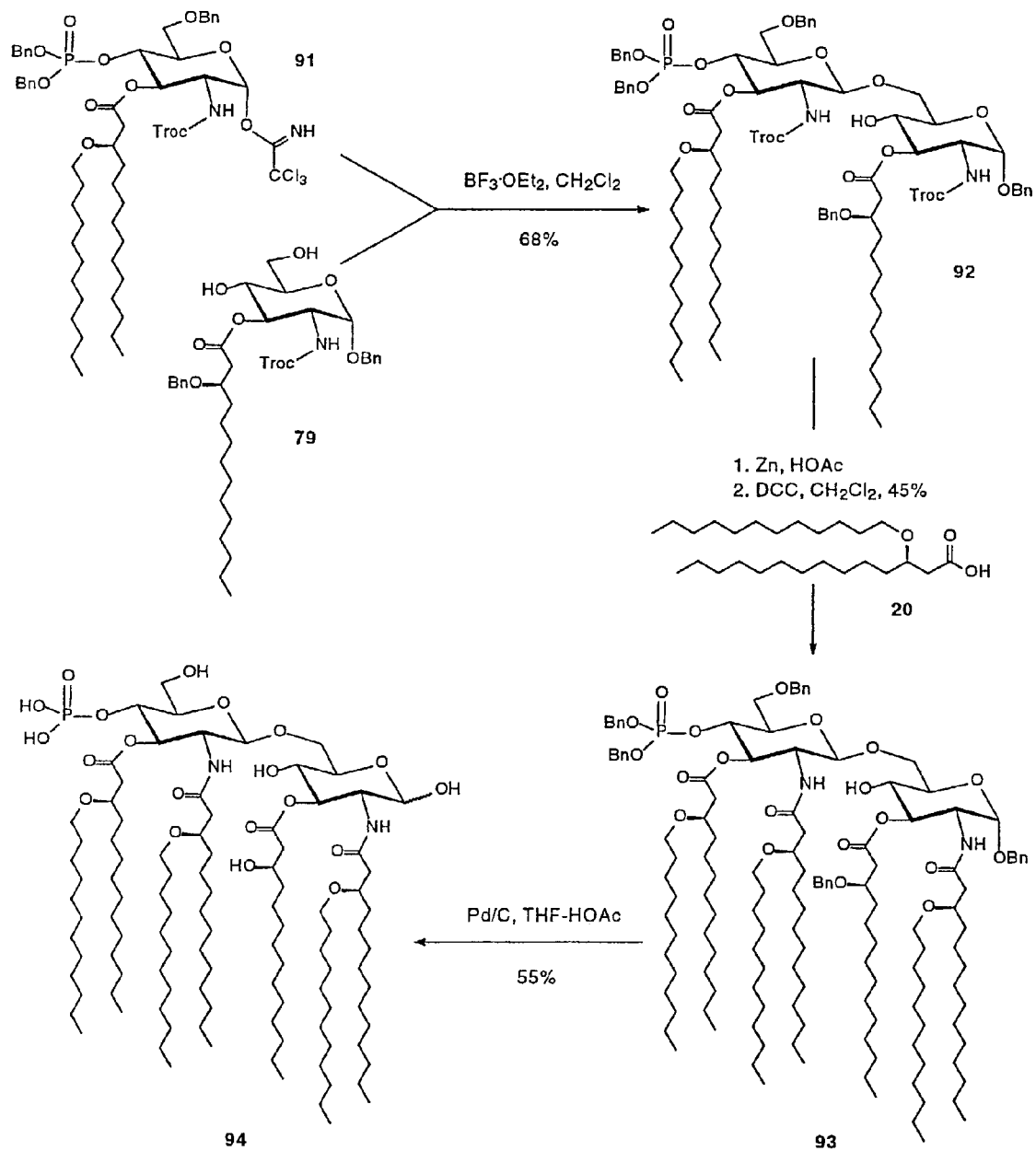
FIG. 26  Synthesis of compound 94

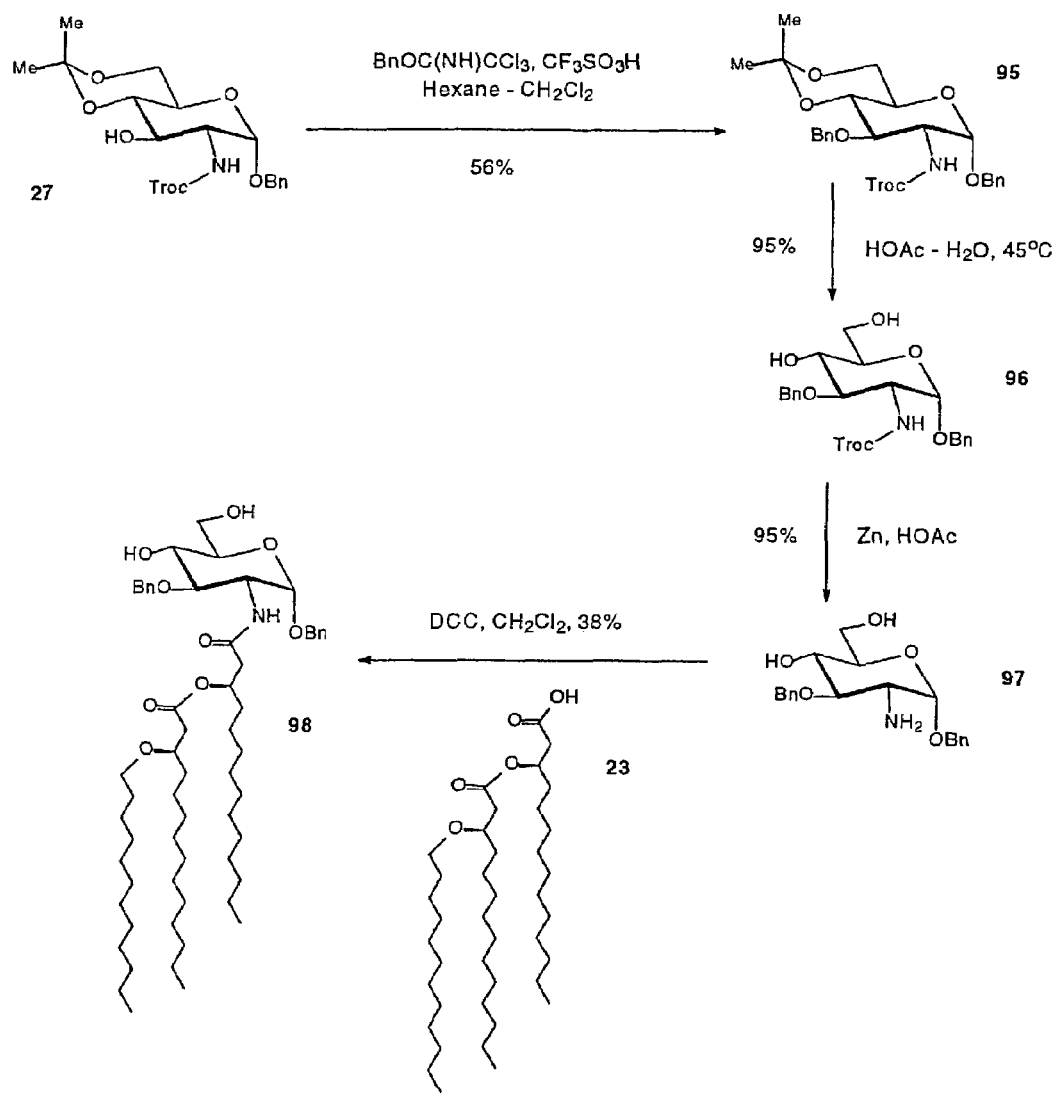
FIG. 27 Synthesis of glycosylation acceptor 98

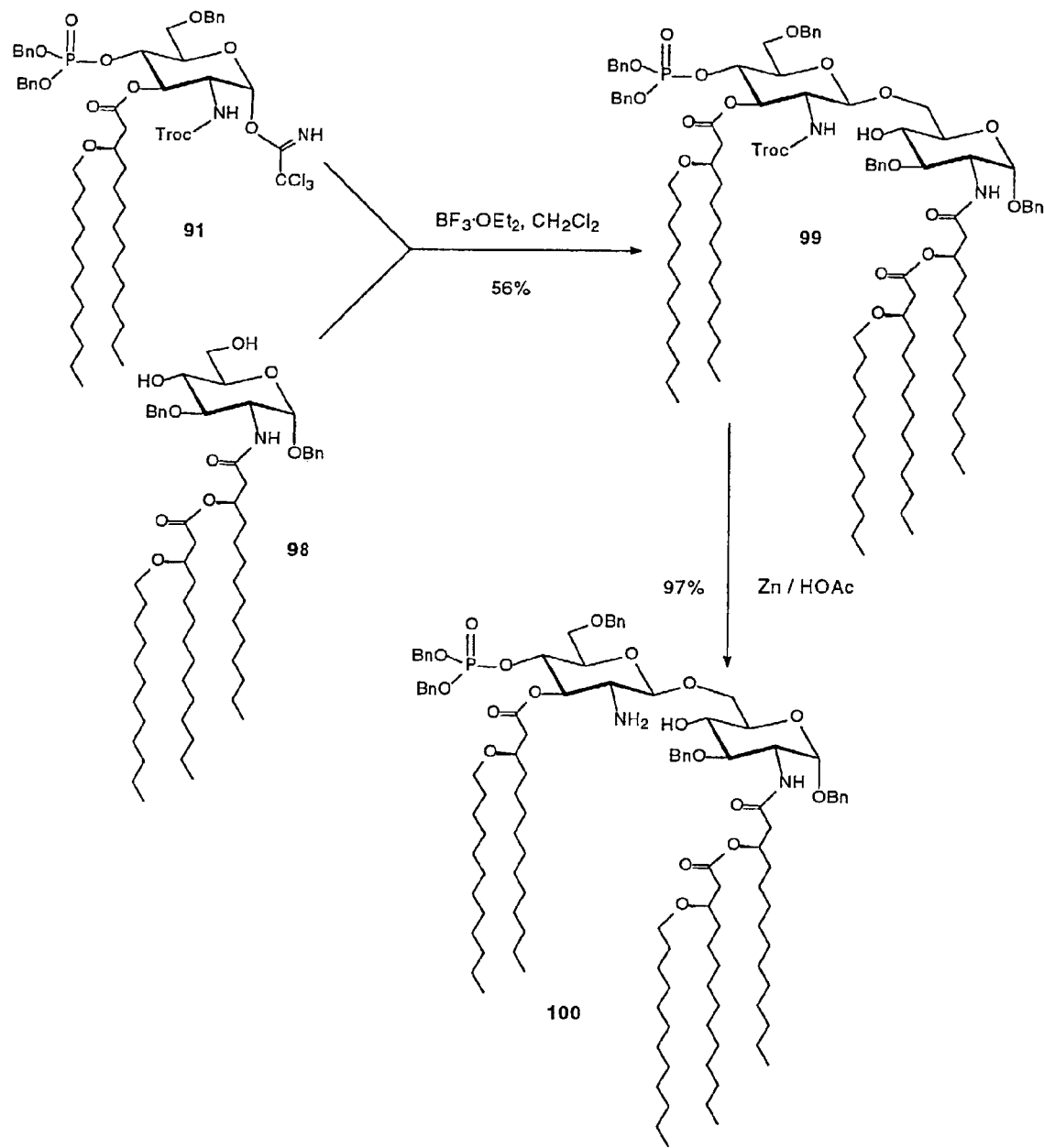
FIG. 28    Synthesis of amine 100

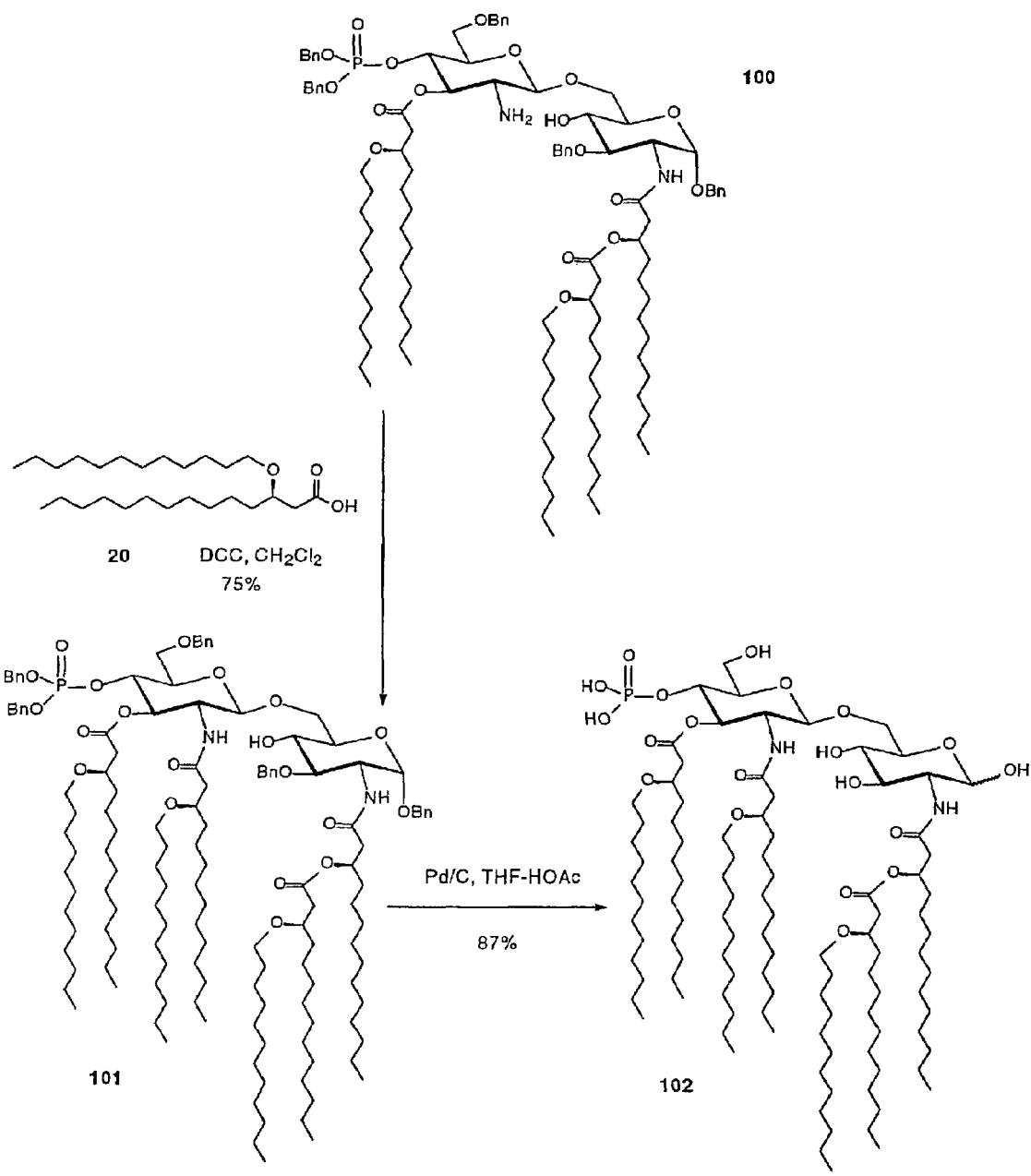
FIG. 29  Synthesis of compound 102

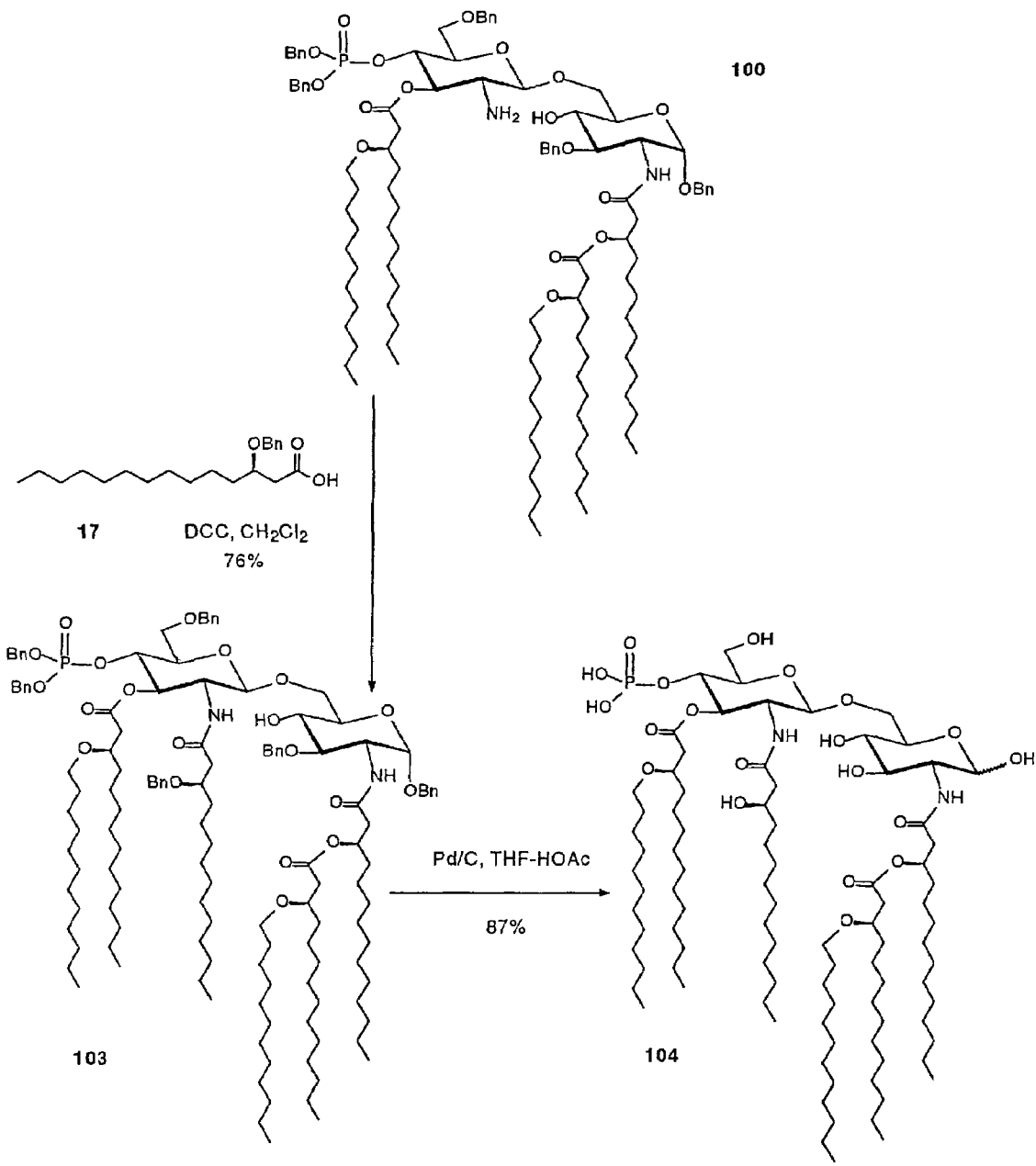
FIG. 30 Synthesis of compound 104

T-cell proliferation (CPM, counts per minute) and Interferon-gamma (IFN-γ, pg/ml) production in mice immunized with liposomal vaccine which contains MUC1-based synthetic lipopeptide BP1-148 as antigen, adjuvanted with Lipid-A analogs 33, 48, 58 or Natural Lipid-A T-cell proliferation (CPM, counts per minute) and Interferon-gamma (IFN-γ, pg/ml) production in mice immunized with liposomal vaccine which contains MUC1-based synthetic lipopeptide BP1-148 as antigen, adjuvanted with Lipid-A analogs 48, 54, 70, 77, 86 or Natural Lipid-A

T-cell proliferation (CPM, counts per minute) and Interferon-gamma (IFN-γ, pg/ml) production in mice immunized with liposomal vaccine which contains MUC1-based synthetic lipopeptide BP1-148 as antigen, adjuvanted with Lipid-A analogs 86, 94, 102, 104 or Natural Lipid-A

H₂N-STAPPAHGVTSAPPDTRPAPGSTAPPK(Pal)G-OH
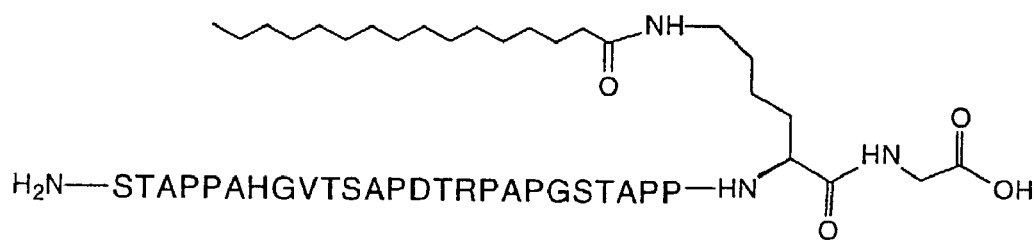
BP1-148
FIG. 34  Structure of lipopeptide BP1-148, a modified 25-amino-acid sequence derived from tumor-associated MUC1 mucin (single letter codes of amino acids)

BP1-231 / Malaria NSP-1 (20-39):  H$_2$N-VTHESYQELVKKLEALEDAVK(Pal)G-OH

BP1-232 / Malaria LS1.2 1742-1760:  H$_2$N-HTLETVNNISDVNDFQISKYK(Pal)G-OH

BP1-233 / HepA VP1 (75-92):  H$_2$N-GESRHTSDHMSIYKFMGRK(Pal)G-OH

BP1-235 / HBc Ag CTL epitope:  H$_2$N-STLPETTVVRRK(Pal)G-OH

BP1-230 / TB 38 KDa antigen (350-369):  H$_2$N-DQVHFQPLPPAVVKLSDALIK(Pal)G-OH

BP1-219:  H$_2$N-GVTSAPDT(Tn)RPAPGSTAS(Lipo)S(Lipo)L-OH

BP1-217:  H$_2$N-GVTSAPDTRPAPGSTAS(Lipo)S(Lipo)L-OH

BP1-223:  H$_2$N-GVT(Tn)S(Tn)APDTRPAPGS(Tn)T(Tn)AS(Lipo)S(Lipo)L-OH

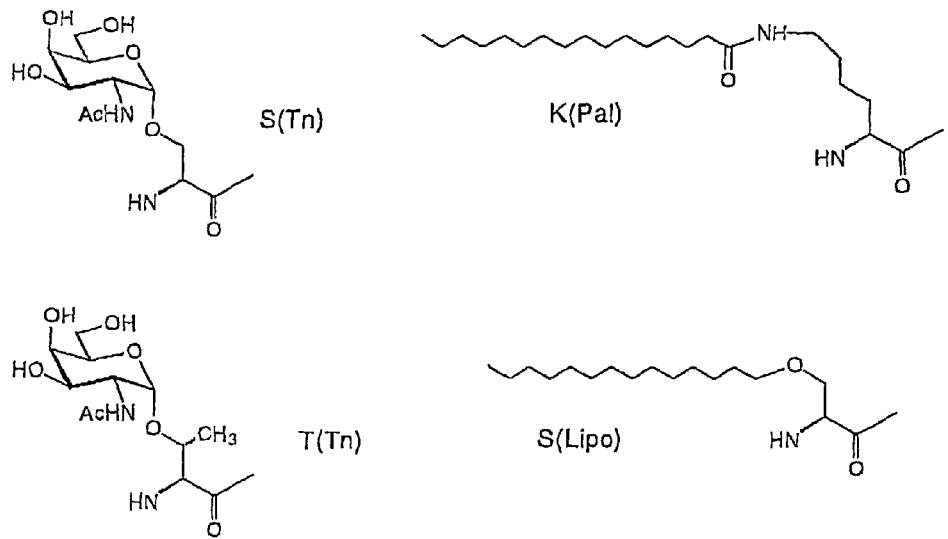

FIG. 35  Some examples of peptides and glycopeptides derived from viral antigens and MUC1 protein that can be incorporated into liposome formulations

```
                      SEQUENCE LISTING

<160> NUMBER OF SEQ ID NOS: 1

<210> SEQ ID NO 1
<211> LENGTH: 27
<212> TYPE: PRT
<213> ORGANISM: Artificial
<220> FEATURE:
<223> OTHER INFORMATION: Synthetic lipopeptide comprising human mucin
      Muc1 repeat sequence
<220> FEATURE:
<221> NAME/KEY: MISC_FEATURE
<222> LOCATION: (26)..(26)
<223> OTHER INFORMATION: Lys is modified by Palmitoyl.

<400> SEQUENCE: 1

Ser Thr Ala Pro Pro Ala His Gly Val Thr Ser Ala Pro Asp Thr Arg
1               5                   10                  15

Pro Ala Pro Gly Ser Thr Ala Pro Pro Lys Gly
            20                  25
```

SYNTHETIC LIPID-A-ANALOGS AND USES THEREOF

This application is a non-provisional application of the provisional U.S. application Ser. No. 60/164,928 filed on Nov. 15, 1999. This prior provisional application is hereby incorporated by reference in its entirety.

FIELD OF THE INVENTION

The present invention relates to novel synthetic structural mimics of bacterial Lipid-A and methods of synthesis of such analogs. Bacterial Lipid-A compositions are being widely used as adjuvant to enhance the immune responses to various antigens used in vaccine formulations. A synthetic adjuvant, being a single chemically defined entity, leads to the required homogeneity for vaccine formulations of either liposomal origin or normal admixtures. This invention includes the design and synthesis of Lipid-A analogs, with much lower toxicity but with adjuvant properties comparable to those of the natural Lipid-A.

These synthetic structures incorporate unnatural lipids, unnatural chemical linkages and combinations of lipid chains that are not found among natural lipid-A structures.

BACKGROUND OF THE INVENTION

Lipopolysaccharide (LPS) is a unique glycolipid found exclusively in the outer leaflet of the outer membrane of Gram-negative bacteria. Structurally[1a,b], bacterial LPS molecule has three main regions: the O-antigen region, the core region and the Lipid-A region. The O-antigen region is a strain-specific polysaccharide moiety and determines the antigenic specificity of the organism. The core region is an oligosaccharide chain and may play a role in maintaining the integrity of the outer membrane. The Lipid-A region is conserved and functions as a hydrophobic anchor holding lipopolysaccharide in place.

LPS is known to trigger many pathophysiological events in mammals, either when it is injected or when is accumulated due to Gram-negative bacterial infection[1b]. Before the discovery of Lipid-A component of LPS the term "endotoxin" was generally used to describe the effects of the LPS. The endotoxin from Gram-negative bacteria is heat-stable, cell associated, pyrogenic and potentially lethal. In addition to its endotoxic activities, LPS also exhibits various biological activities, which include immuno adjuvant activity, B-lymphocyte mitogenesis, macrophage activation, interferon production, tumor regression, etc. While both the O-antigen and the core regions modulate the toxic activity of the LPS, it is generally believed that the hydrophobic Lipid-A moiety is responsible for these pathophysiological effects of the endotoxin[2a, b].

Lipid-A consists of a β-(1,6)-linked D-glucosamine disaccharide phosphorylated at 1-O- and 4'-O-positions. Hydroxylated and non-hydroxylated fatty acids are linked to the hydroxyl and amino groups of the disaccharide to confer hydrophobicity to the Lipid-A. FIG. 1 shows two examples of natural Lipid-A structures, compound A[2a,b] isolated from *E. coli*, and compound B[4a-d] isolated from *Salmonella* strains. Takada and Kotani have conducted a thorough study of structural requirements of Lipid-A for endo-toxicity and other biological activities[5a], thanks to the availability of synthetic Lipid-A analogs due to the efforts of various groups[6-10]. Ribi et al[5b] showed that the minimal structure required for toxicity was a bisphosphorylated β-(1,6)-linked di-glucosamine core to which long chain fatty acids are attached. It appears that an optimal number of lipid chains, in the form of either hydroxy acyl or acyloxyacyl groups, are required on the disaccharide backbone in order to exert strong endotoxic and related biological activities of Lipid-A[6]. For immunoadjuvant activity, however, the structural requirements of Lipid-A do not appear to be as rigid as those required for endotoxic activity and IFN-α/β or TNF-inducing properties[5]. Removal of all fatty acids, however, abrogates all biological activities normally attributed to Lipid-A.

In addition, removal of either phosphate group results in significant loss of toxicity without a corresponding loss of adjuvant activity. Bioassays on monophosphoryl Lipid-A showed that, while it was 1000 times less potent on a molar basis in eliciting toxic and pyrogenic responses, it was comparable to diphosphoryl Lipid-A (and endotoxin itself) in immunostimulating activities[11a]. It is known that the diphosphoryl Lipid-A from *E. coli* and *Salmonella* strains are highly toxic, but the monophosphoryl Lipid-A from *E. coli* has reduced toxicity while retaining the numerous biological activities that are normally associated with LPS[11b, c, d].

The potent biological activities of Lipid-A have directed numerous research efforts toward developing useful applications. For example, the inhibition of Lipid-A biosynthesis is a new target activity for antibacterial drugs[12, 13], and the drugs of future that function through this inhibitory mechanism will constitute a new class of antibiotics[14, 15]. The immunostimulating activity of Lipid-A has been investigated in order to develop new therapeutic anti-tumor agents[16, 17] and immunoadjuvants by using modified Lipid-A structures and analogs. Furthermore, therapeutic agents of Lipid-A analogs have been investigated for treatment of sepsis[18] based on their abilities to inhibit the interaction with macrophages, and as antagonists for the toxic activity of Lipid-A. Recently, Eisai[19] developed a potent synthetic Lipid-A antagonist for the treatment of sepsis.

There is a need for effective treatment for Lipid-A/LPS associated disorders, and for a potent adjuvant without the associated toxicity. The high toxicity of unmodified Lipid-A from natural source prevents its general use as a pharmaceutical. A major drawback with the naturally derived Lipid-A is in accessing sufficient material with pharmaceutically acceptable purity, reproducible activity and stability. Naturally derived Lipid-A is a mixture of several components of cell wall including those of Lipid-A with varying number of lipid chains. Such heterogeneity in natural Lipid-A product is attributed to two sources: (1) biosynthetic variability in the assembly of the Lipid-A moiety and (2) loss of fatty acids from Lipid-A backbone during processing and purification. Consequently, it is difficult to control the manufacturing process in terms of reproducibility of composition of the mixture, which has significant bearing in biological activity and toxicity. For example, a reduction in adjuvant activity leads to reduction in immune response to an antigen that is formulated with Lipid-A as an adjuvant. The loss of a significant number of lipid chains during the processing of natural Lipid-A could result in the loss of adjuvant and other biological activities. Thus, it appears that lipid chains of Lipid-A molecules play a significant role in adjuvanticity such as internalization of antigens into macrophages and other antigen presenting cells (APC), leading to powerful immune responses.

While it is recognized that Lipid-A analogs are structurally complex, chemical synthesis is perhaps the best alternative to overcome the difficulties associated with accessing Lipid-A from natural sources. Natural combination of lipids refers to the lipid diversity that exists in nature. There is no lipid diversity in the synthetic lipids of present invention as they carry a uniform of contingent of lipids, which are of similar carbon length. The present invention relates to the design and synthesis of some new mono-phosphorylated Lipid-A analogs, each carrying a combination of unnatural lipids, such as (I) and (II) (FIG. 3) or significantly, an unnatural combination of lipids (FIG. 4). The following features distinguish the synthetic Lipid-A structures disclosed in this invention from those obtained from natural sources and/or reported in the prior art in the field.

1) Mono-phosphorylated: A chemically unmodified Lipid-A structure from nature carries two phosphate groups at 1- and 4'-position, while the synthetic Lipid-A analogs in the present invention carry one phosphate group at 4'-position.
2) A combination of unnatural lipids: Molecules, such as compounds 33 and 102 (FIG. 3), contain at least one novel and unnatural lipid (I or II).
3) An unnatural combination of lipids: This refers to those Lipid-A analogs that carry lipids of uniform chain length, a combination that is not found in nature and their synthesis is not known in the prior art. Compounds 54 and 86 (FIG. 4) fall into this category. Compound 70 (FIG. 19) is similar, but it also contains an n-propyl group at 3-O-position and is an example of Lipid-A analog that incorporates a short unnatural alkyl group with an unnatural ether linkage.

All synthetic Lipid-A structures disclosed in this invention are expected to be mimics of naturally occurring *E. coli* derived and/or *Salmonella* derived Lipid-A structures (FIG. 1).

SUMMARY OF THE INVENTION

Though there are several publications detailing the minimal structure required for Lipid-A molecules for adjuvant activity with low toxicity, there has been no systematic study of structural features needed to maintain this activity.

A structurally defined molecule as an adjuvant is not commercially available for use with human therapeutic vaccines although some promising adjuvants are currently under clinical investigation. One example of such promising adjuvants is a natural Lipid-A product purified from bacterial cultures. The natural Lipid-A adjuvant product contains a mixture of several Lipid-A components with varying number of lipid chains. Lipid chain esters, which are attached to the carbohydrate core-, can be cleaved during controlled hydrolysis of cell wall, leading to the formation of many components. One of the major problems associated with these, preparations is the inconsistency in composition and performance as an adjuvant, the latter being highly critical to the effectiveness of vaccine based therapies. Other added factors such as high production costs and the difficulty in determining active ingredients in the final pharmaceutical composition render such adjuvants from natural sources commercially unattractive.

Synthetic Lipid-A analogs have several advantages over naturally derived adjuvant preparations. Synthetic compound is chemically defined with single structure and thus facilitates its tracking and control from manufacturing to final formulation. Synthetic product is cost effective and is easily adaptable for commercial scale-up while maintaining the consistency in both quality and performance.

Under the present invention novel Lipid-A analogs are designed, synthesized and finally incorporated into liposome vaccines containing the cancer associated mucin (MUC1) derived antigen, as a lipopeptide, to evaluate their adjuvanticity. Salient features of the present invention are described as follows.

New Lipid Structures

Though on any given natural Lipid-A structure the contingent of lipids are never of uniform length or structure, the most commonly found lipid in nature is (R)-3-hydroxy-tetradecanoic acid (3-hydroxy myristic acid) and its 3-O-acylated derivatives. Lipid diversity contributes to by far the most significant variations among natural Lipid-A structures. While they are all linked through ester and amide bonds to the hydroxy and amino groups of the sugar respectively, variations include the number of lipids attached, the length of each lipid chain and the functional groups contained within the lipid chains. It is believed that these variations contribute to various biological functions of the entire Lipid-A molecule and more importantly to its adjuvant properties. Chemically speaking, ester linkages are labile as they are vulnerable to hydrolysis under physiological conditions. Gradual loss of lipid chains may slowly reduce the activity of the adjuvant under long storage of the vaccines thus diminishing their shelf life. Introduction of unnatural but stable ether linkages in place of esters, or combinations of both may enhance the stability of the adjuvant and may result in the longer shelf life for the vaccine formulations. A major advantage in the synthesis of a Lipid-A analog is that a molecule may be designed to achieve effectiveness as an adjuvant, safety and stability using the diversity in lipid chains and their linkages.

Incorporating these features, we have designed new synthetic lipid acids with general formulae (3) and (4) (FIG. 2) for building synthetic Lipid-A analogs. Compounds 5 and 23 were prepared in this invention as two specific examples of general structures (3) and (4). Compound 5 contains an aspartic acid moiety, which can be viewed as an b-amino acid. Its absolute configuration corresponds to (R)-3-hydroxy-tetradecanoic acid and thus compound 5 is considered to be a mimic of (R)-3-acyloxy-tetradecanoic acid. Compound 23 is a tri-lipid fatty acid containing an ether linkage, incorporated to enhance the stability of the whole molecule. Though ester based tri-lipid constructs have not so far been discovered among natural Lipid-A analogs, their presence may not be entirely excluded. The present invention also focuses on the synthesis of Lipid-A with a uniform lipid contingent in order to compare the adjuvant activities of those that exhibit lipid diversity.

Lipid-A Analogs with New Lipid Acid Attachments

Lipids of general formulae (3) and (4) (FIG. 2) are of new design and thus the corresponding Lipid-A structures that incorporate them are all distinctive. Two types of Lipid-A analogs, monosaccharide (1) and disaccharide (2) (FIG. 3), have been designed and synthesized as part of the invention.

The monosaccharide derivative of structure (1) where at least one of $R_1$ and $R_2$ is independently chosen from structures (I) and (II) (FIG. 3) features the non-reducing end sugar of the natural Lipid-A structure. Compound 33 (FIG. 9) is an example of such structures.

And the disaccharide derivative of structure (2) where at least one of $R_1$, $R_2$, $R_3$, $R_4$ and $R_5$ is independently chosen from structures (I) and (II) (FIG. 3) is a monophosphorylated analog of natural Lipid-A structure. Compounds 58 (FIG. 16), 77 (FIG. 21), 102 (FIG. 29) and 104 (FIG. 30) are some examples with such structural features.

Lipid-A Analogs with Uniform Lipid Contingent

The lipid diversity of Lipid-A renders the molecule too complex and impractical for large-scale preparation through chemical synthesis. One of the main features of compounds designed as part of this invention is that the lipid substituents on 2-amino, 2'-amino, and 3'-O positions of the disaccharide backbone are identical and are composed of either ether or ester-linked di-lipid structure fragments. Such features are summarized in FIG. 4. The compound has the general formula (2) where $R_1$, $R_4$ and $R_5$ are identically having the di-lipid structure (III). Specific compounds are prepared in this invention as representative examples, such as structure 54 (FIG. 15), 70 (FIG. 19), 86 (FIG. 24) and 94 (FIG. 26).

A New Process for the Preparation of Lipid-A Analogs

The invention includes new processes for the synthesis of Lipid-A analogs (1) and (2). Disclosed herein are general synthetic routes to prepare variously substituted Lipid-A analogs of the invention. Different analogs can be easily obtained by using alternative starting materials. Details are illustrated in drawing figures and examples.

The process for the synthesis of monosaccharide derivative 33 is illustrated in FIG. 9 and the disaccharide derivative 48 in FIG. 10-FIG. 13. An important feature of this new process is the general strategy of using combinations of different carbohydrate building blocks, protecting group strategies and reagents to accomplish specific structures. For example, the 4,6-benzylidene protection on glucosamine derivative offers the freedom of selective ring opening to free the 4-OH on which the phosphate group may be introduced. Benzyl ester protected phosphate group, which is introduced through a two-step procedure, also offers the advantage of being easily deprotected, together with other benzyl groups on the molecule, at the final stage of the synthesis through catalytic hydrogenation. More examples are described in FIG. 14-FIG. 21 for the synthesis of compounds 54, 58, 70 and 77.

This process has been further modified to provide a more efficient procedure, which is particularly useful for the preparation of compounds with identical substituents on both amino groups of the carbohydrate backbone. FIGS. 22-24 illustrate the synthesis of compound 86 using this modified process.

In this modified process the phosphate group is introduced on the monosaccharide derivative before the glycosidic linkage is formed, and the glycosylation acceptor, which has both 4-OH and 6-OH groups unprotected (e.g. compound 79 in FIG. 22), is prepared through a simplified pathway. The steps involved in the whole process are reduced, especially at the disaccharide stage at which the material becomes more expensive and practically more difficult to handle. The process is designed for large-scale production and has been proven to be very efficient at gram-scale synthesis of a Lipid-A analog. Additional examples of compounds 94, 102 and 104, prepared using this modified process, are described in FIGS. 25-30.

The strategic intermediates disclosed in this invention are used in the synthesis of Lipid-A analogs and are not known in the literature.

Liposome Formulations

Liposomes are globular particles formed by the physical self-assembly of polar lipids, which define the membrane organization in liposomes. Liposomes may be formed as unilamellar or multi-lamellar vesicles of various sizes. Such liposomes, though constituted of small molecules having no immunogenic properties of their own, behave like macromolecular particles and display strong immunogenic characteristics.

Taking advantage of the self-assembling properties of lipids, one or more immunogens may be attached to the polar lipids that in turn become part of the liposome particle. Each immunogen comprises one or more antigenic determinants (epitopes). These epitopes may be B-cell epitopes (recognized by antibodies) or T-cell epitopes (recognized by T-cells). The liposome can act to adjuvant the immune response elicited by the associated immunogens. It is likely to be more effective than an adjuvant that is simply mixed with an immunogen, as it will have a higher local effective concentration.

Moreover, a hapten may be attached in place of the aforementioned immunogen. Like an immunogen, a hapten comprises an antigenic determinant, but by definition is too small to elicit an immune response on its own (typically, haptens are smaller than 5,000 daltons). In this case, the lipid moiety may act, not only as an adjuvant, but also as an immunogenic carrier, the conjugate of the hapten and the lipid acting as a synthetic immunogen (that is, a substance against which humoral and/or cellular immune responses may be elicited).

Even if the lipid does not act as an immunogenic carrier, the liposome borne hapten may still act as a synthetic antigen (that is, a substance which is recognized by a component of the humoral or cellular immune system, such as an antibody or T-cell). The term "antigen" includes both haptens and immunogens.

Thus, the invention contemplates a liposome whose membrane comprises a Lipid A analogue as disclosed herein, and at least one B-cell or T-cell epitope.

We have designed several synthetic antigens in the form of lipo-peptides, glyco-lipids and glyco-lipo-peptides that form the liposome membrane. Similarly, synthetic Lipid-A molecules of well-defined structural characteristics can be anchored into the liposome membrane.

Unlike the bacterial adjuvant preparations, a synthetic Lipid-A analog contributes a structurally well-defined lipids to the liposome membrane. Such defined structures not only reduce the burden of re-affirming the 'active' membrane components after formulation, but also contribute to the definition of liposome membrane. Such liposomes may be designated as totally synthetic vaccine formulations' containing synthetic Lipid-A analog as an adjuvant and a synthetic lipopeptide as an antigen.

Epitope

The epitopes of the present invention may be B-cell or T-cell epitopes, and they may be of any chemical nature, including without limitation peptides, carbohydrates, lipids, glycopeptides and glycolipids. The epitope may be identical to a naturally occurring epitope, or a modified form of a naturally occurring epitope.

B-cell peptide epitopes are typically at least five amino acids, more often at least six amino acids, still more often at least seven or eight amino acids in length, and may be continuous ("linear") or discontinuous ("conformational") (the latter being formed by the folding of a protein to bring non-contiguous parts of the primary amino acid sequence into physical proximity). T-cell peptide epitopes are linear and usually 8 to 15, more often 9-11 amino acids in length.

Epitopes of interest include those specific to or otherwise associated with a pathogen, or a tumor. An epitope may be said to be associated with a particular infectious disease if it is presented by an intracellular, surface, or secreted antigen of the organism which causes the disease, or in the case of a virus, if it is associated with viral particles or is specific to a cell infected by the virus.

It may be said to be associated with a particular tumor if it is presented by an intracellular, surface or secreted antigen of said tumor. It need not be presented by all cell lines of the tumor type in question, or by all-cells of a particular tumor, or throughout the entire life of the tumor. It need not be specific to the tumor in question. An epitope may be said to be "tumor associated" in general if it is so associated with any tumor (cancer, neoplasm).

The term "disease associated epitope" also includes any non-naturally occurring epitope which is sufficiently similar to an epitope naturally associated with the disease in question so that cytotoxic lymphocytes which recognize the natural disease epitope also recognize the similar non-natural epitope. Similar comments apply to "tumor associated epitope".

An epitope may be said to be specific to a particular source (such as a disease-causing organism or a tumor), if it is associated more frequently with that source than with other sources. Absolute specificity is not required, provided that a useful prophylactic, therapeutic or diagnostic effect is still obtained.

In the case of a "tumor-specific" epitope, it is more frequently associated with that tumor that with other tumors, or with normal cells. Preferably, there should be a statistically significant (p=0.05) difference between its frequency of occurrence in association with the tumor in question, and its frequency of occurrence in association with (a) normal cells of the type from which the tumor is derived, and (b) at least one other type of tumor. An epitope may be said to be "tumor-specific" in general is it is associated more frequently with tumors (of any or all types) than with normal cells. It need not be associated with all tumors.

The term "tumor specific epitope" also includes any non-naturally occurring epitope which is sufficiently similar to a naturally occurring epitope specific to the tumor in question (or as appropriate, specific to tumors in general) so that cytotoxic lymphocytes stimulated by the similar epitope will be essentially as specific as CTLs stimulated by the natural epitope.

In general, tumor-versus-normal specificity is more important than tumor-versus-tumor specificity as (depending on the route of administration and the particular normal tissue affected), higher specificity generally leads to fewer adverse effects. Tumor-versus-tumor specificity is more important in diagnostic as opposed to therapeutic uses.

The reference to a CTL epitope as being "restricted" by a particular allele of MHC, such as HLA-A1, indicates that such epitope is bound and presented by the allelic form in question. It does not mean that said epitope might not also be bound and presented by a different allelic form of MHC, such as HLA-A2, HLA-A3, HLA-B7, or HLA-B44.

The term "specific" is not intended to connote absolute specificity, merely a clinically useful difference in probability of occurrence in association with a pathogen or tumor rather than in a matched normal subject.

Pathogens may be submicrobial (e.g., viruses), microbial (e.g., fungi, protozoa), or multicellular (e.g, worms, arthropods, etc.). Tumors may be of mesenchymal or epithelial origin. Cancers include cancers of the colon, rectum, cervix, breast, lung, stomach, uterus, skin, mouth, tung, lips, larynx, kidney, bladder, prostate, brain, and blood cells.

Naturally occurring epitopes may be identified by a divide-and-test process. One starts with a protein known to be antigenic or immunogenic. One next tests fragments of the protein for immunological activity. These fragments may be obtained by treatment of the protein with a proteolytic agent, or, if the peptide sequence is known, one may synthetically prepare smaller peptides corresponding to subsequences of the protein. The tested fragments may span the entire protein sequence, or just a portion thereof, and they may be abutting, overlapping, or separated.

If any of the fragments are immunologically active, the active fragments may themselves be subjected to a divide-and-test analysis, and the process may be continued until the minimal length immunologically active sequences are identified. This approach may be used to identify either B-cell or T-cell epitopes, although the assays will of course be different. Geysen teaches systematically screening all possible oligopeptide (pref. 6-10 a.a.) abutting or overlapping fragments of a particular protein for immunological activity in order to identify linear epitopes. See WO 84/03564.

It is also possible to predict the location of B-cell or T-cell peptide epitopes if an amino acid sequence is available. B-cell epitopes tend to be in regions of high local average hydrophilicity.

See Hopp and Wood, Proc. Nat. Acad. Sci. (USA) 78: 3824 (1981); Jameson and Wolf, CABIOS, 4: 181 (1988). T-cell epitopes can be predicted on the basis of known consensus sequences for the peptides bound to MHC class I molecules of cells of a particular haplotype. See e.g., Slingluff, WO98/33810, especially pp. 15-16; Parker, et al., "Scheme for ranking potential HLA-A2 binding peptides based on independent binding of individual peptide side chains", J. Immunol. 152: 163 (1994).

Naturally occurring T-cell epitopes may be recovered by dissociating them from their complexes with MHC class I molecules and then sequencing them, e.g., by mass spectroscopic techniques.

Generally speaking, in addition to epitopes which are identical to the naturally occurring disease- or tumor-specific epitopes, the present invention embraces epitopes which are different from but substantially identical with such epitopes, and therefore disease- or tumor-specific in their own right. It also includes epitopes which are not substantial identical to a naturally occurring epitope, but which are nonetheless cross-reactive with the latter as a result of a similarity in 3D conformation.

An epitope is considered substantially identical to a reference epitope (e.g., a naturally occurring epitope) if it has at least 10% of an immunological activity of the reference epitope and differs from the reference epitope by no more than one non-conservative substitution.

If it is a CTL epitope, it may incorporate further nonconservative substitutions which are suggested by a known binding motif of the pertinent MHC molecule. Kast, et al., J. Immunol, 152:3904-12 (1994) sets forth HLA-A specific peptide binding motifs for the HLA molecules A1, A2.1, A3, A11 and A24. Engelhard, et al., in Sette, ed., Naturally Processed Peptides, 57:39-62 (1993) explored the features that determined binding to HLA-A2.1 and HLA-B7. See also Hobohim et al; Eur. J. Immunol., 23:127'-6 (1993); Kawakami, et al., J. Immunol., 154:3961-8 (1995). Based on these and other sources, the preferred and tolerated AAs for various HLA molecules include (but are not limited to) the following:

TABLE 10

| Molecule | Position | Preferred AA | tolerated AA |
| --- | --- | --- | --- |
| A1 | 2 | T, S, M | |
| | 3 | D, E | A, S |
| | 9 | Y | |
| A2.1 | 2 | L, M | I, V, A, T |
| | 9 | L, V, I | A, M, T |
| A3 | 2 | L, M, I, V, S A, T, F | C, G, D |
| | 9 | K, R, Y, H, F | A |
| A11 | 2 | M, L, I, V, S A, T, G, N | C, D, F |
| | 9 | K | R, H, Y |
| A24 | 2 | Y, F, W | M |
| | 9 | F, L, I, W | |
| B7 | 1 | A | M, S, R, L |
| | 2 | P | V |
| | 3 | R | A, K, S, M |
| | 9 | L | I, A, V |

TABLE 10-continued

| Molecule | Position | Preferred AA | tolerated AA |
|---|---|---|---|
| B8 | 3 | K | not known |
|  | 5 | K | not known |
|  | 9 | L | not known |
| B27 | 2 | R | not known |
|  | 9 | R, K, H | not known |
| B35 | 2 | P | not known |
|  | 9 | Y | not known |
| B53 | 2 | P | not known |

If a position is not listed, studies revealed a greater variability of AAs than for the listed positions. For listed positions, AAs not listed may be tolerated, especially if they are conservative or semi-conservative substitutions for "preferred" or "tolerated" AAs.

Conservative substitutions are herein defined as exchanges within one of the following five groups:
I. Small aliphatic, nonpolar or slightly polar residues:
Ala, Ser, Thr, Pro, Gly
II. Polar, negatively charged residues: and their amides
Asp, Asn, Glu, Gln
III. Polar, positively charged residues:
His, Arg, Lys
IV. Large, aliphatic, nonpolar residues:
Met, Leu, Ile, Val, Cys
V. Large, aromatic residues:
Phe, Tyr, Trp
Within the foregoing groups, the following substitutions are considered "highly conservative":
Asp/Glu
His/Arg/Lys
Phe/Tyr/Trp
Met/Leu/Ile/Val Semi-conservative substitutions are defined to be exchanges between two of groups (I)-(V) above which are limited to supergroup (A), comprising (I), (II) and (III) above, or to supergroup (B), comprising (IV) and (V) above. Also, Ala is considered a semi-conservative substitution for all non group I amino acids.

It will be appreciated that highly conservative substitutions are less likely to affect activity than other conservative substitutions, conservative substitutions are less likely to affect activity than merely semi-conservative substitutions, and semi-conservative substitutions less so than other non-conservative substitutions. In addition, single substitutions are less likely to affect activity than are multiple mutations.

Although a substitution mutant, either single or multiple, of the peptides of interest may not have quite the potency of the original peptide, such a mutant may well be useful.

Substitutions are not limited to the genetically encoded, or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

A non-genetically encoded amino acid is considered a conservative substitution for a genetically encoded amino acid if it is more similar in size (volume) and hydrophilicity to the original amino acid, and to other amino acids in the same exchange group, than it is to genetically encoded amino acids belonging to other exchange groups.

Substantially identical peptide epitopes may be identified by a variety of techniques, some of which do not depend on preexisting knowledge of the binding motif. Thus, it is known in the art that one may synthesize all possible single substitution mutants of a known peptide epitope. For a nonpeptide, there are (20×9−1=179) such mutants. Geysen, et al., Proc Nat. Acad. Sci. (USA), 81:3998-4002 (1984). While the effects of different substitutions are not always additive, it is reasonable to expect that two favorable or neutral single substitutions at different residue positions in the epitope can safely be combined in most cases.

Both naturally occurring and non-naturally occurring peptide epitopes may be identified, if a suitable antibody or other receptor is available, by screening a peptide combinatorial library for peptides bound by the target. Humoral peptide epitopes may be identified by screening a combinatorial peptide phage library for specific binding to a target monoclonal antibody known to recognize the antigen of interest. Preferably, the library is prescreened to eliminate peptides which bind the antibody other than at the epitope binding site of the antibody; this can be done by eliminating phage which bind to a second, control antibody of the same isotype.

Similarly, to identify CTL peptide epitopes, one may synthesize a family of related single or multiple substitution mutants, present the mixture to the HLA-A2.1 positive lymphoblastoid cell line T2 (or other cell line capable of presenting specific CTL epitopes), and expose the T2 cells to CTLs of the desired specificity. If the T2 cells are lysed, the effective epitopes may be identified either by direct recovery from the T2 cells or by a progressive process of testing subsets of the effective peptide mixtures. Methods for the preparation of degenerate peptides are described in Rutter, U.S. Pat. No. 5,010,175, Haughten, et al., Proc. Nat. Acad. Sci. (USA), 82:5131-35 (1985), Geysen, et al., Proc. Nat. Acad. Sci. (USA), 81:3998-4002 (1984); WO86/06487; WO86/00991.

Multiple mutagenesis may be used to screen a few residue positions intensely or a larger number of positions more diffusely. One approach is to explore at least a representative member of each a.a. type at each position, e.g., one representative of each of exchange groups I-V as hereafter defined. Preferably, Gly and Pro are screened in addition to one other group I residue. Preferably, at least one screened residue is an H-bonding residue. If a positive mutant features a particular representative, like amino acids can be explored in a subsequent library. If, for example, a Phe substitution improves binding, Tyr and Trp can be examined in the next round.

The person of ordinary skill in the art, in determining which residues to vary, may also make comparisons of the sequences of the naturally processed MHC associated peptides, and may obtain 3D structures of the MHC: peptide: TCR complexes, in order to identify residues involved in MHC or TCR binding. Such residues may either be left alone, or judiciously mutated in an attempt to enhance MHC or TCR binding.

An extensive discussion of carbohydrate haptens appears in Wong, U.S. Pat. No. 6,013,779.

Adjuvanticity of Lipid-A Analogs

It is generally understood that a synthetic antigen of low molecular weight is weakly immunogenic, which is the biggest obstacle to the success of a fully synthetic vaccine. One way to improve the immunogenicity of such a synthetic antigen is to deliver it in the environment of an adjuvant. The primary target of those new synthetic Lipid-A analogs in the present invention is their adjuvant properties. An ideal adjuvant is believed to non-specifically stimulate the immune system of the host, which upon the subsequent encounter of any foreign antigen can produce strong and specific immune response to that foreign antigen. Such strong and specific immune response, which is also characterized by its memory, can be produced only when T-lymphocytes (T-cells) of the host immune system are activated. Here we choose T-cell blastogenesis and IFN-γ production as two important parameters for measuring the immune response.

Experimentally T-cell blastogenesis measures DNA synthesis that directly relates to T-cell proliferation, which in turn is the direct result of the T-cell activation. On the other hand, IFN-γ is a major cytokine secreted by T-cells when they are activated. There fore, both T-cell blastogenesis and IFN-γ production indicate T-cell activation, which suggests the ability of an adjuvant in helping the host immune system to induce a strong and specific immune response to any protein-based antigen. By using a synthetic lipopeptide antigen, H$_2$N-STAPPAHGVTSAPDTRPAPGSTAPPK(Pal)G-OH SEQ ID NO:1 (FIG. 34, single letter amino acid codes are defined in Table 8), a modified 25-amino-acid sequence that is derived from tumor-associated MUC1 mucin, we were able to evaluate the adjuvant properties of the synthetic Lipid-A analogs disclosed in this invention. Based on the data of T-cell blastogenesis and IFN-γ level (FIGS. 31-33) obtained through preliminary in vivo/in vitro studies, it is amply demonstrated that synthetic Lipid-A structures 48, 54, 70, 86, 102 and 104 are as effective, as adjuvants, as the Lipid-A preparations of bacterial origin.

The compound is considered an adjuvant if it significantly (p=0.05) increases the level of either T-cell blastogenesis or of interferon gamma production in response to at least one liposome/immunogen combination relative to the level elicited by the immunogen alone. Preferably, it does both. Preferably, the increase is at least 10%, more preferably at least 50%, still more preferably, at least 100%.

Preliminary in vivo toxicity evaluation of synthetic Lipid-A analog 86 has shown that its toxicity is much lower than that of natural Lipid-A product obtained from bacteria *Salmonella* (Table 4, Example 99). Thus, there are many advantages Associated with the totally synthetic and novel Lipid-A structures disclosed in this invention, in terms of efficacy, safety, stability and compliance of such vaccine formulations with regulatory guidelines.

Preferably, the toxicity of the lipid compounds of the present invention is not more than 50% that of said natural Lipid-A product; more preferably it is less than 10% that of the latter.

The in vivo studies of the synthetic compounds disclosed in this invention have been limited to the assessment of their effectiveness as adjuvant. But they may have broader applications in other areas such as anti-tumor agents, LPS/Lipid-A antagonists, inhibitors for Lipid-A biosynthesis and thus useful as novel antibiotics. Results of various biological activities will be disclosed in due course.

Pharmaceutical Methods and Preparations

Applicants hereby incorporate by reference the discussion at pp. 32-46 of WO98/33810.

The preferred animal subject of the present invention is a primate mammal. By the term "mammal" is meant an individual belonging to the class Mammalia, which, of course, includes humans. The invention is particularly useful in the treatment of human subjects, although it is intended for veterinary uses as well. By the term "non-human primate" is intended any member of the suborder Anthropoidea except for the family Hominidae. Such non-human primates include the superfamily Ceboidea, family Cebidae (the New World monkeys including the capuchins, howlers, spider monkeys and squirrel monkeys) and family Callithricidae (including the marmosets); the superfamily Cercopithecoidea, family Cercopithecidae (including the macaques, mandrills, baboons, proboscis monkeys, mona monkeys, and the sacred hunaman monkeys of India); and superfamily Hominoidae, family Pongidae (including gibbons, orangutans, gorillas, and chimpanzees). The rhesus monkey is one member of the macaques.

The term "protection", as used herein, is intended to include "prevention," "suppression" and "treatment." "Prevention" involves administration of the protein prior to the induction of the disease. "Suppression" involves administration of the composition prior to the clinical appearance of the disease. "Treatment" involves administration of the protective composition after the appearance of the disease.

It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." It should also be understood that to be useful, the protection provided need not be absolute, provided that it is sufficient to carry clinical value. An agent which provides protection to a lesser degree than do competitive agents may still be of value if the other agents are ineffective for a particular individual, if it can be used in combination with other agents to enhance the level of protection, or if it is safer than competitive agents.

The composition may be administered parentally or orally, and, if parentally, either systemically or topically. Parenteral routes include subcutaneous, intravenous intradermal, intramuscular, intraperitoneal, intranasal, transdermal, or buccal routes. One or more such routes may be employed. Parenteral administration can be, e.g., by bolus injection or by gradual perfusion over time. Alternatively, or concurrently, administration may be by the oral route. The immunization is preferably accomplished initially by intramuscular injection followed by intradermal injection, although any combination of intradermal and intramuscular injections may be used.

It is understood that the suitable dosage of a immunogen of the present invention will be dependent upon the age, sex, health, and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This will typically involve adjustment of a standard dose, e.g., reduction of the dose if the patient has a low body weight.

Prior to use in humans, a drug will first be evaluated for safety and efficacy in laboratory animals. In human clinical studies, one would begin with a dose expected to be safe in humans, based on the preclinical data for the drug in question, and on customary doses for analogous drugs (if any). If this dose is effective, the dosage may be decreased, to determine the minimum effective dose, if desired. If this dose is ineffective, it will be cautiously increased, with the patients monitored for signs of side effects. See, e.g., Berkow, et al., eds., *The Merck Manual,* 15th edition, Merck and Co., Rahway, N.J., 1987; Goodman, et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985), which references and references cited therein, are entirely incorporated herein by reference.

The total dose required for each treatment may be administered in multiple doses (which may be the same or different) or in a single dose, according to an immunization schedule, which may be predetermined or ad hoc. The schedule is selected so as to be immunologically effective, i.e., so as to be sufficient to elicit an effective immune response to the antigen and thereby, possibly in conjunction with other agents, to provide protection. The doses adequate to accomplish this are defined as "therapeutically effective doses." (Note that a schedule may be immunologically effective even though an individual dose, if administered by itself, would not be effective, and the meaning of "therapeutically effective dose" is best interpreted in the context of the immunization schedule.) Amounts effective for this use will depend on, e.g., the peptide composition, the manner of administration, the stage and severity of the disease being treated, the weight and general state of health of the patient, and the judgment of the prescribing physician.

Typically, the daily dose of an active ingredient of a pharmaceutical, for a 70 kg adult human, is in the range of 10 nanograms to 10 grams. For immunogens, a more typical daily dose for such a patient is in the range of 10 nanograms to 10 milligrams, more likely 1 microgram to 10 milligrams. However, the invention is not limited to these dosage ranges.

It must be kept in mind that the compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

The doses may be given at any intervals which are effective. If the interval is too short, immunoparalysis or other adverse effects can occur. If the interval is too long, immunity may suffer. The optimum interval may be longer if the individual doses are larger. Typical intervals are 1 week, 2 weeks, 4 weeks (or one month), 6 weeks, 8 weeks (or two months) and one year. The appropriateness of administering additional doses, and of increasing or decreasing the interval, may be reevaluated on a continuing basis, in view of the patient's immunocompetence (e.g., the level of antibodies to relevant antigens).

A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019369, incorporated herein by reference.

The appropriate dosage form will depend on the disease, the immunogen, and the mode of administration; possibilities include tablets, capsules, lozenges, dental pastes, suppositories, inhalants, solutions, ointments and parenteral depots. See, e.g., Berker, supra, Goodman, supra, Avery, supra and Ebadi, supra, which are entirely incorporated herein by reference, including all references cited therein.

BRIEF DESCRIPTION OF THE DRAWINGS

FIG. 1 Examples of natural Lipid-A structures, A from *E. coli* and B from *Salmonella* strains FIG. 2 New lipid acids of general formulae (3) and (4) and two examples thereof FIG. 3 Monosaccharide and disaccharide Lipid-A analogs containing new lipid structures and two examples thereof FIG. 4 Disaccharide Lipid-A analogs containing uniform di-lipid chains and two examples thereof FIG. 5 Synthesis of lipid 5

FIG. 6 Synthesis of lipids

FIG. 7 Synthesis of tri-lipid 23

FIG. 8 Synthesis of glucosamine derivatives

FIG. 9 Synthesis of compound 33

FIG. 10 Synthesis of glycosylation acceptors

FIG. 11 Synthesis of glycosylation donor 43

FIG. 12 Synthesis of disaccharide 45

FIG. 13 Synthesis of compound 48

FIG. 14 Synthesis of disaccharide 51

FIG. 15 Synthesis of compound 54

FIG. 16 Synthesis of compound 58

FIG. 17 Synthesis of glycosylation acceptor 64

FIG. 18 Synthesis of disaccharide 67

FIG. 19 Synthesis of compound 70

FIG. 20 Synthesis of amine 73

FIG. 21 Synthesis of compound 77

FIG. 22 Synthesis of glycosylation 79

FIG. 23 Synthesis of glycosylation donor 83

FIG. 24 Synthesis of compound 86

FIG. 25 Synthesis of glycosylation donor 91

FIG. 26 Synthesis of compound 94

FIG. 27 Synthesis of glycosylation acceptor 98

FIG. 28 Synthesis of amine 100

FIG. 29 Synthesis of compound 102

FIG. 30 Synthesis of compound 104

FIG. 35 Examples of peptides and glycopeptides derived from viral and tumor antigens that can be incorporated into liposome formulations.

DETAILED DESCRIPTIONS OF THE PREFERRED EMBODIMENTS OF THE INVENTION

Detailed Description of the Figures

Figure 31:
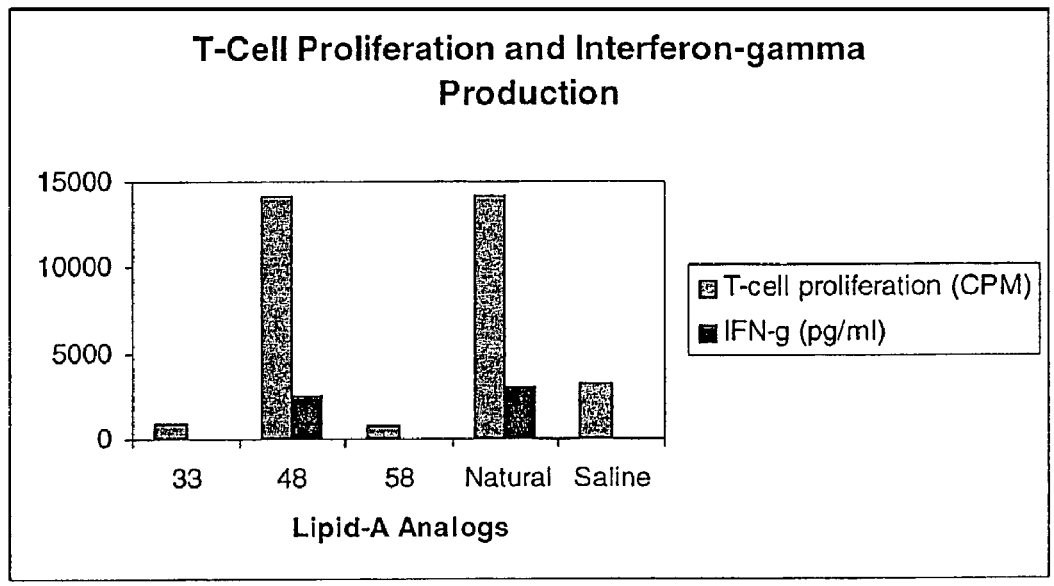
FIG. 31 T-cell proliferation (CPM, counts per minute) and Interferon-gamma (IFN-$\gamma$, pg/ml) production in mice immunized with MUC1-based liposomal vaccine adjuvanted with Lipid-A analogs 33, 48, 58 or Natural Lipid-A FIG. 32 T-cell proliferation (CPM, counts per minute) and Interferon-gamma (IFN-$\gamma$, pg/ml) production in mice immunized with MUC1-based liposomal vaccine adjuvanted with Lipid-A analogs 48, 54, 70, 77, 86 or Natural Lipid-A FIG. 33 T-cell proliferation (CPM, counts per minute) and Interferon-gamma (IFN-$\gamma$, pg/ml) production in mice immunized with MUC1-based liposomal vaccine adjuvanted with Lipid-A analogs 86, 94, 102, 104 or Natural Lipid-A FIG. 34 Structure of lipopeptide BP1-148, a modified 25-amino-acid sequence derived from tumor-associated MUC1 mucin (single letter codes of amino acids)

Chemical Synthesis of Lipid-A Analogs (FIG. 5-FIG. 30).

An invariant structural feature of Lipid-A molecule is its $\beta$-(1,6)-linked D-glucosamine disaccharide backbone. While this structure is bacterial in origin, this disaccharide in its pure form probably has no relevance to the range of biological activities displayed by the lipid structure. The lipid chains perhaps provide the basic mechanism through which the disaccharide exhibits a wide range of properties. Thus, only the lipid chains play a quantitative role through the promotion of the Lipid-A properties. A wide range of lipids may fill this need, while only in their numbers the lipids seem to quantitatively influence the properties of the molecule. We have synthesized and examined the influence of a range of lipids both natural (compound 13-15 and 17 in FIG. 6) and unnatural (5 in FIGS. 5, 20 and 23 in FIG. 7) and a range of linkages through which the lipids are linked together and to the carbohydrate core.

The most commonly found lipid in Lipid-A structures from nature is (R)-3-hydroxy-myristic acid. The 3-hydroxy group is further acylated with lipids of different lengths. Compound 5 (FIG. 5) is designed employing the natural stereochemistry of aspartic acid. Since the three dimensional orientation of the amino group in 5 is identical to that of the hydroxyl group in (R)-3-hydroxy myristic acid, 5 is expected to be a stereostructural mimic of (R)-3-acyloxy myristic acid.

The preparation of 5 is described in FIG. 5. Commercially available aspartic acid derivative 1 was coupled with nonylamine by using isobutyl chloroformate as an activating reagent to obtain 2 in 79% yield. The removal of Fmoc group from 2 followed by coupling with tetradecanoic acid provided 4. The tert-butyl protecting group was removed by treatment with TFA to give 5 in 97% yield.

FIG. 6 describes the synthesis of (R)-3-hydroxy-myristic acid derivative. Reformatsky reaction[20] of dodecanal with ethyl bromoacetate gave 6, which was hydrolyzed to racemic 3-hydroxymyristic acid 7. Optical resolution of 7 was achieved according to the known procedure[21a, b]. The diastereomers of its dehydroabietylamine salt were separated through fractional crystallization and the diastereomeric purity of the salt was monitored by melting point and/or NMR spectroscopy. Base and acid treatment of the salt gave R-isomer 8 in >95% enantiomeric excess (e.e.), which was converted to phenacyl ester 9 in 92% yield. Acylation of the 3-hydroxy group with various acyl chlorides in pyridine in the presence of DMAP gave 10-12 which upon treatment with zinc powder gave free lipid acids 13-15[22, 23]. On the other hand 9 was treated with benzyl trichloroacetimidate in the presence of trifluoromethyl sulphonic acid to give the 3-benzyloxy derivative 16 which was subsequently converted to its free acid 17[24].

FIG. 7 illustrates the synthesis of novel di-lipid 20 and tri-lipid 23 containing unnatural ether linkage. The reaction of 9 with triflate 18 in the presence of potassium carbonate gave 19 which was de-protected to give the di-lipid acid 20. Asymmetric synthesis of 21[25a, b, c] from dodecanal and allyl bromide in the presence of chiral reagent (−)-DIPCl at −78° C. afforded the product with ~85% e.e. in about 70% yield. The enantiomeric excess was determined from its optical rotation data and the NMR data of its methyl trifluoromethyl phenyl acetic acid [(R)-(+)-MTPA]ester[26, 27]. 21 and 20 were coupled in the presence of DCC and DMAP in dichloromethane to form 22 in 81% yield. Oxidative cleavage of the double bond in 22 gave the tri-lipid free acid 23 in 61% yield. Among the reported Lipid-A structures from nature, the presence of a tri-lipid moiety is not yet known.

FIG. 8 shows the general procedure used to prepare the glucosamine derivatives. These derivatives are well known and they are prepared essentially according to the procedures described in literatures[28, 29].

In FIG. 9 the synthesis of a monosaccharide analog 33 of the non-reducing end of Lipid-A structure is described. Compound 26 was coupled with tetradecanoic acid in the presence DCC and DMAP to afford 29 in 91% yield. The reductive removal of Troc-group in 29 with zinc powder in acetic acid, followed by coupling with lipid acid 5, furnished compound 30 in 60% yield. Regioselective benzylidene-ring opening with sodium cyanoborohydride and etherial HCl solution afforded the 4-OH compound 31 in 86%. A two step phosphate group introduction[30] was effected by reacting 31 with dibenzyl diisopropylphsophoramidite to form phosphite, followed by oxidation with m-chloroperbenzoic acid (m-CPBA) to give 32 in 66% yield. Catalytic hydrogenation to remove benzyl protecting groups of 32 gave the monosaccharide Lipid-A analog 33 in 79% yield.

FIG. 10 describes the preparation of two glycosylation acceptors to be used in the synthesis of monophosphorylated disaccharide Lipid-A analogs. The glucosamine derivative 34 31 was readily available from glucosamine hydrogen chloride. Regioselective introduction of trityl group in 6-O-position of 34 in the presence to DMAP and pyridine at 40° C. gave 35 in 90% yield. Benzylation with benzyl bromide and sodium hydride, followed by treatment with 80% acetic acid at 110° C. gave 37. The phthalimido group was removed by treatment with hydrazine in ethanol at reflux to give free amine 38, which was coupled in the presence of DCC with lipid acids 15 and 14 to provide 39 and 40, respectively.

The preparation of glycosylation donor 43 is shown in FIG. 11. Compound 28 was coupled with 14 in the presence of DCC and DMAP to obtain 41 in very good yield. Allyl, group was then removed in two steps, first the isomerization of allyl double bond by treating with Ir(I) complex and then hydrolysis in the presence of NBS. Treatment of 42 with trichloroacetonitrile and DBU afforded 43 in 81% yield.

The complete synthesis for disaccharide Lipid-A analog 48 is illustrated in FIG. 12 and FIG. 13. The glycosylation reaction between 39 and 43 with trifluoroboron diethyl etherate as the catalyst furnished the desired disaccharide 44 in 65% yield (FIG. 12). The Troc-protection group in 43, which served as a neighbour participating group, controlled the outcome of the stereochemistry of this glycosylation reaction to provide b-glycoside, exclusively. The removal of Troc-group in 44, followed by coupling with lipid acid 13 in the presence of DCC, gave compound 45. The selective benzylidene ring opening with sodium cyanoborohydride/HCl provides the 4'-OH compound 46 (FIG. 13). The phosphate group was introduced through phosphite formation and subsequent oxidation giving 47 in 85% yield. Final debenzylation with palladium on charcoal and hydrogen in THF-acetic acid afforded the monophosphorylated Lipid-A analog 48.

The whole strategy described above is very efficient in constructing disaccharide Lipid-A analogs, and it is also very flexible to adapt variations in the lipid contingent by using a few common building blocks. The same strategy was used to prepare two other analogs 54 and 58, which are described in FIG. 14-FIG. 16.

Compared to the proposed structure of *Salmonella*-type Lipid-A (FIG. 1), compound 48 (FIG. 13) has no lipid attached at the 3-O-position while the rest of the lipid substitution pattern remains the same. Compound 54 (FIG. 15) has the same substitution pattern as 48 except that in 54 all the lipids are of identical length ($C_{14}$). The repetition of lipids can be advantageous for large-scale preparation of the compound. Compound 58 (FIG. 16) carries an unnatural aspartic acid based lipid, but it may be considered as a close mimic of 54.

In order to introduce another lipid acid to 3-O-position of the disaccharide backbone, a different protecting strategy in the reducing end sugar has been employed. FIG. 17 shows the preparation of a new glycosylation acceptor 64. From 59, 3-O-allylation, removal of benzylidene group, and regioselective introduction of a trityl group gave 60. Benzylation of 4-OH group in 60 with benzyl bromide and sodium hydride, followed by the removal of trityl group afforded 62. The phthalimido group in 62 was cleaved by treatment with hydrazine in refluxing ethanol giving free amine compound 63 which was acylated with 14 in the presence of DCC to produce 64. The allyl group at 3-O-position provides the freedom of introducing a lipid to 3-O-position at any stage during the synthesis and if not removed, the allyl group will undergo catalytic hydrogenation to n-propyl group and it remains as a permanent appendage to the molecule.

Using the same procedure as described for the synthesis of compound 48, coupling of 43 and 64 gave the desired disaccharide 65 in 88% yield (FIG. 18). Through reductive cleavage of Troc-group, acylation of the free amine, 65 was converted to 67 which finally led to Lipid-A analog 70 after a series of transformations including reductive benzylidene ring opening, phosphate group introduction and hydrogenation (FIG. 19). Analog 70 has an n-propyl group on 3-O-position connected through an ether linkage. Compounds with such short simple alkyl chain connected through an ether linkage have not been reported before for Lipid-A analogs either from natural sources or through chemical synthesis.

FIG. 20 illustrates the strategy of introducing a lipid acid at 3-O-position of the disaccharide backbone. The allyl group of 65 was removed by treatment with Ir(I) complex, followed by NBS to give 71. The coupling of 71 with 17 in the presence of DCC and DMAP gave 72 in 71% yield, which following the treatment with zinc in acetic acid formed the free amine 73. By carrying out the same series of reactions as described above, compound 73 was converted to the final structure 77 (FIG. 21)

In the process of preparing several other Lipid-A analogs a new simplified strategy has been adapted for the synthesis of 86 as shown in FIG. 22-FIG. 24. In FIG. 22 the glycosyl acceptor 79 was prepared in two steps from 27 through acylation at 3-O-position and removal of 4,6-isopropylidene group.

FIG. 23 describes the preparation of new glycosyl donor 83 which is complete with benzyl protected phosphate group at 4-O-position. Selective opening of benzylidene ring in 41 using sodium cyanoborohydride and dry HCl gave compound 80 in good yield. Benzyl protected phosphate group was then introduced into 4-O-position to form 81 in 85% yield. De-allylation followed by the reaction with trichloroacetonitrile and DBU formed the new glycosylation donor 83.

The coupling reaction between 79 and 83 (FIG. 24) was carried out in the presence of trifluoroboron etherate as catalyst to form the desired disaccharide 84 in 66% yield. Reductive removal of Troc-groups, followed by the coupling with lipid acid 14, afforded compound 85 which, following debenzylation, gave the Lipid-A analog 86.

In the modified strategy, the phosphate group was introduced before the formation of glycosidic linkage. The glycosylation of acceptor with two free hydroxy groups proceeded with both regioselectivity and stereoselectivity forming only (1→6)-connected-b-glycoside. In doing so the synthetic steps were reduced at the disaccharide stage. This process becomes very efficient for Lipid-A analogs with identical substituents on 2- and 2'-amines, which may be introduced simultaneously.

Using this same procedure another Lipid-A analog 94 was prepared (FIG. 25, FIG. 26). The difference between compounds 86 and 94 is that in the latter the di-lipid moieties contain ether linkages. Though the ether linkage is not known in naturally derived Lipid-A structures, it confers better stability to Lipid-A structures than the natural ester linkage. In addition, the ether linkage is not susceptible to hydrolytic conditions and is more hydrophobic. Consequently, the lipid moiety with ether linkage attains better stability and may display better adjuvant characteristics than its natural counterpart. In FIG. 25 the preparation of glycosylation donor 91 is described. Starting with the coupling of 28 with lipid acid 20 (→87), through benzylidene ring opening (→88), phosphate group introduction (→89), de-allylation (→90) and imidate formation, compound 91 was obtained. As described above the glycosylation reaction of 79 and 91 furnished the disaccharide 92 (FIG. 26), which through the Troc-group removal, acylation with lipid acid 20, and final debenzylation, afforded Lipid-A analog 94.

Using the modified strategy, two more synthetic examples of Lipid-A analogs are described in FIG. 27-FIG. 30. In FIG. 27 the preparation of a new glycosylation acceptor 98 is described. A benzyl group was introduced at the 3-O-position of 27 using benzyl trichloroacetimidate and trifluoromethyl sulfonic acid to provide 95. Both the isopropylidene and Troc-group were removed to form the free amine 97, which upon coupling with the tri-lipid acid 23 afforded the glycosyl acceptor 98.

The glycosylation reaction between 91 and 98 in the presence of trifluoroboron etherate gave the desired disaccharide 99 in 56% yield (FIG. 28), which upon treatment with activated zinc in acetic acid provided the amino compound 100. Acylation of the amino-group with 20 (FIG. 29) and 17 (FIG. 30) gave 101 and 103, respectively. Complete de-protection of 101 and 103 furnished two Lipid-A analogs 102 and 104, respectively.

Both compound 102 and 104 carry tri-lipid moieties on the amino-group at the reducing end sugar. There have been no reports of naturally occurring Lipid-A structures with tri-lipid components nor have any chemically synthesized structures been reported. It is believed that the number of lipid chains attached to the carbohydrate core quantitatively modulates the biological activities of Lipid-A analogs. Whether the presence of a tri-lipid moiety on Lipid-A structure has a net quantitative effect on biological activities still remains to be investigated. We believe that the tri-lipid structural fragment does not significantly alter biological properties of Lipid-A structures. Our preliminary in vivo test results show that both compounds 102 and 104 have exhibited adjuvant characteristics similar to those of Lipid-A preparation of bacterial origin as well as to those of synthetic analog 86.

Figure 32:
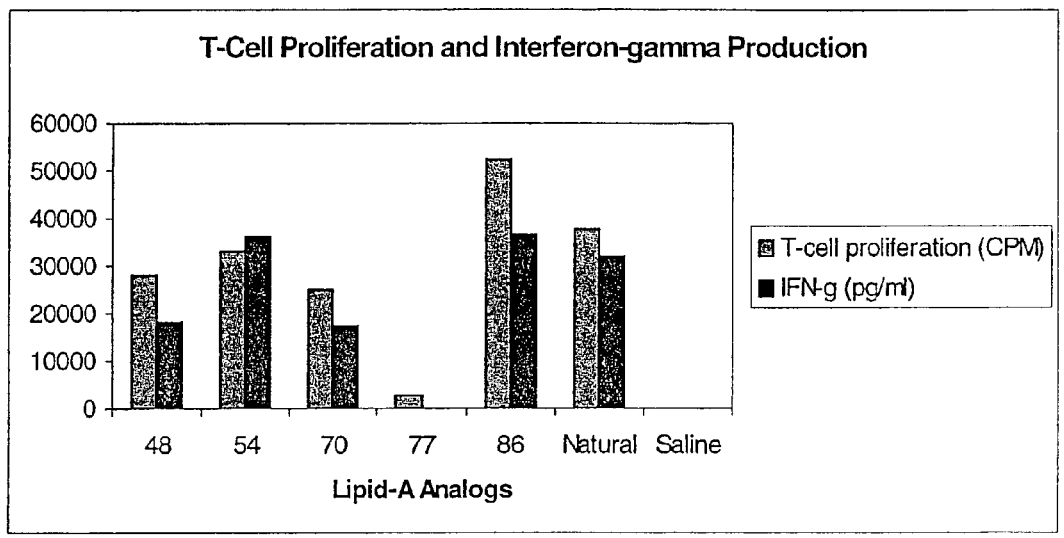
Figure 33:
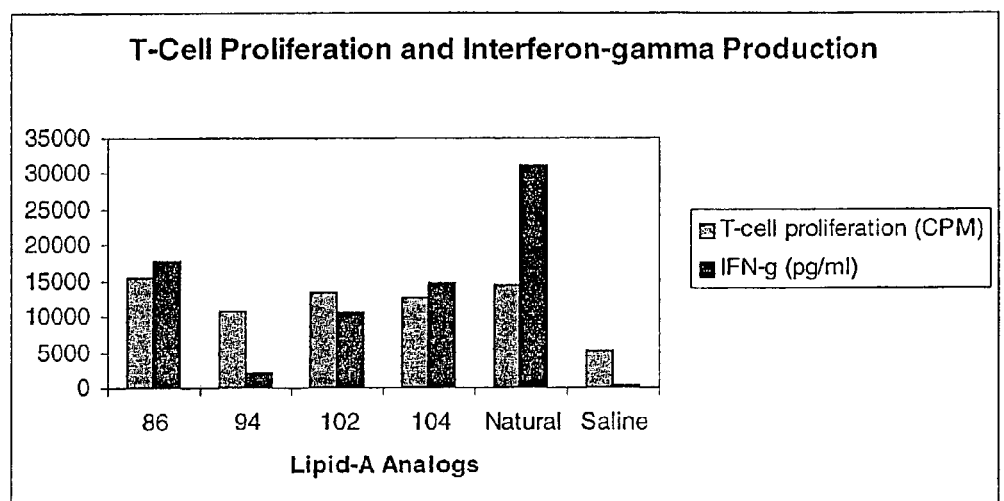

Biological Test Results (FIGS. 31-33)

Liposome formulations have been used to evaluate the adjuvant properties of various synthetic Lipid-A structures and the immune responses to a synthetic lipopeptide antigen BP-148, $H_2$N-STAPPAHGVTSAPDTRPAPGSTAPPK(Pal)G-OH (FIG. 34), a modified 25-amino-acid sequence derived from tumor-associated MUC1 mucin. The commercially available Lipid-A product, which is currently under clinical evaluation as an adjuvant for vaccine programs, was used for comparison. The natural Lipid-A product, purchased from AVANTI, contained a mixture of Lipid-A analogs extracted from *Salmonella* bacterial cell wall and is designated as Natural Lipid-A in this invention.

Thus, the liposomal formulations containing the synthetic lipopeptide antigen, BP1-148, and Lipid-A analogs 33, 48, 54, 58, 70, 77, 86, 94, 102, 104 or Natural Lipid-A, were used to immunize mice to measure their immune response in terms of T-cell blastogenesis and interferon-gamma (IFN-γ) production. The compounds were tested in three groups at different time and their preliminary results are shown separately in FIGS. 31-33. As the variations are attributed to different factors such as animal groups and experimental factors, the data from different groups will not be compared.

T-cell blastogenesis and high levels of IFN-γ production in mice after the introduction of such liposomal formulations amply demonstrated that synthetic Lipid-A structures 48, 54, 70, 86, 102 and 104 have similar adjuvant activity compared to Natural Lipid-A. As shown in FIG. 31-FIG. 33, liposomal vaccine formulations containing those synthetic Lipid-A analogs 48, 54, 70, 86, 102 and 104 induce significant T-cell blastogenesis and high levels of interferon-gamma. The values of CPM (counts per minute) and IFN-γ (pg/ml) are comparable to those observed for the formulations containing Natural Lipid-A. The formulations containing the synthetic Lipid-A analog 94 (FIG. 33) also induce significant T-cell blastogenesis, although the production of interferon-gamma level is low. Further testing of compound 94 is necessary to provide unambiguous result of its adjuvant properties. Compound 33, 77 and 58 are inactive in both T-cell blastogenesis and interferon-gamma production.

Compound 86 seems to be slightly more active than all the other synthetic Lipid-A analogs tested in the second group shown in (FIG. 32). In a direct comparison with natural Lipid-A, synthetic analog 86 exhibited similar values in both T-cell blastogenesis and IFN-γ production. Structurally, compound 86 has a total of seven lipid chains, including a 3-hydroxyl myristic acid moiety on 3-O-position of the disaccharide backbone. Compound 54 and compound 70 are structurally very close to compound 86, except that compound 54 has no lipid chain on 3-O-position and compound 70 has a simple n-propyl group on 3-O-position. Comparable results in both T-cell blastogenesis and Interferon-gamma (IFN-γ) production are obtained for compounds 54, 70 and 86 (FIG. 32). This observation indicates that the nature of the substitute group on 3-O-position of the Lipid-A disaccharide backbone probably has little effect on the adjuvanticity of Lipid-A analogs. In addition, compounds 48 and 70 (FIG. 32), both having the same substitution pattern but differing only in lipid chain length, are almost identical in performance. This result confirms our belief that slight variations in lipid chain length do not affect much the adjuvant properties of Lipid-A analogs.

As shown in FIG. 33, compounds 102 and 104 also demonstrated similar results in comparison to both compound 86 and Natural Lipid-A. Interestingly, both compounds 102 and 104 contain an unnatural tri-lipid fatty acid moiety on the 2-N-position of the disaccharide backbone. In addition, unnatural ether linkage instead of the natural ester linkage, is also incorporated for the lipid-lipid connection in those multi-lipid fatty acid moieties. The finding that compound 102 and 104 display similar adjuvanticity as the Natural Lipid-A product further proves our idea that slight variations in the lipid portion of Lipid-A structures do not affect the adjuvant property of these molecules. These results are extremely useful in designing new Lipid-A mimics that may provide structurally simpler, more stable, and biologically more active molecules.

Synthetic analogs 33, 58 and 77 contain aspartic acid based lipids. The observed weak responses to these liposomal formulations are primarily attributed to their poor incorporation into liposomes as a result of their poor solubility. Different formulation techniques may be needed to assure their efficient incorporation into liposomes and to re-evaluate their adjuvant properties.

EXAMPLES

General: Melting points were not corrected. All air and moisture sensitive reactions were performed under nitrogen atmosphere. Anhydrous THF, DMF and dichloromethane were purchased from Aldrich and other dry solvents were prepared in the usual way. ACS grade solvents were purchased from Fisher and used for chromatography without distillation. TLC plates (silica gel 60 $F_{254}$, thickness 0.25 mm, Merck) and flash silica gel 60 (35-75 μm) for column chromatography were purchased from Rose Scientific, Canada. $^1$H and $^{31}$P spectra were recorded either on a Brucker AM 300 MHz or Varian Unity 500 MHz or Brucker DRX 600 MHz spectrometers with TMS as internal standard for proton chemical shifts. Optical rotations were measured on a Perkin-Elmer 241 Polarimeter at room temperature (20-22° C.).

Elemental analysis data were obtained from the Micro-analytical laboratory in the University of Alberta. Electron-spray mass spectrometric analyses were performed either on a MS50B or MSD1 SPC mass spectrometers.

Example 1 Preparation of Compound 2

A solution of 1 (3.16 g, 7.69 mmol) in dry THF (35 ml) was cooled to −20° C. N-Methyl morpholine (0.76 ml, 0.70 g, 6.92 mmol) and isobutyl chloroformate (0.94 g, 0.90 ml, 6.92 mmol) were added. The mixture was stirred for 5 min. and nonylamine (1.27 ml, 0.99 g, 6.92 mmol) in dry THF (2 ml) was added to the above solution. The mixture was stirred at −20° C. for 1 h. Methanol (3 ml) was added and the reaction mixture was concentrated in vacuo. The residue was purified by flash chromatography (hexane:ethyl acetate, 2:1) to give 2 (3.27 g, 79%). TLC: $R_f$0.44 (hexane:ethyl acetate, 3:1). $[\alpha]_D^{22}$=+16.9 (c 0.64, chloroform). $^1$H NMR (300 MHz, CDCl$_3$): δ 0.88 (t, J=6.5 Hz, 3H, CH$_3$), 1.42 (br s, 12H, 6CH$_2$), 1.50 (br s, 11H, 3CH$_3$, CH$_2$), 2.59 (dd, J=16.0, 6.5 Hz, 1H, Asp-β-H), 2.93 (dd, J=16.0, 3.5 Hz, 1H, Asp-β'-H), 3.24 (m, 2H, NCH$_2$), 4.22 (t, J=7.0 Hz, 1H, Fmoc-CH), 4.45 (m, 3H, OCH$_2$, Asp-α-H), 5.96 (d J=7.0 Hz, 1H, NH), 6.45 (m, 1H, NH), 7.29-7.79 (m, 8H, Ar—H). Anal. calcd for C$_{32}$H$_{44}$N$_2$O$_5$ (536.71): C, 71.61; H, 8.26; N, 5.22. Found: C, 71.68; H, 8.51; N, 5.27.

Example 2 Preparation of Compound 3

Compound 2 (9.50 g, 19.47 mmol) was dissolved in dry THF (40 ml). Piperidine (10 ml) was added and the mixture stirred at room temperature for 1 h. The solvent was removed and the residue was purified by flash chromatography (hexane:ethyl acetate, 1:1 and then 5% methanol in dichloromethane) to give 3 (5.64 g, 92%). TLC: $R_f$=0.38 (5% methanol in dichloromethane), $[\alpha]$=D$^{22}$=−41.0 (c 0.59, chloroform). $^1$H NMR (300 MHz, CDCl$_3$): δ 0.86 (t, J=6.5 Hz, CH$_3$), 1.22 (br s, 12H, 6CH$_2$), 1.45 (s, 9H, 3, CH$_3$) 1.55 (m, 2H, CH$_2$), 1.68 (s, 2H, NH$_2$), 2.46 (dd, J=16.0, 8.0 Hz, 1H, Asp-β-H), 2.83 (dd, J=16.0, 4.0 Hz, 1H, Asp-β'-H), 3.20 (m, 2H, NCH$_2$), 3.80 (dd, J=8.0, 4.0 Hz, 1H, Asp-α-H), 7.36 (br s, 1H, NH). Anal. calcd for C$_{17}$H$_{34}$N$_2$O$_3$ (314.47): C, 64.93; H, 10.90; N, 8.90. Found: C, 65.01; H, 11.20; N, 8.96.

Example 3 Preparation of Compound 4

Tetradecanoic acid (4.51 g, 19.78 mmol) was dissolved in dry THF (50 ml). N-Methyl morpholine (3.78 ml, 3.47 g, 34.40 mmol) was added and the solution was cooled to −25° C. Isobutyl chloroformate (2.34 ml, 2.47 g, 18.06 mmol) was added dropwise and the mixture was stirred for five min. A solution of 3 (5.40 g, 17.20 mmol) in dry THF (50 ml) was added dropwise to the above solution. The mixture, after stirring at −25° C. for 30 min, was allowed to warm up to room temperature within 1 h. Methanol (5 ml) was then added and the reaction mixture was stirred for five min further. It was concentrated in vacuo and the residue was purified by flash chromatography (dichloromethane actone, 30:1 and 25:1) to give 4 (7.21 g, 80%). TLC: $R_f$=0.37, (hexane:ethyl acetate, 3:1). $[\alpha]_D^{22}$=−14.4 (c 0.61, chloroform). $^1$H NMR (300 MHz, CDCl$_3$): δ 0.87 (t, J=6.5 Hz, 6H, 2CH$_3$), 1.25 (br s, 32H, 16 CH$_2$), 1.46 (br s, 11H, 3CH$_3$, CH$_2$), 1.54 (m, 2H, CH$_2$), 2.21 (t, J=7.5 Hz, 2H, CH$_2$), 2.52 (dd, J=16.5, 7.0 Hz, 1H, Asp-β-H); 2.84 (dd, J=16.5, 4.0 Hz, 1H, Asp-β'-H), 3.21 (m, 2H, NCH$_2$), 4.71 (m, 1H, Asp-α-H), 6.63 (t, J=5.0 Hz, 1H, NH), 6.84 (d, J=7.0 Hz, 1H, NH). Anal. calcd for C$_{31}$H$_{60}$N$_2$O$_5$ (524.83): C, 70.94; H, 11.52; N, 5.34. Found: C, 70.84; H, 11.87; N, 5.28.

Example 4 Preparation of Compound 5

Compound 4 (7.74 g, 14.77 mmol) was dissolved in trifluoroacetic acid-water (95:5, v/v, 180 ml) and the solution was stirred at room temperature for 4 h. The solvent was then removed and the residue was purified by flash chromatography (2 to 4% methanol in dichloromethane) to give 5 (6.71 g, 97%). TLC: $R_f$=0.33 (5% methanol in chloroform). $[\alpha]_D^{22}$=−27.5 (c 0.24, chloroform). $^1$H NMR (300. MHz, CDCl$_3$): δ 0.88 (t, J=6.5 Hz, 6H, 2CH$_3$), 1.26 (br s, 32H, 16 CH$_2$), 1.48 (m, 2H, CH$_2$), 1.62 (m, 2H, CH$_2$), 1.24 (t, J=7.5 Hz, 2H, CH$_2$), 2.69 (dd, J=−16.5, 7.0 Hz, 1H, Asp-1-H), 2.89 (dd, J=16.5, 4.0 Hz, 1H, Asp-β'-H), 3.21 (m, 2H, NCH$_2$), 4.79 (m, 1H, Asp-α-H), 6.95 (t, J=5.5 Hz, 1H, NH), 7.05 (d, J=7.5 Hz, 1H, NH). Anal. calcd C$_{27}$H$_{52}$N$_2$O$_4$ (468.72): C, 69.19; —H, 11.18; N, 5.98. Found: C, 69.14; H, 11.28; N, 5.95.

Example 5 Preparation of Compound 8

(1) Compound 6: Zinc powder (19.6 g, 299 mmol) was added to a mixture of dodecanal (25.0 g, 136 mmol.), ethyl bromoacetate (25.0 g, 150 mmol.), and 150 mL THF in presence of nitrogen atmosphere. The reaction flask was clamped into a sonication bath and the sonication was started. Iodine (3.5 g, 27.2 mmol.) was added slowly into the reaction flask. After 2-3 minutes of sonication the reaction was initiated vigorously. Then the sonication was stopped and the reaction flask was removed from the sonicator bath. Zinc was filtered off and washed with THF (10 mL) for 6-7 times. The combined filtrates were concentrated in vacuo. A pale yellow viscous liquid was resulted to which hexane (200 mL) was added and shaken well for 5 min. A white solid precipitated out, which was filtered off and washed with hexane (3×15 mL). The combined filtrate and washings were concentrated to dryness and the residue was purified by column chromatography (10% ethyl acetate in hexane) to afford the pure compound 6 (22.2 g, 60%). TLC: $R_f$=0.25 (10% ethyl acetate in hexane). $^1$H NMR (300 MHz, CDCl$_3$): δ=0.88 (t, J=6.5 Hz, CH$_3$), 1.26 (m, 16H), 1.28 (t, J=6.5 Hz, 3H, CH$_3$), 1.40-1.50 (m, 4H), 2.40 (dd, J=16.0, 7.0 Hz, 1H), 2.50 (dd, J=16.0, 3.0 Hz, 1H), 3.05 (s, 1H, OH), 4.00 (m, 1H, H-3), 4.17 (q, J=6.5 Hz, 2H).

(2) Compound 7: 3-Hydroxy-myristic ester 6 (122.0 g, 0.5 mmol) was dissolved in ethanol (800 ml) and KOH (33.6 g) was added. The reaction mixture was refluxed for 1 h and then 10% HCl (1000 ml) was added after cooling in an ice bath. A white solid precipitated out which was filtered off and dried briefly (192.0 g). The solid was recrystallized with boiling hexane (800 ml) to give a white crystalline compound 7 (98.2 g, 90%). TLC: $R_f$=0.35 (5% methanol in dichloromethane). $^1$H NMR (300 MHz, DMSO-d$_6$): δ=0.88 (t, J=6.5 Hz, CH$_3$), 1.25 (m, 20H), 2.20 (dd, J=15.0, 7.5 Hz, 1H), 2.28 (dd, J=15.0, 5.5 Hz, 1H), 3.80 (br s, 1H), 4.55 (br s, 1H).

(3) 3-hydroxy-myristic acid-dehydroabietyl amine salt: Pure dehydroabietyl amine (purified according to lit.$^{21b}$, 131.0 g, 459.6 mmol) was dissolved in a mixture of hexane (3.0 L) and diethyl ether (1.5 L). Compound 7 (110.0 g, 450.8 mmol) was dissolved in diethyl ether (3.0 L) and added to the above amine solution with stirring. Crystallization started immediately after the addition. The stirring was stopped and the reaction mixture left at room temperature for 1 h. The white solid was filtered out and washed with hexane:diethyl ether mixture (1:1). The precipitate was dissolved in methanol (500 ml) (heated to dissolve) and then hexane:diethyl ether mixture (1:1, 700 ml) was added. The mixture was kept in the refrigerator (−9° C.) overnight. A white solid precipitated out which was collected by filtration. The recystalization of the solid was repeated until there was no further rise in melting point. The final yield of the pure (R)-salt was 38 g, 40%. m.p. 131.5-132° C. $^1$H NMR (600 MHz, CDCl$_3$) δ: 0.85 (t, J=6.5 Hz, 3H, CH$_3$), 1.00 (s, 3H, CH$_3$), 1.19 (d, J=6.5 Hz, 6H, 2CH$_3$), 1.25 (s, 3H, CH$_3$), 1.25-1.70 (m), 2.10 (dd, J=15.0, 10.0 Hz, 1H), 2.27 (m, 2H), 2.63 (d, J=12.5 Hz, 1H), 2.79 (m, 2H), 2.87 (m, 2H), 3.81 (m, 1H), 6.40 (br s, 3H), 6.85 (d, J=1.5 Hz, 1H), 6.95 (dd, J=8.0, 1.5 Hz, 1H), 7.12 (d, J=8.0 Hz, 1H). A single set of double doublet peaks at 2.10 ppm is characteristic of only one isomer present. For the salt formed from racemic 3-hydroxy myristic acid, two sets of double doublet peaks will appear at this position. NMR can be used here to detect the separation efficiency.

(4) Compound 8: The salt of dehydroabietyl amine and myristic acid (38.0 g) was taken into a 2 L round bottomed flask and saturated aqueous sodium carbonate (1000 ml) and diethyl ether (800 ml) were added. The mixture was stirred vigorously for 30 min. The water layer and ether layer were separated and the solid was collected. The solid was washed with water (300 ml), ether (3×100 ml) and dried briefly. The solid was treated with 1 L of 2% HCl (aq.) and ethyl acetate (1.5 L) till the solid dissolved completely. The aqueous layer was separated and extracted with ethyl acetate (2×150 ml). The organic layer was dried with anhydrous sodium sulfate and concentrated to give R-rich acid that was recrystallized from ethyl acetate and hexane to provide 8 (16.5 g) in ~95% e.e. $[\alpha]_D^{20}$=−15.5 (c 1.0, CHCl$_3$).

Example 6 Preparation of Compound 9

Compound 8 (16.0 g, 65.6 mmol) was dissolved in anhydrous ethyl acetate and bromoacetophenone (15.66 g, 78.7 mmol) and triethyl amine (7.95 g, 78.7 mmol) were added under N$_2$ atmosphere. The reaction mixture was allowed to stir overnight. A white solid was precipitated out which was filtered off and washed with ethyl acetate (3×10 ml). The combined washings and filtrate was evaporated to get a pale yellow solid which was purified to give 9 (22.0 g, 92%) as white crystalline solid by silica gel chromatography (ethyl acetate:hexane, 1:8). TLC: $R_f$=0.42 (ethyl acetate:hexane, 1:3). $[\alpha]_D^{20}$=−5.7 (c 1.0, chloroform). $^1$H NMR (300 MHz, CDCl$_3$): δ=0.88 (t, J=6.5 Hz, 3H, CH$_3$), 1.30 (br s, 16H), 1.40-1.60 (m, 4H), 2.57 (dd, J=15.0, 9.0 Hz, 1H), 2.70 (dd, J=15.0, 3.0 Hz, 1H), 3.45 (d, J=3.5 Hz, 1H), 4.18 (m, 1H, H-3), 5.37 (d, J=16.0 Hz, 1H), 5.49 (d, J=16.0 Hz, 1H), 7.50 (m, 2H), 7.64 (m, 1H), 7.92 (m, 2H).

Example 7 Preparation of Compound 10

Compound 9 (500 mg, 1.381 mmol) was dissolved in pyridine (5 ml) and to this solution 4-dimethylaminopyridine (DMAP, 8.46 mg, 0.068 mmol) was added. The resulting mixture was then cooled in an ice bath for 5 minutes before lauroyl chloride (383 μl, 1.657 mmol) was added dropwise. When the addition of lauroyl chloride ended, the entire mixture was left with stirring at room temperature overnight. TLC of reaction mixture in the next morning showed the presence of starting lipid 9. The reaction was then cooled down to 0° C. and at this temperature it was treated with some more lauroyl chloride (160 μl). Subsequently, the reaction mixture was removed from the bath and left to react for 3 hours further at room temperature. To stop the reaction, methanol (1 ml) was added and 10 minutes later reaction mixture was concentrated to dryness by evaporator. The residue was then applied on silica gel for chromatographic purification (ethyl acetate:hexane; 1:9) to provide compound 10 (524 mg, 70%). Yield of reaction could be higher if the impure fraction (320 mg) was purified again. TLC: $R_f$=0.34 (ethyl acetate:hexane, 1:9). $[\alpha]_D^{20}$=+1.0 (c 1.0, chloroform). $^1$H NMR (300 MHz, CDCl$_3$): δ=0.88 (t, J=6.5 Hz, 6H, 2CH$_3$), 1.30 (m, 0.34H), 1.65 (m, 4H), 2.30 (t, J=6.5 Hz, 2H), 2.72 (dd, J=15.5, 5.5 Hz, 1H), 2.78 (dd, J=15.5, 7.5 Hz, 1H), 5.30 (m, 1H, H-3), 5.35 (s, 2H), 7.47 (m, 2H), 7.63 (m, 1H), 7.90 (m, 2H).

Example 8 Preparation of Compound 11

Compound 9 (16.0 g, 44.2 mmol) was dissolved in pyridine (150 ml) and DMAP (270 mg, 2.2 mmol) was added. Tetradecanoyl chloride (13.1 g, 53.0 mmol) was added dropwise while keeping the reaction mixture in cold water bath. The reaction mixture was stirred for 3 h at room temperature. When TLC indicated the completion of the reaction, methanol (20 ml) was added to quench the reaction and allowed to stir for 30 min. The solvents were removed to dryness and the residue was dissolved in 800 ml-ethyl acetate and washed with ice water (2×100 ml). The aqueous layer was back extracted with ethyl acetate (3×100 ml). The combined organic layer was dried over anhydrous sodium sulphate and the solvent was removed in vacuo. The colourless residue obtained was purified on a silica gel chromatography (ethyl acetate:hexane, 1:10) to give the pure compound 11 (23.0 g, 92%). TLC: $R_f$=0.54 (ethyl acetate:hexane, 5:1). $[\alpha]_D^{20}$=+0.95 (c 2.0, chloroform). $^1$H NMR (300 MHz, CDCl$_3$): δ=0.88 (t, J=6.5 Hz, 6H; 2CH3), 1.26 (br s, 38H), 1.65 (m, 4H), 2.31 (t, J=6.5H, 2H), 2.72 (dd, J=16.0, 5.5 Hz, 1H), 2.79 (dd, J=16.0, 7.5 Hz, 1H), 5.32 (m, 1H, H-3), 5.34 (s, 2H), 7.35 (m, 2H), 7.61 (m, 1H), 7.90 (m, 2H).

Example 9 Preparation of Compound 12

Compound 12 was synthesized by following exactly the same procedure described for the preparation of compound 10, except that lauroyl chloride was replaced by palmitoyl chloride. When the reaction between compound 9 (500 mg, 1.381 mmol) and palmitoyl chloride (628.5 µl) was completed, the residue from solvent removal was re-dissolved in ethyl acetate and washed with water. The organic layer was dried over Na$_2$SO$_4$ and concentrated. Desired product, compound 12; was obtained as colourless solid (463.4 mg, 56%) from silica gel column purification using ethyl acetate-hexane (1:9) for elution. Additional desired product (563.6 mg) was obtained in slightly impure form. TLC: $R_f[\alpha]_D^{20}$=+2.0 (c 1.0, chloroform). $^1$H NMR (300 MHz, CDCl$_3$): δ=0.88 (t, J=6.5 Hz, 6H, 2CH$_3$), 1.30 (br s, 42H), 1.65 (m, 4H), 2.31 (t, J=6.5 Hz, 2H), 2 72 (dd, J=15.0, 5.5 Hz, 1H), 2.78 (dd, J=15.0, 7.5 Hz, 1H), 5.30 (m, 1H, H-3), 5.35 (s, 2H), 7.48 (m, 2H), 7.61 (m, 1H), 7.90 (m, 2H).

Example 10 Preparation of Compound 13

Compound 10 (510 mg) was dissolved in 80% acetic acid in ethyl acetate (18 ml) and Zn powder (1.0 g) was added. The entire mixture was left with good stirring overnight. Next morning the reaction was treated with additional Zn powder (400 mg) and stirred for 5 hours further. The solid was then filtered off and washed with generous amount of ethyl acetate. The filtrate was concentrated to dryness. The remainder was purified on flash silica column (ethyl acetate:hexane:acetic acid, 1:10:1%) to yield compound 13 (327 mg, 82%) as colourless solid on cooling at 0° C. TLC: $R_f$=0.22 (ethyl acetate:hexane, 1:9) $[\alpha]_D^{20}$=−1.2 (c 1.0, chloroform). $^1$H NMR (300 MHz, CDCl$_3$—CD$_3$OD): δ=0.88 (t, J=6.5 Hz, 6H, 2CH$_3$), 1.30 (br s, 34H), 1.62 (m, 4H), 2.30 (t, J=6.5 Hz, 2H), 2.52 (dd, J=15.5, 5.5 Hz, 1H), 2.60 (dd, J=15.5, 7.5 Hz, 1H), 5.22 (m, 1H, H-3).

Example 11 Preparation of Compound 14

The mixture of compound 11 (23.0 g), zinc powder (50 g) and glacial acetic acid (350 ml) was stirred at room temperature for 2 h. Zinc powder was filtered off and washed with ethyl acetate (100 ml). Combined filtrates were concentrated under reduced pressure and co-evaporated with toluene twice. Residue as colourless viscous liquid was purified by silica gel chromatography (2% methanol in dichloromethane). The pure compound 14 (16.5 g, 90%) was obtained as a white solid after evaporation of the solvent. TLC: $R_f$=40 (ethyl acetate hexane, 1:3). $[\alpha]_D^{20}$=−1.25 (c 2.0, CHCl$_3$) $^1$NMR (300 Mz, CDCl$_3$): δ=0.88 (t, J=6.5 Hz, 6H, 2CH$_3$), 1.30 (br s, 38H), 1.40-1.55 (m, 4H), 2.47 (dd, J=16.5, 9.0 Hz, 1H), 2.58 (dd, J=16.5, 3.0 Hz, 1H), 4.05 (m, 1H, H-3).

Example 12 Preparation of Compound 15

Compound 12 (429.9 mg, 0.716 mmol) was dissolved in ethyl acetate (4.4 ml) and acetic acid (17.6 ml) was added. After an addition of Zn powder (2.1 g) was made, the mixture was stirred at room temperature overnight. Zn was then removed by filtration and washed with generous amount of ethyl acetate. The filtrate was concentrated and purified on flash silica gel column (ethyl acetate:hexane:acetic acid, 1:10:1%) to give compound 15 (245 mg, 72%). TLC: $R_f$=0.25 (ethyl acetate:hexane, 1:10). $[\alpha]_D^{20}$=−1.3 (c 1.0, chloroform). $^1$H NMR (300 MHz, CDCl$_3$): δ=0.88 (t, J=6.5 Hz, 6H, 2CH$_3$), 1.23 (br s, 42H), 1.62 (m, 4H), 2.28 (t, J=6.5 Hz, 2H), 2.56 (dd, J=16.0, 5.5 Hz, 1H), 2.64 (dd, J=16.0, 7.5 Hz, 1H), 5.20 (m, 1H, H-3).

Example 13 Preparation of Compound 16

Compound 9 (5.0 g, 13.8 mmol), benzyl trichloroacetimidate (7.0 g, 27.6 mmol), molecular sieve powder (4 Å, 3.0 g), anhydrous dichloromethane (100 ml) and anhydrous hexane (100 ml) were taken in a 250 ml round bottomed flask and stirred for 30 min under N$_2$ atmosphere. Cooled to 0° C. and trifluoromethyl sulfonic acid (0.414 g, 2.8 mmol) was added and stirred for 5 h at 0° C. When there was no further improvement, in the formation of product shown on TLC, the reaction was quenched with triethyl amine (2 ml). The reaction mixture was filtered through a small celite bed, washed thoroughly with dichloromethane and the combined filtrate and washings were concentrated. The colorless residue obtained was purified on a silica column (ethyl acetate:hexane, 1:10) to obtain pure 16 (6.0 g, 96%) as a shiny white solid. TLC: $R_f$=0.36 (hexane:ethyl acetate, 6:1). $[\alpha]_D^{20}$=−7.4 (c 2.0, chloroform). $^1$H NMR (300 MHz, CDCl$_3$): δ=0.88 (t, J=6.5 Hz, 3H, CH$_3$), 1.25 (br s, 18H), 1.62 (m, 2H), 2.66 (dd, J=15.0, 5.5 Hz, 1H), 2.80 (dd, J=15.0, 7.5 Hz, 1H), 3.95 (m, 1H), 4.54 (d, J=11.5 Hz, 1H), 4.60 (d, J=11.5 Hz, 1H), 5.27 (d, J=15.5 Hz, 1H), 5.35 (d, J=15.5 Hz, 1H), 7.32 (m, 5H, Ar—H), 7.47 (m, 2H), 7.60 (m, 1H), 7.90 (m, 2H).

Example 14 Preparation of Compound 17

By following the same procedure described for the preparation of compound 14, compound 17 was prepared from compound 16 (6.0 g) in the presence of zinc powder (10.0 g) and glacial acetic acid (100 ml). Reaction was completed in 30 min. After the work up, the colourless residue was purified on a silica column with ethyl acetate:hexane: acetic acid (2:8:1%) as solvent system. Evaporation of the solvent afforded 17 as a white solid in 65% yield. TLC: $R_f$=0.45 (hexane:ethyl acetate, 4:1). $[\alpha]_D^{20}$=−5.4 (c 2.0, chloroform).

¹H NMR (300 MHz, CDCl₃): δ=0.88 (t, J=6.5 Hz, 3H, CH₃), 1.26 (br s, 18H), 1.60 (m, 2H), 2.55 (dd, J=15.5, 5.5 Hz, 1H), 2.64 (dd, J=15.5, 6.5 Hz, 1H), 3.87 (m, 1H), 4.58 (s, 2H), 7.30 (m, 5H, Ar—H).

Example 15 Preparation of Compound 19

(1) Compound 18: A mixture of dodecyl alcohol (810.0 mg, 4.348 mmol), pyridine (394 µl) and CH₂Cl₂ (0.5 ml) was slowly added to a cooled solution of trifluoromethyl sulfonic acid anhydride (triflic anhydride, 1.433 ml in 8.0 ml of CH₂Cl₂) at 0° C. over 15 minutes period. The resulting mixture was then stirred at the same temperature for 20 minutes at which time the reaction appeared as slightly orange suspension and its TLC indicated the absence of dodecyl alcohol. Cooled hexane (20 ml) was added. Solid was then removed by filtering through a Na₂SO₄ bed and washed with some more hexane. The removal of solvent provided crude triflate product as clear liquid. After drying further under high vacuum the amount of crude triflate 18 was 1.433 g. TLC: $R_f$=0.77 (hexane:ethyl acetate, 10:1).

(2) Compound 19: Lipid 9 (1.05 g; 2.989 mmol) and Na₂SO₄ (7.0 g) in dry 1,2-dichoroethane (25 ml) was stirred for 5 minutes before crude triflate 18 solution (1.433 g in 2.0 ml of dry 1,2-dichoroethane) was added. The resulting suspension was stirred at room temperature over weekend. It was then heated at 80° C. for 2 hours. Still some lipid 9 remained in the reaction mixture, but the reaction was terminated. Solid was filtered through a Na₂SO₄ bed and washed with CH₂Cl₂ (150 ml). Combined filtrates were washed with saturated NaHCO₃ (20 ml), water (50 ml), and dried over Na₂SO₄. Remainders from solvent removal were purified on flash silica gel column (CH₂Cl₂: hexane, 1:1) to give slightly impure 19 which was re-purified on a second column (CH₂Cl₂: hexane, 4:1) to render pure 19 (1.05 g, 69%). TLC: $R_f$=0.29 (hexane/ethyl acetate, 10:1). $[\alpha]_D^{20}$=−3.8 (c 1.0, chloroform). ¹H NMR (300 MHz, CDCl₃): δ=0.88 (t, J=6.5 Hz, 6H, 2CH₃), 1.26 (br s, 36H), 1.55 (m, 4H), 2.60 (dd, J=15.5, 5.5 Hz, 1H), 2.74 (dd, J=15.5, 7.5 Hz, 1H), 3.46 (m, 2H), 3.76 (m, 1H), 5.30 (d, J=16.5 Hz, 1H), 5.39 (d, J=16.5 Hz, 1H), 7.49 (m, 1H), 7.61 (m, 1H), 7.91 (m, 2H).

Example 16 Preparation of Compound 20

Using the same procedure described for the synthesis of compound 14, compound 20 was prepared from the reaction of compound 19 (1.02 g; 1.922 mmol) with Zn powder (1.12 g) in acetic acid (12.0 ml). After stirring at room temperature overnight, Zn was removed and combined filtrates were evaporated to dryness. Residue was applied on flash silica gel column for purification, initially with 9H₂Cl₂:hexane (8:1) to remove all impurities with high $R_f$ value and later ethyl acetate:hexane (1:5) to elute desired produce 20 in 88% yield (741.5 mg). TLC: $R_f$=0.20 (dichloromethane:hexane, 8:1). $[\alpha]_D^{20}$=−4.8 (c 1.0, chloroform). ¹H NMR (300 MHz, CDCl₃): δ=0.88 (t, J=6.5 Hz, 6H, 2CH₃), 1.27 (br s, 36H), 1.56 (m, 4H), 2.54 (d, J=6.0 Hz, 2H), 3.50 (m, 2H), 3.69 (m, 1H).

Example 17 Preparation of Compound 21

(−)-DIP-Cl (9.6 g, 30 mmol) was dissolved in anhydrous diethyl ether (35 ml, freshly distilled over Na/benzophenone) under nitrogen atmosphere. The mixture was cooled to −40° C. (dry ice/acetone) Allyl magnesium bromide (Aldrich, 1.0 M solution in diethyl ether considered as 0.9 M solution and hence 27.7 ml, 25 mmol) was added slowly to the above cooled solution. The reaction mixture was allowed to warm to room temperature and stirring was continued for 30 min (total stirred for 1.0 h). Meanwhile dodecanal (4.41 ml, 3.68 g, 20 mmol) was dissolved in dry diethyl ether and cooled to 0° C. using an ice bath.

The above reaction mixture which was stirred at room temperature for 30 min was cooled to, −78° C. and the cooled dodecanal solution was added slowly within 15 min and the stirring was continued at −78° C. for 1.0 h. When TLC (ethyl acetate:hexane, 1:15) showed almost completion of the reaction, the cold bath was removed and the reaction mixture allowed to stir for 5-10 min. Saturated aqueous sodium acetate solution (5.0 ml) and hydrogen peroxide (50%, 5.0 ml) were added slowly and cautiously and stirred for 5 min. The addition of sodium acetate solution and hydrogen peroxide was repeated at every 5 min. intervals of time, total 20 ml of sodium acetate and 15 ml of hydrogen peroxide were added. During the addition of these reagents, the reaction mixture become warmer and care should be taken that the temperature does not rise too high (if necessary use ice bath to cool). The resultant mixture was extracted with diethyl ether (3×20 ml). The combined ether extracts were washed with water and brine (1×25 ml) and dried over anhydrous sodium sulfate (60 g) and concentrated to obtain a colorless oily compound. Purification by silica gel column chromatography using 10% hexane in ethyl acetate afforded pure 21 as colorless viscous oil in 60% yield. TLC: $R_f$=0.26 (hexane/ethyl acetate, 15:1). $[\alpha]_D^{20}$=+4.9 (c 0.57, chloroform). ¹H NMR (300 MHz, CDCl₃): δ=0.88 (t, J=6.5 Hz, 3H, CH₃), 1.28 (br s, 18H), 1.46 (m, 2H), 2.09-2.18 (m, 1H), 2.30 (m, 1H), 3.63 (m, 1H, OH), 5.13 (m, 2H), 5.83 (m, 1H).

Example 18 Preparation of Compound 22

Compound 20 (250 mg, 0.61 mmol) and 21 (272 mg, 1.21 mmol) were dissolved in dry dichloromethane (5 ml). DCC (377 mg, 1.83 mmol) and DMAP (15.0 mg, 0.12 mmol) were added and the mixture was stirred at room temperature for 24 h. The reaction was quenched by adding water (0.3 ml) and methanol (5 ml) and the mixture stirred for 10 min. The solution was concentrated to dryness in vacuo by codistillation with chloroform (10 ml) twice and the residue treated with hexane (10 ml). The solid was filtered out and the filtrate concentrated in vacuo. The residue was purified by flash silica gel chromatography (hexane ethyl acetate, 30:1) to give 22 (302 mg, 81%). TLC: $R_f$=0.33 (hexane/ethyl acetate, 3:1). $[\alpha]_D^{20}$=+8.2 (c 1.0, chloroform). ¹H NMR (300 MHz, CDCl₃): δ=0.89 (t, J=6.5 Hz, 9H, 3CH₃), 1.26 (br s, 54H). 1.52 (m, 6H), 2.31 (m, 2H), 2.36 (dd, J=15.5, 6.5 Hz, 1H), 3.43 (m, 2H), 3.68 (m, 1H), 4.93 (m, 1H), 5.07 (m, 2H), 5.75 (m, 1H). ES-MS calcd for C₄₁H₈₀O₃:620.6. Found: 621.9 (M+H⁺).

Example 19 Preparation of Compound 23

Compound 22 (280 mg, 0.45 mmol) was dissolved in hexane (10 ml) and acetic acid (2 ml) and Aliquat (3 drops) was added. The mixture was cooled to 0° C. and potassium permanganate solution (980 mg in 15 ml water) was added. The reaction mixture was stirred at 0° C. for 6 h. When the reaction was complete, sodium sulfite (2.5 g) and hydrogen chloride solution (6 N, 5 ml) were added. The dark brown solid disappeared and the mixture became a clear solution. The mixture was extracted with hexane (30 ml×3) and with dichloromethane (30 ml×3). Both hexane and dichloromethane extracts contained product and they were washed, separately, with saturated sodium chloride solution (20 ml), dried with sodium sulfate and concentrated in vacuo. The combined residue was purified by flash silica gel chromatography (ethyl acetate:hexane, 1:3) to give 23 (176 mg, 61%). TLC: $R_f$=0.30 (ethyl acetate:hexane, 1:3). $[\alpha]_D^{20}$=2.4 (c 0.5, chloroform) $^1$H NMR (300 MHz, CDCl$_3$): δ=0.8 (t, J=6.5 Hz, 39H, 3CH$_3$), 1.27 (br s, 54H). 1.48-1.65 (m, 6H), 2.38 (dd, J=15.0, 6.0 Hz, 1H), 2.53 (dd, J=15.0, 7.0 Hz, 1H), 2.57 (dd, J=15.5, 5.5 Hz, 1H), 2.66 (dd, J=15.5, 7.0 Hz, 1H), 3.42 (m, 2H), 3.67 (m, 1H), 5.22 (m, 1H). ES-MS calcd for C$_{40}$H$_{78}$O$_5$: 638.6. Found: 639.3 (M+H$^+$).

Example 20 Preparation of Compound 26

(1) D-glucosamine hydrogen chloride (195 g, 0.88 mmol) and sodium bicarbonate (152 g, 1.89 mmol) were dissolved in water (2 L) in plastic container with mechanic stirring. To this mixture trichloroethoxy carbonyl chloride (180 g, 0.85 mmol) was slowly added within 35 min. After the end of addition, stirring was continued for 1.5 h. The reaction mixture was then acidified by 10% HCl solution (300 ml). The solid was filtered off and washed with water (800 ml) and diethyl ether (500 ml), dried at 50° C. under vacuo to give the N-Troc-protected D-glucosamine (275 g, 91%) which was used directly for the next step reaction.

(2) Compound 24: Hydrochloric acid (g) was bubbled into benzyl alcohol (30 ml, 282 mmol) for 12 min at 0° C. to provide about 1.45 g of HCl. This benzyl alcohol and acid solution was then added to an around bottom flask containing N-Troc-protected D-glucosamine (10.0 g, 28.2 mmol). The mixture as suspension was heated at 100° C. for 25 min. and upon the heating, the suspension gradually became a clear solution. After cooling the reaction at room temperature for 30 min. it was treated with hexane (200 ml) and vigorously swirled. Discarded the upper organic layer and kept the milky solid remained at the bottom of the flask. Repeated this treatment twice on the milky solid with different solvents [(ethyl acetate:hexane (1:4, 50 ml) and ethyl acetate (50 ml)]. Further treatment of the milky solid with hexane (200 ml) gave 24 (8.72 g, 70%) as crude product which was free from benzyl alcohol and used in the next step reaction.

(3) Compound 26: Compound 24 (3.14 g, 7.06 mmol) was suspended in dry acetonitrile (50 ml). Benzaldehyde dimethyl acetal (3.21 ml, 21.38 mmol) and p-toluene sulfonic acid (50 mg, 0.26 mmol) were added. The mixture was stirred at room temperature for 4 h, and triethyl amine (1 ml) was added to quench the reaction. The solvent was then removed and the residue was purified through recrystallization from ethyl acetate and hexane to give 26 (3.63 g, 96%). $^1$H NMR (300 MHz, CDCl$_3$) δ=2.52 (s, 1H, OH), 3.59 (m, 1H), 3.77 (dd, J=10.0, 10.0 Hz, 1H), 3.85-4.00 (m, 3H), 4.25 (dd, J=11.0, 5.5 Hz, 1H), 4.55 (d, J=12.0 Hz, 1H), 4.60-4.84 (m, 3H), 4.99 (d, J=3.5 Hz, 1H, H-1), 5.30 (d, J=10.0 Hz, 1H, NH), 5.57 (s, 1H), 7.25-7.50 (m, 10H, Ar—H).

Example 21 Preparation of Compound 27

A mixture of crude 24 (1.35 g, 3.04 mmol) and anhydrous CaSO$_4$ (0.6 g) in anhydrous CH$_2$Cl$_2$ (16 ml) was stirred at room temperature for 5 minutes. To this suspension, 2,2-dimethoxy propane (1.2 ml, 9.12 mmol) was added and followed by an addition of p-toluene sulfonic acid monohydrate (62 mg, 0.30 mmol). The resulting mixture was then allowed to react for 1.5 hours. The reaction mixture was then neutralized with solid NaHCO$_3$ and solid was then filtered off and washed with CH$_2$Cl$_2$. Residue from solvent and reagent removal was purified on flash silica gel column (ethyl acetate: hexane; 1:2) to give compound 27 as colorless foam (1.19 g, 81%). TLC: $R_f$=0.67 (hexane:ethyl acetate, 3:2). $[\alpha]_D^{20}$=+104.2 (c 1.0, chloroform). $^1$H NMR (300 MHz, CDCl$_3$): δ=1.45 (s, 3H, CH$_3$), 1.55 (s, 3H, CH$_3$), 3.59-3.88 (m, 5H), 3.93 (ddd, J=9.5, 9.5, 3.5 Hz, 1H, H-2), 4.49 (d, J=11.5 Hz, 1H), 4.65 (d, J=12.0 Hz, 1H), 4.72 (d, J=11.5 Hz, 1H), 4.80 (d, J=12.0 Hz, 1H), 4.93 (d, J=3.5 Hz, 1H, H-1), 5.32 (d, J=9.5 Hz, 1H, NH), 7.20 (m, 5H, Ar—H).

Example 22 Preparation of Compound 28

(1) Compound 25: Hydrochloric acid (g) was bubbled into allyl alcohol (190 ml) at 0° C. for about 30 minutes to provide approximate 9.5 g of HCl. This allyl alcohol and HCl solution was transferred into a round bottom flask containing N-Troc-protected-D-glucosamine (see Example 20/(1), 69 g; 194.58 mmol). The whole mixture appeared as suspension and it became clear solution after 5 minutes immersion in 104° C. bath. Heating was continued for 35 minutes at the same temperature. After removing the reaction mixture from the bath and let it cooled to room temperature, allyl alcohol was then removed by evaporator. Co-evaporation with toluene was also performed to remove any moisture to provide crude 25 as brownish flakes, which was used directly in the next step reaction. TLC: $R_f$=0.64 (10% methanol in dichloromethane).

(2) Compound 28: The above crude 25 was then dissolved in CH$_3$CN (600 ml) and treated with benzaldehyde dimethyl acetate (87 ml) and p-toluene sulfonic acid monohydrate (490 mg, 2.40 mmol) at room temperature for 6.5 hours. Reaction mixture was then treated with solid NaHCO$_3$ (12 g) to obtain the alkaline pH. Solid was filtered off and washed with acetone and combined filtrates were concentrated to dryness. Desired product 28, as colourless solid (45.74 g, 49%), was obtained from ethanol (275 ml) recrystallization. TLC: $R_f$=0.22 (hexane/ethyl acetate, 3:1). $[\alpha]_D^{20}$=+69.3 (c 1.0, chloroform). $^1$H NMR (300 MHz, CDCl$_3$): δ=2.50 (br s, 1H, OH), 3.56 (dd, J=9.5, 9.5 Hz, 1H), 3.75 (dd, J=10.0, 10.0 Hz, 1H), 3.82-4.04 (m, 4H), 4.18-4.30 (m, 2H), 4.68 (d, J=11.5 Hz, 1H), 4.82 (d, J=11.5 Hz, 1H), 4.92 (d, J=3.5 Hz, 1H, H-1), 5.25 (d, J=10.0 Hz, 1H, NH), 5.28-5.35 (m, 2H), 5.55 (s, 1H), 5.89 (m, 1H), 7.38 (m, 3H), 7.50 (m, 2H).

Example 23 Preparation of Compound 29

Tetradecanoic acid (1.29 g, 5.55 mmol) and 26 (2.00 g, 3.76 mmol) were dissolved in dry dichloromethane (50 ml) under nitrogen. To the solution were added dicyclohexyl carbodiimide (DCC, 1.17 g, 5.66 mmol) and 4-dimethylaminopyridine (DMAP, 0.23 g, 1.89 mmol). The mixture was stirred at room temperature for 2 h and the solid was filtered and washed with dichloromethane (4 ml). The filtrate was concentrated in vacuo and the residue purified by silica gel chromatography (hexane:ethyl acetate, 6:1) to give 29 (2.53 g, 91%). TLC: $R_f$=0.40 (hexane:ethyl acetate, 6:1). $[\alpha]_D^{22}$=+44.7 (c 0.57, chloroform). $^1$H NMR (300 MHz, CDCl$_3$): δ 0.89 (t, J=6.5 Hz, 3H, CH$_3$). 1.25 (m, 20H), 1.57 (m, 2H, CH$_2$), 2.30 (m, 2H, CH$_2$), 3.72 (dd, J=10.0, 10.0. Hz, 1H, H-4), 3.79 (dd, J=10.0, 10.0 Hz, 1H, H-6), 3.97 (ddd, J=10.0, 10.0, 5.5 Hz, 1H, H-5), 4.05 (ddd, J=10.0, 10.0, 3.5 Hz, 1H, H-2), 4.21 (dd, J=10.0, 5.5 Hz, 1H, H-6'), 4.54 (d, J=11.5 Hz, 1H, CHHPh), 4.66, 4.71 (2d, J=12.0 Hz, each 1H, Cl$_3$CCH$_2$O), 4.76 (d, J=11.5 Hz, 1H, CHHPh), 4.97 (d, J=3.5 Hz, 1H, H—), 5.35 (d, J=10.0. Hz, 1H, NH), 5.41 (dd, J=10.0, 10.0 Hz, 1H, H-3), 5.53 (s, 1H, CHPh), 7.30-7.45 (m, 10H, Ar—H). Anal. calcd for $C_{37}H_{50}Cl_3NO_8$ (743.16): C, 59.80; H, 6.78; N, 1.88. Found: C, 60.03; H, 6.63; N, 1.97.

Example 24 Preparation of Compound 30

Compound 29 (2.49 g, 3.35 mmol) was converted to 30 by activated Zinc (6.56 g, 100.9 mmol) and 80% acetic acid in ethyl acetate (150 ml) as its described for the preparation of 13. Reaction was completed in 6 hours and with a usual work up residue was obtained. It was then lyophilized from dioxane to give the free amine compound (1.83 g, 96%). TLC: $R_f$=0.41 (5% methanol in dichloromethane).

The above amino compound (900 mg, 1.59 mmol) was re-dissolved in dry $CH_2Cl_2$-DMF (4:1, 100 ml). To this amine solution and under nitrogen atmosphere, compound 5 (1.15 g, 2.46 mmol) and DCC (528 mg, 2.46 mmol) were added. The reaction mixture was stirred at room temperature for 48 h. The removal of solvent gave the residue which was purified by repeated flash chromatography (initially with 3 to 5% acetone in chloroform and subsequently with 8 to 10% acetonitrile in dichloromethane) to give 30 (1.08 g, 62%). TLC: $R_f$=0.42 (5% methanol in dichloromethane). $[\alpha]_D^{22}$=+31.0 (c 0.29, chloroform). $^1$H NMR (300 MHz, CDCl$_3$): δ 0.86 (t, J=6.5 Hz, 9H, 3CH$_3$), 1.23 (m, 52H, 26 CH$_2$), 1.45-1.65 (m, 6H, 3CH$_2$), 2.18-2.35 (m, 5H, 2CH$_2$, Asp-β-H), 2.70 (dd, J=15.0, 3.5 Hz, 1H, Asp-β'-H), 3.16 (m, 2H, NCH$_2$), 3.68 (dd, J=10.0, 10.0 Hz, 1H, H-4), 3.75 (dd, J=10.0, 10.0 Hz, 1H, H-6), 3.93 (ddd, J=10.0, 10.0, 3.5 Hz, 1H, H-5), 4.20 (dd, J=10.0, 3.5 Hz, 1H, H-6'), 4.30 (ddd, J=10.0, 10.0, 3.5 Hz, 1H, H-2), 4.58, 4.70 (2d, J=11.0 Hz, each 1H, CH$_2$Ph), 4.60 (m, 1H, Asp-β-H), 4.97 (d, J=3.5 Hz, 1H, H-1), 5.32 (dd, J=10.0, 10.0 Hz, 1H, H-3), 5.50 (s, 1H, CHPh), 6.13 (d, J=10.0 Hz, 1H, NH), 6.97 (t, J=5.0 Hz, 1H, NH), 7.25-7.44 (m, 11H, NH, Ar—H). ES-MS calcd for $C_{61}H_{99}N_3O_9$: 1017.7. Found: 1019.3 (M+H).

Example 25 Preparation of Compound 31

To a solution of 30 (150 mg, 0.15 mmol) in dry THF-CHCl$_3$ (6:1, 24 ml), molecular sieves (4A, 0.5 g) were added and the mixture was stirred at room temperature for 20 minutes. Sodium cyanoborohydride (188 mg, 3.00 mmol) was added and the mixture was cooled to 0° C. where the HCl(g)/Et$_2$O was added dropwise slowly till no gas was evolved. Additional sodium cyanoborohydride (400 mg) was added, followed by slow addition of HCl (g)/Et$_2$O until no gas was formed. The mixture was poured into saturated sodium bicarbonate solution (50 ml) and extracted with ethyl acetate (100 ml×3). The organic layer was washed with saturated sodium chloride solution (15 ml), dried over sodium sulfate, concentrated. The residue was purified by flash chromatography (1 to 2% methanol in dichloromethane) to give 31 (130 mg, 86%). TLC: $R_f$=0.46 (dichloromethane: methanol, 95:3, developed for two times). $[\alpha]_D^{22}$=+30.7 (c 0.46, chloroform). $^1$H NMR (300 MHz, CDCl$_3$): δ 0.89 (t, J=6.5 Hz, 9H, 3CH$_3$), 1.25 (br. s, 52H, 26 CH$_2$), 1.45 (m, 2H, CH$_2$), 1.60 (m, 4H, 2CH$_2$), 2.21 (m, 2H, CH$_2$), 2.30 (m, 2H, CH$_2$), 2.35 (dd, J=15.0, 7.0 Hz, 1H, Asp-1-H), 2.71 (dd, J=15.0, 3.5 Hz, 1H, Asp-β'-H), 2.72 (d, J=3.0 Hz, 1H, OH), 3.17 (m, 2H, NCH$_2$), 3.65-3.87 (m, 4H, H-4, H-5, 2H-6), 4.25 (ddd, J=10.5, 9.5, 3.5 Hz, 1H, H-2), 4.54-4.73 (m, 5H, 2CH$_2$Ph, Asp-α-H), 4.96 (d, J=3.5 Hz, 1H, H-1), 5.13 (dd, J=10.5, 9.0 Hz, 1H, H-3), 6.13 (d, J=9.0 Hz, 1H, NH), 7.02 (t, J=5.5 Hz, 1H, NH), 7.28-7.40 (m, 11H, NH, Ar—H). Anal. calcd for $C_6H_{101}N_3O_9$: C, 71.80; H, 9.98 N, 4.12. Found: C, 71.66; H, 10.39; N, 4.48. ES-MS calcd 1019.8. Found 1021.1 (M+H).

Example 26 Preparation of Compound 32

To compound 31 (125 mg, 0.123 mmol) in dry dichloromethane (10 ml) were added 1H-tetrazole (26 mg, 0.37 mmol) and dibenzyl diisopropylphosphoramidite (86.3 mg, 0.084 ml, 0.25 mmol). The mixture was stirred at room temperature for 30 min and then cooled to 0° C. m-Chloroperbenzoic acid (m-CPBA, 55%, 136 mg, 0.44 mmol) was added and the mixture was stirred for 30 min at 0° C. The mixture was then poured into 10% sodium hydrogen sulfite (20 ml) and extracted with dichloromethane (20 ml×3). The organic layer was washed with saturated sodium bicarbonate solution (10 ml), dried with sodium sulfate and concentrated. The residue was purified by repeated flash chromatography (hexane:acetone, 6:1 and 4:1; toluene:acetone, 10:1 and 8:1) to give 32 (104 mg, 66%). TLC: $R_f$=0.20 (toluene:acetone, 8:1). $[\alpha]_D^{22}$=+23.7 (c 0.59, chloroform). $^1$H NMR (300 MHz, CDCl$_3$): δ 0.89 (m, 9H, 3CH$_3$), 1.25 (m, 52H, 26 CH$_2$), 1.44 (m, 2H, CH$_2$), 1.63 (m, 2H, CH$_2$), 1.74 (m, 2H, CH$_2$), 2.14 (t, J=7.0 Hz, 2H, CH$_2$), 2.22 (m, 2H, CH$_2$), 2.31 (dd, J=15.0, 6.5 Hz, 1H, Asp-1-H), 2.72 (dd, J=15.0, 3.5 Hz, 1H, Asp-β'-H), 3.17 (m, 2H, NCH$_2$), 3.68 (m, 2H, 2H-6), 3.95 (m, 1H, H-5), 4.28 (ddd, J=10.5, 9.5, 3.5 Hz, 1H, H-2), 4.47 (d, J=12.0, 1H, CHHPh), 4.55, (d, J=12.0 Hz, 1H, CHHPh), 4.60 (m, 3H, H-4 Asp-α-H, CHHPh), 4.72 (d, 1H, J=11.5 Hz, 1H, CHHPh), 4.90 (m, 4H, 2CH$_2$Ph), 4.99 (d, J=3.5 Hz, 1H, H-1), 5.34 (dd, J=10.5, 9.0 Hz, 1H, H-3), 6.13 (d, J=9.5 Hz, 1H, NH), 7.03 (t, J=5.5 Hz, 1H, NH), 7.28-7.42 (m, 21H, NH, Ar—H). Anal. calcd for $C_{75}H_{114}N_3O_{12}P$ (1280.72): C, 70.34; H, 8.97; N, 3.28. found: C, 70.54; H, 8.90; N, 3.26.

Example 27 Preparation of Compound 33

To the solution of 32 (30 mg, 0.023 mmol) in a mixture of methanol:ethyl acetate:acetic acid (2:1:0.3, 80 ml), palladium on carbon (5%, 50 mg) was added. The mixture was stirred under hydrogen atmosphere at room temperature for 24 h. The solid was filtered off and the filtrate was concentrated. The residue was lyophilized from dioxane:chloroform (10:1, 30 ml) to give 33 (17 mg, 79%). TLC: $R_f$=0.27 (chloroform methanol: water, 2:1:0.1) $[\alpha]_D^{22}$=+310.8 (c 0.074, chloroform methanol, 4:1).

For the a-isomer: $^1$H NMR (500 MHz, CDCl$_3$—CD$_3$OD, 1:1): δ 0.89 (t, J=7.0 Hz, 9H, 3CH$_3$), 1.28 (br. s, 52H, 26 CH$_2$), 1.49 (m, 2H, CH$_2$), 1.60 (m, 4H, 2CH$_2$), 2.23 (t, J=7.5 Hz, 2H, CH$_2$), 2.35 (m, 2H, CH$_2$), 2.49 (dd, J=14.0, 5.0 Hz, 1H, Asp-β-H), 2.61 (dd, J=14.0, 6.0 Hz, 1H, Asp-β'-H), 3.17 (m, 2H, NCH$_2$), 3.72 (m, 2H, 2H-6), 3.96 (m, 1H, H-5), 4.12 (dd, J=10.5, 3.5 Hz, 1H, H-2), 4.28 (m, 1H, H-4), 4.65 (m, 1H, Asp-α-H), 5.10 (d, J=3.5 Hz, 1H, H-1), 5.32 (dd, J=10.5, 9.5 Hz, 1H, H-3). $^{31}$P NMR (202.3 MHz, DMSO-d$_6$): δ −0.02 ppm. ES-MS calcd for $C_{47}H_{90}N_3O_{12}P$: 919.6. Found 921.1 (M+H).

Example 28 Preparation of Compound 35

To a solution of 34$^{31}$ (1.0 g, 3.50 mmol) in dry pyridine (10 ml), triphenylmethyl chloride (836 mg, 3.0 mmol) and DMAP (30.5 mg, 0.25 mmol) were added. The mixture was stirred at room temperature for 20 h. Additional trityl chloride (418 mg, 1.25 mmol) and DMAP (30.5 mg, 0.25 mmol) were added and the mixture was stirred at 40° C. for 4 h. The solvent was removed by codistillation with toluene and the residue was purified by flash chromatography (hexane:ethyl acetate, 1:1) to give 35 (1.42 g, 88%). TLC: $R_f$=0.36 (hexane: ethyl acetate, 1:1). $[\alpha]_D^{22}$=−48.3 (c 0.6, chloroform). $^1$H NMR (300 MHz, CDCl$_3$): δ 2.70 (br. s, 1H, OH), 3.00 (br s, 1H, OH), 3.44-3.53 (m, 2H, 2H-6), 3.59 (m, 1H, H-5), 3.65 (dd, J=9.5, 9.0 Hz, 1H, H-4), 4.21 (dd, J=9.5, 8.0 Hz, 1H, H-2), 4.55, 4.95 (2 d, J=12.0 Hz, each 1H, CH$_2$Ph), 5.23 (d, J=8.0 Hz, 1H, H-1), 7.10-7.80 (m, 24H, Ar—H). Anal. calcd for C$_{40}$H$_{35}$NO$_7$.1.3H$_2$O (641.72): C, 72.23; H, 5.70; N, 2.10. Found: C, 72.24; H, 5.92; N, 1.83.

Example 29 Preparation of Compound 36

Sodium hydride (120 mg, 5.02 mmol) and benzyl bromide (0.86 g, 0.60 ml, 5.02 mmol) were added to dry DMF (10 ml). To this solution, a solution of 35 (1.34 g, 2.09 mmol) in DMF (8 ml) was added dropwise within 3 minutes. The mixture was stirred at room temperature for 1 h and treated further with an additional amount of benzyl bromide (0.43 g, 0.30 ml, 2.51 mmol) and sodium hydride (60 mg, 2.51 mmol). The reaction mixture was allowed to prolong for another 2 hours. Methanol (2 ml) was added and the mixture was stirred for 10 more minutes. The reaction was then poured into ice water (100 ml) and extracted with diethyl ether (60 ml×3). Combined ether layers were washed with ice water (15 ml×3), dried with sodium sulfate and concentrated. The residue was purified by flash chromatography (hexane:ethyl acetate, 5:1) to give 36 (1.55 g, 90%). TLC: $R_f$=0.60 (hexane ethyl acetate, 3:1). $[\alpha]_D^{22}$=+5.5 (c 0.8, chloroform). $^1$H NMR (300 MHz, CDCl$_3$): δ 3.32 (dd, J=10.0, 4.5 Hz, 1H, H-6a), 3.60 (m, 1H, H-5), 3.68 (dd, J=10.0, 1.8 Hz, 1H, H-6b), 4.03 (dd, J=9.5, 8.2 Hz, 1H, H-2), 4.33 (m, 2H, H-3, H-4), 4.43 (d, J=12.0 Hz, 1H, CHHPh), 4.47 (d, J=10.0 Hz, 1H CHHPh), 4.61 (d, J=12.0 Hz, 1H, CHHPh), 4.72 (d, J=10.0 Hz, 1H, CHHPh), 4.80 (d, J=12.0 Hz, 1H, CHHPh), 4.94 (d, J=12.0 Hz, 1H, CHHPh), 5.20 (d, J=8.2 Hz, 1H, H-1), 6.84-7.80 (m, 34H, Ar—H). Anal. calcd for C$_{14}$H$_{47}$NO$_7$.1.3H$_2$O (821.97): C, 76.72; H, 5.91; N, 1.66. Found: C, 76.56; H, 6.13; N, 1.52.

Example 30 Preparation of Compound 37

The solution of 36 (1.42 g, 1.73 mmol) in acetic acid-water (4:1, 60 ml) was stirred at 110° C. for 1 h. The solvent was removed by codistillation with toluene and the residue was purified by flash chromatography (hexane:ethyl acetate, 2:1) to give 37 (700 mg, 70%). TLC: $R_f$=0.31 (hexane:ethyl acetate, 2:1). $[\alpha]_D^{22}$=+16.0 (c 0.25, chloroform). $^1$H NMR (300 MHz, CDCl$_3$): δ 1.90 (dd, J=6.5, 6.5 Hz, 1H, OH), 3.54 (m, 1H, H-5), 3.73 (dd, J=9.5, 9.0 Hz, 1H, H-4), 3.78 (m, 1H, H-6a), 3.93 (m, 1H, H-6b), 4.19 (dd, J=10.0, 8.5 Hz, 1H, H-2), 4.36 (dd, J=10.0, 9.0 Hz, 1H, H-3), 4.43 (d, J=12.0 Hz, 1H, CHHPh), 4.50 (d, J=12.0 Hz, 1H, CHHPh), 4.73 (d, J=11.0 Hz, 1H, CHHPh), 4.76 (J=12.0 Hz, 1H, CHHPh), 4.79 (d, J=12.0 Hz, 1H, CHHPh), 4.90 (d, J=11.0 Hz, 1H, CHHPh), 5.20 (d, J=8.5 Hz, 1H, H-1), 6.80-7.80 (m, 19H, Ar—H). Anal. calcd for C$_{35}$H$_{33}$NO$_7$.0.8H$_2$O (579.65): C, 70.76; H, 5.87; N, 2.35. Found: C, 70.74; H, 6.14; N, 2.20.

Example 31 Preparation of Compound 38

To the solution of 37 (0.60 g, 1.04 mmol) in 95% ethanol (40 ml) was added hydrazine monohydrate (2.06 g, 2.0 ml, 41.2 mmol). The mixture was refluxed for 2 h and then the solvent was removed in vacuo. The residue was purified by flash chromatography (1 to 2% methanol in dichloromethane) to give 38 (450 mg, 97%). TLC: $R_f$=0.20 (2% methanol in dichloromethane). $[\alpha]_D^{22}$=−9.4 (c 0.35, chloroform). $^1$H NMR (300 MHz, CDCl$_3$): δ 1.75 (br. s, 3H, OH, NH$_2$), 2.92 (dd, J=9.0, 8.0 Hz, 1H, H-2), 3.43 (m, 1H, H-5), 3.49 (dd, J=9.5, 9.5 Hz, 1H, H-4), 3.66 (dd, J=9.5, 9.0 Hz, 1H, H-3), 3.76 (dd, J=12.0, 5.0 Hz, 1H, H-6a), 3.91 (dd, J=12.0, 2.5 Hz, 1H, H-6b), 4.39 (d, J=8.0 Hz, 1H, H-1), 4.63 (d, J=11.5 Hz, 1H, CHHPh), 4.70 (d, J=11.0 Hz, 1H, CHHPh), 4.74 (d, J=11.0 Hz, 1H, CHHPh), 4.86 (d, J=11.0 Hz, 1H, CHHPh), 4.88 (d, J=11.5 Hz, 1H, CHHPh), 4.99 (d, J=11.0 Hz, 1H, CHHPh), 7.35 (m, 15H, Ar—H). Anal. calcd for C$_{27}$H$_{31}$NO$_5$ (449.55): C, 72.14; H, 6.95; N, 3.15. Found: C, 72.34; H, 7.15; N, 3.12.

Example 32 Preparation of Compound 39

Compound 38 (400 mg, 0.89 mmol), 15 (401 mg, 0.83 mmol) and DCC (275 mg, 1.34 mmol) were dissolved in dry dichloromethane (10 ml) and the resulting mixture was stirred at room temperature for 3 h. The solid was filtered off and washed with dichloromethane (4 ml). The filtrate was concentrated and the residue was purified by silica gel chromatography (0.5 to 1% methanol in dichloromethane) to give 39 (576 mg, 76%). TLC: $R_f$=0.30 (2% methanol in dichloromethane). $[\alpha]_D^{22}$=−2.6 (c 0.7, chloroform). $^1$H NMR (300 MHz, CDCl$_3$): δ 0.88 (t, J=6.5 Hz, 6H, 2CH$_3$), 1.25 (br. s, 42H, 21CH$_2$), 1.55 (m, 4H, 2CH$_2$), 2.14 (m, 2H, CH$_2$), 2.28 (dd, J=15.0, 6.0 Hz, 1H, CHH), 2.36 (dd, J=15.0, 6.0 Hz, 1H, CHH), 3.48 (m, 2H, H-2, H-5), 3.59 (dd, J=9.0, 9.0 Hz, 1H, H-4), 3.71 (dd, J=11.5, 4.5 Hz, 1H, H-6a), 3.87 (dd, J=11.5, 2.5 Hz, 1H, H-6b), 4.10 (dd, J=1.0.0, 9.0 Hz, 1H, H-3), 4.60 (d, J=12.0 Hz, 1H, CHHPh), 4.65 (d, J=11.5 Hz, 2H, 2CHHPh), 4.80 (d, J=11.5 Hz, 1H, CHHPh), 4.81 (d, J=11.5 Hz, 1H, CHHPh), 4.83 (d, J=12.0 Hz, 1H, CHHPh), 4.95 (d, J=8.0 Hz, 1H, H-1), 5.04 (m, 1H, lipid-3-H), 5.90 (d, J=8.0 Hz, 1H, NH), 7.35 (m, 15H, Ar—H). Anal. calcd for C$_{57}$H$_{17}$NO$_8$.0.3H$_2$O (914.32): C, 74.44; H, 9.60; N, 1.52. Found: C, 74.38; H, 9.85; N, 1.56.

Example 33 Preparation of Compound 40

To the solution of compound 38 (410 mg, 0.913 mmol) in dry dichloromethane (30 ml), compound 14 (623 mg, 1.37 mmol) and DCC (564 mg, 2.74 mmol) were added. The mixture was stirred at room temperature for 24 hours. The solid was filtered off and washed with dichloromethane (4 ml). The filtrate was concentrated and the residue was purified by silica gel chromatography (0.5 to 1% methanol in dichloromethane) to give 40 (664 mg, 82%). TLC: $R_f$=0.33 (2% 1% methanol in dichloromethane). $[\alpha]_D^{22}$=−3.2 (c 0.6, chloroform). $^1$H NMR (300 MHz, CDCl$_3$): δ 0.90 (t, J=7.0 Hz, 6H, 2CH$_3$), 1.25 (m, 38H, 19 CH$_2$), 1.55 (m, 4H, 2CH$_2$), 1.89 (dd, J=7.0, 6.0 Hz, 1H, OH), 2.15 (m, 2H, CH$_2$), 2.27 (dd, J=15.0, 5.5 Hz, 1H, CHH), 2.36 (dd, J=15.0, 6.0 Hz, 1H, CHH), 3.46 (m, 1H, H-5), 3.52 (m, 1H, H-4), 3.59 (dd, J=10.0, 9.0 Hz, 1H, H-3), 3.70 (m, 1H, H-6a), 3.86 (m, 1H, H-6b), 4.10 (dd, J=10.0, 8.0 Hz, 1H, H-2), 4.60 (d, J=12.0 Hz, 1H, CHHPh), 4.64 (d, J=11.5 Hz, 1H, CHHPh), 4.65 (d, J=11.5 Hz, 1H, CHHPh), 4.81 (d, J=11.5 Hz, 2H, 2CHHPh), 4.83 (d, J=12.0 Hz, 1H, CHHPh), 4.95 (d, J=8.0 Hz, 1H, H-1), 5.04 (m, 1H, lipid-3-H), 5.92 (d, J=8.0 Hz, 1H, NH), 7.30 (m, 15H, Ar—H). Anal. calcd for: C$_{55}$H$_{83}$NO$_8$ (886.26): C, 74.47; H, 9.44; N, 1.58. Found: C, 74.25; H, 9.44; N, 1.64.

Example 34 Preparation of Compound 41

Compound 28 (312 mg, 0.65 mmol), 14 (200 mg, 0.44 mmol), DCC (136 mg, 0.66 mmol) and DMAP (27 mg, 0.22 mmol) were dissolved in dry dichloromethane (5 ml). The mixture was stirred at room temperature for 4 h. The solid was filtered off and washed with ethyl acetate (5 ml) The filtrate was concentrated and the residue was purified by flash chromatography (hexane ethyl acetate, 8:1) to give 41 (398 mg, 98%). TLC: $R_f$=0.69 (hexane:ethyl acetate, 3:1). $[\alpha]_D^{22}$=+32.0 (c 0.5, chloroform). $^1$H NMR (300 MHz, CDCl$_3$): δ 0.90 (t, J=6.5 Hz, 6H, 2CH$_3$), 1.2.5 (m, 38H, 19 CH$_2$), 1.52 (m, 4H, 2CH$_2$), 2.16 (t, J=7.5 Hz, 2H, CH$_2$), 2.50 (dd, J=16.0, 6.0 Hz, 1H, CHH), 2.63 (dd, J=16.0, 6.0 Hz, 1H, CHH), 3.71 (dd, J=9.5, 9.5 Hz, 1H, H-4), 3.78 (dd, J=10.0, 10.0 Hz, 1H, H-6a), 3.94 (m, 1H, H-5), 3.98-4.08 (m, 2H, H-2, CHHCH=CH$_2$), 4.21 (m, 1H, CHHCH=CH$_2$), 4.29 (dd, J=10.0, 5.0 Hz, 1H, H-6b), 4.69, 4.76 (2 d, J=12.0 Hz, each 1H, Troc-CH$_2$), 4.94 (d, J=3.6 Hz, 1H, H-1), 5.16 (m, 1H, lipid-3-H), 5.30 (m, 2H, CH=CH$_2$), 5.39 (dd, J=9.5, 9.5 Hz, 1H, H-3), 5.42 (d, J=10.0 Hz, 1H, NH), 5.53 (s, 1H, CHPh), 5.90 (m, 1H, CH=CH$_2$), 7.30-7.35 (m, 15H, Ar—H). Anal. calcd for C$_{47}$H$_{74}$Cl$_3$NO$_{10}$ (919.46): C, 61.40; H, 8.11; N, 1.52. Found: C, 61.40; H, 8.19; N, 1.58.

Example 35 Preparation of Compound 42

[Bis(methyldiphenylphosphine)](1,5-cyclooctadiene) iridium(I) hexafluorophosphate (37 mg, 0.044 mmol) was suspended in dry THF (5 ml) and hydrogen gas was bubbled in for 5 min to give a yellowish solution, which was added to the solution of 41 (400 mg, 0.44 mmol) in dry THF (5 ml). The mixture was stirred at room temperature for 2 hours. Water (0.5 ml) and N-bromosuccinimide (NBS, 117 mg, 0.66 mmol) were then added and the reaction was stirred for 1 hour longer. Remainder obtained from solvent removal was dissolved in ethyl acetate (200 ml) and washed with saturated sodium bicarbonate solution (20 ml×2). Combined organic layers were dried with sodium sulfate and concentrated. The residue was purified by flash chromatography (hexane:ethyl acetate, 4:1 and 3:1) to give 42 (314 mg, 82%) as an anomeric mixture in a ratio of a/b 4:1. TLC: $R_f$=0.36 (hexane:ethyl acetate, 3:1) $[\alpha]_D^{22}$=−9.6 (c 1.0, chloroform). $^1$H NMR (300 MHz, CDCl$_3$) for the a-isomer: d 0.88 (t, J=6.5 Hz, 6H, 2CH$_3$), 1.24 (m, 38H, 19 CH$_2$), 1.50 (m, 4H, 2CH$_2$), 2.16 (t, J=7.5 Hz, 2H, CH$_2$), 2.49 (dd, J=15.0, 5.0 Hz, 1H, CHH), 2.60 (dd, J=15.0, 7.0 Hz, 1H, CHH), 3.65 (d, J=4.0 Hz, 1H, OH), 3.70 (dd, J=9.5, 9.5 Hz, 1H, H-4), 3.77 (dd, J=10.0, 10.0 Hz, 1H, H-6a), 4.03 (m, 1H, H-2), 4.17 (m, 1H, H-5), 4.28 (dd, J=10.0, 4.5 Hz, 1H, H-6b), 4.67, 4.75 (2 d, J=12.0 Hz, each 1H, Troc-CH$_2$), 5.15 (m, 1H, lipid-3-H), 5.35 (dd, J=4.0, 4.0 Hz, 1H, H-1), 5.43 (dd, J=9.5, 9.5 Hz, 1H, H-3), 5.51 (s, 1H, CHPh), 5.81 (d, J=10.0 Hz, 1H, NH), 7.32-7.47 (m, 5H, Ar—H). Anal. calcd for C$_{44}$H$_{70}$Cl$_3$NO$_{10}$ (879.39): C, 60.10; H, 8.02; N, 1.59. Found: C, 60.11; H, 8.09; N, 1.61.

Example 36 Preparation of Compound 43

To a solution of 42 (2.50 g, 2.88 mmol) in dry dichloromethane (30 ml), trichloroacetonitrile (8.64 g, 6.0 ml, 60.0 mmol) and DBU (10 drops) were added. The mixture was stirred at room temperature for 2 h and concentrated in vacuo (not to dryness). The residue was purified by flash chromatography (hexane:ethyl acetate:triethylamine, 6:1:1% and 5:1:15) to give 43 (2.40 g, 81%). TLC: $R_f$=0.25 (hexane:ethyl acetate, 8:1). $[\alpha]_D^{22}$=+35.0 (c 1.0, chloroform). $^1$H NMR (300 MHz, CDCl$_3$): δ 0.90 (t, J=7.0 Hz, 6H, 2CH$_3$), 1.25 (m, 38 Hz, 19 CH$_2$), 1.50 (m, 4H, 2CH$_2$), 2.20 (t, J=7.5 Hz, 2H, CH$_2$), 2.56 (dd, J=15.5, 5.5 Hz, 1H, CHH), 2.65 (dd, J=15.5, 7.0 Hz, 1H, CHH), 3.81 (dd, J=10.0, 10.0 Hz, 1H, H-4), 3.83 (dd, J=10.0, 10.0 Hz, 1H, H-6a), 4.06 (m, 1H, H-5), 4.25 (ddd, J=10.0, 9.0, 4.0 Hz, 1H, H-2), 4.36 (dd, H=10.0, 5.0 Hz, 1H, H-6b), 4.63, 4.78 (2 d, J=12.0 Hz, each 1H, Troc-CH$_2$), 5.18 (m, 1H, lipid-3-H), 5.45 (dd, J=10.0, 10.0 Hz, 1H, H-3), 5.56 (d, J=9.0 Hz, 1H, NH), 5.58 (s, 1H, CHPh), 6.42 (d, J=4.0 Hz, 1H, H-1), 7.30-7.45 (m, 5H, Ar—H), 8.73 (s, H, NH). Anal. calcd for C$_{46}$H$_{70}$Cl$_6$N$_2$O$_{10}$ (1023.78): C, 53.97; H, 6.89; N, 2.74. Found: C, 53.80; H, 6.77; N, 2.80.

Example 37 Preparation of Compound 44

To the solution of 39 (269 mg, 0.295 mmol) and 43 (452 mg, 0.442 mmol) in dry dichloromethane (6 ml) was added molecular sieves (4 A, 1.0 g). The mixture was stirred under nitrogen at room temperature for 20 min and then cooled to 0° C. Trifluoroboron etherate solution (0.15 M in CH$_2$Cl$_2$, 0.5 ml) was added dropwise and reaction mixture was stirred at 0° C. for 30 minutes. It was then treated with triethylamine (0.05 ml). The solid was filtered off and washed with dichloromethane. The filtrate was concentrated and the residue was purified by precipitation from ethyl acetate and by silica gel chromatography (1.5% methanol in dichloromethane) to give 44 (340 mg, 65%). TLC: $R_f$=0.31 (2% methanol in dichloromethane). $[\alpha]_D^{22}$=−13.3 (c 0.7, chloroform). $^1$H NMR (300 MHz, CDCl$_3$+CD$_3$OD): δ 0.88 (t, J=6.5 Hz, 12H, 4 CH$_3$), 1.24 (m, 72H, 36 CH$_2$), 1.52 (m, 8H, 4 CH$_2$), 1.70 (m, 4H, 2CH$_2$), 1.94 (m, 4H, 2CH$_2$), 2.16 (m, 4H, 2CH$_2$), 2.27 (dd, J=15.0, 6.0 Hz, 1H, CHH), 2.35 (dd, J=15.0, 6.5 Hz, 1H, CHH), 2.49 (dd, J=15.5, J=5.5 Hz, 2H, CHH), 2.59 (dd, J=15.5, 7.0 Hz, 1H, CHH), 3.35-4.14 (m, 10H, H-2, H-3, H-4, H-5, 2H-6, H-2', —H-4', H-5', H-6'a), 4.31 (dd, J=10.5, 5.5 Hz, 1H H-6'b), 4.53 (d, J=8.0 Hz, 1H, H-1'), 4.57-4.69 (m, 5H, Cl$_3$CCH$_2$, 3 CHHPh), 4.75 (d, J=11.5 Hz, 1H, CHHPh), 4.78 (d, J=11.0, 1H, CHHPh), 4.88 (d, J=12.0 Hz, 1H, CHHPh), 4.89 (d, J=8.0 Hz, 1H, H-1), 5.04 (m, 1H, lipid-3-H), 5.18 (m, 2H, H-3', lipid-3-H), 5.48 (s, 1H, CHPh), 7.25-7.45 (m, 20H, Ar—H). Anal. calcd for C$_{101}$H$_{155}$Cl$_3$N$_2$O$_{17}$.2H$_2$O (1775.70): C, 66.95; H, 8.84; N, 1.55. Found: C, 66.83; H, 8.63; N, 1.66.

Example 38 Preparation of Compound 45

Using the same procedure described for the preparation of 30, compound 45 was synthesized. Initially crude amine was obtained from 44 (224 mg, 0.126 mmol) treated with activated Zinc (5.0 g) and 80% acetic acid in ethyl acetate (500 ml) for 60 hours at room temperature. It was lyophilized from dioxane to give the amino compound (192 mg, 95%). Later, this amine compound (212 mg, 0.132 mmol) and 13 (115 mg, 0.238 mmol) in the presence of DCC (122 mg, 0.60 mmol) and dry dichloromethane (10 mg) were converted to compound 45 in 48 hours at room temperature. Pure 45 (160 mg, 60%) was obtained from silica gel chromatographic purification (3% acetone in chloroform) of crude 45. TLC: $R_f$=0.30 (2% methanol in dichloromethane). $[\alpha]_D^{22}$=−8.9 (c 0.73, chloroform). $^1$H NMR (300 MHz, CDCl$_3$): δ 0.88 (t, J=6.5 Hz, 18H, 6CH$_3$), 1.10-1.90 (m, 126H, 63 CH$_2$), 2.14 (t, J=7.0 Hz, 4H, 2CH$_2$), 2.26 (m, 6H, 3CH$_2$), 2.50 (dd, J=15.5, 5.5 Hz, 1H, CHH), 2.59 (dd, J=15.5, 7.5 Hz, 1H, CHH), 3.40-4.14 (m, 10H, H-2, H-3, H-4, H-5, 2H-6, H-2', H-4', H-5', H-6'a), 4.27 (dd, J=11.0, 5.0 Hz, 1H, H-6'b), 4.60 (d, J=11.5 Hz, 2H, 2 CHHPh), 4.66 (d, J=12.0 Hz, 1H, CHHPh), 4.73 (d, J=8.0 Hz, 1H, H-1'), 4.74 (d, J=11.5 Hz, 1H, CHHPh), 4.75 (d, J=11.5 Hz, 1H, CHHPh), 4.82 (d, J=8.0 Hz, 1H, H-1), 4.86 (d, J=12.0 Hz, 1H, CHHPh), 5.05 (m, 2H, 2 lipid-3-H), 5.15 (m, 1H, lipid-3-H), 5.25 (dd, J=10.0, 10.0 Hz, 1H, H-3'), 5.48 (s, 1H, CHPh), 5.94 (d, J=9.0 Hz, 1H, NH), 6.06 (d, J=9.0 Hz, 1H, NH), 7.25-7.43 (m, 20H, Ar—H). Anal. calcd for $C_{124}H_{202}N_2O_{18}\cdot 1.5H_2O$ (2008.96): C, 73.15; H, 10.14; N, 1.37. Found: C, 73.06; H, 9.95; N, 1.22.

Example 39 Preparation of Compound 46

To a solution of 45 (148 mg, 0.074 mmol) in dry THF (8 ml) was added molecular sieves (4 A, 1.0 g). The mixture was stirred at room temperature under nitrogen for 20 min. Sodium cyanoborohydride (340 mg, 5.41 mmol) was added and the mixture was cooled to 0° C. HCl(g)/Et$_2$O solution (~3 ml) was added dropwise slowly till no gas was evolved. The mixture was then poured into saturated sodium bicarbonate solution (50 ml) and extracted with dichloromethane (100 ml×3). Combined organic layers were washed with saturated sodium chloride solution (20 ml) and dried with sodium sulfate, and concentrated. The residue was purified by flash chromatography (gradient elution with chloroform:acetone, from 100:2 to 100:5) to give 46 (79 mg, 53%). TLC: R$_f$=0.16 (chloroform:acetone, 100:5). $[\alpha]_D^{22}$=−16.0 (c 0.2, chloroform). $^1$H NMR (500 MHz, CDCl$_3$): δ 0.89 (t, J=6.5 Hz, 18H, 6CH$_3$), 1.08-1.94 (m, 126H, 63 CH$_2$), 2.13-2.36 (m, 10H, 5 CH$_2$), 2.51 (dd, J=15.0, 5.0 Hz, 1H, CHH), 2.58 (dd, J=15.0, 8.0 Hz, 1H, CHH), 3.32 (br. s, 1H, OH), 3.43-3.77 (m, 8H, H-2, H-4. H-5, 2H-6, H-4', H-5', H-6'a), 3.86 (ddd, J=10.0, 8.5, 8.5 Hz, 1H, H-2'), 3.92 (dd, J=9.0, 9.0 Hz, 1H, H-3), 4.08 (dd, J=11.0, 2.5 Hz, 1H, H-6'b), 4.61 (d, J=11.5 Hz, 1H, CHHPh), 4.55 (d, J=12.0 Hz, 1H, CHHPh), 4.56 (d, J=8.5 Hz, 1H, H-1'), 4.57 (d, J=11.5 Hz, 1H, CHHPh), 4.60 (d, J=11.5 Hz, 1H, CHHPh), 4.64 (d, J=11.5 Hz, 1H, CHHPh), 4.72 (d, J=11.5 Hz, 1H, CHHPh), 4.73 (d, J=11.5 Hz, 1H, CHHPh), 4.79 (d, J=7.5 Hz, 1H, H-1), 4.83 (d, J=12.5 Hz, 1H, CHHPh), 4.95 (dd, J=10.5, 9.0 Hz, 1H, H-3'), 4.99-5.08 (m, 2H, 2 lipid-3-H), 5.11 (m, 1H, lipid-3-H), 5.77 (d, J=8.5 Hz, 1H, NH), 5.93 (d, J=8.5 Hz, 1H, NH), 7.30 (m, 20H, Ar—H). Anal. calcd for $C_{124}H_{204}N_2O_{18}$ (2010.98): C, 74.06; H, 10.22; N, 1.39. Found: C, 73.74; H, 10.57; N, 1.43.

Example 40 Preparation of Compound 47

By following the same procedure described for the preparation of 32, compound 47 was obtained from the reaction of 46 (68 mg, 0.034 mmol) with 1H-tetrazole (10 mg, 0.144 mmol), dibenzyl diisopropylphosphoramidite (33 mg, 0.032 ml, 0.096 mmol) and m-chloroperbenzoic acid (59 mg, ~55%, 0.19 mmol) in dry dichloromethane (3 ml). After stirring for 1 hour at 0° C., the work up rendered residue which was purified by repeated silica gel chromatography (gradient elution with 1 to 5% acetone in chloroform and toluene:acetone, from 18:1 to 12:1) gave 47 (65 mg, 85%). TLC: R$_f$=0.22 (5% acetone in chloroform) $[\alpha]_D^{22}$=−4.0 (c 0.4, chloroform). $^1$H NMR (300 MHz, CDCl$_3$): δ 0.90 (m, 18H, 6CH3), 1.25 (m, 114H, 57CH$_2$), 1.45-1.70 (m, 12H, 6 CH$_2$), 2.10-2.50 (m, 12H, 6CH$_2$), 3.52-3.93 (m, 9H, H-2, H-3, H-4, H-5, H-6a, H-2', H-5', 2H-6'), 4.09 (br. d, J=11.0 Hz, 1H, H-6b), 4.43 (m, 3H, CH$_2$Ph, H-4'), 4.56-4.91 (m, 12H, 6 CH$_2$Ph), 4.78 (d, J=7.5 Hz, 1H, H-1'), 4.98 (d, J=8.5 Hz, 1H, H-1), 5.05 (m, 2H, 2 lipid-3-H), 5.16 (m, 1H, lipid-3-H), 5.39 (dd, J=10.0, 9.0 Hz, 1H, H-3'), 5.88 (d, J=8.5 Hz, 1H, NH), 6.08 (d, J=7.5 Hz, 1H, NH), 7.25 (m, 30H, Ar—H). Anal. calcd for $C_{138}H_{217}N_2O_{21}P$ (2271.21): C, 72.98; H, 9.63; N, 1.23. Found: C, 72.83; H, 9.60; N, 1.23.

Example 41 Preparation of Compound 48

To a solution of 47 (48 mg, 0.021 mmol) in THF-HOAc (10:1, 90 ml) was added palladium on carbon (5%, 70 mg). The mixture was stirred at room temperature under hydrogen atmosphere for 24 h. The solid was filtered off and the filtrate was concentrated in vacuo. The residue was purified by flash chromatography (chloroform:methanol: water, 4:1:0 and then 3:1:0.1) to give 48 (25 mg, 68%). TLC: R$_f$=0.38 (chloroform:methanol: water, 3:1:0.1). $[\alpha]_D^{22}$=+8.0 (c 0.1, chloroform:methanol, 4:1). ES-MS calcd for $C_{96}H_{181}N_2O_{21}P$: 1729.3. Found: 1728.3 (M−H) (negative mode).

Example 42 Preparation of Compound 49

To a solution of 40 (290 mg, 0.328 mmol) and 43 (503 mg, 0.492 mmol) in dry dichloromethane (6 ml) was added molecular sieves (4 A, 0.5 g). The mixture was stirred under nitrogen at room temperature for 20 min. Trifluoroboron etherate solution (0.1 M in CH$_2$Cl$_2$, 1.3 ml) was added dropwise within 20 min. The mixture was stirred for 1 h and then poured into saturated sodium bicarbonate solution (10 ml) and extracted with dichloromethane (20 ml×3). Combined organic layers were dried with sodium sulfate and concentrated. The residue was purified by silica gel chromatography (0.5 to 1% methanol in dichloromethane) to give 49 (457 mg, 80%). TLC: R$_f$=0.21 (3% acetone in chloroform). $[\alpha]_D^{22}$=−17.8 (c 0.6, chloroform). $^1$H NMR (300 MHz, CDCl$_3$): δ 0.90 (t, J=7.0 Hz, 12H, 4 CH$_3$), 1.25 (m, 76H, 38 CH$_2$), 1.52 (m, 8H, 4 CH$_2$), 2.15 (m, 4H, 2CH$_2$), 2.26, 2.35 (2 dd, J=14.0, 6.0 Hz, each 1H, CH$_2$), 2.48 (dd, J=15.0, 5.5 Hz, 1H, CHH), 2.58 (dd, J=15.0, 7.0 Hz, 1H, CHH), 3.34-3.78 (m, 8H, H-2, H-3, H-4, H-5, H-6a, H-2', H-4', H-6'a), 4.02-4.13 (m, 2H, H-6b, H-5'), 4.30 (dd, J=10.5, 5.0 Hz, 1H, H-6'b), 4.52 (d, J=8.0 Hz, 1H, H-1'), 4.57-4.90 (m, 8H, 3CH$_2$Ph, Troc-CH$_2$), 4.89 (d, J=8.0 Hz, 1H, H-1) 5.02 (m, 1H, lipid-3-H), 5.15 (m, 3H, NH, H-3', lipid-3-H), 5.55 (s, 1H, CHPh), 6.00 (d, J=8.0 Hz, 1H, NH), 7.25-7.45 (m, 20H, Ar—H). Anal. calcd for $C_{99}H_{151}Cl_3N_2O_{17}$ (1747.64): C, 68.04; H, 8.71; N, 1.60. Found: C, 67.92, H, 8.85; N, 1.64.

Example 43 Preparation of Compound 50

Compound 50 was synthesized from 49 (740 mg, 0.424 mmol) treated with activated Zinc (5.0 g, 76.5 mmol) and 80% acetic acid in ethyl acetate (400 ml) at room temperature for 60 hours as its described for the preparation of 13. Crude 50 (666 mg, 100%) obtained from solvent removal was lyophilized from dioxane and used without any further purification.

Example 44 Preparation of Compound 51

In a similar method as described for 45, compound 50 (175 mg, 0.11 mmol) was coupled with 14 (101 mg, 0.22 mmol) in presence of DCC (68 mg, 0.33 mmol) in dry dichloromethane (5 ml). After usual work-up and silica gel chromatography (1% methanol in dichloromethane) gave 51 (150 mg, 67%). TLC: R$_f$=0.27 (2% methanol in dichloromethane). $[\alpha]_D^{22}$=−14.2 (c 0.5, chloroform). $^1$H NMR (300 MHz, CDCl$_3$): δ 0.90 (t, J=7.0 Hz, 18H, 6CH$_3$), 1.25 (m, 114H, 57CH$_2$), 1.53 (m, 12H, 6CH$_2$), 2.15 (t, J=7.0 Hz, 4H, 2CH$_2$), 2.23-2.39 (m, 6H, 3CH$_2$), 2.56 (dd, J=15.5, 5.5 Hz, 1H, CHH), 2.60 (dd, J=15.5, 7.0 Hz, 1H, CHH), 3.37-4.00 (m, 9H, H-2, H-3, H-4, H-5, H-6a, H-2', H-4', H-5', H-6'a), 4.09 (dd, J=11.0, 2.0 Hz, 1H, H-6b), 4.27 (dd, J=11.0, 4.5 Hz, 1H, H-6'b), 4.58-4.88 (m, 7H, 3CH$_2$Ph, H-1'), 4.82 (d, J=7.5 Hz, 1H, H-1), 5.00-5.09 (m, 2H, 2 lipid-3-H), 5.16 (m, 1H, lipid-3-H), 5.26 (dd, J=10.0, 10.0 Hz, 1H, H-3'), 5.47 (s, 1H, CHPh), 5.93 (d, J=8.5 Hz, 1H, NH), 6.06 (d, J=8.0 Hz, 1H, NH), 7.25-7.45 (m, 20H, Ar—H). Anal. calcd for $C_{124}H_{202}N_2O_{18}\cdot 0.5H_2O$ (2008.96): C, 73.80; H, 10.14; N, 1.39. Found: C, 73.64; H, 9.88; N, 1.41.

Example 45 Preparation of Compound 52

In a similar method as described for 31, compound 51 (135 mg, 0.067 mmol) was treated with sodium cyanoborohydride (211 mg, 3.36 mmol) and HCl (g)/Et$_2$O in dry THF:CHCl$_3$ (4:1, 50 ml) at room temperature. After usual work-up and flash chromatography (2 to 5% acetone in chloroform) afforded 52 (112 mg, 83%). TLC: R$_f$=0.20 (2% methanol in dichloromethane). $[\alpha]_D^{22}$=−13.5 (c 0.6, chloroform). $^1$H NMR (300 MHz, CDCl$_3$): δ 0.89 (t, J=6.5 Hz, 18H, 6CH$_3$), 1.25 (m, 114H, 57CH$_2$), 1.50 (m, 12H, 6CH$_2$), 2.14 (t, J=7.0 Hz, 2H, CH$_2$), 2.23-2.60 (m, 10H, 5 CH$_2$), 3.33 (d, J=3.3 Hz, 1H, OH), 3.44-3.96 (m, 10H, H-2, H-3, H-4, H-5, H-6a, H-2', H-4', H-5', 2H-6'), 4.09 (dd, J=10.0, 2.0 Hz, 1H, H-6b), 4.49-4.86 (m, 9H, 4 CH$_2$Ph, H-1'), 4.80 (d, J=7.5 Hz, 1H, H-1), 4.92-5.18 (m, 4H, H-3', 3 lipid-3-H), 5.80 (d, J=9.0 Hz, 1H NH), 5.95 (d, J=8.5 Hz, 1H, NH), 7.30 (m, 20H, Ar—H). Anal. calcd for C$_{124}$H$_{204}$N$_2$O$_{18}$.H$_2$O (2010.98): C, 73.40; —H, 10.23; N, 1.38. Found: C, 73.40; H, 10.04; N, 1.38.

Example 46 Preparation of Compound 53

In a similar method as described for 32, compound 52 (61 mg, 0.030 mmol) was treated with 1H tetrazole (12.6 mg, 0.18 mmol) and dibenzyl diisopropylphosphoramidite (42 mg, 0.041 ml, 0.12 mmol) in dry dichloromethane (3.0 ml) and then subsequently with m-CPBA (75 mg, 55%, 0.24 mmol). After usual work-up and silica gel chromatography (1 to 5% acetone in chloroform and then toluene: acetone, from 18:1 to 12:1) afforded 53 (58 mg, 85%). TLC: R$_f$=0.17 (1% acetone in chloroform). $[\alpha]_D^{22}$=−3.1 (c 0.35, chloroform). $^1$H NMR (300 MHz, CDCl$_3$): δ 0.87 (t, J=6.5 Hz, 18H, 6CH$_3$), 1.24 (m, 114H, 57CH$_2$), 1.40-1.57 (m, 12H, 6 CH$_2$), 2.11-2.50 (m, 12H, 6CH$_2$), 3.52-3.94 (m, 9H, H-2, H-3, H-4, H-5, H-6a, H-2', H-5', 2H-6'), 4.09 (dd, J=11.0, 2.0 Hz, 1H, H-6b), 4.44 (m, 3H, CH$_2$Ph, H-4'), 4.56-4.90 (m, 12H, 6CH$_2$Ph), 4.78 (d, J=8.0 Hz, 1H, H-1'), 4.98 (d, J=8.0 Hz, 1H, H-1), 5.05 (m, 2H, 2 lipid-3-H), 5.16 (m, 1H, lipid-3-H), 5.39 (dd, J=10.0, 9.0 Hz, 1H, H-3'), 5.88 (d, J=8.5 Hz, 1H, NH), 6.08 (d, J=8.0 Hz, 1H, NH), 7.25 (m, 30H, Ar—H). Anal. calcd for C$_{138}$H$_{217}$N$_2$O$_{21}$P.0.5H$_2$O (2271.21): C, 72.69; H, 9.63; N, 1.22. Found: C, 72.45; H, 9.32; N, 1.19.

Example 47 Preparation of Compound 54

In a similar method as described for 33, compound 53 (54 mg, 0.028 mmol) was converted to 54 (30 mg, 62%) using palladium on carbon (5%, 70 mg) in THF:acetic acid, 10:1 (90 ml) in hydrogen atmosphere. TLC: R$_f$=0.35 (chloroform: methanol: water, 3:1:0.1). $[\alpha]_D^{22}$=10 (c 0.1, chloroform: methanol, 4:1). ES-MS calcd for C$_{96}$H$_{181}$N$_2$O$_{21}$P: 1729.3. Found: 1728 (M−H) (negative mode).

Example 48 Preparation of Compound 55

In a similar method as described for 30, compound 50 (300 mg, 0.19 mmol) was coupled with 5 (222 mg, 0.475 mmol) in dichloromethane:DMF (4:1, 50 ml). Silica gel chromatography (2 to 6% acetone in chloroform) gave 55 (256 mg, 66%). TLC: R$_f$=0.33 (chloroform:acetone, 9:1). $[\alpha]_D^{22}$=−24.0 (c 0.2, chloroform:methanol, 5:1). $^1$H NMR (300 MHz, CDCl$_3$: CD$_3$OD, 4:1): δ 0.98 (t, J=6.5 Hz, 18H, 6CH$_3$), 1.25 (m, 108H, 54 CH$_2$), 1.40-1.60 (m, 14H, 7CH$_2$), 2.07-2.63 (m, 12H, 6CH$_2$), 3.12 (t, J=7.0 Hz, 2H, NCH$_2$), 3.45-3.90 (m, 9H, H-2, H-3, H-4, H-5, H-6a, H-2', H-4', H-5', H-6'a), 4.10 (dd, J=11.0, 2.0 Hz, 1H, H-6b), 4.31 (dd, J=11.0, 5.5 Hz, 1H, H-6'b), 4.48 (t, J=6.5 Hz, 1H, Asp-α-H), 4.56-4.87 (m, 7H, 3CH$_2$Ph, H-1'), 4.85 (d, J=8.0 Hz, 1H, H-1), 5.08-5.19 (m, 2H, 2 lipid-3-H), 5.34 (dd, J=10.0, 10.0 Hz, 1H, H-3'), 5.51 (s, 1H, CHPh), 7.20-7.45 (m, 20H, Ar—H). Anal. calcd for C$_{123}$H$_{200}$N$_4$O$_{18}$.H$_2$O (2022.95): C, 72.38; H, 9.97; N, 2.74. Found: C, 72.19; H, 9.68; N, 2.70.

Example 49 Preparation of Compound 56

In a similar method as described for 31, compound 55 (220 mg, 0.109 mmol) was treated with sodium cyanoborohydride (1.37 g, 21.78 mmol) and HCl (g)/Et$_2$O in dry THF CHCl$_3$ (4:1, 50 ml) at room temperature to afford 56 (150 mg, 68%). TLC: R$_f$=0.20 (2% methanol in dichloromethane). $[\alpha]_D^{22}$=−14.0 (c 0.2, chloroform). $^1$H NMR (300 MHz, CDCl$_3$—CD$_3$OD, δ: 1): δ 0.72 (t, J=6.5 Hz, 18H, 6CH$_3$), 1.10 (m, 108H, 54CH$_2$), 1.21-1.46 (m, 14H, 7CH$_2$), 1.96-2.39 (m, 12H, 6CH$_2$), 2.15 (d, J=6.0 Hz, 1H, OH), 2.95 (m, 2H, NCH$_2$), 3.30-3.77 (m, 10H, H-2, H-3, H-4, H-5, H-6a, H-2', H-4', H-5', 2H-6'), 3.96 (dd, J=11.0, 2.0 Hz, 1H, H-6b), 4.31 (m, 1H, Asp-α-H), 4.35-4.68 (m, 9H, 4 CH$_2$Ph, H-1), 4.48 (d, J=8.0 Hz, 1H, H-1'), 4.86 (dd, J=10.0, 9.0 Hz, 1H, H-3'), 4.96 (m, 2H, 2 lipid-3-H), 7.10 (m, 20H, Ar—H). Anal. calcd for C$_{123}$H$_2$O$_2$N$_4$O$_{18}$.1.5H$_2$O (202.4.96): C, 72.00; H, 10.07; N, 2.73. Found: C, 71.97; H, 9.91; N, 2.69.

Example 50 Preparation of Compound 57

In a similar method as described for 32, compound 56 (85 mg, 0.042 mmol) was converted to 57 (80 mg, 83%). TLC: R$_f$=0.37 (chloroform:acetone, 9:1). $[\alpha]_D^{22}$=−6.2 (c 0.4, chloroform). $^1$H NMR (300 MHz, CDCl$_3$): δ 0.88 (m, 18H, 6CH$_3$), 1.23 (m, 108H, 54CH$_2$), 1.25-1.60 (m, 14H, 7CH$_2$), 2.12-2.57 (m, 12H, 6CH$_2$), 3.15 (m, 2H, NCH$_2$), 3.48-3.92 (m, 9H, H-2, H-3, H-4, H-5, H-6a, H-2', H-5', 2H-6'), 4.10 (br. d, J=11.0 Hz, 1H, H-6b), 4.37-4.90 (m, 16H, H-1, H-1', H-4', Asp-α-H, 6CH$_2$Ph), 5.08 (m, 2H, 2 lipid-3-H), 5.32 (dd, J=10.0, 9.0 Hz, 1H, H-3'), 6.20 (d, J=8.0 Hz, 1H, NH), 6.62 (d, J=8.0 Hz, 1H, NH), 7.08 (m, 2H, 2NH), 7.25 (m, 30H, Ar—H). Anal. calcd for C$_{137}$H$_{215}$N$_4$O$_{21}$P.1.5H$_2$O (2285.19): C, 71.16; H, 9.50; N, 2.42. Found: C, 71.02; H, 9.43; N, 2.23.

Example 51 Preparation of Compound 58

In a similar method as described for 33, compound 57 (52 mg, 0.023 mmol) was converted to 58 (32 mg, 80%). TLC: R$_f$=0.29 (chloroform:methanol:water, 3:1:0.1). $[\alpha]_D^{22}$=−10.0 (c 0.1, chloroform:methanol, 4:1). ES-MS calcd for C$_{95}$H$_{179}$N$_4$O$_{21}$P 1743.3. Found: 1742 (M−H) (negative mode).

Example 52 Preparation of Compound 60

(1) Compound 59: To a solution of 34 (15.95 g, 40.13 mmol) in dry acetonitrile (250 ml), benzaldehyde dimethyl acetal (18.32 g, 18.01 ml, 120.4 mmol) and p-toluenesulfonic acid (328 mg, 1.73 mmol) were added. After stirring at room temperature and under nitrogen atmosphere for 1.5 hours, reaction was terminated by an addition of triethyl amine (2 ml). It was then concentrated in vacuo and the residue was purified by silica gel chromatography (hexane:ethyl acetate, 7:3) to give 59 (13.93 g, 71%).

(2) Solution of 59 (2.02 g, 4.14 mmol) in dry DMF (15 ml) was added dropwise within 10 min to a mixture of sodium hydride (230 mg, 9.58 mmol), allyl bromide (0.75 g, 0.50 ml, 6.21 mmol) and dry DMF (20 ml). The reaction mixture was then stirred at room temperature for 3 hours. Similar work-up as described for 36 and purification by silica gel chromatography (hexane:ethyl acetate, 5:1) gave the 3-O-allyl compound (1.79 g, 82%).

(3) The 3-O-allyl compound (5.79 g, 11.0 mmol) was treated with acetic acid-water (4:1, 130 ml) at 65° C. for 6 h. The solvent was removed and the residue was purified by flash chromatography (hexane:ethyl acetate, 1:2) to give 4,6-dihydroxy compound (4.91 g, 95%).

(4) Compound 60: To a solution of the above 4,6-dihydroxy compound (4.79 g, 10.91 mmol) in dry pyridine (50 ml), triphenylmethyl chloride (6.38 g, 22.86 mmol) and DMAP (266 mg, 2.18 mmol) were added. The reaction mixture was stirred at room temperature for 6 hours and then at 35° C. for 16 hours. Residue from solvent removal was purified by silica gel chromatography (hexane:ethyl acetate, 4:1) to give 60 (5.87 g, 79%). TLC: $R_f$=0.66 (hexane:ethyl acetate, 1:2). $[\alpha]_D^{22}$=–37.2 (c 1.0, chloroform). $^1$H NMR (300 MHz, CDCl$_3$): δ 2.71 (d, J=2.8 Hz, 1H, OH), 3.46 (m, 2-H, 2H-6), 13.59 (m, 1H, H-5), 3.80 (m, 1H, H-4), 3.95 (m, 1H, CHHCH=CH$_2$), 4.15 (dd, J=10.0, 8.5 Hz, 1H, H-3), 4.16 (m, 1H, CHHCH=CH$_2$), 4.25 (dd, J=10.0, 8.0 Hz, 1H, H-2), 4.55 (d, J=12.0 Hz, CHHPh), 4.84 (d, J=12.0 Hz, 1H, CHHPh), 4.85 (m, 1H, CHH=CH), 5.02 (m, 1H CHH=CH), 5.19 (d, J=8.0 Hz, 1H, H-1), 5.59 (m, 1H, CH$_2$=CH), 7.09-7.90 (m, 24H, Ar—H). Anal. calcd for C$_{43}$H$_{39}$NO$_7$ (681.78): C, 75.75; H, 5.76; N, 2.04. Found: C, 75.37; H, 5.67; N, 2.04.

Example 53 Preparation of Compound 61

To a mixture of sodium hydride (200 mg, 8.33 mmol), benzyl bromide (1.01 g, 0.70 ml, 8.35 mmol) and dry DMF (20 ml), a solution of 60 (3.80 g, 5.57 mmol) in dry DMF (20 ml) was added dropwise within 10 min. After stirring for 3 hours at room temperature, methanol (4 ml) was added and stirring was continued for 10 minutes further. Reaction was then poured into ice-cooled saturated sodium chloride solution (500 ml) and extracted with dichloromethane (200 ml×3). Combined organic layers were dried with sodium sulfate and concentrated. The residue was purified by flash chromatography (hexane:ethyl acetate, 4:1) to give 61 (2.45 g, 57%). TLC: $R_f$=0.67 (hexane ethyl acetate, 2:1). $[\alpha]_D^{22}$=–37.2 (c 1.0, chloroform). $^1$H NMR (300 MHz, CDCl$_3$): δ 3.32 (dd, J=10.0, 3.5 Hz, 1H, H-6a), 3.62 (m, 1H, H-5), 3.69 (dd, J=10.0, 1.0 Hz, 1H, H-6b), 3.93 (m, 1H, CHHCH=CH$_2$), 3.96 (m, 1H, H-4), 4.25 (m, 1H, CHHCH=CH$_2$), 4.27 (dd, J=10.5, 8.5 Hz, 1H, H-2), 4.42 (dd, J=10.5, J=8.5 Hz, 1H, H-3), 4.44 (d, J=10.0 Hz, 1H, CHHPh), 4.66 (d, J=12.0, Hz, 1H, CHHPh), 4.70 (d, J=10.0 Hz, 1H, CHHPh), 4.83 (m, 1H, CHH=CH), 4.99 (d, J=12.0 Hz, 1H, CHHPh), 5.02 (m, 1H, CHH=CH), 5.27 (d, J=8.5 Hz, 1H, H-1), 5.59 (m, 1H, CH$_2$=CH), 6.92-7.90 (m, 29H, Ar—H). Anal. calcd for C$_{50}$H$_{45}$NO$_7$·0.5H$_2$O (771.91): C, 76.90; H, 5.94; N, 1.79. Found: C, 76.72; H, 6.11; N, 1.78.

Example 54 Preparation of Compound 62

Compound 61 (1.50 g, 1.94 mmol) was dissolved in acetic acid:water: allyl alcohol (8:2:1, 220 ml) and this solution was heated at 110° C. for 1 h. The solvent was then removed in vacuo and the residue was purified by flash chromatography (hexane:ethyl acetate, 2.5:1 and then 2:1) to give 62 (0.90 g, 87%). TLC: $R_f$=0.33 (hexane:ethyl acetate, 2:1) $[\alpha]_D^{22}$=–16.3 (c 1.0, chloroform). $^1$H NMR (300 MHz, CDCl$_3$): δ 1.90 (dd, J=6.0, 6.0 Hz, 1H, OH), 3.52 (m, 1H, H-6a), 3.65 (dd, J=9.5, 8.5 Hz, 1H, H-4), 3.75 (m, 1H, H-5), 3.90 (m, 2H, H-6b, CHHCH=CH$_2$), 4.20 (m, 2H, H-3, CHHCH=CH$_2$), 4.28 (dd, J=10.0, 8.0 Hz, 1H, H-2), 4.52 (d, J=12.0 Hz, 1H, CHHPh), 4.68 (d, J=10.5 Hz, 1H, CHHPh), 4.79 (d, J=12.0 Hz, 1H, CHHPh), 4.80 (m, 1H, CHH=CH), 4.84 (d, J=10.5 Hz, 1H, CHHPh), 5.00 (m, 1H, CHH=CH), 5.23 (d, J=8.0 Hz, 1H, H-1), 5.55 (m, 1H, CH$_2$=CH), 7.10-7.85 (m, 14H, Ar—H). Anal. calcd for C$_{31}$H$_{31}$NO$_7$·0.7H$_2$O (529.59): C, 68.67; H, 6.02; N, 2.58. Found: C, 68.46; H, 5.93; N, 2.53.

Example 55 Preparation of Compound 63

To the solution of 62 (0.90 g, 1.70 mmol) in 95% ethanol (60 ml) was added hydrazine monohydrate (3 ml). The mixture was heated under refluxing for 2 hours. Solvent was then removed in vacuo and the residue was purified by flash chromatography (1% methanol in dichloromethane) to give 63 (525 mg, 77%). TLC: $R_f$=0.28 (3% methanol in dichloromethane) $[\alpha]_D^{22}$=–17.0 (c 0.5, chloroform). $^1$H NMR (300 MHz, CDCl$_3$): δ 1.75 (s, 3H, NH$_2$, OH), 2.87 (dd, J=9.5, 8.0 Hz, 1H, H-2), 3.35 (dd, J=9.5, 9.5 Hz, 1H, H-4), 3.36 (m, 1H, H-5), 3.57 (dd, J=9.5, 9.5 Hz, 1H, H-3), 3.72 (dd, J=12.0, 4.0 Hz, 1H, H-6a), 3.88 (dd, J=12.0, 2.5 Hz, 1H, H-6b), 4.24 (m, 1H, CHHCH=CH$_2$), 4.36 (d, J=8.0 Hz, 1H, H-1), 4.42 (m, 1H, CHHCH=CH$_2$), 4.62 (d, J=11.5 Hz, 1H, CHHPh), 4.64 (d, J=11.0 Hz, 1H, CHHPh), 4.82 (d, J=11.0 Hz, 1H, CHHPh), 4.88 (d, J=11.5 Hz, 1H, CHHPh), 5.18-5.33 (m, 2H, CH$_2$=CH), 5.97 (m, 1H, CH$_2$=CH), 7.30 (m, 10H, Ar—H).

Example 56 Preparation of Compound 64

In a similar method as described for 40, compound 63 (510 mg, 1.28 mmol) was coupled with 14 (870 mg, 1.92 mmol) in presence of DCC (659 mg, 3.20 mmol) to give 64 (853 mg, 80%) after silica gel chromatography (2 to 5% acetone in chloroform) TLC: $R_f$=0.38 (% methanol dichloromethane). $[\alpha]_D^{22}$=–6.0 (c 1.0, chloroform). $^1$H NMR (300 MHz, CDCl$_3$): δ 0.89 (t, J=6.5 Hz, 6H, 2CH$_3$), 1.25 (br. s, 38H, 19 CH$_2$), 1.59 (m, 4H, 2CH$_2$), 1.86 (t, J=7.0 Hz, 1H, OH), 2.23 (t, J=7.5 Hz, 2H, CH$_2$), 2.37 (dd, J=15.0, 5.5 Hz, 1H, CHH), 2.48 (dd, J=15.0, 5.5 Hz, 1H, CHH), 3.40 (m, 2H, H-2, H-5), 3.52 (dd, J=9.5, 8.5 Hz, 1H, H-4), 3.70 (m, 1H, H-6a), 3.85 (m, 1H, H-6b), 4.00 (dd, J=10.0, 8.5 Hz, 1H, H-3), 4.14 (m, 1H, CHHCH=CH$_2$), 4.26 (m, 1H, CHHCH=CH$_2$), 4.59 (d, J=11.5 Hz, 1H, CHHPh), 4.63 (d, J=11.0 Hz, 1H, CHHPh), 4.82 (d, J=11.0 Hz, 1H, CHHPh), 4.83 (d, J=11.5 Hz, 1H, CHHPh), 4.96 (d, J=8.0 Hz, 1H, H-1), 5.08 (m, 1H, lipid-3-H), 5.13 (m, 1H, CHH=CH), 5.23 (m, 1H, CHH=CH), 5.88 (m, 1H, CH=CH$_2$), 6.00 (d, J=8.0 Hz, 1H, NH), 7.35 (m, 10H, Ar—H). Anal. calcd for C$_{51}$H$_{81}$NO$_8$O$_8$·0.7H$_2$O (836.20): C, 72.17; H, 9.78; N, 1.65. Found: C, 72.07; H, 9.81; N, 1.72.

Example 57 Preparation of Compound 65

In a similar method as described for 44, compound 65 was prepared using the imidate 43 (1.15 g, 1.12 mmol) and the glycosyl acceptor 64 (652 mg, 0.75 mmol) with BF$_3$ etherate (0.15 M in CH$_2$Cl$_2$, 3.5 ml). Silica gel chromatography (1 to 2% acetone in chloroform) yielded 65 (1.30 g, 83%). TLC: $R_f$=0.36 (6% acetone in chloroform). $[\alpha]_D^{22}$=–18.6 (c 0.5, chloroform). $^1$H NMR (300 MHz, CDCl$_3$): δ 0.86 (t, J=6.5 Hz, 12H, 4 CH$_3$), 1.22 (br. s, 76H, 38 CH$_2$), 1.53 (m, 8H, 4 CH$_2$), 2.15 (t, J=7.5 Hz, 2H, CH$_2$), 2.20 (t, J=7.5H, 2H, CH$_2$), 2.32 (dd, J=14.0, 5.5 Hz, 1H, CHH), 2.42 (dd, J=14.0, 6.0 Hz, 1H, CHH), 2.47 (dd, J=15.0, 5.0 Hz, 1H, CHH), 2.57 (dd, J=15.0, 7.0 Hz, 1H, CHH), 3.34-4.21 (m, 12H, H-2, H-3, H-4, H-5, 2H-6, H-2', H-4', H-5', H-6'a, CH$_2$CH=CH$_2$), 4.30 (dd, J=10.0, 5.0 Hz, 1H, H-6'b), 4.51 (d, J=8.5 Hz, 1H, H-1'), 4.57 (m, 4H, 2CHHPh, Cl$_3$CCH$_2$O), 4.78 (d, J=11.0 Hz, 1H, CHHPh), 4.85 (d, J=11.5 Hz, 1H, CHHPh), 4.88 (d, J=8.0 Hz, 1H, H-1), 5.00-5.25 (m, 5H, H-3', 2 lipid-3-H, $CH_2$=CH), 5.45 (s, 1H, CHPh), 5.85 (m, 1H, CH=$CH_2$), 6.00 (d, J=8.0 Hz, 1H, NH), 7.30 (m, 15H, Ar—H). Anal. calcd for $C_{95}H_{149}Cl_3N_2O_{17}$ (1697.58): C, 67.21; H, 8.85; N, 1.65. Found: C, 66.99; H, 8.96; N, 1.65.

Example 58 Preparation of Compound 67

(1) Compound 66: In the similar method as described for 50, compound 65 (350 mg, 0.206 mmol) was treated with activated Zinc (9.0 g) and 80% acetic acid in ethyl acetate (500 ml) at room temperature to give 66 (314 mg, 100%), which was used directly in the next step.

(2) Compound 67: Compound 66 (304 mg, 0.20 mmol), 14 (191 mg, 0.42 mmol) and DCC (130 mg, 0.62 mmol) were dissolved in dry dichloromethane (10 ml). The mixture was stirred at room temperature for 24 hours and the solid was filtered off. The filtrate was concentrated and the residue was purified by flash chromatography (2% acetone in chloroform) to give 67 (220 mg, 56%). TLC: $R_f$=0.25 (5% acetone in chloroform). $[\alpha]_D^2$=−16.0 (c 0.5, chloroform). $^1$H NMR (300 MHz, CDCl$_3$): δ 0.89 (t, J=6.5 Hz, 18H, 6CH$_3$), 1.23 (br. s, 114H, 57CH$_2$), 1.55 (m, 12H, 6CH$_2$), 2.13-2.48 (m, 10H, 5 CH$_2$), 2.50 (dd, J=15.0, 5.5 Hz, 1H, CHH), 2.59 (dd, J=15.0, 7.5 Hz, 1H, CHH)), 3.38-4.24 (m, 12H, H-2, H-3, H-4, H-5, 2H-6, H-2', H-4', H-5', H-6'a, $CH_2$CH=$CH_2$), 4.30 (dd, J=10.5, 5.5 Hz, 1H, H-6'b), 4.58 (d, J=11.0 Hz, 1H, CHHPh), 4.59 (d, J=12.0 Hz, 1H, CHHPh), 4.73 (d, J=8.5 Hz, 1H, H-1'), 4.77 (d, J=12.0 Hz, 1H, CHHPh), 4.83 (d, J=8.0 Hz, 1H, H-1), 4.85 (d, J=11.0 Hz, 1H, CHHPh), 4.99-5.30 (m, 6H, H-3', $CH_2$=CH, 3 lipid-3-H), 5.48 (s, 1H, CHPh), 5.87 (m, 1H, $CH_2$=CH), 5.91 (d, J=8.5 Hz, 1H, NH), 6.07 (d, J=8.0 Hz, 1H, NH), 7.35 (m, 15H, Ar—H). Anal. calcd for $C_{120}H_{200}N_2O_{18}$ (1958.90): C, 73.58; H, 10.30; N, 1.43. Found: C, 73.40; H, 10.70; N, 1.39.

Example 59 Preparation of Compound 68

In a similar way as described for 31, compound 67 (194 mg, 0.10 mmol) was converted to 68 (130 mg, 67%). TL: $R_f$=0.22 (8% acetone in chloroform). $[\alpha]_D^{22}$=−9.6 (c 0.5, chloroform). $^1$H NMR (600 MHz, CDCl$_3$): δ 0.89 (t, J=7.0 Hz, 18H, 6CH$_3$), 1.25 (br s, 114H, 57CH$_2$), 1.49-1.58 (m, 12H, 6CH$_2$), 2.21 (t, J=8.0 Hz, 2H, CH$_2$), 2.26 (m, 3H, CH$_2$, CHH), 2.27 (t, J=8.0 Hz, 2H, CH$_2$), 2.33 (dd, J=14.0, 6.0 Hz, 1H, CHH), 2.36 (dd, J=15.0, 6.5 Hz, 1H, CHH), 2.43 (dd, J=15.0, 6.5 Hz, 1H, CHH), 2.50 (dd, J=16.5, 6.50 Hz, 1H, CHH), 2.53 (dd, J=16.5, 8.0 Hz, 1H, CHH), 3.28 (d, J=3.0 Hz, 1H, OH), 3.43 (m, 2H, H-4, H-5'), 3.54 (m, 2H, H-2, H-6a), 3.62 (ddd, J=10.0, 9.0, 3.0 Hz, 1H, H-4'), 3.71 (m, 3H, H-5, 2H-6'), 3.84 (m, 2H, H-3, H-2'), 4.06 (dd, J=11.0, 2.5 Hz, 1H, H-6b), 4.10-4.20 (m, 2H, $CH_2$CH=$CH_2$), 4.52 (d, J=12.0 Hz, 1H, CHHPh), 4.58 (m, 4H, H-1', 3CHHPh), 4.74 (d, J=10.5 Hz, 1H, CHHPh), 4.80 (d, J=8.0 Hz, 1H, H-1), 4.83 (d, J=11.5 Hz, 1H, CHHPh), 4.95 (dd, J=10.0, 9.0 Hz, 1H, H-3'), 5.02 (m, 1H, lipid-3-H), 5.10 (m, 3H, 2 lipid-3-H, CHH=CH), 5.22 (m, 1H, CHH=CH), 5.77 (d, J=9.0 Hz, 1H, NH), 5.85 (m, 1H, CH$_2$=CH), 5.98 (d, J=8.0 Hz, 1H, NH), 7.30 (m, 15H, Ar—H). Anal. calcd for $C_{120}H_2O_2N_2O_{18}$ (1960.92): C, 73.50; H, 10.38; N, 1.43. Found: C, 73.25; H, 10.95; N, 1.60.

Example 60 Preparation of Compound 69

In a similar way as described for 32, compound 68 (117 mg, 0.060 mmol) was converted to 69 (81 mg, 61%) which was purified by repeated flash chromatography (initially with 1 to 3% acetone in chloroform and then with toluene: acetone, from 15:1 to 12:1 and subsequently with hexane: acetone, from 6:1 to 5:1). TLC: $R_f$=0.46 (9% acetone in chloroform). $[\alpha]_D^{22}$=−4.8 (c 0.33, chloroform). $^1$H NMR (300 MHz, CDCl$_3$): δ 0.89 (t, J=6.5 Hz, 18H, 6CH$_3$), 1.25 (br. s, 114H, 57CH$_2$), 1.45-1.55 (m, 12H, 6CH$_2$), 2.19-2.51 (m, 12H, 6CH$_2$), 3.45-4.23 (m, 12H, H-2, H-3, H-4, H-5, 2H-6, H-2', H-5', 2H-6', $CH_2$CH=$CH_2$), 4.50 (m, 3H, H-4', $CH_2$Ph), 4.58 (d, J=12.5 Hz, 2H, 2CHHPh), 4.75 (d, J=11.0 Hz, 1H, CHHPh), 4.80 (d, J=8.0 Hz, 1H, H-1), 4.88 (m, 5H, 5 CHHPh), 4.99 (d, J=8.0 Hz, 1H, H-1'), 5.05-5.26 (m, 5H, 3 lipid-3-H, $CH_2$=CH), 5.41 (dd, J=10.0, 9.0 Hz, 1H, H-3'), 5.86 (m, 1H, $CH_2$=CH), 5.93 (d, J=8.0 Hz, 1H, NH), 6.09 (d, J=7.5 Hz, 1H, NH), 7.30 (m, 25H, Ar—H). Anal. calcd for $C_{134}H_{215}N_2O_{21}P$ (2221.15): C, 72.416; H, 9.76; N, 1.26. Found: C, 72.21; H, 9.92; N, 1.27.

Example 61 Preparation of Compound 70

In a similar method as described for 33, compound 69 (73 mg, 0.035 mmol) was converted to 70 (55 mg, 95%). TLC: $R_f$=0.35 (chloroform:methanol: water, 3:1:0.1). $[\alpha]_D^{22}$=+6.0 (c 0.1, chloroform:methanol, 4:1). ES-MS calcd for $C_{99}H_{187}N_2O_{21}P$: 1771.3. Found (negative mode): 1770.3 (M−H), 1771.3 (M−H, isotopic peak).

Example 62 Preparation of Compound 71

In a similar method as described for 42, compound 65 (350 mg, 0.195 mmol) was converted to 71 (200 mg, 62%). TLC: $R_f$=0.30 (5% acetone in chloroform). $[\alpha]_D^{22}$=−25.7 (c 0.83, chloroform). $^1$H NMR (300 MHz, CDCl$_3$): δ 0.90 (t, J=6.5 Hz, 12H, 4 CH$_3$), 1.25 (br. s, 76H, 38 CH$_2$), 1.55 (m, 8H, 4 CH$_2$), 1.70 (s, 1H, OH), 2.17 (t J=7.0 Hz, 2H, CH$_2$), 2.26 (t, J=7.0 Hz, 2H, CH$_2$), 2.43 (m, 2H, CH$_2$), 2.50 (dd, J=14.0, 5.5 Hz, 1H, CHH), 2.60 (dd, J=15.0, 7.5 Hz, 1H, CHH), 3.40-3.90 (m, 9H, H-2, H-3, H-4, H-5, H-6a, H-2', H-4', H-5', H-6'a), 4.13 (br. d, J=10.0 Hz, 1H, H-6b), 4.34 (dd, J=−10.0, 5.0 Hz, 1H, H-6'b), 4.51, 4.52 (2 d, J=8.5 Hz, each 1H, H-1, H−1'), 4.60 (d, J=12.5 Hz, 1H, CHHPh), 4.66 (m, 3H, CHHPh, Cl$_3$CCH$_2$O), 4.90 (d, J=12.5 Hz, 1H, CHHPh), 4.98 (d, J=11.5 Hz, 1H, CHHPh), 5.04-5.25 (m, 3H, H-3', 2 lipid-3-H), 5.49 (s, 1H, CHPh), 6.02 (d, J=5.0 Hz, 1H, NH), 7.40 (m, 15H, Ar—H). Anal. calcd for $C_{92}H_{145}Cl_3N_2O_{17}$·0.8H$_2$O (1657.52): C, 66.09; H, 8.84; N, 1.67. Found: C, 66.06; H, 8.84; N, 1.64.

Example 63 Preparation of Compound 72

In a similar method as described for 28, compound 71 (670 mg, 0.405 mmol) was coupled with 17 (270 mg, 0.81 mmol) in presence of DCC (208 mg, 1.01 mmol) and DMAP (25 mg, 0.20 mmol) The reaction was completed in 72 h. Silica gel chromatography (dichloromethane:hexane:acetone, 2:1:3%; and 1% methanol in dichloromethane) afforded 72 (570 mg, 71%). TLC: $R_f$=0.60 (dichloromethane:hexane:acetone, 10:5:1). $[\alpha]_D^{22}$=−20.0 (c 1.0, chloroform). $^1$H NMR (600 MHz, CDCl$_3$): δ 0.88 (t, J=7.0 Hz, 15H, 5 CH$_3$), 1.25 (m, 74H, 37 CH$_2$), 1.53 (m, 10H, 5 CH$_2$), 2.17 (t, J=7.5 Hz, 2H, CH$_2$), 2.22 (dd, J=15.0, 6.0 Hz, 1H, CHH), 2.24 (t, J=7.5 Hz, 2H, CH$_2$), 2.34 (dd, J=15.0, 6.5 Hz, 1H, CHH), 2.45 (dd, J=16.0, 5.0 Hz, 1H, CHH), 2.50 (dd, J=15.5, 5.5 Hz, 1H, CHH), 2.55 (dd, J=16.0, 7.5 Hz, 1H, CHH), 2.59 (dd, J=15.5, 7.5 Hz, 1H, CHH), 3.38 (ddd, J=10.0, 10.0, 5.0 Hz, 1H, H-5'), 3.56 (m, 2H, H-4, H-5), 3.62 (m, 1H, H-2), 3.64 (dd, J=10.0, 10.0 Hz, 1H, H-4'), 3.69 (dd, J=11.0, 5.0 Hz, 1H, H-6a), 3.76 (dd, J=10.0, 10.0 Hz, 1H, H-6'a), 3.83 (m, 1H, lipid-3-H), 3.95 (m, 1H, H-2'), 4.05 (br. d, J=11.0 Hz, 1H, H-6b), 4.32 (dd, J=10.0, 5.0 Hz, 1H, H-6'b), 4.45 (d, J=11.0 Hz, 1H, CHHPh), 4.48 (d, J=11.0 Hz, 2H, 2CHHPh), 4.51 (d, J=8.0 Hz, 1H, H-1), 4.59 (d, J=8.0 Hz, 1H, H-1'), 4.60-4.67 (m, 4H, 2CHHPh, $Cl_3CCH_2O$), 4.85 (d, J=12.0 Hz, 1H, CHHPh), 5.01 (m, 1H, lipid-3-H), 5.12 (d, J=9.0 Hz, 1H, NH), 5.19 (m, 4H, H-3, H-3', 2. lipid-3-H), 5.48 (s, 1H, CHPh), 5.71 (d, J=8.0 Hz, 1H, NH), 7.20-7.45 (m, 20H, Ar—H). Anal. calcd for $C_{113}H_{177}Cl_3N_2O_{19}$ (1974.00): C, 68.76; H, 9.04; N, 1.42. Found: C, 68.68; H, 9.10; N, 1.39.

Example 64 Preparation of Compound 74

(1) Compound 73: In the similar method as described for 50, compound 72 (550 mg, 0.279 mmol) was treated with activated Zinc (9.0 g) and 80% acetic acid in ethyl acetate (500 mg) at room temperature to give 73 (500 mg, 100%). TLC: $R_f$=0.12 (2% methanol in dichloromethane).

(2) Compound 74: Compound 73 (270 mg, 0.15 mmol), 5 (211 mg, 0.45 mmol) and DCC (139 mg, 0.68 mmol) were dissolved in dry $CH_2Cl_2$:DMF (4:1, 15 ml) and the mixture was stirred at room temperature for 24 h. The solvent was removed and the residue was purified by silica gel chromatography (3 to 7% acetone in chloroform) to give 74 (220 mg, 65%). TLC: $R_f$=0.15 (8% acetone in chloroform). $[\alpha]_D^{22}$=−20.0 (c 0.5, chloroform). $^1$H NMR (600 MHz, $CDCl_3$): δ 0.90 (m, 21H, $7CH_3$), 1.25 (m, 126H, 63 $CH_2$), 1.50 (m, 14H, $7CH_2$), 2.13 (m, 2H, $CH_2$), 2.16-2.25 (m 5H, $2CH_2$, CHH), 2.31 (dd, J=15.5, 7.0 Hz, 1H, CHH), 2.36 (dd, J=15.0, 7.0 Hz, 1H, CHH), 2.45 (dd, J=16.0, 5.0 Hz, 1H, CHH), 2.50 (m, 2H, 2CHH), 2.55 (dd, J=15.5, 5.5 Hz, 1H, CHH), 2.60 (dd, J=15.0, 7.5 Hz, 1H, CHH), 3.17 (m, 2H, $NCH_2$), 3.42 (ddd, J=10.0, 10.0, 5.0 Hz, 1H, H-5'), 3.52 (dd, J=10.0, 9.0 Hz, 1H, H-4), 3.61 (dd, J=10.0, 10.0 Hz, 1H, H-4'), 3.64 (m, 2H, H-5, H-2'), 3.73 (m, 1H, H-6a), 3.75 (dd, J=10.0, 10.0 Hz, 1H, H-6'a), 3.82 (m, 1H, lipid-3-H), 4.06 (m, 2H, H-2. H-6b), 4.33 (dd, J=10.0, 5.0 Hz, 1H, H-6'b), 4.44 (d, J=11.5 Hz, 1H, CHHPh), 4.46 (d, J=11.5 Hz, 1H, CHHPh), 4.47 (m, 1H, Asp-α-H), 4.49 (d, J=11.5 Hz, 1H, CHHPh), 4.57 (d, J=11.5H, 1H, CHHPh), 4.67 (d, J=12.5 Hz, 1H, CHHPh), 4.73 (d, J=8.0 Hz, 1H, H-1), 4.85 (d, J=12.5 Hz, 1H, CHHPh), 4.89 (d, J=8.5 Hz, 1H, H-1'), 5.06 (m, 1H, lipid-3-H), 5.13 (m, 2H, 2 lipid-3-H), 5.21 (dd, J=10.0, 9.0 Hz, 1H, H-3), 5.38 (dd, J=10.0, 10.0 Hz, 1H, H-3'), 5.47 (s, 1H, CHPh), 5.97 (d, J=9.0 Hz, 1H, NH), 6.46 (d, J=8.0 Hz, 1H, NH), 7.05 (t, J=5.0 Hz, 1H, NH), 7.10 (d, J=8.0 Hz, 1H, NH), 7.22-7.45 (m, 20H, Ar—H). Anal. calcd for $C_{137}H_{226}N_4O_{20}$ (2249.31): C, 73.15; H, 10.13; N, 2.49. Found: C, 73.00; H, 10.51; N, 2.41.

Example 65 Preparation of Compound 75

In a similar way as described for 31, compound 74 (140 mg, 0.062 mmol) was treated with sodium cyanoborohydride (780 mg, 12.4 mmol) and HCl (g)/$Et_2O$ in dry THF (25 ml) at room temperature to give 75 (90 mg, 64%). TLC: $R_f$=0.17 (10% acetone in chloroform). $[\alpha]_D^{22}$=−16.0 (c 0.5, chloroform). $^1$H NMR (300 MHz, $CDCl_3$): δ 0.89 (t, J=6.5 Hz, 21H, $7CH_3$), 1.25 (br. s, 126H, 63 $CH_2$) 1.40-1.60 (m, 14H, $7CH_2$), 2.15-2.60 (m, 14H, $7CH_2$), 3.15 (m, 2H, $NCH_2$), 3.33 (d, J=3.0 Hz, 1H, OH), 3.43-4.12 (m, 11H, H-2, H-4, H-5, 2H-6, H-2', H-4', H-5', 2H-6', lipid-3-H), 4.41-4.59 (m, 6H, Asp-α-H, 5 CHHPh), 4.61 (d, J=11.0 Hz, 1H, CHHPh), 4.65 (d, J=12.0 Hz, 1H, CHHPh), 4.70 (d, J=8.5 Hz, 1H, H-1), 4.77 (d, J=8.0 Hz, 1H, H-1'), 4.85 (d, J=12.0 Hz, 1H, CHHPh), 5.04-5.21 (m, 4H, H-3, H-3', 2 lipid-3-H), 5.96 (d, J=9.0 Hz, 1H, NH), 6.31 (d, J=8.0 Hz, 1H, NH), 7.08 (t, J=5.0 Hz, 1H, NH), 7.15-7.30 (m, 21H, NH, Ar—H). Anal. calcd for $C_{137}H_{228}N_4O_{20}$ (2251.32): C, 73.09; H, 10.21; N, 2.48. Found: C, 73.31; H, 10.77; N, 2.41.

Example 66 Preparation of Compound 76

In a similar way as described for 32, compound 75 (120 mg, 0.053 mmol) was converted to 76 (81 mg, 60%) which was purified by repeated flash chromatography (initially with 3% acetone in chloroform and then with toluene:acetone from 10:1 to 8:1). TLC: $R_f$=0.30 (9% acetone in chloroform). $[\alpha]_D^{22}$=−10.9 (c 0.33, chloroform). $^1$H NMR (600 MHz, $CDCl_3$): δ 0.90 (t, J=7.0 Hz, 21H, $7CH_3$), 1.25 (br. s, 126H, 63 $CH_2$), 1.45-1.60 (m, 14H, $7CH_2$), 2.15-2.55 (m, 14H, $7CH_2$), 3.16 (m, 2H, $NCH_2$), 3.51-4.10 (m, 10H, H-2, H-4, H-5, 2H-6, H-2', H-5'; 2H-6', lipid-3-H), 4.38-4.50 (m, 7H, H-4', 6 CHHPh), 4.55 (d, J=11.0 Hz, 1H, CHHPh), 4.65 (d, J=12.5 Hz, 1H, CHHPh), 4.70 (d, J=8.0 Hz, 1H, H-1), 4.84 (d, J=12.5 Hz, 1H, CHHPh), 4.87-4.92 (m, 5H, Asp-α-H, H-1', 3 CHHPh), 5.07 (m, 2H, 2 lipid-3-H), 5.18 (dd, J=10.0, 10.0 Hz, 1H, H-3), 5.31 (dd, J=10.0, 10.0 Hz, 1H, H-3'), 5.93 (d, J=9.0 Hz, 1H, NH), 6.51 (d, J=8.0 Hz, 1H, NH), 7.03 (t, J=5.5 Hz, 1H, NH), 7.09 (d, J=7.0 Hz, 1H, NH), 7.16-7.33 (m, 30H, Ar—H). Anal. calcd for $C_{151}H_{241}N_4O_{23}P$ (2511.55): C, 72.21; H, 9.67; N, 2.23. Found: C, 72.13; H, 9.82; N, 2.17.

Example 67 Preparation of Compound 77

In the same way as described for 33, compound 76 (70 mg, 0.03 mmol) was converted to 77 (42.5 mg, 78%). TLC: $R_f$=0.37 (chloroform:methanol: water, 3:1:0.1), $[\alpha]_D^{22}$=−11.0 (c 0.1, chloroform:methanol, 4:1). ES-MS calcd for $C_{1-9}H_{205}N_4O_{23}P$: 1969.5. Found (negative mode): 1968.5 (M−H), 1969.5 (M−H, isotopic peak).

Example 68 Preparation of Compound 78

The lipid acid 17 (1.5 g, 4.5 mmol), the sugar compound 27 (3.18 g, 7.8 mmol), EDCI (1.3 g, 6.8 mmol) and DMAP (0.275 g, 2.2 mmol) were taken in anhydrous dichloromethane (40 ml) and stirred for 3 hours at room temperature under nitrogen atmosphere. TLC indicated the completion of the reaction. The solvent was removed in vacuo and the colourless residue was purified silica gel chromatography (10% ethyl acetate in hexane) to give 78 (2.4 g, 70%). TLC: $R_f$=0.54 (hexane:ethyl acetate, 3:1). $[\alpha]_D^{20}$=+69.1 (c 0.53, chloroform). $^1$H NMR (300 MHz, $CDCl_3$): δ=0.88 (t, J=6.5 Hz, 3H, $CH_3$), 1.25 (br s, 18H), 1.32 (s, 3H, $CH_3$), 1.43 (s, 3H, $CH_3$), 1.51 (m, 2H), 2.42 (dd, J=15.5, 5.5 Hz, 1H), 2.68 (dd, J=15.5, 6.5 Hz, 1H), 3.71-3.86 (m, 5H), 4.02 (ddd, J=10.0, 10.0, 3.5 Hz, 1H, H-2), 4.45 (d, J=11.5 Hz, 1H), 4.49 (d, J=12.0 Hz, 1H), 4.55 (d, J=12.0 Hz, 1H), 4.58 (d, J=11.5 Hz, 1H), 4.69 (d, J=12.0 Hz, 1H), 4.71 (d, J=12.0 Hz, 1H), 4.92 (d, J=3.5 Hz, 1H, H-1), 5.24 (dd, J=10.0, 10.0 Hz, 1H, H-3), 5.32 (d, J=10.0 Hz, 1H, NH), 7.30 (m, 10H, Ar—H).

Example 69 Preparation of Compound 79

Compound 78 (2.4 g) and 80% acetic acid in ethyl acetate (50 ml) was stirred at 35° C. for 2 hours. The solvent was then removed under reduced pressure and co-evaporated with toluene. The colorless residue obtained was purified by silica gel chromatography (10% acetone in toluene) to give 79 (2.1 g, 85%). TLC: $R_f$=0.25 (toluene:acetone, 4-1). $[\alpha]_D^{20}$=+54.6 (c 2.0, chloroform). $^1$H NMR (300 MHz, $CDCl_3$): δ=0.88 (t, J=6.5 Hz, $CH_3$), 1.25 (br s, 18H, $9CH_2$), 1.51 (m, 2H, $CH_2$), 1.99 (br s, 1H, OH), 2.49 (dd, J=14.5, 4.5 Hz, 1H), 2.61 (dd, J=14.5, 7.5 Hz, 1H), 3.01 (br s, 1H, OH), 3.62-3.95 (m, 6H), 4.98 (d, J=12.0 Hz, 1H), 4.50 (d, J=12.0 Hz, 1H), 4.53 (d, J=12.0 Hz, 1H), 4.62 (d, J=12.0 Hz, 1H), 4.67 (d, J=12.0 Hz, 1H), 4.94 (d, J=3.5 Hz, 1H, H-1), 5.15 (dd, J=10.0, 9.0 Hz, 1H, H-3), 5.29 (d, J=9.0 Hz, 1H, NH). 7.30 (m, 10H, Ar—H).

Example 70 Preparation of Compound 80

In a similar method as described for 46, compound 41 (1.45 g, 1.60 mmol) was treated with sodium cyanoborohydride (1.0 g, 15.96 mmol) and freshly saturated solution of diethyl ether with hydrogen chloride gas to give 80 (1.23 g, 85%) after flash silica gel chromatography (initially with hexane:ethyl acetate, 5:1 and then 4:1). TLC: $R_f$=0.20 (hexane:ethyl acetate, 4:1). $[\alpha]_D^{20}$=+47.5 (c 1.0, CHCl$_3$). $^1$H NMR (300 MHz, CDCl$_3$): δ 0.88 (t, J=6.5 Hz, 6H, 2CH$_3$), 1.25 (br s, 38H, 19 CH$_2$), 1.50 (m, 4H, 2CH$_2$), 2.28 (t, J=7.5 Hz, 2H, CH$_2$), 2.48 (dd, J=14.0, 4.0 Hz, 1H), 2.58 (dd, J=14.0, 7.5 Hz, 1H), 3.27 (d, J=3.5 Hz, 1H, OH), 3.70-3.86 (m, 4H), 3.92-4.03 (m, 2H), 4.58 (d, J=12.0 Hz, 1H), 4.64 (d, J=12.0 Hz, 1H), 4.66 (d, J=12.0 Hz, 1H), 4.76 (d, J=12.0 Hz, 1H), 4.92 (d, J=3.5 Hz, 1H, H-1), 5.13 (m, 2H), 5.19-5.31 (m, 2H, CH$_2$=CH), 5.40 (d, J=9.5 Hz, 1H, NH), 5.88 (m, 1H, CH$_2$=CH), 7.30 (m, 5H, Ar—H). ES-MS calcd for C$_{47}$H$_{76}$Cl$_3$NO$_{10}$: 919.5. Found: 920.8 (M+H).

Example 71 Preparation of Compound 81

In a similar way as described for 47, compound 80 (1.20 g, 1.30 mmol) was treated with 1H tetrazole and dibenzyl diisopropylphosphoramidite (900 mg, 0.875 ml, 2.61 mmol) in dry dichloromethane (12 ml) and followed by with m-CPBA (1.63 g, 55%, 5.22 mmol) to give 81 (1.33 g, 86%) after flash silica gel chromatography (initially hexane:ethyl acetate, 4:1 and then 3:1). TLC: $R_f$=0.31 (hexane:ethyl acetate, 3:1). $[\alpha]_D^{20}$+35.0 (c 1.0, CHCl$_3$). $^1$H NMR (300 MHz, CDCl$_3$): δ 0.88 (t, J=6.5 Hz, 6H, 2CH$_3$), 1.24 (br s, 38H, 19 CH$_2$), 1.50 (m, 4H, 2CH$_2$), 2.17 (t, J=7.0 Hz, 2H, CH$_2$), 2.41 (dd, J=16.5, 5.5 Hz, 1H), 2.51 (dd, J=16.5, 7.5 Hz, 1H), 3.66 (dd, J=11.0, 4.5 Hz, 1H), 3.74 (dd, J=11.0, 2.0 Hz, 1H), 3.91 (m, 1H), 4.00 (m, 2H), 4.20 (m, 1H), 4.44 (d, J=12.0 Hz, 1H), 4.53 (m, 1H, H-4), 4.54 (d, J=12.0, 1H), 4.63 (d, J=12.0, 1H), 4.88-4.95 (m, 5H), 5.11 (m, 1H), 5.20-5.32 (m, 2H, CH$_2$=CH), 5.35 (dd, J=10.5, 9.0 Hz, 1H, H-3), 5.41 (d, J=9.5 Hz, 1H, NH), 5.88 (m, 1H, CH$_2$=CH), 7.30 (m, 15H, Ar—H). ES-MS calcd for C$_{61}$H$_{89}$Cl$_3$NO$_{13}$P: 1179.6. Found: 1181.0 (M+H).

Example 72 Preparation of Compound 82

In a similar way as described for 42, compound 81 (1.30 g, 1.10 mmol) was dissolved in dry THF (10 ml) and treated with [bis(methyldiphenylphosphine] (1,5-cyclooctadiene) iridium (I) hexafluorophosphate (14 mg, 0.0165 mmol), followed by the treatment with water (0.5 ml) and N-succinimide (NBS, 294 mg, 1.62 mmol) to give 82 (950 mg, 76%). TLC: $R_f$=0.31 (ethyl acetate hexane, 1:2). $[\alpha]_D^{20}$+17.5 (c 1.0, CHCl$_3$). $^1$H NMR (300 MHz, CDCl$_3$): δ 0.88 (t, J=6.5 Hz, 6H, 2CH$_3$), 1.24 (br s, 38H, 19 CH$_2$), 1.50 (m, 4H, 2CH$_2$), 2.18 (t, J=7.0 Hz, 2H, CH$_2$), 2.39 (m, 2H, CH$_2$), 3.59 (dd, J=11.0, 6.0 Hz, 1H), 3.71 (dd, J=11.0, 1.5 Hz, 1H), 3.94 (m, 1H), 4.16 (m, 1H), 4.40 (m, 3H), 4.49 (d, J=12.0 Hz, 1H), 4.65 (d, J=12.0 Hz, 1H), 4.72 (d, J=12.0 Hz, 1H), 4.90 (m, 4H), 5.09 (m, 1H), 5.39 (t, J=3.5 Hz, 1H, H-1), 5.37 (dd, J=10.0, 9.5 Hz, 1H, H-3), 5.70 (d, J=9.5 Hz, 1H, NH), 7.30 (m, 15H, Ar—H). ES-MS calcd for C$_{58}$H$_{85}$Cl$_3$NO$_{13}$P: 1139.5. Found: 1141.0 (M+H).

Example 73 Preparation of Compound 83

In a similar method as described for 43, compound 82 (920 mg, 0.81 mmol) was treated with trichloroacetonitrile (2 ml) and DBU (4 drops). Purification by flash silica gel chromatography (hexane:ethyl acetate, 4:1, 3.5:1 and 3:1, with 0.5% of triethyl amine) afforded 83 (700 mg, 68%). TLC: $R_f$=0.36 (hexane ethyl acetate, 3:1). $[\alpha]_D^{20}$=+12.5 (c 0.4, CHCl$_3$). $^1$H NMR (300 MHz, CDCl$_3$): δ 0.88 (t, J=6.5 Hz, 6H, 2CH$_3$), 1.24 (br s, 38H, 19 CH$_2$), 1.50 (m, 4H, 2CH$_2$), 2.19 (t, J=7.0 Hz, 2H, CH$_2$), 2.46 (m, 2H, CH$_2$), 3.71 (m, 2H), 4.04 (m, 1H). 4.15 (ddd, J=1.0, 8.5, 3.5 Hz, 1H, H-2), 4.43 (d, J=12.0 Hz, 1H), 4.52 (d, J=12.0 Hz, 1H), 4.61 (d, J=12.0 Hz, 1H), 4.71 (ddd, J=9.5, 9.5, 9.5 Hz, 1H, H-4), 4.77 (d, J=12.0 Hz, 1H). 4.94 (m, 4H), 5.12 (m, 1H), 4.39 (dd, J=10.0, 9.5 Hz, 1H, H-3), 5.65 (d, J=8.5 Hz, 1H, NH), 6.47 (d, J=3.5 Hz, 1H, H-1), 7.32 (m, 15H, Ar—H), 8.72 (s, 1H, NH). ES-MS calcd for C$_{60}$H$_{85}$Cl$_6$N$_2$O$_{13}$P: 1282.4. Found: 1284.0 (M+H).

Example 74 Preparation of Compound 84

In a similar way as described for 44, the imidate 83 (190 mg, 0.148 mmol) and 79 (112 mg, 0.148 mmol) were treated with trifluoroboron diethyl etherate in dichloromethane solution (0.1 M, 0.4 ml) to give 84 (172 mg, 66%). TLC: $R_f$=0.25 (hexane ethyl acetate, 2.5:1). $[\alpha]_D^{20}$=+17.5 (c 2.0, CHCl$_3$). $^1$H NMR (600 MHz, CDCl$_3$): δ 0.88 (t, J=6.5 Hz, 9H, 3CH$_3$), 1.24 (br s, 56H, 28CH$_2$), 1.42-1.62 (m, 6H, 3CH$_2$), 2.23 (m, 2H, CH$_2$), 2.38 (dd, J=15.0, 8.0 Hz, 1H), 2.46 (dd, J=15.0, 4.0 Hz, 1H), 2.47 (dd, J=15.0, 5.0 Hz, 1H), 2.63 (dd, J=15.0, 7.5 Hz, 1H), 3.00 (s, 1H, OH), 3.48 (m, 1H, lipid-3-H), 3.61 (dd, J=11.0, 5.5 Hz, 1H), 3.65 (m, 2H), 3.78 (dd, J=11.0, 2.0 Hz, 1H), 3.83 (m, 3H), 3.94 (ddd, J=10.0, 10.0, 4.0 Hz, 1H, H-2), 4.06 (br d, J=10.0 Hz, 1H), 4.42 (ddd, J=9.5, 9.5, 9.5 Hz, 1H, H-4'), 4.45 (d, J=12.0 Hz, 1H), 4.50 (m, 4H), 4.52 (d, J=12.0 Hz, 1H), 4.57 (d, J=12.0 Hz, 1H), 4.66 (d, J=12.0 Hz, 1H), 4.72 (m, 2H), 4.90 (m, 6H), 5.15 (dd, J=10.0, 10.0 Hz, 1H, H-3), 5.19 (m, 1H, lipid-3-H), 5.25 (d, J=10.0 Hz, 1H, NH), 5.38 (d, J=10.0, 10.0 Hz, 1H, H-3'), 5.61 (d, J=8.0 Hz, 1H, NH), 7.30 (m, 25H, Ar—H). The assignment was based on $^1$H–$^1$H COSY spectrum.

For structural proof, compound 84 was treated with acetic anhydride and pyridine to give its mono-acetate. TLC: $R_f$=0.30 (toluene:acetone, 8:1). $[\alpha]_D^{20}$=+21.4 (c 0.4, CHCl$_3$). $^1$H NMR (300 MHz, CDCl$_3$): δ 0.88 (t, J=6.5 Hz, 9H, 3CH$_3$), 1.23 (br s, 56H, 28CH$_2$), 1.50 (m, 6H, 3CH$_2$), 1.80 (s, 3H, CH$_3$), 2.18 (t, J=7.0 Hz, 2H, CH$_2$), 2.44 (m, 3H), 2.53 (dd, J=16.0, 7.0 Hz, 1H), 3.45 (m, 1H), 3.61 (m, 3H), 3.80 (m, 2H), 3.97 (m, 3H), 4.42 (m, 1H), 4.49 (m, 6H), 4.58-4.75 (m, 5H), 4.89 (m, 2H), 4.91 (m, 2H), 4.96 (d, J=3.5 Hz, 1H, H-1), 5.05 (dd, J=10.0, 10.0 Hz, 1H, H-4), 5.24 (d, J=10.0 Hz, 1H, NH), 5.32 (dd, J=10.0, 10.0 Hz, 2H, H-3, H-3'), 5.70 (d, J=8.0 Hz, 1H, NH), 7.30 (m, 25H, Ar—H).

Example 75 Preparation of Compound 85

Compound 84 (30 mg, 0.017 mmol) was dissolved in acetic acid (10 ml) and treated with zinc (1.0 g) at room temperature for 30 min. The solid was filtered off and washed with dichloromethane (50 ml). The solvent was removed and the residue purified by flash silica gel chromatography (1% to 3% methanol in dichloromethane) to give the free amine compound (20 mg, 78%).

The solution of the above free amine compound (19 mg, 0.012 mmol), 14 (22.5 mg, 0.049 mmol) and DCC (10.2 mg, 0.049 mmol) in dry dichloromethane (3 ml) was stirred at room temperature for 20 h. The solvent was removed and the residue purified by repeated flash silica gel chromatography (initially with 0.5% to 2% methanol in dichloromethane and then hexane acetone, 6:1) to give 85 (16 mg, 54%). TLC: $R_f$=0.43 (4% methanol in dichloromethane) $[\alpha]_D^{20}$=+30.0 (c 0.25, CHCl$_3$). $^1$H NMR (600 MHz, CDCl$_3$): δ 0.90 (m, 21H, 7CH$_3$), 1.25 (m, 132H, 66 CH$_2$), 1.50 (m, 14H, 7CH$_2$), 2.18 (dd, J=8.5, 3.5 Hz, 1H), 2.20-2.37 (m, 9H), 2.41 (dd, J=14.5, 7.5 Hz, 1H), 2.44 (dd, J=15.5, 4.5 Hz, 1H), 2.48 (dd, J=15.5, 3.5 Hz, 1H), 2.63 (dd, J=15.5, 7.0 Hz, 1H), 3.58-3.63 (m, 2H), 3.67 (m, 1H), 3.72-3.79 (m, 4H), 3.81-3.86 (m, 2H), 4.00 (dd, J=11.0, 2.5 Hz, 1H), 4.24 (ddd, J=10.5, 9.0, 3.5 Hz, 1H, H-2), 4.38 (ddd, J=9.0, 9.0, 9.0 Hz, 1H, H-4'), 4.44 (d, J=12.0, 1H), 4.44 (d, J=11.5 Hz, 1H), 4.45 (d, J=12.0 Hz, 1H), 4.51 (d, J=12.0 Hz, 1H), 4.54 (d, J=11.5 Hz, 1H), 4.70 (d, J=12.0 Hz, 1H), 4.88 (m, 5H), 4.99 (d, J=8.0 Hz, 1H, H-1'), 5.05 (m, 1H), 5.13 (m, 2H), 5.18 (dd, J=10.5, 9.0 Hz, 1H, H-3), 5.34 (dd, J=10.5, 9.0 Hz, 1H, H-3'), 5.92 (d, J=9.0 Hz, 1H, NH), 6.27 (d, J=7.5 Hz, 1H, NH), 7.30 (m, 25H, Ar—H). ES-MS calcd for C$_{145}$H$_{237}$N$_2$O$_{23}$P: 2405.7. Found: 1204.4 (M+2H$^+$).

Example 76 Preparation of Compound 86

In a similar method as described for 48, compound 85 (12.0 mg, 0.005 mmol) was converted to 86 (9.5 mg, 97%). $R_f$=0.46 (chloroform:methanol: water, 3:1:1). $[\alpha]_D^{20}$=−6.6 (c 0.1, chloroform/methanol, 4:1). ES-MS calcd for C$_{110}$H$_{207}$N$_2$O$_{23}$P: 1955.5. Found: 1954.5 (M−H, negative mode).

Example 77 Preparation of Compound 87

In a similar method as described for 78, lipid acid 20 (547.9 mg, 1.33 mmol) was treated with EDCI (286.82 mg, 1.33 mmol), DMAP (85.36 mg, 1.15 mmol) and 28 (706.14 mg, 1.46 mmol) in dry CH$_2$Cl$_2$ (14.0 ml) to give 87 (1.08 g, 92%) after flash chromatography (ethyl acetate:hexane, 1:9). TLC: $R_f$=0.31 (ethyl acetate:hexane, 1:7). $[\alpha]_D^{20}$=+33.1 (c 1.0, chloroform). $^1$H NMR (300 MHz, CDCl$_3$): δ 0.88 (t, J=6.5 Hz, 6H, 2, CH$_3$), 1.25 (m, 36H), 1.40 (m, 4H), 2.35 (dd, J=15.0, 6.0 Hz, 1H), 2.60 (dd, J=15.0, 6.5 Hz, 1H), 3.28 (m, 1H), (3.41 (m, 1H), 3.63 (m, 1H), 3.72 (dd, J=9.5, 9.5 Hz, 1H), 3.79 (dd, J=10.0, 10.0 Hz, 1H), 3.91-4.10 (m, 3H), 4.23 (m, 1H), 4.23 (m, 1H), 4.30 (dd, J=10.0, 4.5 Hz, 1H), 4.67 (d, J=12.0 Hz, 1H), 4.76 (d, J=12.0 Hz, 1H), 4.94 (d, J=3.5 Hz, 1H, H-1), 5.23-5.29 (m, 3H), 5.41 (dd, J=10.0, 10.0 Hz, 1H, H-3), 5.52 (s, 1H), 5.90 (m, 1H), 7.34 (m, 3H), 7.44 (m, 2H).

Example 78 Preparation of Compound 88

Acetonitrile (140 ml) was added to 87 (1.655 g; 1.863 mmol) and cooled 0° C. To this suspension was added BH$_3$.Me$_2$NH (550.8 mg, 9.49 mmol), stirred for three minutes and then treated slowly with BF$_3$.OEt$_2$ (1.2 ml). After the addition, the reaction was allowed to stir at 0° C. and then 45 minutes at room temperature. The clear reaction mixture was poured into a separate funnel containing saturated NaHCO$_3$ (50.0 ml), the water layer was then separated and washed with ethyl acetate (150 ml). Combined organic layers were concentrated to dryness and its remainder was purified by flash silica gel chromatography (ethyl acetate:hexane, 1:7) to give compound 88 (1.25 g, 72%). TLC: $R_f$=0.14 (hexane:ethyl acetate, 7:1). $[\alpha]_D^{20}$=+35.6 (c 1.0, chloroform). $^1$H NMR (300 MHz, CDCl$_3$): δ 0.88 (m, 6H, 2CH$_3$), 1.25 (m, 36H), 1.50-1.60 (m, 4H), 2.45 (dd, J=15.0, 5.0 Hz, 1H), 2.67 (dd, J=15.0, 7.0 Hz, 1H), 3.04 (d, J=2.5 Hz, 1H), 3.42 (m, 2H), 3.66-3.87 (m, 6H), 4.00 (m, 2H), 4.20 (m, 1H), 4.58 (d, J=12.0 Hz, 1H), 4.64 (d, J=12.0 Hz, 1H), 4.68 (d, J=12.0 Hz, 1H), 4.73 (d, J=12.0 Hz, 1H), 4.94 (d, J=3.5 Hz, 1H, H-1), 5.12-5.33 (m, 4H), 5.90 (m, 1H), 7.30 (m, 5H).

Example 79 Preparation of Compound 89

In a similar method as described for 32, compound 88 (1.21 g; 1.364 mmol) was treated with 1H-tetrazole (288 mg; 4.11 mmol), dibenzyl diisopropylphosphoramidite (916 µl) and then with m-CPBA (942 mg, 5.456 mmol). Flash silica gel column (acetone:hexane, 1:7) provided compound 89 in 72% yield. TLC: $R_f$=0.53 (hexane/ethyl acetate, 4:1). $[\alpha]_D^{20}$=+37.6 (c 1.0, chloroform). $^1$H NMR (300 MHz, CDCl$_3$): δ 0.88 (t, J=6.5 Hz, 6H. 2CH$_3$), 1.25 (m, 36H), 1.40 (m, 4H), 2.31 (dd, J=16.0, 6.5 Hz, 1H), 2.53 (dd, J=16.0, 6.0 Hz, 1H), 3.19 (m, 1H), 3.33 (m, 1H), 3.55 (m, 1H), 3.72 (m, 2H), 3.90-4.04 (m, 3H), 4.20 (m, 1H), 4.46 (d, J=12.0 Hz, 1H), 4.53-4.63 (m, 3H), 4.81 (d, J=12.0 Hz, 1H), 4.92 (m, 5H), 5.21-5.33 (m, 3H), 5.39 (dd, J=10.0, 10.0 Hz, 1H, H-3), 5.90 (m, 1H), 7.30 (m, 15H, Ar—H).

Example 80 Preparation of Compound 90

In a similar method as described for 42, compound 89 (1.13 g, 0.98 mmol) was treated with saturated solution of [bis(methyldiphenylphosphine)](1,5-cyclooctadiene) iridium(I) hexafluoro-phosphate (25.2 mg, 0.03 mmol) with hydrogen gas in anhydrous THF (23 ml) and followed by the usual work up. Impurities from crude 90 were partially extracted into hexane and this step was repeated a few times until pure 90 was obtained in 79% yield (860.8 mg). TLC: $R_f$=0.48 (hexane:ethyl acetate, 4:1). $[\alpha]_D^{20}$=+16.2 (c 0.5, chloroform). $^1$H NMR (300 MHz, CDCl$_3$): δ 0.88 (t, J=6.5 Hz, 6H, 2CH$_3$), 1.25 (br s, 36H), 1.45 (m, 4H), 2.30 (dd, J=16.0, 6.0 Hz, 1H), 2.51 (dd, J=16.0, 6.0 Hz, 1H), 3.19 (m, 1H), 3.32 (m, 0.1H), 3.53-3.65 (m, 3H), 3.75 (dd, J=11.0, 2.0 Hz, 1H), 3.94 (m, 1H), 4.17 (m, 1H), 4.42 (d, J=12.0 Hz, 1H), 4.45 (m, 1H, H-4), 4.52 (d, J=12.0 Hz, 1H), 4.57 (d, J=12.0 Hz, 1H), 4.72 (d, J=12.0 Hz, 1H), 4.86-4.95 (m, 4H), 5.28 (dd, J=3.5, 3.5 Hz, 1H, H-1), 5.33 (d, J=10.0 Hz, 1H, NH), 5.40 (dd, J=10.5, 9.5 Hz, 1H, H-3), 7.30 (m, 15H, Ar—H).

Example 81 Preparation of Compound 91

In a similar method as described for 43, compound 90 (900 mg, 0.82 mmol) was treated with trichloroacetonitrile (1 ml) and DBU (4 drops) at room temperature for 2 h. The solvent was removed and the residue purified by flash silica gel chromatography (ethyl acetate:hexane, 1:4 and 1:3.5, with 0.5% triethyl amine) to give 91 (626 mg, 61%). TLC: $R_f$=0.30 (ethyl acetate hexane, 1:3). $[\alpha]_D^{20}$=+42.7 (c 2.0, chloroform). $^1$H NMR (300 MHz, CDCl$_3$): δ=0.88 (t, J=6.5 Hz, 6H, 2CH$_3$), 1.25 (br s, 36H), 1.40 (m, 4H), 2.37 (dd, J=15.5, 6.0 Hz, 1H), 2.53 (dd, J=15.5, 6.0 Hz, 1H), 3.21 (m, 1H), 3.34 (m, 1H), 3.57 (m, 1H), 3.73 (d, J=2.5 Hz, 2H), 4.04 (m, 1H), 4.15 (ddd, J=9.5, 8.5, 3.5 Hz, 1H, H-2), 4.45 (d, J=12.0 Hz, 1H), 4.50 (d, J=12.0 Hz, 1H). 4.53 (d, J=12.0 Hz, 1H), 4.80 (m, 1H), 4.83 (d, J=12.0 Hz, 1H), 4.95 (m, 4H), 5.30 (d, J=8.5 Hz, 1H, NH), 5.43 (dd, J=10.5, 9.5 Hz, 1H, H-3), 6.45 (d, J=3.5 Hz, 1H, H-1), 7.30 (m, 15H, Ar—H), 8.75 (s, 1H, NH).

Example 82 Preparation of Compound 92

In a similar method as described for 44, the mixture of imidate 91 (221.1 mg, 0.17 mmol), compound 79 (109.7 mg, 0.15 mmol) and molecular sieves (4 A, 500 mg) in anhydrous CH$_2$Cl$_2$ (4 ml) was treated with diluted BF$_3$ diethyl etherate solution (75 µl). This diluted BF$_3$ etherate solution was prepared by diluting 50 µl BF$_3$ etherate solution with 300 µl of anhydrous CH$_2$Cl$_2$. Followed by usual work up and silica gel chromatography (ethyl acetate:CH$_2$Cl$_2$:hexane, 1:1:2) afforded pure compound 92 (183.1 mg, 68%). TLC: R$_f$=0.35 (ethyl acetate:hexane, 1:2). [α]$_D^{20}$=+21.2 (c 0.5, chloroform). $^1$H NMR (500 MHz, CDCl$_3$): δ=0.88 (t, J=6.5 Hz, 9H, 3CH$_3$), 1.26 (m, 54H), 1.42-1.60 (m, 6H), 2.34 (dd, J=16.0, 6.0 Hz, 1H), 2.44 (dd, J=16.0, 5.0 Hz, 1H), 2.47 (dd, J=15.0, 5.0 Hz, 1H), 2.63 (dd, J=15.0, 7.5 Hz, 1H), 3.11 (d, J=3.5 Hz, 1H, OH), 3.21 (m, 1H), 3.35 (m, 1H), 3.54 (m, 1H), 3.65 (m, 3H), 3.82 (m, 4H), 3.92 (ddd, J=10.0, 10.0, 3.5 Hz, 1H, H-2), 4.07 (br d, J=9.5 Hz, 1H), 4.45 (d, J=11.5 Hz, 1H), 4.47-4.61 (m, 7H), 4.65 (d, J=12.0 Hz, 1H), 4.65 (m, 1H), 4.70 (d, J=11.5 Hz, 1H), 4.80 (d, J=8.0 Hz, 1H, H-1'), 4.90 (m, 5H), 5.16 (dd, J=9.5H, 9.5 Hz, 1H), 5.26 (d, J=10.0 Hz, 1H, NH), 5.37 (m, 2H). 7.30 (m, 25H, Ar—H).

Example 83 Preparation of Compound 93

In a similar method as described for 85, compound 92 (173.9 mg) was converted into its free amino compound with Zn powder (475 mg) and acetic acid (4 ml). The mixture of the amine compound was coupled with lipid acid 20 (251 mg, 0.58 mmol) using DCC (205.83 mg, 1.0 mmol). After usual work up and silica gel chromatography (acetone:hexane:chloroform, provided pure 93 (96.3 mg, 45%). TLC: R$_f$=0.30 (hexane dichloromethane:acetone, 6:2:1) [α]$_D^{20}$=+22.0 (c 1.0, chloroform). $^1$H NMR (500 MHz, CDCl$_3$): δ=0.88 (t, J=6.5 Hz, 21H, 7CH$_3$), 1.24 (m, 126H), 1.30-1.50 (m, 14H), 2.21-2.31 (m, 4H), 2.32 (dd, J=16.0, 6.5 Hz, 1H), 2.42 (dd, J=15.0, 5.0 Hz, 1H), 2.50 (dd, J=15.5, 5.5 Hz, 1H), 2.61 (dd, J=15.5, 7.0 Hz, 1H), 3.18 (m, 1H), 3.28-3.41 (m, 5H), 3.49-3.56 (m, 4H), 3.61-3.87 (m, 8H), 4.02 (m, 1H), 4.28 (ddd, J=10.5, 9.5, 3.5 Hz, 1H, H-2), 4.43 (m, 4H), 4.51 (d, J=11.5 Hz, 1H), 4.53 (d, J=11.5 Hz, 1H), 4.69 (d, J=11.5 Hz, 1H), 4.83 (d, J=8.0 Hz, 1H, H-1'), 4.89 (m, 5H), 5.19 (dd, J=10.5, 9.5 Hz, 1H), 5.36 (dd, J=10.5, 9.5 Hz, 1H), 6.44 (d, J=9.5 Hz, 1H, NH), 6.57 (d, J=7.5 Hz, 1H, NH), 7.30 (m, 25H, Ar—H).

Example 84 Preparation of Compound 94

In a similar method as described for 33, compound 93 (60.8 mg, 0.027 mmol) was converted to 94 which was purified by silica gel chromatography (chloroform:methanol: water acetic acid, 15:1:0.1:0.1) to give pure 94 (26.9 mg, 55%) TLC: R$_f$=0.32 (chloroform:methanol: water:acetic acid, 10:1:0.1:0.1). [α]$_D^{20}$=+15.0 (c 1.0, chloroform). ES-MS calcd for C$_{104}$H$_{201}$N$_2$O$_{20}$P: 1829.5. found: 1829.5 (negative mode, M-H, $^{13}$C isotopic peak).

Example 85 Preparation of Compound 95

Compound 27 (500 mg, 1.03 mmol) and benzyl trichloroacetimidate (521 mg, 2.06 mmol) were dissolved in dry dichloromethane:hexane, 1:2 (15 ml) and molecular sieves (4 Å, ~1.0 g) was added. The mixture was stirred at room temperature for 15 min and trifluoromethane sulfonic acid (460 mg, 28 µl, 0.31 mmol) was added. The reaction was continued for 2 h and then triethyl amine (0.2 ml) was added. The solid was filtered off through celite and washed with dichloromethane. The filtrate was concentrated in vacuo and the residue purified by flash silica gel chromatography to give 95 (300 mg, 56%). TLC: R$_f$=0.36 (ethyl acetate:hexane, 1:4). [α]$_D^{20}$=+93.8 (c 0.8, CHCl$_3$). $^1$H NMR (300 MHz, CDCl$_3$): δ=1.45 (s, 3H, CH$_3$), 1.55 (s, 3H, CH$_3$), 3.62 (dd, J=10.0, 8.5 Hz, 1H), 3.70-3.88 (m, 5H), 3.98 (ddd, J=10.0, 10.0, 3.5 Hz, 1H), 4.47 (d, J=12.0 Hz, 1H), 4.63 (d, J=12.0 Hz, 1H), 4.68 (d, J=12.0 Hz, 1H), 4.71 (d, J=12.0 Hz, 1H), 4.75 (d, J=12.0 Hz, 1H), 4.86 (d, J=12.0 Hz, 1H), 4.93 (d, J=3.5 Hz, 1H, H-1), 5.09 (d, J=10.0 Hz, 1H, NH), 7.30 (m, 10H, Ar—H).

Example 86 Preparation of Compound 96

Compound 95 (280 mg, 0.49 mmol) was treated with acetic acid:water (4:1, 20 ml) at 45° C. for 2 h. Usual work-up and flash silica gel chromatography (toluene:acetone, 4:1) gave 96 (247 mg, 95%). TLC: R$_f$=0.20 (toluene:acetone, 3:1). [α]$_D^{20}$=+90.0 (c 0.5, CHCl$_3$). $^1$H NMR (300 MHz, CDCl$_3$): δ=2.00 (br s, 1H, OH), 2.60 (br s, 1H, OH), 3.62-3.73 (m, 3H), 3.81 (br s, 2H), 3.98 (ddd, J=10.0, 10.0, 4.0 Hz, 1H, H-2), 4.50 (d, J=11.5 Hz, 1H), 4.66 (d, J=12.0 Hz, 1H), 4.70 (d, J=11.5 Hz, 1H), 4.72 (d, J=12.0 Hz, 1H), 4.77 (d, J=11.5 Hz, 1H), 4.82 (d, J=11.5 Hz, 1H), 4.93 (d, J=4.0 Hz, 1H, H-1), 5.19 (d, J=10.0 Hz, 1H, NH), 7.30 (m, 10H, Ar—H). ES-MS calcd for C$_{23}$H$_{26}$Cl$_3$NO$_7$: 533.1. Found: 533.8 (M+H).

Example 87 Preparation of Compound 97

Compound 96 (450 mg, 0.84 mmol) was dissolved in acetic acid (30 mg) and treated with zinc (6.0 g) at room temperature for 6 h. The solid was filtered off and washed with acetic acid, and the filtrate was concentrated in vacuo. The residue was passed through a short silica gel column (6% to 8% dichloromethane in methanol) to give 97 (300 mg, 95%). TLC: R$_f$=0.20 (6% methanol in dichloromethane). [α]$_D^{20}$=+133.0 (c 0.2, methanol). $^1$H NMR (300 MHz, CD$_3$OD): δ=3.10 (dd, J=10.0, 3.5 Hz, 1H, H-2), 3.57-3.82 (m, 5H), 4.60 (d, J=11.5 Hz, 1H), 4.69 (d, J=11.0 Hz, 1H), 4.75 (d, J=11.5 Hz, 1H), 5.06 (d, J=11.0 Hz, 1H), 5.23 (d, J=3.5 Hz, 1H, H-1), 7.35 (m, 10H, Ar—H).

Example 88 Preparation of Compound 98

In a similar method as described for 55, compound 97 (100 mg, 0.28 mmol) was treated with 23 (162 mg, 0.25 mmol) and DCC (209 mg, 1.02 mmol) in dichloromethane:dimethyl formamide (5:1, 6 ml). The usual work up followed by flash silica gel chromatography (chloroform:acetone, 9:1) afforded 98 (93 mg, 38%). TLC: R$_f$=0.30 (dichloromethane:methanol, 100:2). [α]$_D^{20}$=+52.0 (c 0.4, chloroform). $^1$H NMR (300 MHz, CDCl$_3$): δ=0.88 (t, J=6.5 Hz, 6H, 2CH$_3$), 1.25 (br s, 54H), 1.45-1.60 (m, 6H), 2.00 (m, 1H, OH), 2.29 (dd, J=15.5, 5.5 Hz, 1H), 2.40 (m, 3H), 2.50 (d, J=1.5 Hz, 1H, OH), 3.37 (t, J=6.5 Hz, 2H), 3.61-3.80 (m, 5H), 4.30 (ddd, J=9.5, 9.5, 3.5 Hz, 1H, H-2), 4.48 (d, J=12.0 Hz, 1H), 4.65 (d, J=11.5 Hz, 1H), 4.70 (d, J=12.0 Hz, 1H), 4.73 (d, J=11.5 Hz, 1H), 4.89 (d, J=3.5 Hz, 1H, H-1), 5.07 (m, 1H), 5.96 (d, J=8.5 Hz, 1H, NH), 7.30 (m, 10H, Ar—H). ES-MS calcd for C$_{60}$H$_{101}$NO$_9$: 979.7. Found: 980.9 (M+H).

Example 89 Preparation of Compound 99

In a similar method as described for 44, the mixture, 91 (188 mg, 0.15 mmol), 98 (93 mg, 0.10 mmol) molecular sieves (4 Å, 1.0 g) and dry dichloromethane (3 ml) was treated with BF$_3$ etherate solution (0.05 M in dichloromethane, 0.6 ml). The usual work up followed by repeated flash silica gel chromatography (hexane:ethyl acetate, 2.5:1 and 2:1; toluene:acetone, 8:1) to give 99 (109 mg, 56%). TLC: R$_f$=0.33 (hexane:ethyl acetate, 2:1). [α]$_D^{20}$=+24.0 (c 0.3, chloroform). $^1$H NMR (500 MHz, CDCl$_3$): δ=0.88 (t, J=6.5 Hz, 15H, 5 CH₃), 1.25 (m, 90H), 1.40-1.58 (m, 10H), 2.25-2.45 (m, 6H), 2.95 (br s, 1H, OH), 3.21 (m, 1H), 3.36 (m, 3H), 3.47-3.53 (m, 2H), 3.57-3.67 (m, 4H), 3.72 (m, 2H), 3.80 (m, 2H), 4.03 (br d, J=11.0 Hz, 1H), 4.25 (ddd, J=10.0, 9.0, 35 Hz, 1H, H-2), 4.44 (d, J=111.5 Hz, 1H), 4.48 (m, 3H), 4.59 (m, 2H), 4.67 (d, J=11.5 Hz, 1H), 4.69 (d, J=11.5 Hz, 1H), 4.75 (d, J=11.5 Hz, 1H), 4.85-4.92 (m, 6H), 5.04 (m, 1H), 5.36 (m, 2H), 5.80 (d, J=9.0 Hz, 1H, NH), 7.30 (m, 25H, Ar—H).

Example 90 Preparation of Compound 100

In a similar method as described for 45, compound 99 (95 mg, 0.046 mmol) was converted into its free amino compound 100 using zinc powder (2.0 g) and acetic acid (20 ml). The crude compound was freeze dried from dioxane to give 100 (85 mg, 97%). TLC: R$_f$=0.11 (2% methanol in dichloromethane).

Example 91 Preparation of Compound 101

In a similar method as described for 45, the free amino compound, 100 (42 mg, 0.02 mmol) was coupled with lipid acid, 20 (36.8 mg, 0.09 mmol) using DCC (28 mg, 0.13 mmol) in dry dichloromethane (3 ml). The usual work up followed by flash silica gel chromatography (hexane:chloroform:acetone, 6:3:1.5) afforded 101 (38 mg, 75%). TLC: R$_f$=0.50 (hexane:chloroform acetone, 6:3:2). $[α]_D^{20}$=+21.2 (c 0.4, chloroform). ¹H NMR (600 MHz, CDCl₃): δ=0.86 (m, 21H, 7CH₃), 1.23-1.60 (m, 140H), 2.20-2.39 (m, 8H), 2.47 (dd, J=15.5, 5.5 Hz, 1H), 3.17 (m, 1H), 3.31-3.39 (m, 5H), 3.50-3.67 (m, 7H), 3.68-3.78 (m, 4H), 3.84 (dd, J=11.0, 3.5 Hz, 1H), 3.96 (dd, J=11.0, 3.0 Hz, 1H), 4.21 (ddd, J=10.5, 9.0, 3.0 Hz, 1H, H-2), 4.40 (d, J=12.0 Hz, 1H), 4.43 (d, J=12.0 Hz, 1H), 4.44 (m, 1H), 4.47 (d, J=12.0 Hz, 1H), 4.64 (d, J=12.0 Hz, 1H), 4.65 (d, J=12.0 Hz, 1H), 4.87 (m, 7H), 5.03 (m, 1H), 5.34 (dd, J=10.5H, 9.0 Hz, 1H), 5.75 (d, J=9.0 Hz, 1H, NH), 6.57 (d, J=9.0 Hz, 1H, NH), 7.30 (m, 25H, Ar—H).

Example 92 Preparation of Compound 102

In a similar method as described for 33, under hydrogen atmosphere compound 101 (20 mg, 8.78 μmol) was converted to 102 by palladium on charcoal (5%, 50 mg) in THF-acetic acid (10:1, 50 ml) for 24 h. Usual work-up and flash silica gel chromatography purification (chloroform:methanol:water: acetic acid, 9:1:0.1:0.1 and 8:1:0.1:0.1) gave 102 (12 mg, 75%). TLC: R$_f$=0.38 (chloroform:methanol: water:ammonium hydroxide, 7:3:0.4:0.2). $[α]_D^{20}$=+2.0 (c 0.2, chloroform:methanol, 4:1). ES-MS calcd for $C_{104}H_{201}N_2O_{20}P$: 1829.4. found: 1829.5 (negative mode, M−H, ¹³C isotopic peak).

Example 93 Preparation of Compound 103

In a similar method as described for 101, compound 100 (42 mg, 0.02 mmol) and 17 (30 mg, 0.09 mmol) were treated with DCC (28 mg, 0.134 mmol) in dry dichloromethane (3 ml) to give 103 (37 mg, 76%) which was purified through repeated flash silica gel chromatography (hexane:ethyl acetone, 2:1; hexane:acetone, 3:1). TLC: R$_f$=0.39 (hexane: chloroform:acetone, 6:3:2). $[α]_D^{20}$=+21.2 (c 0.4, chloroform). ¹H NMR (600 MHz, CDCl₃): δ=0.86 (m, 18H, 6CH₃), 1.23-1.60 (m, 120H), 2.23 (dd, J=15.0, 6.5 Hz, 1H), 2.25-2.39 (m, 7H), 2.44 (dd, J=15.5, 5.5 Hz, 1H), 3.17 (m, 1H), 3.34 (m, 3H), 3.50-3.76 (m, 12H), 3.89 (dd, J=11.0, 3.0 Hz, 1H), 4.20 (ddd, J=10.0, 9.0, 3.0 Hz, 1H, H-2), 4.37 (d, J=11.5 Hz, 1H), 4.39-4.43 (m, 3H), 4.46 (d, J=11.5 Hz, 1H), 4.51 (d, J=8.0 Hz, 1H), 4.53 (d, J=11.5 Hz, 1H), 4.61 (d, J=11.5 Hz, 1H), 4.65 (d, J=12.0 Hz, 1H), 4.82-4.90 (m, 6H), 5.03 (m, 1H), 5.22 (dd, J=10.0, 9.0 Hz, 1H), 5.71 (d, J=9.0 Hz, 1H, NH), 6.38 (d, J=8.0 Hz, 1H, NH), 7.30 (m, 30H, Ar—H).

Example 94 Preparation of Compound 104

In a similar way as described for 102, compound 103 (16 mg, 7.27 μmol) was treated with palladium on charcoal (50 mg) under hydrogen atmosphere in THF:acetic acid (10:1, 50 ml) to give 104 (10.5 mg, 87%) which was purified by flash silica gel chromatography (chloroform:methanol: water:acetic acid, 9:1:0.1:0.1, 8:10.1:0.1 and 6:1:0.1:0.1). TLC: R$_f$=0.20 (chloroform:methanol: water:ammonium hydroxide, 7:3:0.4:0.2). $[α]_D^{20}$=−3.5 (c 0.2, chloroform:methanol, 4:1). ES-MS calcd for $C_{92}H_{177}N_2O_{20}P$: 1661.3. found: 1661.3 (negative mode, M−H, ¹³C isotopic peak).

Example 95 Preparation of Liposomal Formulations

Synthetic Lipid-A analogs 33, 48, 54, 58, 70, 77, 86, 94, 102, 104 and the commercial Lipid-A product Natural Lipid-A, were incorporated into liposomal formulations. The Natural Lipid-A was purchased from AVANTI and it contained a mixture of Lipid-A analogs extracted from *Salmonella* bacterial cell wall.

Typically, the liposomal formulation was composed of 400 μg of MUC1-based lipopeptide BP1-148, H₂N-STAPPAH-GVTSAPDTRPAPGSTAPPK(Pal)G-OH, 200 μg of Lipid-A analog, 6.94 mg of cholesterol, 1.46 mg of dimyristoyl phosphatidylglycerol (DMPC) and 11.62 mg of dipalmitoyl phosphatidylcholine (DPPC) per 1 ml of saline (0.9% NaCl solution).

The liposomal constructs were formulated by first dissolving the phospholipids, cholesterol and Lipid A analog in tert-butanol at about 53° C. Lipopeptide and water (5%, v/v) were then added to the tert-butanol solution. The resulting clear 95% tert-butanol solution was injected into about 4 volumes of rapidly stirred water at about 50° C., using a glass syringe with an 18-gauge needle. The small unilamellar vesicles (SUV) formed in this process were cooled, sterilized by filtration through a 0.22 μm membrane filter, filled into vials and lyophilized. The dry powder was re-hydrated with sterile saline before injection, resulting in the formation of multilamellar large vesicles (MLV). The liposomes formed are used to immunize mice.

Example 96 Mice Immunized with Liposomal Vaccines

Groups of C57-Black mice were immunized subcutaneously with the liposomal vaccine containing 40 μg of MUC1-based lipopeptide BP1-148 (FIG. 34), which has the peptide sequence of H₂N-STAPPAHGVTSAPDTRPAPGSTAPPK (Pal) G-OH, and 20 μg of Lipid-A analog per dose. Nine days after vaccine injection mice were sacrificed and lymphocytes were taken from the draining lymph nodes (local response) or from the spleens (systemic response) to determine the immune response in each group. The lymphocytes taken from immunized mice were incubated in in vitro cultures in the presence of MUC1-based boosting antigen BP1-151, which has the peptide sequence H₂N-STAPPAHGVTSAPDTRPA-PGSTAPPK-OH.

Example 97 Measurement of T-Cell Proliferation

T-cell proliferation was evaluated using a standard ³H thymidine incorporation assay. Briefly, nylon wool passed inguinal lymph node lymphocytes from each mouse were added to a culture containing 106 native mitomycin C treated syngeneic splenocytes, which serves as antigen presenting cells (APCs). To each well 20 µg of MUC1-based boosting peptide BP1-151, H$_2$N-STAPPAHGVTSAPDTRPAPG-STAPPK-OH (single letter amino acid code, Table 8), was added for positive control; and cultures containing no antigen or peptide BP1-72, which has the peptide sequence H$_2$N-EAIQPGCIGGPKGLPGLPGP-OH, were used as negative control. The culture was incubated for 72 h in a total volume of 250 µl well, followed by adding 1 µCi of $^3$H-thymidine in a volume of 50 µl. The plates were incubated for an additional 18-20 h. Cells were harvested and [$^3$H]dTh incorporation was measured by liquid scintillation counter. T-cell proliferation results corresponding to various liposomal vaccines adjuvanted, with different Lipid-A analogs are summarized in Tables 1-Table 3 and FIG. 31-FIG. 33.

LIST OF TABLES

Table 1 T-cell proliferation and Interferon-gamma production of Lipid-A analogs 33, 48 and 58

Table 2 T-cell proliferation and Interferon-gamma production of Lipid-A analogs 48, 54, 70, 77 and 86

Table 3 T-cell proliferation and Interferon-gamma production of Lipid-A analogs 86, 94, 102 and 104

Table 4 Comparison of lethal toxicity of synthetic and natural Lipid-A analogs

Table 5 Common abbreviations used in the text

Table 6 List of structures of Lipid-A analogs prepared in this invention

Table 7 List of IUPAC names of compounds prepared in this invention

Table 8 Single letter and three letter codes for amino acids

Table 9: Enumeration of Some Preferred Embodiments

TABLE 1

T-cell proliferation and Interferon-gamma production of Lipid-A analogs 33, 48 and 58

| Lipid-A Analogs | T-cell-Proliferation (CPM) | Interferon-gamma (IFN-γ, pg/ml) |
| --- | --- | --- |
| 33 | 822 | 0 |
| 48 | 14112 | 2430 |
| 58 | 686 | 0 |
| Natural Lipid-A | 14172 | 2938 |
| saline | 3274 | 0 |

TABLE 2

T-cell proliferation and Interferon-gamma production of Lipid-A analogs 48, 54, 70, 77 and 86

| Lipid-A analogs | T-cell-Proliferation (CPM) | Interferon-gamma (IFN-γ, pg/ml) |
| --- | --- | --- |
| 48 | 28149 | 18261 |
| 54 | 32976 | 36166 |
| 70 | 25034 | 17321 |
| 77 | 2565 | 0 |
| 86 | 52382 | 36461 |
| Natural Lipid-A | 37851 | 31741 |
| Saline | 183 | 0 |

Examples 98 Measurement of Interferon-Gamma (IFN-γ) Production

Interferon-gamma (IFN-γ) levels were determined in the cell culture supernatants using enzyme-linked immunoabsorbent assay (ELISA). 96-Well plates were coated with 50 µl of catcher Mabs in 50 µl of R4.6AZ at 37° C. for 30 min. The plates were then washed and incubated with test samples for 45 min. After two washes the second biotinylated antibody, XMG1.2 was added. After washing, peroxidase-conjugated streptavidin was added and incubated again for 30 min. Finally, 100 µl of horseradish peroxidase (HRPO) substrate solution was added. The optical density was measured with a Thermomax ELISA reader at 405 nm wavelength in kinetic mode for 10 min. The interferon-gamma (IFN-γ) levels corresponding to various Lipid-A analogs are shown in Table 1-Table 3 and FIG. 31-FIG. 33.

TABLE 3

T-cell proliferation and Interferon-gamma production of Lipid-A analogs 86, 94, 102 and 104

| Lipid-A analogs | T-cell-Proliferation (CPM) | Interferon-gamma (IFN-γ, pg/ml) |
| --- | --- | --- |
| 86 | 15486 | 17697 |
| 94 | 10882 | 2150 |
| 102 | 13389 | 10587 |
| 104 | 12635 | 14669 |
| Natural lipid-A | 14539 | 31166 |
| Saline | 5078 | 362 |

Example 99 Lethal Toxicity of Synthetic and Natural Lipid-A Analogs

Synthetic Lipid-A analog 86 and the Natural Lipid-A (see Example 95 for more detail) were tested for their lethal toxicity. Test methods and results are summarized below (Table 4)

a) Preparation of Lipid-A analog solution: 1 mg of Lipid-A analog was dissolved in 1 ml of 20% DMSO and diluted with saline to obtain 50 µg, 10 µg and 2 µg doses in 0.5 ml.

b) Preparation of Actinomycin D: 5 mg of Actinomycin D was dissolved in 1 ml of ethanol and diluted with saline to obtain a dose at 550 µg/kg in 0.5 ml.

c) Procedure: Various doses of Lipid-A analogs or solvent as control were injected intraperitoneally (i.p.) into C57-Black mice. Twenty minutes later all groups of mice were injected with 500 µl of Actinomycin D. Mice were then observed for mortality or any other symptoms of toxicity.

During the first 24 hour observation period all three mice injected with the high 50 µg dose of Natural Lipid-A as well as two mice injected with 10 µg dose of Natural Lipid-A were found dead (Table 4). The groups of mice injected with all three doses of synthetic Lipid-A analog 86, and mice injected with low 2 µg dose of Natural Lipid-A survived the study. No further mouse death was recorded after 24 hours and the experiment was terminated 4 days later. The results of this study showed that the synthetic Lipid-A analog 86 is much less toxic than the Natural Lipid-A product tested in this experiment.

TABLE 4

Comparison of lethal toxicity of synthetic and natural Lipid-A analogs

| Group | Lipid-A Analog | Dose (µg/µl) | Actinomycin D | No. Survived/No. Tested (+24 h) |
|---|---|---|---|---|
| 1 | 86 | 50/500 | + | 3/3 |
| 2 | 86 | 10/500 | + | 3/3 |
| 3 | 86 | 2/500 | + | 3/3 |
| 4 | Natural | 50/500 | + | 0/3 |
| 5 | Natural | 10/500 | + | 1/3 |
| 6 | Natural | 2/500 | + | 3/3 |
| 7 | Solvent | 0/500 | + | 3/3 |

The above examples described the detailed procedures for the synthesis of Lipid-A analogs and their intermediates, and the procedures to prepare liposomal vaccines, adjuvanted with synthetic Lipid-A analogs, to induce specific immune response in mice. The common abbreviations used in the text of this invention are listed in Table 5. The structures of Lipid-A analogs prepared and tested for their adjuvanticity are listed in Table 6. A complete list of IUPAC names of all compounds prepared in this invention is given in Table 7. For peptide sequence, single letter codes of amino acids are used in the present invention. For reference, please see the list of standard single letter and three letter codes of naturally occurring amino acids in Table 8.

TABLE 5

Common abbreviations used in the text

| All | allyl |
|---|---|
| APC | antigen presenting cell |
| $BF_3OEt_2$ | trifluoroboran diethyl etherate |
| Bn | benzyl |
| $^tBu$ | tert-butyl |
| m-CPBA | m-chloroperbenzoic acid |
| CPM | counts per minute |
| DBU | 1,8-diazabicyclo[5,4,0]undec-7-ene |
| DCC | dicyclohexylcarbodiimide |
| (−)-DIPCl | (−)-B-Chlorodiisopinocamphenylborane |
| DMAP | 4-dimethylaminopyridine |
| DMF | dimethylformamide |
| DMPC | dimyristoyl phosphatidyl glycerol |
| DPPC | dipalmitoyl phosphatidyl choline |
| DMSO | dimethyl sulfoxide |
| EDCI | 1-[3-(dimethylamino)propyl]-3-ethylcarbodiimide hydrochloride |
| ES-MS | electron spray mass spectrometry |
| Et | ethyl |
| Fmoc | 9-fluorenylmethoxylcarbonyl |
| IFN-γ | interferon-gamma |
| LPS | lipopolysaccharide |
| Me | methyl |
| MLV | multilamellar large vesicles |
| NBS | N-bromosuccinimide |
| NMM | N-methyl morpholine |
| NMR | nuclear magnetic resonance |
| Pal | palmitoyl |
| Ph | phenyl |
| Phth | phthalimido |
| iPr | isopropyl |
| Py | pyridine |
| SUV | small unilamellar vesicles |
| Tf | trifluoromethylsulfonyl |
| TFA | trifluoroacetic acid |
| THF | tetrahydrofuran |
| TLC | thin layer chromatography |
| Troc | trichloroethoxycarbonyl |
| Trt | triphenylmethyl |
| p-TsOH | p-toluenesulfonic acid |

TABLE 6

List of structures of Lipid-A analogs prepared in this invention

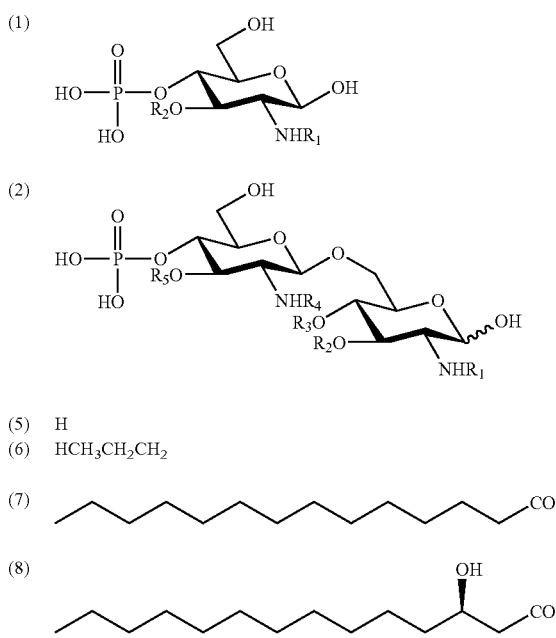

TABLE 6-continued

List of structures of Lipid-A analogs prepared in this invention (9) [structure]

(10) [structure]

(11) [structure]

(12) [structure]

(13) [structure]

(14) [structure]

| Compounds | Structure | $R_1$ | $R_2$ | $R_3$ | $R_4$ | $R_5$ |
|---|---|---|---|---|---|---|
| 33 | (1) | (12) | (7) | N/A | N/A | N/A |
| 48 | (2) | (11) | (5) | (5) | (9) | (10) |
| 54 | (2) | (10) | (5) | (5) | (10) | (10) |
| 58 | (2) | (10) | (5) | (5) | (12) | (10) |
| 70 | (2) | (10) | (6) | (5) | (10) | (10) |
| 77 | (2) | (10) | (8) | (5) | (12) | (10) |
| 86 | (2) | (10) | (8) | (5) | (10) | (10) |
| 94 | (2) | (13) | (8) | (5) | (13) | (13) |
| 102 | (2) | (14) | (5) | (5) | (13) | (13) |
| 104 | (2) | (14) | (5) | (5) | (8) | (13) |
| Natural Lipid-A | (2) | Unident. mixture | Unident. mixture | Unident. mixture | Unident. mixture | Unident. mixture |

TABLE 7

List of IUPAC names of compounds prepared in this invention

| Compound 1 | N-9-Fluorenylmethoxycarbonyl-L-aspartic acid tert-butyl ester |
| Compound 2 | (3S)-3-(9-Fluorenylmethoxycarbonylamino)-4-nonylamino-4-oxo-butyric acid tert-butyl ester |
| Compound 3 | (3S)-3-Amino-4-nonylamino-4-oxo-butyric acid tert-butyl ester |
| Compound 4 | (3S)-3-Tetradecanamido-4-nonylamino-4-oxo-butyric acid tert-butyl ester |
| Compound 5 | (3S)-3-Tetradecanamido-4-nonylamino-4-oxo-butyric acid |
| Compound 6 | 3-Hydroxytetradecanoic acid ethyl ester |
| Compound 7 | 3-Hydroxytetradecanoic acid, or 3-hydroxy-myristic acid |

TABLE 7-continued

List of IUPAC names of compounds prepared in this invention

| | |
|---|---|
| Compound 8 | (3R)-3-Hydroxytetradecanoic acid, (3R)-3-hydroxy-myristic acid |
| Compound 9 | (3R)-3-Hydroxytetradecanoic acid phenacyl ester |
| Compound 10 | (3R)-3-Dodecanoyloxytetradecanoic acid phenacyl ester |
| Compound 11 | (3R)-3-Tetradecanoyloxytetradecanoic acid phenacyl ester |
| Compound 12 | (3R)-3-Hexadecanoyloxytetradecanoic acid phenacyl ester |
| Compound 13 | (3R)-3-Dodecanoyloxytetradecanoic acid |
| Compound 14 | (3R)-3-Tetradecanoyloxytetradecanoic acid |
| Compound 15 | (3R)-3-Hexadecanoyloxytetradecanoic acid |
| Compound 16 | (3R)-3-Benzyloxytetradecanoic acid phenacyl ester |
| Compound 17 | (3R)-3-Benzyloxytetradecanoic acid |
| Compound 18 | Dodecyl trifluromethanesulphonate |
| Compound 19 | (3R)-3-Dodecyloxytetradecanoic acid phenacyl ester |
| Compound 20 | (3R)-3-Dodecyloxytetradecanoic acid |
| Compound 21 | (4R)-4-Hydroxypentadecene-1 |
| Compound 22 | (4R)-4-[(3R)-3-Dodecyloxytetradecanoyloxy]-pentadecene-1 |
| Compound 23 | (3R)-3-[(3R)-3-Dodecyloxytetradecanoyloxy]-tetradecanoic acid |
| Compound 24 | Benzyl 2-deoxy-2-(2,2,2-trichloroethoxycarbonylamino)-α-D-glucopyranoside |
| Compound 25 | Allyl 2-deoxy-2-(2,2,2-trichloroethoxycarbonylamino)-α-D-glucopyranoside |
| Compound 26 | Benzyl 2-deoxy-4,6-di-O-benzylidene-2-(2,2,2-trichloroethoxycarbonylamino)-α-D-glucopyranoside |
| Compound 27 | Benzyl 2-deoxy-4,6-di-O-isopropylidene-2-(2,2,2-trichloroethoxycarbonylamino)-α-D-glucopyranoside |
| Compound 28 | Allyl 2-deoxy-4,6-di-O-benzylidene-2-(2,2,2-trichloroethoxycarbonylamino)-α-D-glucopyranoside |
| Compound 29 | Benzyl 2-deoxy-4,6-di-O-benzylidene-2-(2,2,2-trichloroethoxycarbonylamino)-3-O-tetradecanoyl-α-D-glucopyranoside |
| Compound 30 | Benzyl 2-deoxy-4,6-di-O-benzylidene-2-[(3S)-3-tetradecanamido-4-nonylamino-4-oxo-butanamido]-3-O-tetradecanoyl-α-D-glucopyranoside |
| Compound 31 | Benzyl 6-O-benzyl-2-deoxy-2-[(3S)-3-tetradecanamido-4-nonylamino-4-oxo-butanamido]-3-O-tetradecanoyl-α-D-glucopyranoside |
| Compound 32 | Benzyl 6-O-benzyl-2-deoxy-4-O-(di-O-benzyl-phosphono)-2-[(3S)-3-tetradecanamido-4-nonylamino-4-oxo-butanamido]-3-O-tetradecanoyl-α-D-glucopyranoside |
| Compound 33 | 2-Deoxy-4-O-phosphono-2-[(3S)-3-tetradecanamido-4-nonylamino-4-oxo-butanamido]-3-O-tetradecanoyl-α/β-D-glucopyranose |
| Compound 34 | Benzyl 2-deoxy-2-phthalimido-β-D-glucopyranoside |
| Compound 35 | Benzyl 2-deoxy-2-phthalimido-6-O-triphenylmethyl-β-D-glucopyranoside |
| Compound 36 | Benzyl 2-deoxy-3,4-di-O-benzyl-2-phthalimido-6-O-triphenylmethyl-β-D-glucopyranoside |
| Compound 37 | Benzyl 2-deoxy-3,4-di-O-benzyl-2-phthalimido-β-D-glucopyranoside |
| Compound 38 | Benzyl 2-amino-2-deoxyl-3,4-di-O-benzyl-β-D-glucopyranoside |
| Compound 39 | Benzyl 2-deoxy-3,4-di-O-benzyl-2-[(3R)-3-hexadecanoyloxytetradecanamido]-β-D-glucopyranoside |
| Compound 40 | Benzyl 2-deoxy-3,4-di-O-benzyl-2-[(3R)-3-tetradecanoyloxytetradecanamido]-β-D-glucopyranoside |
| Compound 41 | Allyl 2-deoxy-4,6-di-O-benzylidene-3-O-[(3R)-3-tetradecanoyloxytetradecanoyl]-2-(2,2,2-trichloroethoxycarbonylamino)-α-D-glucopyranoside |
| Compound 42 | 2-Deoxy-4,6-di-O-benzylidene-3-O-[(3R)-3-tetradecanoyloxytetradecanoyl]-2-(2,2,2-trichloroethoxycarbonylamino)-α/β-D-glucopyranose |
| Compound 43 | 2-Deoxy-4,6-di-O-benzylidene-3-O-[(3R)-3-tetradecanoyloxytetradecanoyl]-2-(2,2,2-trichloroethoxycarbonylamino)-α-D-glucopyranosyl trichloroacetimidate |
| Compound 44 | Benzyl 2-deoxy-6-O-{2-deoxy-4,6-di-O-benzylidene-3-O-[(3R)-3-tetradecanoyloxytetradecanoyl]-2-(2,2,2-trichloroethoxycarbonylamino)-β-D-glucopyranosyl}-3,4-di-O-benzyl-2-[(3R)-3-hexadecanoyloxytetradecanamido]-α-D-glucopyranoside |
| Compound 45 | Benzyl 2-deoxy-6-O-{2-deoxy-4,6-di-O-benzylidene-2-[(3R)-3-dodecanoyloxytetradecanamido]-3-O-[(3R)-3-tetradecanoyloxytetradecanoyl]-β-D-glucopyranosyl}-3,4-di-O-benzyl-2-[(3R)-3-hexadecanoyloxytetradecanamido]-β-D-glucopyranoside |
| Compound 46 | Benzyl 2-deoxy-6-O-{6-O-benzyl-2-deoxy-2-[(3R)-3-dodecanoyloxytetradecanamido]-3-O-[(3R)-3-tetradecanoyloxytetradecanoyl]-β-D-glucopyranosyl}-3,4-di-O-benzyl-2-[(3R)-3-hexadecanoyloxytetradecanamido]-β-D-glucopyranoside |
| Compound 47 | Benzyl 2-deoxy-6-O-{6-O-benzyl-4-O-(di-O-benzyl-phosphono)-2-deoxy-2-[(3R)-3-dodecanoyloxytetradecanamido]-3-O-[(3R)-3-tetradecanoyloxytetradecanoyl]-β-D-glucopyranosyl}-3,4-di-O-benzyl-2-[(3R)-3-hexadecanoyloxytetradecanamido]-β-D-glucopyranoside |
| Compound 48 | 2-Deoxy-6-O-{2-deoxy-2-[(3R)-3-dodecanoyloxytetradecanamido]-4-O-phosphono-3-O-[(3R)-3-tetradecanoyloxytetradecanoyl]-β-D-glucopyranosyl}-2-[(3R)-3-hexadecanoyloxytetradecanamido]-α/β-D-glucopyranose |
| Compound 49 | Benzyl 2-deoxy-6-O-{2-deoxy-4,6-di-O-benzylidene-3-O-[(3R)-3-tetradecanoyloxytetradecanoyl]-2-(2,2,2-trichloroethoxycarbonylamino)-β-D-glucopyranosyl}-3,4-di-O-benzyl-2-[(3R)-3-tetradecanoyloxytetradecanamido]-β-D-glucopyranoside |
| Compound 50 | Benzyl 2-deoxy-6-O-{2-amino-2-deoxy-4,6-di-O-benzylidene-3-O-[(3R)-3-tetradecanoyloxytetradecanoyl]-β-D-glucopyranosyl}-3,4-di-O-benzyl-2-[(3R)-3-tetradecanoyloxytetradecanamido]-β-D-glucopyranoside |
| Compound 51 | Benzyl 2-deoxy-6-O-{2-deoxy-4,6-di-O-benzylidene-2-[(3R)-3-tetradecanoyloxytetradecanamido]-3-O-[(3R)-3-tetradecanoyloxytetradecanoyl]-β-D-glucopyranosyl}-3,4-di-O-benzyl-2-(3R)-3-tetradecanoyloxytetradecanamido]-β-D-glucopyranoside |
| Compound 52 | Benzyl 2-deoxy-6-O-{6-O-benzyl-2-deoxy-2-[(3R)-3-tetradecanoyloxytetradecanamido]-3-O-[(3R)-3-tetradecanoyloxytetradecanoyl]-β-D-glucopyranosyl}-3,4-di-O-benzyl-2-[(3R)-3-tetradecanoyloxytetradecanamido]-β-D-glucopyranoside |
| Compound 53 | Benzyl 2-deoxy-6-O-{6-O-benzyl-4-O-(di-O-benzyl-phosphono)-2-deoxy-2-[(3R)-3-tetradecanoyloxytetradecanamido]-3-O-[(3R)-3-tetradecanoyloxytetradecanoyl]-β-D-glucopyranosyl}-3,4-di-O-benzyl-2-[(3R)-3-tetradecanoyloxytetradecanamido]-β-D-glucopyranoside |
| Compound 54 | 2-Deoxy-6-O-{2-deoxy-4-O-phosphono-2-[(3R)-3-tetradecanoyloxytetradecanamido]-3-O-[(3R)-3-tetradecanoyloxytetradecanoyl]-β-D- |

TABLE 7-continued

List of IUPAC names of compounds prepared in this invention

| | |
|---|---|
| | glucopyranosyl}-2-[(3R)-3-tetradecanoyloxytetradecanamido]-α/β-D-glucopyranose |
| Compound 55 | Benzyl 2-deoxy-6-O-{2-deoxy-4,6-di-O-benzylidene-2-[(3S)-3-tetradecanamido-4-nonylamino-4-oxo-butanamido]-3-O-[(3R)-3-tetradecanoyloxytetradecanoyl]-β-D-glucopyranosyl}-3,4-di-O-benzyl-2-[(3R)-3-tetradecanoyloxytetradecanamido]-β-D-glucopyranoside |
| Compound 56 | Benzyl 2-deoxy-6-O-{6-O-benzyl-2-deoxy-2-[(3S)-3-tetradecanamido-4-nonylamino-4-oxo-butanamido]-3-O-[(3R)-3-tetradecanoyloxytetradecanoyl]-β-D-glucopyranosyl}-3,4-di-O-benzyl-2-[(3R)-3-tetradecanoyloxytetradecanamido]-β-D-glucopyranoside |
| Compound 57 | Benzyl 2-deoxy-6-O-{6-O-benzyl-4-O-(di-O-benzyl-phosphono)-2-deoxy-2-[(3S)-3-tetradecanamido-4-nonylamino-4-oxo-butanamido]-3-O-[(3R)-3-tetradecanoyloxytetradecanoyl]-β-D-glucopyranosyl}-3,4-di-O-benzyl-2-[(3R)-3-tetradecanoyloxytetradecanamido]-β-D-glucopyranoside |
| Compound 58 | 2-Deoxy-6-O-{2-deoxy-2-[(3S)-3-tetradecanamido-4-nonylamino-4-oxo-butanamido]-4-O-phosphono-3-O-[(3R)-3-tetradecanoyloxytetradecanoyl]-β-D-glucopyranosyl}-2-[(3R)-3-tetradecanoyloxytetradecanamido]-α/β-D-glucopyranose |
| Compound 59 | Benzyl 2-deoxy-4,6-di-O-benzylidene-2-phthalimido-β-D-glucopyranoside |
| Compound 60 | Benzyl 3-O-allyl-2-deoxy-6-O-triphenylmethyl-2-phthalimido-β-D-glucopyranoside |
| Compound 61 | Benzyl 3-O-allyl-4-O-benzyl-2-deoxy-6-O-triphenylmethyl-2-phthalimido-β-D-glucopyranoside |
| Compound 62 | Benzyl 3-O-allyl-4-O-benzyl-2-deoxy-2-phthalimido-β-D-glucopyranoside |
| Compound 63 | Benzyl 3-O-allyl-2-amino-4-O-benzyl-2-deoxy-β-D-glucopyranoside |
| Compound 64 | Benzyl 3-O-allyl-4-O-benzyl-2-deoxy-2-[(3R)-3-tetradecanoyloxytetradecanamido]-β-D-glucopyranoside |
| Compound 65 | Benzyl 3-O-allyl-4-O-benzyl-2-deoxy-6-O-{2-deoxy-4,6-di-O-benzylidene-3-O-[(3R)-3-tetradecanoyloxytetradecanoyl]-2-(2,2,2-trichloroethoxycarbonylamino)-β-D-glucopyranosyl}-2-[(3R)-3-tetradecanoyloxytetradecanamido]-β-D-glucopyranoside |
| Compound 66 | Benzyl 3-O-allyl-6-O-{2-amino-2-deoxy-4,6-di-O-benzylidene-3-O-[(3R)-3-tetradecanoyloxytetradecanoyl]-β-D-glucopyranosyl}-4-O-benzyl-2-deoxy-2-[(3R)-3-tetradecanoyloxytetradecanamido]-β-D-glucopyranoside |
| Compound 67 | Benzyl 3-O-allyl-4-O-benzyl-2-deoxy-6-O-{2-deoxy-4,6-di-O-benzylidene-2-[(3R)-3-tetradecanoyloxytetradecanamido]-3-O-[(3R)-3-tetradecanoyloxytetradecanoyl]-β-D-glucopyranosyl}-2-[(3R)-3-tetradecanoyloxytetradecanamido]-β-D-glucopyranoside |
| Compound 68 | Benzyl 3-O-allyl-4-O-benzyl-2-deoxy-6-O-{2-deoxy-6-O-benzyl-2-[(3R)-3-tetradecanoyloxytetradecanamido]-3-O-[(3R)-3-tetradecanoyloxytetradecanoyl]-β-D-glucopyranosyl}-2-[(3R)-3-tetradecanoyloxytetradecanamido]-β-D-glucopyranoside |
| Compound 69 | Benzyl 3-O-allyl-4-O-benzyl-2-deoxy-6-O-{2-deoxy-6-O-benzyl-4-O-(di-O-benzyl-phosphono)-2-[(3R)-3-tetradecanoyloxytetradecanamido]-3-O-[(3R)-3-tetradecanoyloxytetradecanoyl]-β-D-glucopyranosyl}-2-[(3R)-3-tetradecanoyloxytetradecanamido]-β-D-glucopyranoside |
| Compound 70 | 2-Deoxy-6-O-{2-deoxy-2-[(3R)-3-tetradecanoyloxytetradecanamido]-4-O-phosphono-3-O-[(3R)-3-tetradecanoyloxytetradecanoyl]-β-D-glucopyranosyl}-3-O-propyl-2-[(3R)-3-tetradecanoyloxytetradecanamido]-α/β-D-glucopyranose |
| Compound 71 | Benzyl 4-O-benzyl-2-deoxy-6-O-{2-deoxy-4,6-di-O-benzylidene-3-O-[(3R)-3-tetradecanoyloxytetradecanoyl]-2-(2,2,2-trichloroethoxycarbonylamino)-β-D-glucopyranosyl}-2-[(3R)-3-tetradecanoyloxytetradecanamido]-β-D-glucopyranoside |
| Compound 72 | Benzyl 4-O-benzyl-3-O-[(3R)-3-benzyloxytetradecanoyl]-2-deoxy-6-O-{2-deoxy-4,6-di-O-benzylidene-3-O-[(3R)-3-tetradecanoyloxytetradecanoyl]-2-(2,2,2-trichloroethoxycarbonylamino)-β-D-glucopyranosyl}-2-[(3R)-3-tetradecanoyloxytetradecanamido]-β-D-glucopyranoside |
| Compound 73 | Benzyl 6-O-{2-amino-2-deoxy-4,6-di-O-benzylidene-3-O-[(3R)-3-tetradecanoyloxytetradecanoyl]-β-D-glucopyranosyl}-4-O-benzyl-3-O-[(3R)-3-benzyloxytetradecanoyl]-2-deoxy-2-[(3R)-3-tetradecanoyloxytetradecanamido]-β-D-glucopyranoside |
| Compound 74 | Benzyl 4-O-benzyl-3-O-[(3R)-3-benzyloxytetradecanoyl]-2-deoxy-6-O-{2-deoxy-4,6-di-O-benzylidene-2-[(3S)-3-tetradecanamido-4-nonylamino-4-oxo-butanamido]-3-O-[(3R)-3-tetradecanoyloxytetradecanoyl]-β-D-glucopyranosyl}-2-[(3R)-3-tetradecanoyloxytetradecanamido]-β-D-glucopyranoside |
| Compound 75 | Benzyl 4-O-benzyl-3-O-[(3R)-3-benzyloxytetradecanoyl]-6-O-{6-O-benzyl-2-deoxy-2-[(3S)-3-tetradecanamido-4-nonylamino-4-oxo-butanamido]-3-O-[(3R)-3-tetradecanoyloxytetradecanoyl]-β-D-glucopyranosyl}-2-deoxy-2-[(3R)-3-tetradecanoyloxytetradecanamido]-β-D-glucopyranoside |
| Compound 76 | Benzyl 4-O-benzyl-3-O-[(3R)-3-benzyloxytetradecanoyl]-6-O-{6-O-benzyl-4-O-(di-O-benzyl-phosphono)-2-deoxy-2-[(3S)-3-tetradecanamido-4-nonylamino-4-oxo-butanamido]-3-O-[(3R)-3-tetradecanoyloxytetradecanoyl]-β-D-glucopyranosyl}-2-deoxy-2-[(3R)-3-tetradecanoyloxytetradecanamido]-β-D-glucopyranoside |
| Compound 77 | 2-Deoxy-6-O-{2-deoxy-2-[(3S)-3-tetradecanamido-4-nonylamino-4-oxo-butanamido]-4-O-phosphono-3-O-[(3R)-3-tetradecanoyloxytetradecanoyl]-β-D-glucopyranosyl}-3-O-[(3R)-3-hydroxytetradecanoyl]-2-[(3R)-3-tetradecanoyloxytetradecanamido]-α/β-D-glucopyranose |
| Compound 78 | Benzyl 3-O-[(3R)-3-benzyloxytetradecanoyl]-2-deoxy-4,6-di-O-isopropylidene-2-(2,2,2-trichloroethoxycarbonylamino)-α-D-glucopyranoside |
| Compound 79 | Benzyl 3-O-[(3R)-3-benzyloxytetradecanoyl]-2-deoxy-2-(2,2,2-trichloroethoxycarbonylamino)-α-D-glucopyranoside |
| Compound 80 | Allyl 6-O-benzyl-2-deoxy-3-O-[(3R)-3-tetradecanoyloxytetradecanoyl]-2-(2,2,2-trichloroethoxycarbonylamino)-α-D-glucopyranoside |

TABLE 7-continued

List of IUPAC names of compounds prepared in this invention

| | |
|---|---|
| Compound 81 | Allyl 6-O-benzyl-4-O-(di-O-benzyl-phosphono)-2-deoxy-3-O-[(3R)-3-tetradecanoyloxytetradecanoyl]-2-(2,2,2-trichloroethoxycarbonylamino)-α-D-glucopyranoside |
| Compound 82 | 6-O-Benzyl-4-O-(di-O-benzyl-phosphono)-2-deoxy-3-O-[(3R)-3-tetradecanoyloxytetradecanoyl]-2-(2,2,2-trichloroethoxycarbonylamino)-α/β-D-glucopyranose |
| Compound 83 | 6-O-Benzyl-4-O-(di-O-benzyl-phosphono)-2-deoxy-3-O-[(3R)-3-tetradecanoyloxytetradecanoyl]-2-(2,2,2-trichloroethoxycarbonylamino)-α-D-glucopyranosyl trichloroacetimidate |
| Compound 84 | Benzyl 6-O-{6-O-benzyl-4-O-(di-O-benzyl-phosphono)-2-deoxy-3-O-[(3R)-3-tetradecanoyloxytetradecanoyl]-2-(2,2,2-trichloroethoxycarbonylamino)-β-D-glucopyranosyl}-3-O-[(3R)-3-benzyloxytetradecanoyl]-2-deoxy-2-(2,2,2-trichloroethoxycarbonylamino)-α-D-glucopyranoside |
| Compound 85 | Benzyl 6-O-{6-O-benzyl-4-O-(di-O-benzyl-phosphono)-2-deoxy-3-O-[(3R)-3-tetradecanoyloxytetradecanoyl]-2-[(3R)-3-tetradecanoyloxytetradecanamido]-α-D-glucopyranosyl}-3-O-[(3R)-3-benzyloxytetradecanoyl]-2-deoxy-2-[(3R)-3-tetradecanoyloxytetradecanamido]-α-D-glucopyranoside |
| Compound 86 | 2-Deoxy-6-O-{2-deoxy-4-O-phosphono-2-[(3R)-3-tetradecanoyloxytetradecanamido]-3-O-[(3R)-3-tetradecanoyloxytetradecanoyl]-β-D-glucopyranosyl}-3-O-[(3R)-3-hydroxytetradecanoyl]-2-[(3R)-3-tetradecanoyloxytetradecanamido]-α/β-D-glucopyranose |
| Compound 87 | Allyl 2-deoxy-4,6-di-O-benzylidene-3-O-[(3R)-3-docyloxytetradecanoyl]-2-(2,2,2-trichloroethoxycarbonylamino)-α-D-glucopyranoside |
| Compound 88 | Allyl 6-O-benzyl-2-deoxy-3-O-[(3R)-3-dodecyloxytetradecanoyl]-2-(2,2,2-trichloroethoxycarbonylamino)-α-D-glucopyranoside |
| Compound 89 | Allyl 6-O-benzyl-4-O-(di-O-benzyl-phosphono)-2-deoxy-3-O-[(3R)-3-dodecyloxytetradecanoyl]-2-(2,2,2-trichloroethoxycarbonylamino)-α-D-glucopyranoside |
| Compound 90 | 6-O-Benzyl-4-O-(di-O-benzyl-phosphono)-2-deoxy-3-O-[(3R)-3-dodecyloxytetradecanoyl]-2-(2,2,2-trichloroethoxycarbonylamino)-α/β-D-glucopyranose |
| Compound 91 | 6-O-Benzyl-4-O-(di-O-benzyl-phosphono)-2-deoxy-3-O-[(3R)-3-dodecyloxytetradecanoyl]-2-(2,2,2-trichloroethoxycarbonylamino)-α-D-glucopyranosyl trichloroacetimidate |
| Compound 92 | Benzyl 6-O-{6-O-benzyl-4-O-(di-O-benzyl-phosphono)-2-deoxy-3-O-[(3R)-3-dodecyloxytetradecanoyl]-2-(2,2,2-trichloroethoxycarbonylamino)-β-D-glucopyranosyl}-3-O-[(3R)-3-benzyloxytetradecanoyl]-2-deoxy-2-(2,2,2-trichloroethoxycarbonylamino)-α-D-glucopyranoside |
| Compound 93 | Benzyl 6-O-{6-O-benzyl-4-O-(di-O-benzyl-phosphono)-2-deoxy-3-O-[(3R)-3-dodecyloxytetradecanoyl]-2-[(3R)-3-dodecyloxytetradecanamido]-β-D-glucopyranosyl}-3-O-[(3R)-3-benzyloxytetradecanoyl]-2-deoxy-2-[(3R)-3-dodecyloxytetradecanamido]-α-D-glucopyranoside |
| Compound 94 | 2-Deoxy-6-O-{2-deoxy-4-O-phosphono-2-[(3R)-3-dodecyloxytetradecanamido]-3-O-[(3R)-3-dodecyloxytetradecanoyl]-β-D-glucopyranosyl}-3-O-[(3R)-3-hydroxytetradecanoyl]-2-[(3R)-3-dodecyloxytetradecanamido]-α/β-D-glucopyranose |
| Compound 95 | Benzyl 3-O-benzyl-2-deoxy-4,6-di-O-isopropylidene-2-(2,2,2-trichloroethoxycarbonylamino)-α-D-glucopyranoside |
| Compound 96 | Benzyl 3-O-benzyl-2-deoxy-2-(2,2,2-trichloroethoxycarbonylamino)-α-D-glucopyranoside |
| Compound 97 | Benzyl 2-amino-3-O-benzyl-2-deoxy-α-D-glucopyranoside |
| Compound 98 | Benzyl 3-O-benzyl-2-deoxy-2-{(3R)-3-[(3R)-3-dodecyloxytetradecanoyloxy]-tetradecanamido}-α-D-glucopyranoside |
| Compound 99 | Benzyl 3-O-benzyl-6-O-{6-O-benzyl-4-O-(di-O-benzyl-phosphono)-2-deoxy-3-O-[(3R)-3-dodecyloxytetradecanoyl]-2-(2,2,2-trichloroethoxycarbonylamino)-β-D-glucopyranosyl}-2-deoxy-2-{(3R)-3-[(3R)-3-dodecyloxytetradecanoyloxy]-tetradecanamido}-α-D-glucopyranoside |
| Compound 100 | Benzyl 6-O-{2-amino-6-O-benzyl-4-O-(di-O-benzyl-phosphono)-2-deoxy-3-O-[(3R)-3-dodecyloxytetradecanoyl]-β-D-glucopyranosyl}-3-O-benzyl-2-deoxy-2-{(3R)-3-[(3R)-3-dodecyloxytetradecanoyloxy]-tetradecanamido}-α-D-glucopyranoside |
| Compound 101 | Benzyl 3-O-benzyl-6-O-{6-O-benzyl-4-O-(di-O-benzyl-phosphono)-2-deoxy-2-[(3R)-3-dodecyloxytetradecanamido]-3-O-[(3R)-3-dodecyloxytetradecanoyl]-β-D-glucopyranosyl}-2-deoxy-2-{(3R)-3-[(3R)-3-dodecyloxytetradecanoyloxy]-tetradecanamido}-α-D-glucopyranoside |
| Compound 102 | 2-Deoxy-6-O-{2-deoxy-4-O-phosphono-2-[(3R)-3-dodecyloxytetradecanamido]-3-O-[(3R)-3-dodecyloxytetradecanoyl]-β-D-glucopyranosyl}-2-{(3R)-3-[(3R)-3-dodecyloxytetradecanoyloxy]-tetradecanamido}-α/β-D-glucopyranose |
| Compound 103 | Benzyl 3-O-benzyl-6-O-{6-O-benzyl-4-O-(di-O-benzyl-phosphono)-2-deoxy-2-[(3R)-3-benzyloxytetradecanamido]-3-O-[(3R)-3-dodecyloxytetradecanoyl]-β-D-glucopyranosyl}-2-deoxy-2-{(3R)-3[(3R)-3-dodecyloxytetradecanoyloxy]-tetradecanamido}-α-D-glucopyranoside |
| Compound 104 | 2-Deoxy-6-O-{2-deoxy-4-O-phosphono-2-[(3R)-3-hydroxytetradecanamido]-3-O-[(3R)-3-dodecyloxytetradecanoyl]-β-D-glucopyranosyl}-2-{(3R)-3-[(3R)-3-dodecyloxytetradecanoyloxy]-tetradecanamido}-α/β-D-glucopyranose |

TABLE 8

Single letter and three letter codes for amino acids

| Amino acid | Single letter code | Three letter code |
|---|---|---|
| L-Alanine | A | Ala |
| L-Cysteine | C | Cys |
| L-Asparatate | D | Asp |
| L-Glutamate | E | Glu |
| L-Phenylalanine | F | Phe |
| L-Glycine | G | Gly |
| L-Histidine | H | His |
| L-Isoleucine | I | Ile |
| L-Lysine | K | Lys |
| L-Leucine | L | Leu |
| L-Methionine | M | Met |
| L-Asparagine | N | Asn |
| L-Proline | P | Pro |

TABLE 8-continued

Single letter and three letter codes for amino acids

| Amino acid | Single letter code | Three letter code |
|---|---|---|
| L-Glutamine | Q | Gln |
| L-Arginine | R | Arg |
| L-Serine | S | Ser |
| L-Threonine | T | Thr |
| L-Valine | V | Val |
| L-Tryptophan | W | Trp |
| L-Tyrosine | Y | Tyr |

TABLE 9

Enumeration of Some Preferred Embodiments

Embodiment 1. A compound of the following formula:

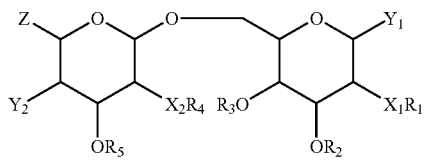

wherein at least one of $R_1$, $R_2$, $R_3$, $R_4$, $R_5$ is chosen from the following structures

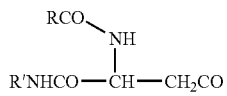   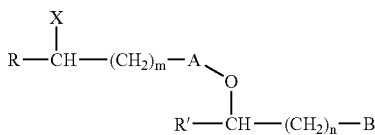

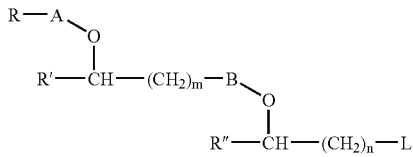

where the remaining $R_1$, $R_2$, $R_3$, $R_4$, and/or $R_5$, if any, are selected from the group consisting of hydrogen, —R, —COR and the following structures

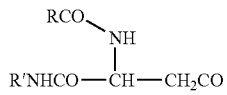   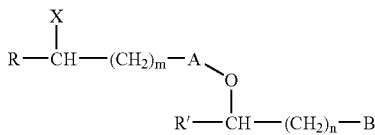

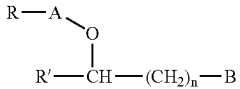   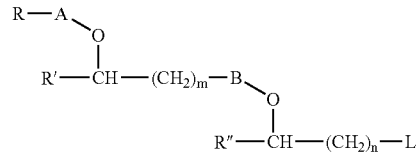

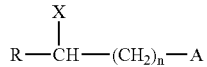

where each R, R', R'' is independently chosen to be a hydrogen, or a substituted or unsubstituted, branched or linear $C_{1-20}$ saturated or unsaturated aliphatic hydrocarbon; A, B and L are independently selected from the group consisting of —CH$_2$—, —C(=O)— and —C(=S)— groups; each X is independently selected from the group consisting of —OH, —SH, —NH$_2$, and -halogen;
m and n are independently selected from the range of integers between 0 and 10 inclusive, $X_1$ and $X_2$ are —O— or —NH—,
$Y_1$ and $Y_2$ are independently selected from the group consisting of —OH, —OP(O)(OH)$_2$, —COOH, —OSO$_3$H, —CH(COOH)$_2$ and —OP(O)(OH)(OCH$_2$CH$_2$NH$_2$),
Z is H, —CH$_2$E, or —CH$_2$MG, where E is -hydrogen, -halogen, —OH, —NH$_2$, —OSO$_3$H, —SO$_3$H, —P(O)(OH)$_2$ or —OP(O)(OH)$_2$;
M is —O—, —S—, —OC(=O)—, —SC(=O)—, —OC=(S)—, or —NHC(=O)—;
G is a -hydrogen, or a substituted or unsubstituted, branched or linear, saturated or unsaturated $C_{1-20}$ aliphatic hydrocarbon. or a physiologically acceptable salt thereof.

TABLE 9-continued

Enumeration of Some Preferred Embodiments

Embodiment 2. A compound of embodiment 1 where $X_1$ and $X_2$ are NH; $Y_1$ is —OH or —OP(O)(OH)$_2$; $Y_2$ is —OH or OP(O)(OH)$_2$; and Z is —CH$_2$OH.

Embodiment 3. A compound of embodiment 1 where the substitution groups and the stereochemistry of substitutions on the sugar rings are defined by the following formula:

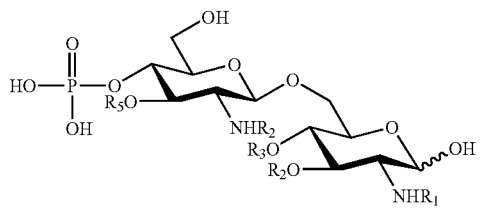

Embodiment 4. A compound of embodiment 3 where at least one of $R_1$, $R_2$, $R_3$, $R_4$ and $R_5$ is chosen from the following groups

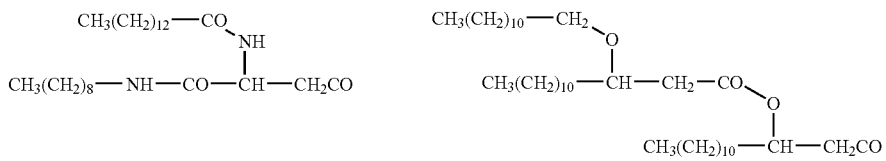

Embodiment 5. A compound of embodiment 4 where $R_1$ is the following group

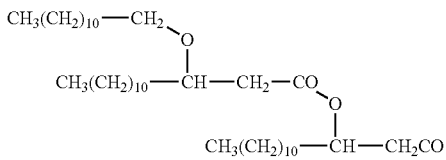

$R_2$ and $R_3$ are hydrogen atoms;
$R_4$ is chosen from the following groups

and R5 is the following group

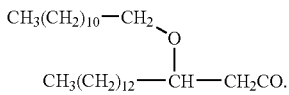

Embodiment 6. A compound of embodiment 5 where $R_4$ is the following group

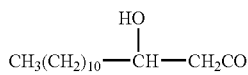

and the absolute configuration of the chiral carbons in group $R_1$, $R_4$ and $R_5$ is (R).

Embodiment 7. A compound of embodiment 5 where $R_4$ is the following group

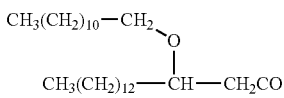

and the absolute configuration of the chiral carbons in group $R_1$, $R_4$ and $R_5$ is (R).

Embodiment 8. A compound of embodiment 4 where $R_1$ and $R_5$ are a group of the following structure

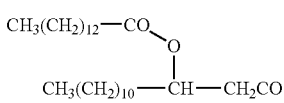

and $R_2$ is a hydrogen atom or the following group

TABLE 9-continued

Enumeration of Some Preferred Embodiments

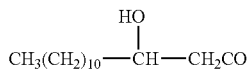

$R_3$ is a hydrogen atom;
and $R_4$ is a group of the following structure

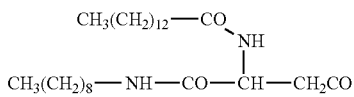

Embodiment 9. A compound of embodiment 8 where $R_2$ is a hydrogen atom, and the absolute configuration of the chiral carbons in group $R_1$ and $R_5$ is (R), while that in group $R_4$ is (S)
Embodiment 10. A compound of embodiment 8 where $R_2$ is a group of the following structure

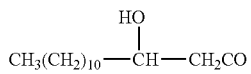

and the absolute configuration of the chiral carbons in group $R_1$, $R_2$ and $R_5$ is (R), while that in group $R_4$ is (S).
Embodiment 11. A compound of the following formula:

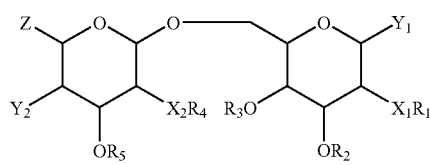

where $R_1 = R_4 = R_5$ and $R_1, R_2, R_3, R_4$ and $R_5$ are chosen from —R, —COR and the following structures

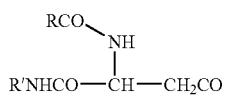

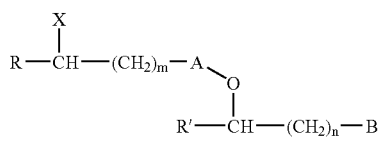

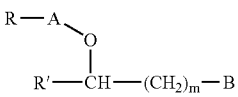

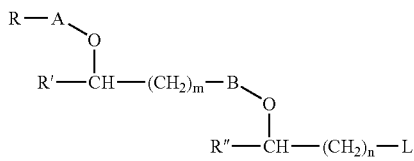

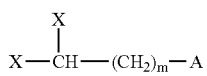

where each R, R', R" is independently a hydrogen, substituted or unsubstituted, branched or linear, saturated or unsaturated $C_{1-20}$ aliphatic hydrocarbon; A, B and L are independently $CH_2$, CO and CS groups; X is —OH, —SH, —$NH_2$ and halogen; m and n are integers between 0 and 10 inclusive.
$X_1$ and $X_2$ are independently O and NH.
$Y_1$ and $Y_2$ are independently group —OH, —OP(O)(OH)$_2$, —COOH, —OSO$_3$H, —CH(COOH)$_2$ and —OP(O)(OH)(OCH$_2$CH$_2$NH$_2$).
Z is H, —CH$_2$E, —CH$_2$MG where E is hydrogen, halogen, —OH, —NH$_2$, —OSO$_3$H, —SO$_3$H, —PO)(OH)$_2$ or —OP(O)(OH)$_2$; M is O, S, OC(O), SC(O), OC(S), or NHC(O); G is a hydrogen, substituted or
unsubstituted, branched or linear, saturated or unsaturated $C_{1-20}$ aliphatic hydrocarbon.
The said compound can be a free acid or a physiologically acceptable salt.
Embodiment 12. A compound of embodiment 11 where $X_1$ and $X_2$ are NH; $Y_1$ is —OH or —OP(O)(OH)$_2$; $Y_2$ is —OH or —OP(O)(OH)$_2$; and Z is —CH$_2$OH.
Embodiment 13. A compound of embodiment 11 where the substitution groups and the stereochemistry of substitutions on the sugar rings are defined by the following formula:

TABLE 9-continued

Enumeration of Some Preferred Embodiments

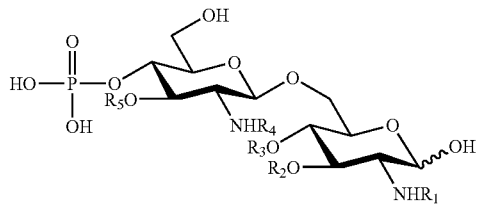

where $R_1 = R_4 = R_5$.
Embodiment 14. A compound of embodiment 13 where $R_1 = R_4 = R_5$ and are chosen from the following structures

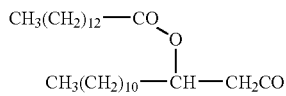 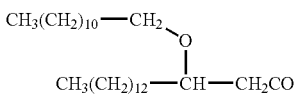

and $R_2$ is a hydrogen atom, n-propyl group or the following structure

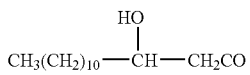

and $R_3$ is a hydrogen atom.
Embodiment 15. A compound of embodiment 14 where $R_2$ is a hydrogen atom, and $R_1$, $R_4$, and $R_5$ are the same group of the following structure

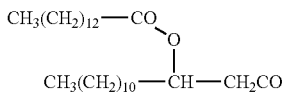

and the absolute configuration of the chiral carbons in group $R_1$, $R_4$, and $R_5$ is (R).
Embodiment 16. A compound of embodiment 14 where $R_2$ is an n-propyl group, and $R_1$, $R_4$, and $R_5$ are the same group of the following structure

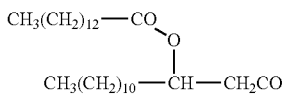

and the absolute configuration of the chiral carbons in group $R_1$, $R_4$, and $R_5$ is (R).
Embodiment 17. A compound of embodiment 14 where $R_2$ is the following group

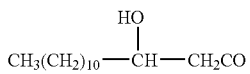

and $R_1$, $R_4$, and $R_5$ are the same group of the following structure

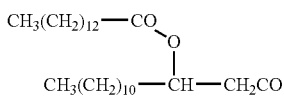

and the absolute configuration of the chiral carbons in group $R_1$, $R_2$, $R_4$, and $R_5$ is (R).
Embodiment 18. A compound of embodiment 14 where $R_2$ is the following group

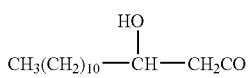

and $R_1$, $R_4$, and $R_5$ are the same group of the following structure

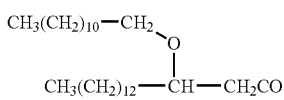

and the absolute configuration of the chiral carbons in group $R_1$, $R_2$, $R_4$, and $R_5$ is (R).
Embodiment 19. A compound of the following formula:

TABLE 9-continued

Enumeration of Some Preferred Embodiments

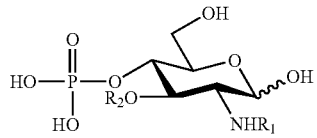

wherein at least one of $R_1$ and $R_2$ is chosen from the following groups

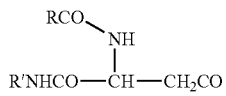     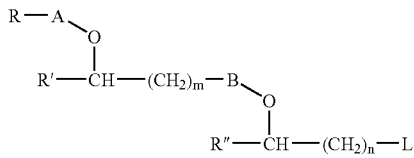

where each R, R', R'' is independently a hydrogen, substituted or unsubstituted, branched or linear, saturated or unsaturated $C_{1-20}$ aliphatic hydrocarbon; A, B and L are independently $CH_2$ and CO groups; m and n are integers between 0 and 10 inclusive, and the remaining $R_1$ or $R_2$ is chosen from hydrogen, group —R, —COR or the following structures

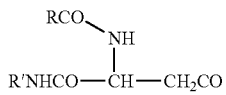     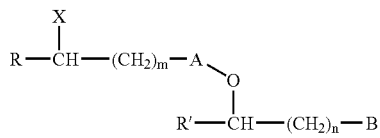

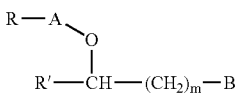   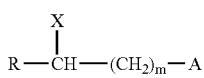   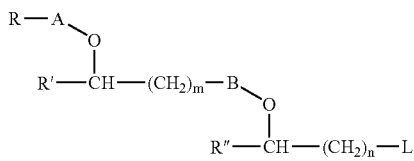

where each R, R', R'' is independently a hydrogen, substituted or unsubstituted, branched or linear, saturated or unsaturated $C_{1-20}$ aliphatic hydrocarbon; A, B and L are independently $CH_2$, CO and CS groups; X is —OH, —SH, —$NH_2$ and halogen; m and n are integers between 0 and 10 inclusive.
Embodiment 20. A compound of embodiment 19 where at least one of $R_1$ and $R_2$ is chosen from the following structures

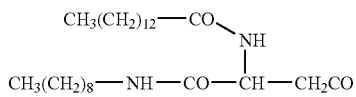     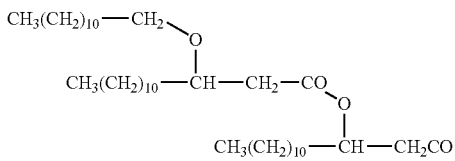

Embodiment 21. A compound of embodiment 20 where $R_1$ is a group of the following structure

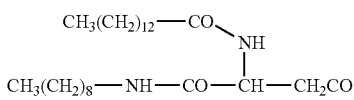

and R2 is a group of $CH_3(CH)_{12}CO$
Embodiment 22. A compound of embodiment 21 where the absolute configuration of the chiral carbon in group $R_1$ is (S)
Embodiment 23. A compound that comprises a substitution group of at least one of the following scructures

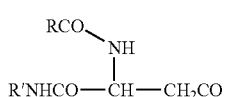     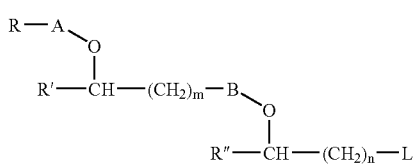

where each R, R', H'' is independently selected from the group consisting of hydrogen, and substituted or unsubstituted, branched or linear, saturated or unsaturated
$C_{1-20}$ aliphatic hydrocarbon; A, B and L are independently selected from the group consisting of —$CH_2$—, —C(=O)—, and —C(=S)— groups; and m and n are independently selected integers between 0 and 10 inclusive.
Embodiment 24. A compound of embodiment 23 where the said substitution group has the following structure TABLE 9-continued Enumeration of Some Preferred Embodiments

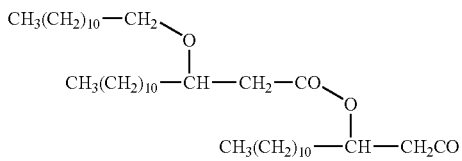

Embodiment 25. A compound of embodiment 23 where the said substitution group has the following structure

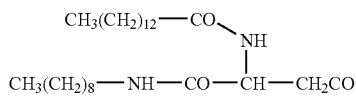

Embodiment 26. A compound of embodiment 24 where the absolutee configuration of the chiral carbons in the said substitution group is (R).
Embodiment 27. A compound of embodiment 25 where the absolute configuration of the chiral carbon in the said substitution group is (S).
Embodiment 28. A compound of che following structure

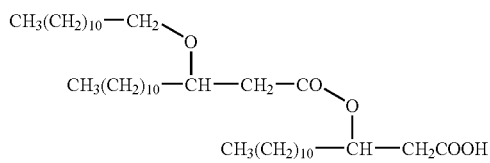

Embodiment 29. A compound of the following structure

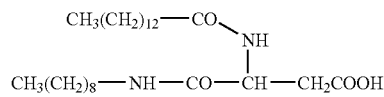

Embodiment 30. A compound of the following formula:

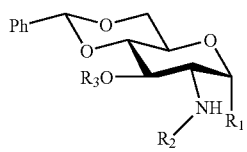

wherein $R_1$ is a group of benzyloxy, allyloxy, hydroxyl, or $OC(NH)CCl_3$; $R_2$ is chosen from the group consisting of hydrogen, —$COOCH_2CCl_3$, or the following structure

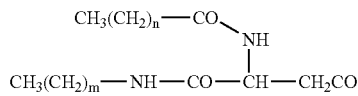

wherein m and n are independently selected integers having values between 0 and 20; and $R_3$ is $CH_3(CH_2)_zCO$ or the following structure

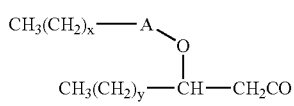

wherein A is —$CH_2$— or —$C(=O)$—, and x, y and z are independently selected integers having values between 0 and 20.
Embodiment 31. A compound of the following formula:

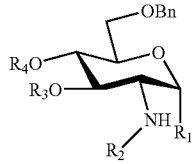

wherein $R_1$ is a group of benzyloxy, allyloxy, hydroxyl, or $OC(NH)CCl_3$; $R_2$ is chosen from a hydrogen atom, TABLE 9-continued Enumeration of Some Preferred Embodiments COOCH$_2$CCl$_3$ or

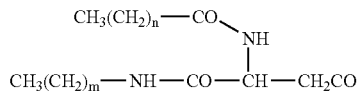

wherein m and n are independent integers having values between 0 and 20;
R$_3$ is CH$_3$(CH$_2$)$_z$CO or the following structure:

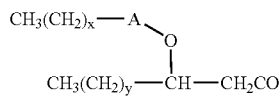

wherein A is —CH$_2$— or —C(=O)—; x, y and z are independently selected integers having values between 0 and 20; and R$_4$ is hydrogen or P(O)(OBn)$_2$.
Embodiment 32. A compound of the following formula:

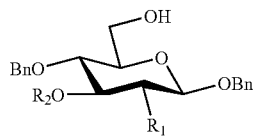

wherein R$_1$ is an amino radical, a phthalamido radical, or the following structure

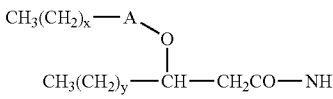

herein A is —CH$_2$— or —C(=O)—; x and y are independently selected integers having values between 0 and 20.
R$_2$ is allyl or benzyl.
Embodiment 33. A compound of the following formula:

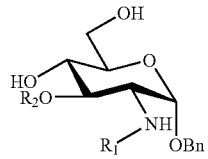

wherein R$_1$ is hydrogen, COOCH$_2$CCl$_3$ or one of the following structures

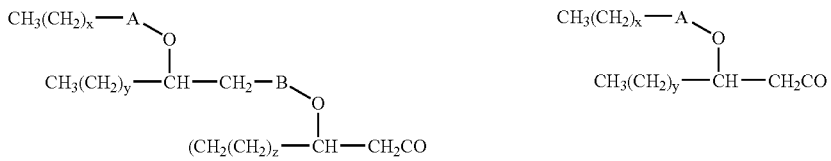

wherein A and B are independently either —CH$_2$— or —C(=O)—; x, y and z are independently selected integers having values between 0 and 20;
R$_2$ is benzyl or the following structure

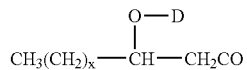

wherein D is a benzyl, CH$_3$(CH$_2$)$_z$ or CH$_3$(CH$_2$)$_y$CO;
x, y and z are independently selected integers having values between 0 and 20.
Embodiment 34. A compound of the following formula:

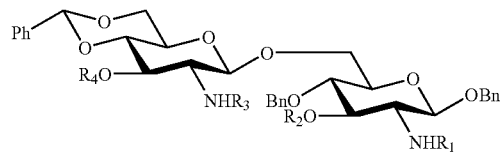

TABLE 9-continued

Enumeration of Some Preferred Embodiments wherein R₁ is a group of the following struccure

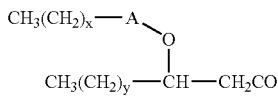

wherein A is —CH₂— or —C(=O)—; x and y are independently selected integers having values between 0 and 20;

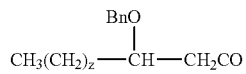

R₂ is hydrogen, allyl, benzyl or the following structure wherein z is an integer between 0 and 20;
R₃ is hydrogen, COOCH₂CCl₃, or one of the following structures

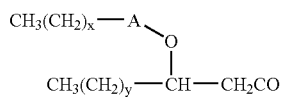  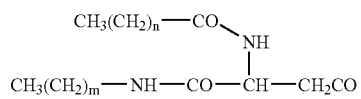

wherein A is —CH₂— or —C(=O)—; m, n, x and y are independently selected integers having values between 0 and 20;
R₄ is a group of the following structure

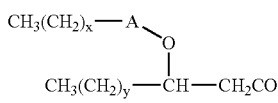

wherein A is —CH₂— or —C(=O)—; x and y are independently selected integers having values between 0 and 20.
Embodiment 35. A compound of che following formula:

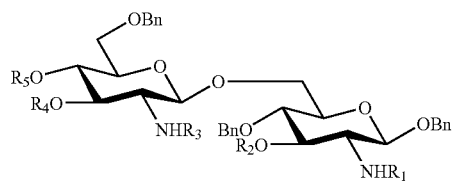

wherein R₁ is a group of the following structure

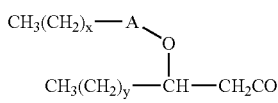

wherein A is —CH₂— or —C(=O)—; x and y are independently selected integers having values between 0 and 20;
R₂ is hydrogen, allyl, benzyl or the following structure

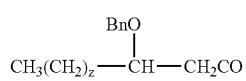

wherein z is an integer between 0 and 20;
R₃ is hydrogen, COOCH₂CCl₃ or one of the following structures

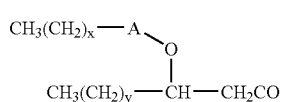  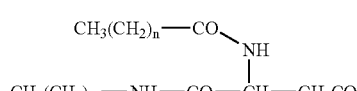

wherein A is —CH₂— or —C(=O)—; m, n, x and y are independently selected integers having values between 0 and 20;
R₄ is a group of the following structure

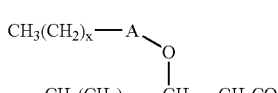

wherein A is —CH₂— or —C(=O)—; x and y are independently selected integers having values between 0 and 20;

TABLE 9-continued

Enumeration of Some Preferred Embodiments $R_5$ is hydrogen or $(BnO)_2P(O)$.
Embodiment 36. A compound of the following formula:

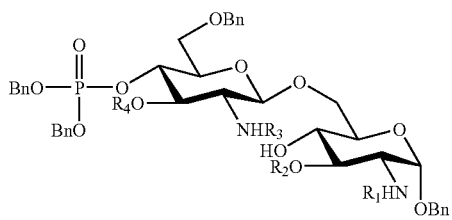

wherein $R_1$ is chosen from the following structures

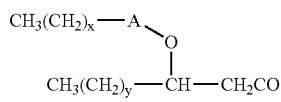         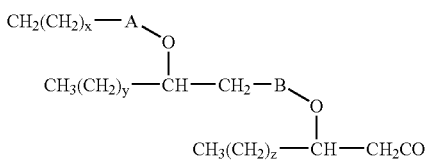

wherein A and B are independently —$CH_2$— or —C(=O)—; x, y and z are independently selected integers having values between 0 and 20;
$R_2$ is a group of benzyl or the following structure

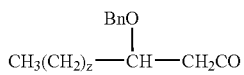

wherein z is an integer between 0 and 20;
$R_3$ is hydrogen, $COOCH_2CCl_3$ or the following structure

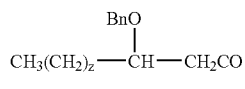         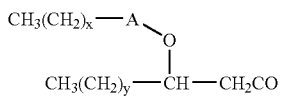

wherein A is $CH_2$ or CO; x, y and z are independent integers having values between 0 and 20;
$R_4$ is a group of the following scructure

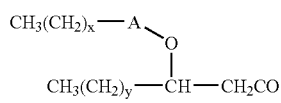

wherein A is $CH_2$ or CO; x and y are independent integers having values between 0 and 20.
Embodiment 37. A process to introduce a phosphate group into the 4-O-position of a hexopyranose derivative, where the said process comprises (1) regioselective reductive ring opening of a hexapyranose derivative, to yield a reactive 4-O position and (2) introduction of a phosphate group at said reactive 4-O position.
Embodiment 38. The process of embodiment 37 where step (1) comprises adding a boron reagent and an acid to a compound with the following structure:

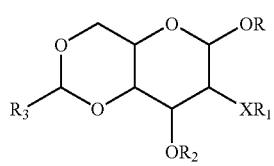

where X is O and NH; R is a substituted or unsubstituted, branched or linear, saturated or unsaturated $C_{1-20}$ aliphatic hydrocarbon, a carbohydrate unit or any protection group; $R_1$ and $R_2$ are any aliphatic or aromatic substitution group, or any protection group; $R_3$ is a phenyl or substituted phenyl group.
Embodiment 39. The process of embodiment 38 where said boron reagent is sodium cyanoboron hydride or a dimethyl amine borane complex.
Embodiment 40. The process of embodiment 38 in which said acid is hydrochloric acid.
Embodiment 41. The process of embodiment 40 in which said acid is provided in a saturaced diethyl ether soluton, trifluoroboron diethyl ether complex.
Embodiment 42. The process of embodiment 37 wherein, after step (2), an oxidizing reagent is added to yield a product with the following structure:

TABLE 9-continued

Enumeration of Some Preferred Embodiments

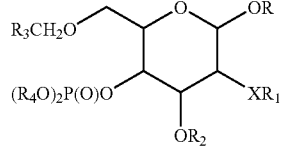

where X, R, $R_1$, $R_2$ and $R_3$ are defined as in the starting material in step (1), $R_4$ is an allyl, or a substituted or unsubstituted benzyl or phenyl group.

Embodiment 43. The process of embodiment 42 in which said oxidizing reagent is meta-chloroperbenzoic acid.

Embodiment 44. A non-naturally occurring liposome, whose membrane comprises: (a) a compound according to any of embodiments 1-36 above; and (b) at least one epitope.

Embodiment 45. The liposome of embodiment 44 in which at least one epitope is a B-cell epitope.

Embodiment 46. The liposome of embodiment 44 in which at least one epitope is a T-cell epitope.

Embodiment 47. The liposome of embodiment 44 in which at least one epitope is a peptide epitope.

Embodiment 48. The liposome of embodiment 44 in which at least one epitope is a carbohydrate, glycopeptide or glycolipid epitome.

Embodiment 49. A pharmaceutical composition comprising a liposome according to embodiment 43, said composition comprising a vaccinologically effective amount of said antigen.

Embodiment 50. The liposome of embodiment 44 where said antigen is a tumor associated antigen.

Embodiment 51. The liposome of embodiment 44 where at least one epitope is derived from MUC1 protein.

Embodiment 52. The liposome of embodiment 51 wherein the epitope is provided by a peptide or lipopeptide which has the amino acid sequence of $H_2N$-STAPPAHGVTSAPDTRPAPGSTAPPK(Pal)G-OH.

Embodiment 53. Use of the liposome of embodiment 51 in the manufacture of a composition for the prevention or treatment of a disease preventable or treatable by eliciting an immune response to said antigen.

Embodiment 54. The use of embodiment 53 in which said lipid A analogue has an adjuvanting effect on the immune response to said antigen.

Embodiment 55. The use of embodiments 53 or 54 in which said disease is a cancer.

REFERENCES 1. a) Stryer, *Biochemistry*, $2^{nd}$ Ed. W. H. Freeman and Co., New York, p 74, 1981.
   b) Christian H. R. Raetz, International Patent, WO 86/05687, 1986.
2. a) E. Th. Rietschel, L. Brade, B. Lindner, and U. Zahringer, 1992. Biochemistry of lipopolysaccharides. In: pp. 3-41, D. C. Morrison and J. L. Ryan (eds.), Bacterial Endotoxic Lipopolysaccharides, Volume I, Molecular Biochemistry and Cellular Biology, CRC Press, Boca Raton, Ann Arbor, London, Tokyo.
   b) H. Takada and S Kotani, 1992. Structure-function relationships of Lipid-A. In: pp. 107-134. ibid
3. a) M. Imoto, S. Kusumoto, T. Shiba, E. T. Rietschel, C. Galanos, and O. Lütderitz, *Tetrahedron Lett.* 1985, 26, 907-908.
   b) M. Imoto, H. Yoshimura, N. Sakaguchi, S. Kusumoto, T. Shiba, *Tetrahedron Lett.* 1985, 26, 1545-1548.
4. a) E. T. Rietschel, H.-W. Wollenweber, H. Brade, U. Zähringer, B. Lindner, U. Seydel, H. Bradaczek, G. Barnickel, H. Labishinski, and P. Giesbrecht. 1984. Structure and conformation of the lipid A component of lipopolysaccharides, pp. 187-220. In E. R. Rietschel (ed.), Handbook of Endotoxin, vol. 1. Chemistry of endotoxin. Elsevier Science Publishers, Amstrerdam.
   b) E. T. Rietschel, H.-W. Wollenweber, R. Russa, H. Brade, and U. Zähringer. *Rev. Infect. Dis.* 1984, 6, 432-438.
   c) U. Seydel, B. Lindner, H.-W. Wollenweber, and E. T. Rietschel, *Eur. J. Biochem.* 1984, 145, 505-509.
   d) S. M. Strain, I. M. Armitage, L. Anderson, K. Takayama, N. Qureshi, and C. R. H. Raetz. *J. Biol. Chem.* 1985, 260, 16089-16098.
5. a) H. Takada, S Kotani, *CRC Critic. Rev. Microbiol.* 1989, 16, 477-523.
   b) E. Ribi, K. Amano, J. L. Cantrell, S. M. Schwartzman, R. Parker and K. Takayama, *Cancer Immunol. Immunother.* 1982, 12, 91-102.
6. S. Kotani et al, *Infect. Immun.* 1986, 52(3), 872-884.
7. a) S. Kotani et al, *Infect. Immun.* 1986, 54; 673.
   b) M. Kiso, S. Tanaka, M. Tanahashi, Y. Fujishima, Y. Ogawa, and A. Hasagawa, *Carbohr. Res.* 1986, 148, 221.
8. a) Y. Fujishima, K. Kigawa, Y. Ogawa, M. Kiso, A. Hasagawa, *Carbohydr. Res.* 1987, 167, 317.
   b) D. Charon, R. Chaby, A. Malinvaud, M. Mondange, and L. Szabó, *Biochemistry*, 1985, 24, 2736.
9. W. J. Christ et al, *Science*, 1995, 268, 80-83.
10. K. Sato et al, *Infect. Immun.* 1995, 63, 2859-2866.
11. a) Georges H. Werner and Pierre Jollés, *Eur. J. Biochem*, 1996, 242, 1-19.
    b) K. Takayama, N. Qureshi, E. Ribi, and J. L. Cantrell, *Rev. Infect. Dis.* 1984, 6, 439-443.
    c) Keat R. Myerr, Alex T. Trachet, U.S. Pat. No. 4,912,094, 1990.
    d) J. T. Ulrich and K. R. Myers, *Pharm. Biotechnol.* 1995, 6, 495-524.
12. Martti Vaara, *Science*, 1996, 274 (8), 939-940.
13. H. Russell Onishi, Barbara A. Pelak, Lynn S, Gerckens, Lynn L. Silver, Frederick M. Kahan, Meng-Hsin Chen, Arthur A. Patchett, Susan M. Galloway, Sheryl A. Hyland, Matt S. Anderson, Christian R. H. Raetz, *Science*, 1996, 274 (8), 980-982.
14. R. C. Goldman, J. O. Capoblanco, C. C. Doran, and A. G. Matthysse. *J. Gen. Microbiol.* 1992, 138: 1527-1533.
15. R. C. Goldman, C. C. Doran, J. O. Capoblanco. *J. Bacterial.* 1988, 170: 2185-2192.
16. K. Takayama, N. Qureshi, E. Ribi, J. L. Cannell, and K. Amano. 1983. Use of endotoxin in cancer immunotherapy and characterization of its nontoxic but active lipid A components. In: pp. 219-233. L. Anderson and F. M. Unger (eds.), Bacterial lipopolysaccharides, American Chemical Society, Washington, D.C.
17. K. Von Esehen. 1992. Monophosphoryl lipid A and immunotherapy. In: D. C. Morrison and J. L. Ryan (eds.), Bacterial Endotoxic Lipopolysaccharides, Volume II, Immunopharmacology and pathophysiology, CRC Press, Boca Raton, Ann Arbor, London, Tokyo.
18. M. P. Fink, Crit. Care Med. 1993, 21 Suppl.: S32-S39.
19 W. J. Christ, T. Kawata, L. D. Hawkins, S, Kobayashi, O. Asano, and D. P. Rossignol. European patent EP-536969-A2. Dement Publications. Ltd.
20. Byung-Hee Han and Philip Boudjouk, J. Org. Chem. 1982, 47, 5036-5032.
21. a) Martine Demary, Germain Puzo, and Jean Asselineau, Nouv. J. Chim, 1978, 2, 373-378.
   b) William J. Gottstein and Lee C. Cheney, J. Org. Chem. 1965, 30, 2072-2073.
22. Makoto Kiso, Shinji Tanaka, Masanori Tanahashi, Yushun Fujishima, Yuji Ogawa and Akira Hasagawa, Carbohydr. Res. 1986, 148, 221-234.
23. Makoto Kiso, Shinji Tanaka, Minoru Fujita, Yushun Fujishima, Yuji Ogawa, Hideharu Ishida and Akira Hasagawa, Carbohydr. Res. 1987, 162, 127-140.
24. Masahiro Imoto et al, Bull. Chem. Soc. Jpn., 1987, 60, 2197-2204.
25. a) Prabhakar K. Jadhav, Mary E. Neville, Robert C. Newton, Subramaniam Sabesan, U.S. Pat. No. 5,158,941, 1992.
   b) Prabhakar K. Jadhav, Krishna S. Bhat, P. Thirumalai Perumal and Herbert C. Brown, J. Org. Chem. 1986, 51, 432-439.
   c) Stephen Hanessian, Ashok Tehim, Ping Chen, J. Org. Chem. 1993, 58, 7768-7781.
26. Bruno Tse, Charles M. Blazey, Ben Tu and James Balkovec, J. Org. Chem. 1997, 62, 3236-3241.
27. James A. Dale and Harry S. Mosher, J. Am. Chem. Soc. 1973, 95, 512-519.
28 Gunter Shüle and Thomas Ziegler, Liebigs Ann. 1996, 1599-1607.
29. Gunter Shüle and Thomas Ziegler, Tetrahedron, 1996, 52, 2925-2936.
30. Willi Bannwarth and Arnold Trzeciak, Helv. Chim. Acta, 1987, 70, 175-196.
31. Tomoya Ogawa and Satoru Nakabayashi, Carbohydr. Res. 1981, 97, 81-86.

No admission is made that any cited reference constitutes prior art. All references cited anywhere in this specification, including patents, published patent applications, and non-patent publications, are hereby incorporated by reference in their entirety, as are any references cited by said cited references.

We claim:

1. A compound of the following formula:

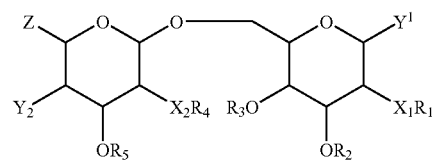

(a) wherein at least one of $R_1$, $R_2$, $R_3$, $R_4$, $R_5$ is selected, independently, from the group consisting of the following structures

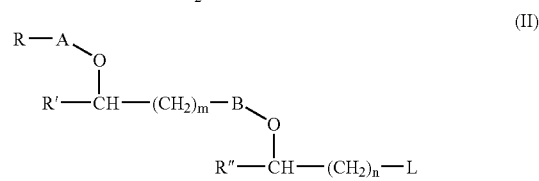

(b) wherein the remaining $R_1, R_2, R_3, R_4,$ and/or $R_5$, if any, are selected independently from the group consisting of hydrogen, —R, —COR and the following structures

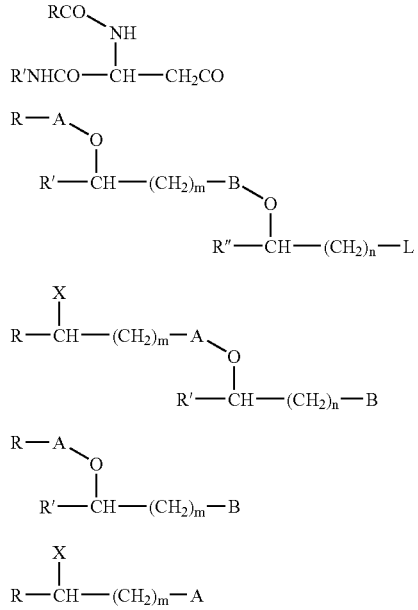

(c)
wherein each R, R', R" is independently chosen to be a substituted or unsubstituted, branched or linear $C_{1-20}$ saturated or unsaturated aliphatic hydrocarbon;

wherein A, B and L are independently selected from the group consisting of —$CH_2$—, —C(=O)— and —C(=S)— groups;

wherein each X is independently selected from the group consisting of —OH, —SH, —$NH_2$, and -halogen;

wherein m and n are independently selected from the range of integers between 0 and 10 inclusive, wherein $X_1$ and $X_2$ are —O— or —NH—;

wherein $Y_1$ and $Y_2$ are independently selected from the group consisting of —OH, —OP(O)(OH)$_2$, —COOH, —OSO$_3$H, —CH(COOH)$_2$ and —OP(O)(OH)(OCH$_2$CH$_2$NH$_2$);

wherein Z is H, —CH$_2$E, or —CH$_2$MG, where E is -hydrogen, -halogen, —OH, —NH$_2$, —OSO$_3$H, —SO$_3$H, —P(O)(OH)$_2$ or —OP(O)(OH)$_2$; M is —O—, —S—, —OC(=O)—, —SC(=O)—, —OC=(S)—, or —NHC(=O)—; G is a -hydrogen, or a substituted or unsubstituted, branched or linear, saturated or unsaturated $C_{1-20}$ aliphatic hydrocarbon;

or a physiologically acceptable salt thereof; wherein said compound, or salt thereof, when administered to mice, increases T-cell proliferation and/or interferon gamma production.

2. A compound of claim 1 where $X_1$ and $X_2$ are NH; $Y_1$ is —OH or —OP(O)(OH)$_2$; $Y_2$ is —OH or —OP(O)(OH)$_2$; and Z is —CH$_2$OH.

3. The compound of claim 2 in which A, B and L are —C(=O)—.

4. The compound of claim 3 in which each R, R', and R" is, independently, an unsubstituted, linear C1-C20 saturated aliphatic hydrocarbon.

5. A compound of claim 1 where the substitution groups and the stereochemistry of substitutions on the sugar rings are defined by the following formula:

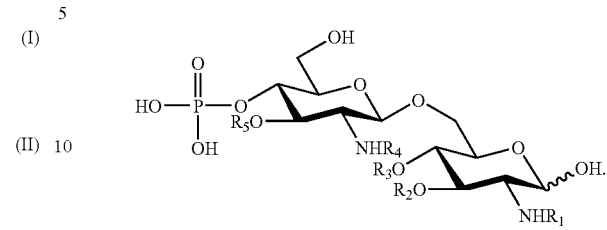

6. A compound of claim 5 where at least one of $R_1, R_2, R_3, R_4$ and $R_5$ is chosen from the following groups

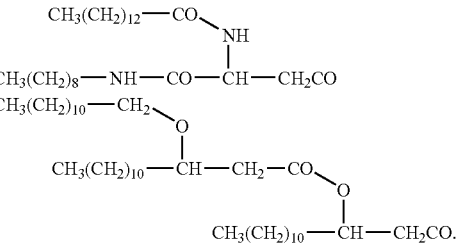

7. A compound of claim 6 where $R_1$ is the following group

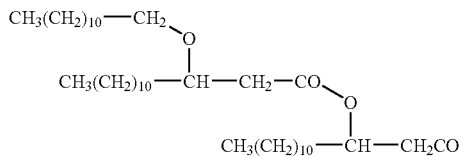

$R_2$ and $R_3$ are hydrogen atoms;
$R_4$ is chosen from the following groups

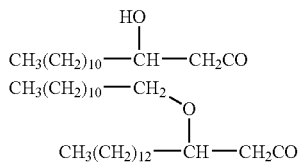

and $R_5$ is the following group

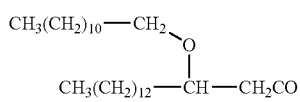

8. A compound of claim 7 where $R_4$ is the following group

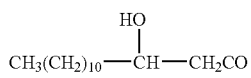

and the absolute configuration of the chiral carbons in group $R_1$, $R_4$ and $R_5$ is (R).

9. A compound of claim 7 where $R_4$ is the following group

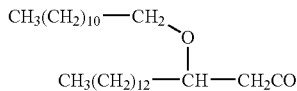

and the absolute configuration of the chiral carbons in group $R_1$, $R_4$ and $R_5$ is (R).

10. A compound of claim 6 where $R_1$ and $R_5$ are a group of the following structure

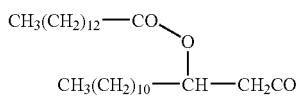

and $R_2$ is a hydrogen atom or the following group

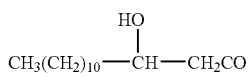

$R_3$ is a hydrogen atom;
and $R_4$ is a group of the following structure

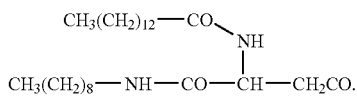

11. A compound of claim 10 where $R_2$ is a hydrogen atom, and the absolute configuration of the chiral carbons in group $R_1$, and $R_5$ is (R), while that in group $R_4$ is (S).

12. A compound of claim 10 where $R_2$ is a group of the following structure

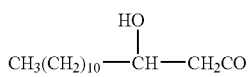

and the absolute configuration of the chiral carbons in group $R_1$, $R_2$ and $R_5$ is (R), while that in group $R_4$ is (S).

13. The compound of claim 1 in which each R, R', and R" is, independently, an unsubstituted, branched or linear, C1-C20 saturated or unsaturated aliphatic hydrocarbon.

14. The compound of claim 1 in which each R, R', and R" is, independently, an unsubstituted, branched or linear, C1-C20 saturated aliphatic hydrocarbon.

15. The compound of claim 1 in which each R, R', and R" is, independently, an unsubstituted, linear, C1-C20 saturated aliphatic hydrocarbon.

16. The compound of claim 1 in which A, B and L are —C(=O)—.

17. The compound of claim 1 in which X1 and X2 are —NH—.

18. The compound of claim 1 in which Y1 and Y2 are —OH or —OP(=O)(OH)2.

19. The compound of claim 1 in which at least one of R1, R2, R3, R4 and R5 is structure (I).

20. The compound of claim 1 in which at least one of R1, R2, R3, R4 and R5 is structure (II).

21. The compound of claim 1 wherein R1 is of structure (I) or (II).

22. The compound of claim 21 wherein R1 is of structure (II).

23. The compound of claim 1 wherein R4 is of structure (I) or (II).

24. The compound of claim 23 wherein R4 is of structure (I).

25. The compound of claim 1 wherein Y1 is —OP(O)(OH)$_2$, —COOH, —OSO$_3$H, or —CH(COOH)$_2$ and Y2 independently is —OP(O)(OH)$_2$, —COOH, —OSO$_3$H, or —CH(COOH)$_2$.

26. The compound of claim 25 wherein Z is not H and, if Z is CH$_2$E, E is not H.

27. The compound of claim 26 wherein, if Z is CH$_2$MG, G is hydrogen.

28. The compound of claim 1 wherein Y1 is —OP(O)(OH)$_2$, —COOH, —OSO$_2$H, or —CH(COOH)$_2$.

29. The compound of claim 1 wherein Y2 is —OP(O)(OH)$_2$, —COOH, —OSO$_3$H, or —CH(COOH)$_2$.

30. A non-naturally occurring liposome, whose membrane comprises: (a) a compound according to claim 1; and (b) at least one epitope.

31. A compound of the following formula:

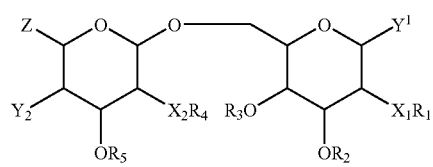

wherein $R_1$=$R_4$=$R_5$ and are one of the following structures

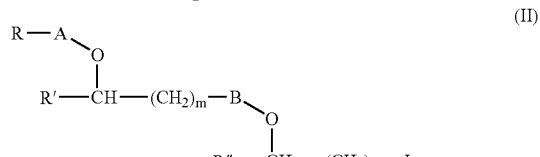

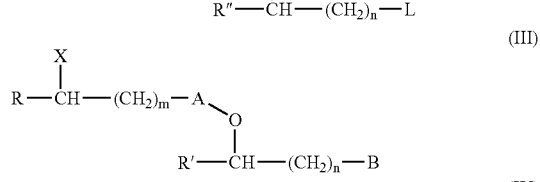

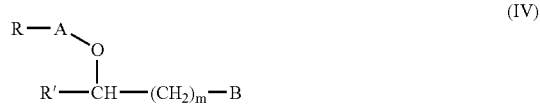

$R_3$ is selected from the group consisting of —R, —COR and the following structures

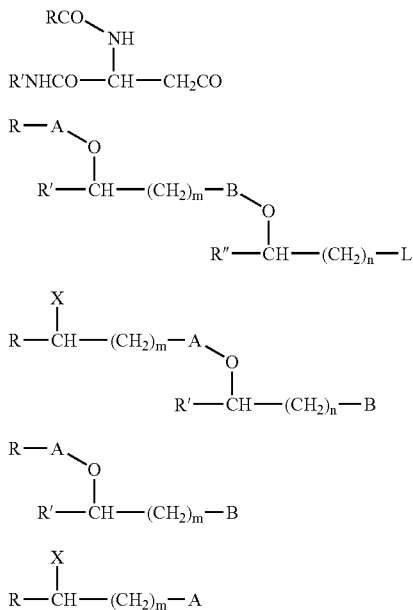

(I)
(II)
(III)
(IV)
(V)

R$_2$ is —R other than hydrogen, —COR, or one of structures (I)-(V), and may differ from R$_3$, wherein each R, R', R" is independently a hydrogen, substituted or unsubstituted, branched or linear, saturated or unsaturated C$_{1-20}$ aliphatic hydrocarbon; A, B and L are independently CH$_2$, CO and CS groups; X is —OH, —SH, —NH$_2$ or halogen; m and n are independently integers between 0 and 10 inclusive;

wherein X$_1$ and X$_2$ are independently O or NH;

wherein Y$_1$ and Y$_2$ are independently selected from the group consisting of —OH, —OP(O)(OH)$_2$, —COOH, —OSO$_3$H, —CH(COOH)$_2$ and —OP(O)(OH) (OCH$_2$CH$_2$NH$_2$);

wherein Z is H, —CH$_2$E, —CH$_2$MG wherein E is hydrogen, halogen, —OH, —NH$_2$, —OSO$_3$H, —SO$_3$H, —P(O)(OH)$_2$ or —OP(O)(OH)$_2$; M is O, S, OC(O), SC(O), OC(S), or NHC(O); and G is a hydrogen, or a substituted or unsubstituted, branched or linear, saturated or unsaturated C$_{1-20}$ aliphatic hydrocarbon;

or a physiologically acceptable salt thereof; wherein said compound, or salt thereof, when administered to mice, increases T-cell proliferation and/or interferon gamma production.

32. A compound of claim 31 where X$_1$ and X$_2$ are NH; Y$_1$ is —OH or —OP(O)(OH)$_2$; Y$_2$ is —OH or —OP(O)(OH)$_2$; and Z is —CH$_2$OH.

33. The compound of claim 32 in which A, B and L are —C(=O)—.

34. The compound of claim 33 in which each R, R', and R" is, independently, an unsubstituted, linear C1-C20 saturated aliphatic hydrocarbon.

35. The compound of claim 34 wherein R2 is structure (I) or structure (II), and may be the same as or different from R1, R4 and R5.

36. A compound of claim 31 where the substitution groups and the stereochemistry of substitutions on the sugar rings are defined by the following formula:

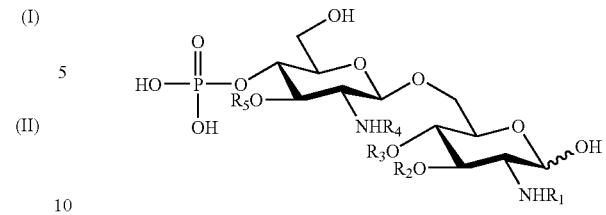

where R$_1$=R$_4$=R$_5$.

37. A compound of claim 36 where R$_1$=R$_4$=R$_5$, and are chosen from the following structures

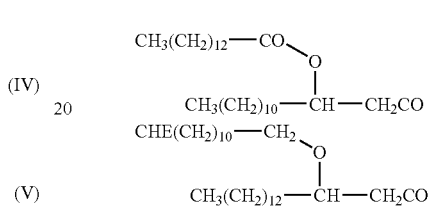

and R$_2$ is, n-propyl group or the following structure

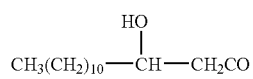

and R$_3$ is a hydrogen atom.

38. A compound of claim 37 R$_1$, R$_4$, and R$_5$ are the same group of the following structure

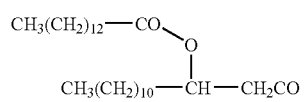

and the absolute configuration of the chiral carbons in group R$_1$, R$_4$, and R$_5$ is (P).

39. A compound of claim 37 where R$_2$ is an n-propyl group, and R$_1$, R$_4$, and R$_5$ are the same group of the following structure

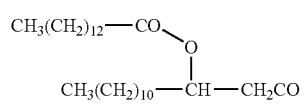

and the absolute configuration of the chiral carbons in group R$_1$, R$_4$, and R$_5$ is (R).

40. A compound of claim 37 where R$_2$ is the following group

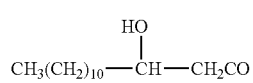

and R$_1$, R$_4$, and R$_5$ are the same group of the following structure

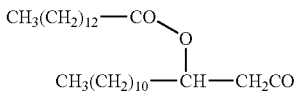

and the absolute configuration of the chiral carbons in group $R_1$, $R_2$, $R_4$, and $R_5$ is (R).

41. A compound of claim 37 where $R_2$ is the following group

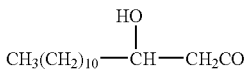

and $R_1$, $R_4$, and $R_5$ are the same group of the following structure

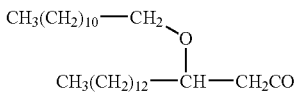

and the absolute configuration of the chiral carbons in group $R_1$, $R_2$, $R_4$, and $R_5$ is (R).

42. The compound of claim 31 in which each R, R', and R" is, independently, an unsubstituted, branched or linear, $C_1$-$C_{20}$ saturated or unsaturated aliphatic hydrocarbon.

43. The compound of claim 31 in which each R, R', and R" is, independently, an unsubstituted, branched or linear, $C_1$-$C_{20}$ saturated aliphatic hydrocarbon.

44. The compound of claim 31 in which each R, R', and R" is, independently, an unsubstituted, linear C1-C20 saturated aliphatic hydrocarbon.

45. The compound of claim 31 in which A, B and L are —C(=O)—.

46. The compound of claim 31 in which X1 and X2 are —NH.

47. The compound of claim 31 in which Y1 and Y2 are —OH or —OP(=O)(OH)2.

48. The compound of claim 31 wherein R2 is structure (I) or structure (II), and may be the same as or different from R1, R4 and R5.

49. The compound of claim 48 wherein R3 is hydrogen.

50. The compound of claim 31 wherein R3 is hydrogen.

51. The compound of claim 31 wherein R3 is not hydrogen.

52. The compound of claim 11 wherein at least one of Y1 and Y2 is —OP(O)(OH)$_2$, —COOH, —OSO$_3$H, or —CH(COOH)$_2$.

53. The compound of claim 52 wherein Z is not H and, if Z is CH$_2$E, E is not H.

54. The compound of claim 53 wherein, if Z is CH$_2$MG, G is hydrogen.

55. A non-naturally occurring liposome, whose membrane comprises: (a) a compound according to claim 31; and (b) at least one epitope.

56. The liposome of claim 55 in which at least one epitope is a B-cell epitope.

57. The liposome of claim 55 in which at least one epitope is a T-cell epitope.

58. The liposome of claim 55 in which at least one epitope is a peptide epitope.

59. The liposome of claim 55 in which at least one epitope is a carbohydrate, glycopeptide or glycolipid epitope.

60. A pharmaceutical composition comprising a liposome according to claim 55, said composition comprising a vaccinologically effective amount of an antigen comprising said epitope.

61. The liposome of claim 55 where said antigen is a tumor associated antigen.

62. The liposome of claim 55 where at least one epitope is derived from MUC1 protein.

63. The liposome of claim 62 wherein the epitope is provided by a peptide or lipopeptide which has the amino acid sequence of H2N-STAPPAHGVTSAPDTRPAPGSTAPPK (Pal) G-OH (SEQ ID NO: 1).

64. A method of preventing or treating a cancer which comprises administering a prophylactically or therapeutically effective amount of the liposome of claim 51, said liposome comprising an antigen comprising said epitope derived from MUC1 protein, said compound or salt thereof being an adjuvant, and having an adjuvanting effect on the immune response to said antigen.

65. The method of claim 64 which is a method of treating cancer, a therapeutically effective amount of the liposome being administered.

66. A compound of the following formula:

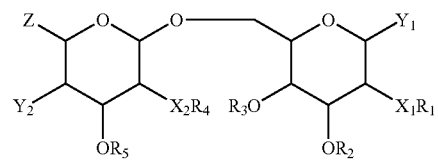

(a) wherein at least one of $R_1$, $R_2$, $R_3$, $R_4$, $R_5$ is selected, independently, from the group consisting of the following structures

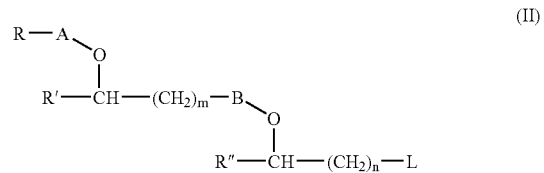

(b) wherein the remaining $R_1$, $R_2$, $R_3$, $R_4$, and/or $R_5$, if any, are selected independently from the group consisting of hydrogen, allyl, benzyl, troc, —R, —COR and the following structures

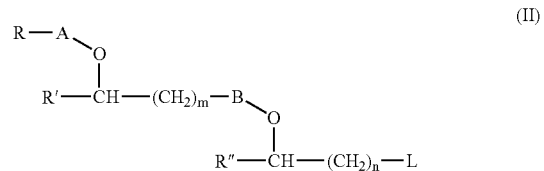

-continued (III)
R—CH(X)—(CH₂)ₘ—A—O—CH(R')—(CH₂)ₙ—B (IV)
R—A—O—CH(R')—(CH₂)ₘ—B (V)
R—CH(X)—(CH₂)ₘ—A (c)

wherein each R, R', R" is independently chosen to be a substituted or unsubstituted, branched or linear $C_{1-20}$ saturated or unsaturated aliphatic hydrocarbon;

wherein A, B and L are independently selected from the group consisting of —CH₂—, —C(=O)— and —C(=S)— groups;

wherein each X is independently selected from the group consisting of —O-benzyl, —OH, —SH, —NH₂, and -halogen;

wherein m and n are independently selected from the range of integers between 0 and 10 inclusive, wherein $X_1$ and $X_2$ are —O— or —NH—;

wherein $Y_1$ and $Y_2$ are independently selected from the group consisting of —O-benzyl, —O—P(=O)(O-benzyl)₂, —OH, —OP(O)(OH)₂, —COOH, —OSO₃H, —CH(COOH)₂ and —OP(O)(OH)(OCH₂CH₂NH₂), and, in the case of Y2, it is alternatively permitted that it and Z together form the structure —O—CH(Ph)—O—CH2-;

wherein Z is H, —CH₂E, or —CH₂MG, where E is -hydrogen, -halogen, —OH, —O-benzyl, —NH₂, —OSO₃H, —SO₃H, —P(O)(OH)₂ or —OP(O)(OH)₂; M is —O—, —S—, —OC(=O)—, —SC(=O)—, —OC=(S)—, or —NHC(=O)—; G is a -hydrogen, or a substituted or unsubstituted, branched or linear, saturated or unsaturated $C_{1-20}$ aliphatic hydrocarbon, except that Z may alternatively form the aforementioned structure with Y2;

or a physiologically acceptable salt thereof;

wherein said compound has a β-(1,6)-linked D-glucosamine disaccharide backbone.

67. A compound of the following formula:

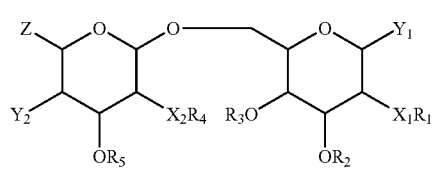

wherein $R_1=R_4=R_5$ and are one of the following structures (I)
RCO—NH
R'NHCO—CH—CH₂CO (II)
R—A—O—CH(R')—(CH₂)ₘ—B—O—CH(R")—(CH₂)ₙ—L (III)
R—CH(X)—(CH₂)ₘ—A—O—CH(R')—(CH₂)ₙ—B (IV)
R—A—O—CH(R')—(CH₂)ₘ—B $R_2$ and $R_3$ are independently selected from the group consisting of -hydrogen, allyl, benzyl, troc, —R, —COR and the following structures (I)
RCO—NH
R'NHCO—CH—CH₂CO (II)
R—A—O—CH(R')—(CH₂)ₘ—B—O—CH(R")—(CH₂)ₙ—L (III)
R—CH(X)—(CH₂)ₘ—A—O—CH(R')—(CH₂)ₘ—B (IV)
R—A—O—CH(R')—(CH₂)ₘ—B (V)
R—CH(X)—(CH₂)ₘ—A wherein each R, R', R" is independently a hydrogen, substituted or unsubstituted, branched or linear, saturated or unsaturated $C_{1-20}$ aliphatic hydrocarbon; A, B and L are independently CH₂, CO and CS groups; X is —O-benzyl, —OH, —SH, —NH₂ or halogen; m and n are independently integers between 0 and 10 inclusive;

wherein $X_1$ and $X_2$ are independently O or NH;

wherein $Y_1$ and $Y_2$ are independently selected from the group consisting of —O-benzyl, —OP(=O)(O-benzyl)₂, —OH, —OP(O)(OH)₂, —COOH, —OSO₃H, —CH(COOH)₂ and —OP(O)(OH)(OCH₂CH₂NH₂), and, in the case of Y2, it is alternatively permitted that it and Z together form the structure —O—CH(Ph)—O—CH2—; and wherein Z is H, —CH$_2$E, —CH$_2$MG wherein E is hydrogen, halogen, —OH, —O-benzyl, —NH$_2$, —OSO$_3$H, —SO$_3$H, —P(O)(OH)$_2$, —OP(O)(O-benzyl)$_2$ or —OP(O)(OH)$_2$; M is O, S, OC(O), SC(O), OC(S), or NHC(O); and G is a hydrogen, or a substituted or unsubstituted, branched or linear, saturated or unsaturated C$_{1-20}$ aliphatic hydrocarbon, except that Z may alternatively form the aforementioned structure with Y2;

or a physiologically acceptable salt thereof;

wherein said compound has a β-(1,6)-linked D-glucosamine disaccharide backbone, with the proviso that R2 is not hydrogen.

68. A compound of the following formula:

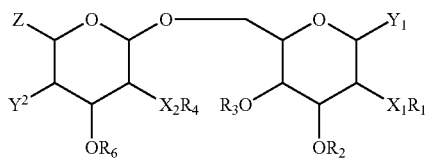

wherein at least one of R$_1$, R$_2$, R$_3$, R$_4$, R$_5$ is selected, independently, from the group consisting of the following structures

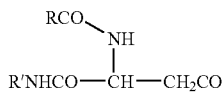
(I)

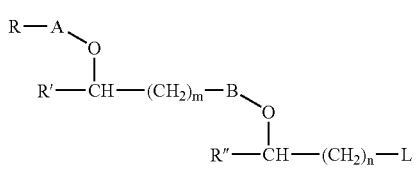
(II)

(b) wherein the remaining R$_1$, R$_2$, R$_3$, R$_4$, and/or R$_5$, if any, are selected independently from the group consisting of hydrogen, —R, —COR and the following structures

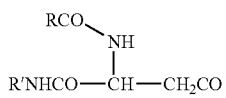
(I)

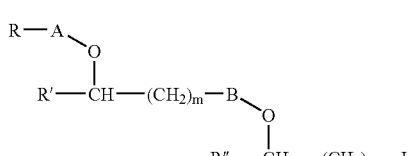
(II)

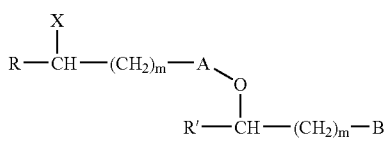
(III)

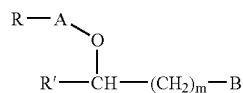
(IV)

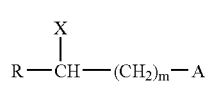
(V)

(c)

wherein each R, R', R" is independently chosen to be a substituted or unsubstituted, branched or linear C$_{1-20}$ saturated or unsaturated aliphatic hydrocarbon;

wherein A, B and L are independently selected from the group consisting of —CH$_2$—, —C(=O)— and —C(=S)— groups;

wherein each X is independently selected from the group consisting of —OH, —SH, —NH$_2$, and -halogen;

wherein m and n are independently selected from the range of integers between 0 and 10 inclusive, wherein X$_1$ and X$_2$ are —O— or —NH—;

wherein Y$_1$ and Y$_2$ are independently selected from the group consisting of —OH, —OP(O)(OH)$_2$, —COOH, —OSO$_3$H, —CH(COOH)$_2$ and —OP(O)(OH)(OCH$_2$CH$_2$NH$_2$);

wherein Z is H, —CH$_2$E, or —CH$_2$MG, where E is -hydrogen, -halogen, —OH, —NH$_2$, —OSO$_3$H, —SO$_3$H, —P(O)(OH)$_2$ or —OP(O)(OH)$_2$; M is —O—, —S—, —OC(=O)—, —SC(=O)—, —OC=(S)—, or —NHC(=O)—; G is a -hydrogen, or a substituted or unsubstituted, branched or linear, saturated or unsaturated C$_{1-20}$ aliphatic hydrocarbon;

or a physiologically acceptable salt thereof;

wherein said compound, or salt thereof, is an adjuvant.

69. A compound of the following formula:

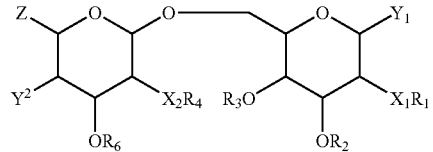

wherein R$_1$=R$_4$=R$_5$ and are one of the following structures

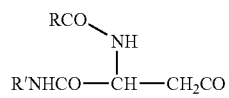
(I)

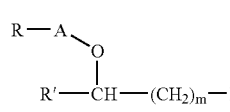
(II)

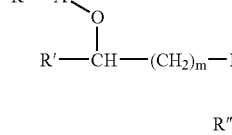

-continued

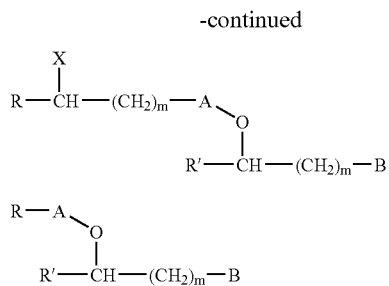

(III)

(IV)

$R_3$ is selected from the group consisting of —R, —COR and the following structures

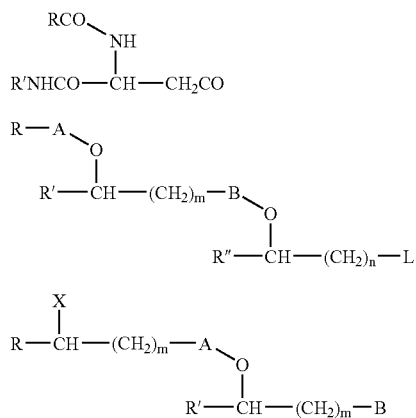

(I)

(II)

(III)

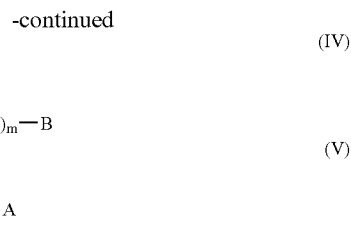

(IV)

(V)

$R_2$ is —R other than hydrogen, —COR, or one of structures (I)-(V), and may differ from $R_3$, wherein each R, R', R" is independently a hydrogen, substituted or unsubstituted, branched or linear, saturated or unsaturated $C_{1-20}$ aliphatic hydrocarbon; A, B and L are independently $CH_2$, CO and CS groups; X is —OH, —SH, —$NH_2$ or halogen; m and n are independently integers between 0 and 10 inclusive;

wherein $X_1$ and $X_2$ are independently O or NH;

wherein Y1 and Y2 are independently selected from the group consisting of —OH, —OP(O)(OH)$_2$, —COOH, —OSO$_3$H, —CH(COOH)$_2$ and —OP(O)(OH)(OCH$_2$CH$_2$NH$_2$);

wherein Z is H, —CH$_2$E, —CH$_2$MG wherein E is hydrogen, halogen, —OH, —NH$_2$, —OSO$_3$H, —SO$_3$H, —P(O)(OH)$_2$ or —OP(O)(OH)$_2$; M is O, S, OC(O), SC(O), OC(S), or NHC(O); and G is a hydrogen, or a substituted or unsubstituted, branched or linear, saturated or unsaturated $C_{1-20}$ aliphatic hydrocarbon;

or a physiologically acceptable salt thereof, wherein said compound, or salt thereof, is an adjuvant.

\* \* \* \* \*